US011634443B2

(12) United States Patent
Phares et al.

(10) Patent No.: US 11,634,443 B2
(45) Date of Patent: Apr. 25, 2023

(54) TREPROSTINIL PRODRUGS

(71) Applicant: United Therapeutics Corporation, Silver Spring, MD (US)

(72) Inventors: Kenneth Robert Phares, Hillsborough, NC (US); Hitesh Batra, Herndon, VA (US); Liang Guo, Vienna, VA (US)

(73) Assignee: United Therapeutics Corporation, Silver Spring, MD (US)

( * ) Notice: Subject to any disclaimer, the term of this patent is extended or adjusted under 35 U.S.C. 154(b) by 0 days.

(21) Appl. No.: 17/001,123

(22) Filed: Aug. 24, 2020

(65) Prior Publication Data

US 2021/0054009 A1 Feb. 25, 2021

Related U.S. Application Data

(60) Provisional application No. 62/976,183, filed on Feb. 13, 2020, provisional application No. 62/890,839, filed on Aug. 23, 2019.

(51) Int. Cl.
| | |
|---|---|
| *C07F 9/6574* | (2006.01) |
| *C07C 59/72* | (2006.01) |
| *C07D 207/16* | (2006.01) |
| *C07D 211/60* | (2006.01) |
| *C07D 265/30* | (2006.01) |
| *C07D 317/40* | (2006.01) |
| *C07D 321/12* | (2006.01) |
| *C07F 9/09* | (2006.01) |
| *A61K 9/00* | (2006.01) |
| *A61K 45/06* | (2006.01) |

(52) U.S. Cl.
CPC .......... *C07F 9/65744* (2013.01); *C07C 59/72* (2013.01); *C07D 207/16* (2013.01); *C07D 211/60* (2013.01); *C07D 265/30* (2013.01); *C07D 317/40* (2013.01); *C07D 321/12* (2013.01); *C07F 9/09* (2013.01); *A61K 9/0019* (2013.01); *A61K 9/0053* (2013.01); *A61K 45/06* (2013.01)

(58) Field of Classification Search
CPC .................................................. C07F 9/65744
See application file for complete search history.

(56) References Cited

U.S. PATENT DOCUMENTS

| | | | |
|---|---|---|---|
| 4,306,075 A | 12/1981 | Aristoff | |
| 5,153,222 A | 10/1992 | Tadepalli et al. | |
| 5,234,953 A | 8/1993 | Crow et al. | |
| 6,054,486 A | 4/2000 | Crow et al. | |
| 6,441,245 B1 | 8/2002 | Moriarty et al. | |
| 6,521,212 B1 | 2/2003 | Cloutier et al. | |
| 6,528,688 B2 | 3/2003 | Moriarty et al. | |
| 6,700,025 B2 | 3/2004 | Moriarty et al. | |
| 6,756,033 B2 | 6/2004 | Cloutier et al. | |
| 6,756,117 B1 | 6/2004 | Barnes | |
| 6,803,386 B2 | 10/2004 | Shorr et al. |
| 6,809,223 B2 | 10/2004 | Moriarty et al. |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 7,879,909 B2 | 2/2011 | Wade et al. |
| 7,999,007 B2 | 8/2011 | Jeffs et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,350,079 B2 | 1/2013 | Walsh |
| 8,410,169 B2 | 4/2013 | Phares et al. |
| 8,461,393 B2 | 6/2013 | Sharma |
| 8,481,782 B2 | 7/2013 | Batra et al. |
| 8,497,393 B2 | 7/2013 | Batra et al. |
| 8,536,363 B2 | 9/2013 | Phares et al. |
| 8,563,614 B2 | 10/2013 | Wade et al. |
| 8,609,728 B2 | 12/2013 | Rothblatt et al. |
| 8,653,137 B2 | 2/2014 | Jeffs et al. |
| 8,658,694 B2 | 2/2014 | Jeffs et al. |
| 8,747,897 B2 | 6/2014 | Kidane et al. |
| 8,765,813 B2 | 7/2014 | Wade et al. |
| 8,940,930 B2 | 1/2015 | Batra et al. |
| 9,029,607 B2 | 5/2015 | McGowan et al. |
| 9,050,311 B2 | 6/2015 | Phares et al. |
| 9,156,786 B2 | 10/2015 | Batra et al. |
| 9,199,908 B2 | 12/2015 | Phares et al. |
| 9,255,064 B2 | 2/2016 | Malinin et al. |
| 9,278,901 B2 | 3/2016 | Phares et al. |
| 9,278,902 B2 | 3/2016 | Tang et al. |
| 9,278,903 B2 | 3/2016 | Tang et al. |
| 9,339,507 B2 | 5/2016 | Olschewski et al. |
| 9,346,738 B2 | 5/2016 | Jain et al. |

(Continued)

FOREIGN PATENT DOCUMENTS

| | | |
|---|---|---|
| WO | WO-00/57701 A1 | 10/2000 |
| WO | WO-2005/007081 A2 | 1/2005 |

(Continued)

OTHER PUBLICATIONS

Newman, A. Developing Solid Oral Dosage Forms (Second Edition), Pharmaceutical Theory and Practice, 2017, pp. 497-518.
Paudel et al., "Manufacturing of solid dispersions of poorly water soluble drugs by spray drying: Formulation and process considerations," International Journal of Pharmaceutics, 2013, 453:253-284.
Sorbera et al., "UT-15. Treatment of Pulmonary Hypertension Treatment of Peripheral Vascular Disease," Drug of the Future, 2001, 26(4), pp. 364-374.
U.S. Appl. No. 17/549,573, filed Dec. 13, 2021, Phares et al.
Moriarty et al., "The Intramolecular Asymmetric Pauson-Khand Cyclization as a Novel and General Stereoselective Route to Benzindene Prostacyclins: Synthesis of UT-15 (Treprostinil)," J. Org. Chem. 2004, 69, 1890-1902.

*Primary Examiner* — Golam M Shameem
(74) *Attorney, Agent, or Firm* — Foley & Lardner LLP

(57) ABSTRACT

Provided are novel prodrugs of treprostinil, as well as methods of making and methods of using these prodrugs.

16 Claims, 38 Drawing Sheets

(56) References Cited

U.S. PATENT DOCUMENTS

| | | |
|---|---|---|
| 9,358,240 B2 | 6/2016 | Olschewski et al. |
| 9,371,264 B2 | 6/2016 | Becker et al. |
| 9,388,154 B2 | 7/2016 | Yiannikouros et al. |
| 9,394,227 B1 * | 7/2016 | Zhang .................. C07C 69/26 |
| 9,422,223 B2 | 8/2016 | Phares et al. |
| 9,505,737 B2 | 11/2016 | Becker et al. |
| 9,624,156 B2 | 4/2017 | Phares et al. |
| 9,643,911 B2 * | 5/2017 | Zhang ................. A61K 9/7023 |
| 9,758,465 B2 | 9/2017 | Laing |
| 9,878,972 B2 | 1/2018 | Phares et al. |
| 9,957,220 B2 * | 5/2018 | Zhang ...................... A61P 9/12 |
| 10,464,877 B2 * | 11/2019 | Zhang .................... A61P 11/06 |
| 10,703,706 B2 * | 7/2020 | Zhang ..................... C07C 69/96 |
| 2008/0200449 A1 | 8/2008 | Olschewski et al. |
| 2008/0280986 A1 | 11/2008 | Wade et al. |
| 2009/0036465 A1 | 2/2009 | Roscigno et al. |
| 2009/0124697 A1 | 5/2009 | Cloutier et al. |
| 2012/0197041 A1 | 8/2012 | Batra et al. |
| 2013/0184295 A1 | 7/2013 | Sprague et al. |
| 2013/0331593 A1 | 12/2013 | Mcgowan et al. |
| 2014/0024856 A1 | 1/2014 | Giust et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0148414 A1 | 5/2015 | Malinin et al. |
| 2015/0299091 A1 | 10/2015 | Batra et al. |
| 2015/0315114 A1 | 11/2015 | Hering et al. |
| 2015/0328232 A1 | 11/2015 | Malinin et al. |
| 2015/0376106 A1 | 12/2015 | Batra et al. |
| 2016/0030355 A1 | 2/2016 | Kidane et al. |
| 2016/0030371 A1 | 2/2016 | Phares et al. |
| 2016/0045470 A1 | 2/2016 | Reddy et al. |
| 2016/0051505 A1 | 2/2016 | Phares et al. |
| 2016/0107973 A1 | 4/2016 | Batra et al. |
| 2016/0129087 A1 | 5/2016 | Christe et al. |
| 2016/0143868 A1 | 5/2016 | Olschewski et al. |
| 2016/0152548 A1 | 6/2016 | Gao et al. |
| 2016/0175319 A1 | 6/2016 | Freissmuth et al. |
| 2017/0095432 A1 | 4/2017 | Phares et al. |
| 2018/0153847 A1 | 6/2018 | Phares et al. |

FOREIGN PATENT DOCUMENTS

| | | |
|---|---|---|
| WO | WO-2014/110491 A1 | 7/2014 |
| WO | WO-2016/038532 A1 | 3/2016 |
| WO | WO-2016/055819 A1 | 4/2016 |
| WO | WO-2016/081658 A1 | 5/2016 |
| WO | WO-2016/105538 A1 | 6/2016 |
| WO | WO-2016/205202 A1 | 12/2016 |
| WO | WO-2018/058124 A1 | 3/2018 |

* cited by examiner

Figure 1A

| No. | Compound | Structure | MW |
|---|---|---|---|
| 1 | Cyclopentyl Carbamate of Treprostinil (Prodrug I) | 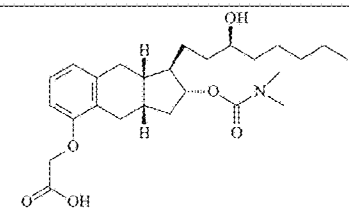 | 461.60 |
| 2 | Side Chain Carbamate of Treprostinil (Prodrug II) | 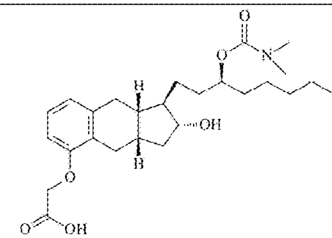 | 461.60 |
| 3 | Glycolamide of Treprostinil (Prodrug VII) | 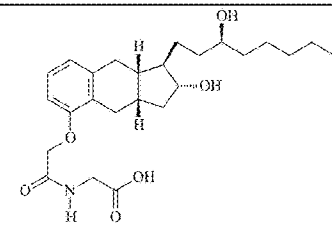 | 447.57 |
| 4 | Treprostinil acetoxy acetic acid prodrug (Prodrug XV) | 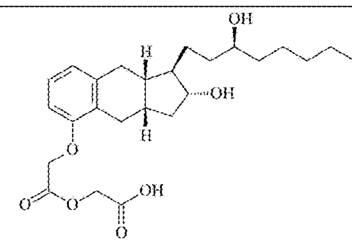 | 448.56 |

Figure 1B

| | | |
|---|---|---|
| 5 | Side chain carbonate ester prodrug of treprostinil<br>(Prodrug IV) | 448.56 |
| 6 | Cyclopentyl carbonate ester prodrug of treprostinil<br>(Prodrug III) | 448.56 |
| 7 | Side chain N-methyl carbamate ester prodrug of treprostinil<br>(Prodrug VIII) | 447.57 |

| 8 | Treprostinil alanine amide prodrug (Prodrug X) |  | 461.60 |
| --- | --- | --- | --- |
| 9 | Treprostinil valine amide prodrug (Prodrug XI) |  | 489.65 |
| 10 | Treprostinil aspartic acid amide prodrug (Prodrug XII) |  | 505.61 |

Figure 1D

| # | Structure | Name | MW |
|---|---|---|---|
| 11 | | Treprostinil serine amide prodrug (Prodrug XIII) | 477.60 |
| 12 | | Treprostinil sulfonamide prodrug (Prodrug XIV) | 467.62 |
| 13 | | Treprostinil side chain ethyl carbonate (Prodrug XVI) Chemical Formula: $C_{26}H_{38}O_7$ Molecular Weight: 462.58 | 462.58 |

Figure 1E

| 14 | Side Chain Isopropyl Carbonate of Treprostinil<br><br>(Prodrug XVII)<br><br>Chemical Formula: $C_{27}H_{40}O_7$<br>Molecular Weight: 476.61 | [structure] | 476.61 |
|---|---|---|---|
| 15 | Treprostinil side-chain phosphate ester<br><br>(Prodrug VI)<br><br>Chemical Formula: $C_{23}H_{35}O_8P$<br>Molecular Weight: 470.50 | [structure] | 470.50 |

Figure 1F

| | | |
|---|---|---|
| 16 | Phosphonooxy methyl ether of treprostinil<br><br>(Prodrug XVIII)<br><br>Chemical Formula: $C_{24}H_{37}O_9P$<br>Molecular Weight: 500.52 | 500.52 |
| 17 | Treprostinil piperidine ester<br><br>(Prodrug XIX)<br><br>Chemical Formula: $C_{29}H_{43}NO_6$<br>Molecular Weight: 501.66 | 501.66 |

Figure 1G

| | | |
|---|---|---|
| 18 | Treprostinil hemi-succinate ester (Prodrug XX) Chemical Formula: $C_{27}H_{38}O_8$ Molecular Weight: 490.59 | 490.59 |
| 19 | Treprostinil phosphonooxyy ethyl ether (Prodrug XXI) Chemical Formula: $C_{25}H_{39}O_9P$ Molecular Weight: 514.55 | 514.55 |
| 20 | Treprostinil Cyclopentyl Succinate (Prodrug XXII) Chemical Formula: $C_{27}H_{38}O_8$ Molecular Weight: 490.6 | 490.59 |

| | | |
|---|---|---|
| Treprostinil Side Chain Bi-piperidine Carbamate (Prodrug XXIII) Chemical Formula: $C_{34}H_{52}N_2O_6$ Molecular Weight: 584.8 |  | 584.80 |
| Treprostinil Cyclic Carbonate (Prodrug XXIV) Chemical Formula: $C_{24}H_{32}O_6$ Molecular Weight: 416.51 |  | 416.51 |
| Treprostinil Cyclopentyl Naproxen Ester (Prodrug XXV) |  | 602.77 |

| 24 | Treprostinil Side Chain isobutylphenylpropionic acid Ester<br><br>(Prodrug XXVI)<br><br>(Mix of diastereomers ~1:1)<br><br>Chemical Formula: $C_{36}H_{50}O_6$<br>Molecular Weight: 578.79 |  | 578.79 |
| --- | --- | --- | --- |
| 25 | Treprostinil Side Chain (6-methoxynaphthalen-2-yl)propanoic acid Ester<br><br>(Prodrug XXVII)<br><br>Chemical Formula: $C_{37}H_{46}O_7$<br>Molecular Weight: 602.77 |  | 602.77 |

Figure 1J

| 26 | Treprostinil Cyclic Phenyl Phosphate-I (Prodrug XXVIII) Chemical Formula: $C_{29}H_{37}O_7P$ | | 528.58 |
|---|---|---|---|
| 27 | Treprostinil Side Chain L-Valine Ester (Prodrug XXIX) Chemical Formula: $C_{28}H_{43}NO_6$ | | 489.65 |

| 28 | Treprostinil Side Chain Glycine Ester (Prodrug XXX) Chemical Formula: $C_{25}H_{37}NO_6$ |  | 447.57 |
|---|---|---|---|
| 29 | Treprostinil Side Chain L-Alanine Ester (Prodrug XXXI) Chemical Formula: $C_{26}H_{39}NO_6$ |  | 461.60 |

| 30 | Treprostinil side chain succinate ester N,N-dimethylamide (Prodrug XXXII) |  | 517.66 |
| --- | --- | --- | --- |
| 31 | Treprostinil side chain succinate ester morpholine amide (Prodrug XXXIII) |  | 559.70 |
| 32 | Treprostinil side chain succinate ester N-methylpiperazine amide (Prodrug XXXIV) |  | 572.74 |

Figure 1M

| 33 | Treprostinil side chain lysine ester (Prodrug XXXV) | | 518.70 |
|---|---|---|---|
| 34 | Treprostinil side chain proline ester (Prodrug XXXVI) | | 487.64 |
| 35 | Treprostinil side chain beta-Alanine ester (Prodrug XXXVII) | | 461.60 |

Figure 1N

| 36 | Treprostinil hemi-succinate carbamate (Prodrug XXXVIII) | | 491.58 |
|---|---|---|---|
| 37 | Treprostinil hemi-succinate carbonate (Prodrug XXXIX) | | 492.57 |
| 38 | Treprostinil mono-mer PEG carbonate (Prodrug XL) | | 492.6 |

| 39 | Treprostinil di-mer PEG carbonate (Prodrug XLI) |  | 536.7 |
| --- | --- | --- | --- |
| 40 | Treprostinil carboxamide (Prodrug XLII) |  | 433.55 |
| 41 | Treprostinil acetate ester (Prodrug XLIII) |  | 432.56 |

Figure 1P

| 42 | Treprostinil hydroxymethyl acetate ester (Prodrug XLIV) | | 448.56 |
|---|---|---|---|
| 43 | Treprostinil methyl ether (Prodrug XLV) | | 404.55 |
| 44 | Treprostinil propyl ether (Prodrug XLVI) | | 432.60 |

Figure 1Q

| | | |
|---|---|---|
| 45 | Treprostinil ethyl ether (Prodrug XLVII) | [structure] | 418.57 |
| 46 | Treprostinil 4-toluate ester (Prodrug XLVIII) | [structure] | 508.66 |
| 47 | Treprostinil pivaldehyde (Prodrug XLIX) | [structure] | 474.64 |

Figure 1R

| 48 | Treprostinil morpholinoethyl ether (Prodrug L) | | 503.68 |
|---|---|---|---|
| 49 | Treprostinil medoxomil ether (Prodrug LI) | | 502.60 |
| 50 | Treprostinil pivoxil ether (Prodrug LII) | | 504.66 |

Figure 1S

| 51 | Treprostinil ring methyl ether (Prodrug LIII) | | 404.55 |
|---|---|---|---|
| 52 | Treprostinil phenol ether hydroxymethyl acetate ester (Prodrug LIV) | | 540.65 |
| 53 | Treprostinil proprionic ester (Prodrug LV) | | 446.58 |

Figure 1T

| 54 | Treprostinil benzoic acid ether<br>(Prodrug LVI) | | 510.63 |
|---|---|---|---|
| 55 | Treprostinil acetic acid ether<br>(Prodrug LVII) | | 448.56 |
| 56 | Treprostinil SC 4-hydroxypiperidine carbamate<br>(Prodrug LVIII) | | 517.66 |

Figure 1U

| 57 | Treprostinil SC ethanol carbamate (Prodrug LIX) | | 477.60 |
|---|---|---|---|
| 58 | Treprostinil SC m-hydroxy benzoic ester (Prodrug LX) | | 510.63 |
| 59 | Treprostinil SC o-hydroxy benzoic ester (Prodrug LXI) | | 510.63 |

| 60 | Treprostinil SC p-trifluoromethyl benzoic ester (Prodrug LXII) |  | 562.63 |
| 61 | Treprostinil SC p-trifluoromethoxybenzoic ester (Prodrug LXIII) |  | 578.63 |
| 62 | Treprostinil SC p-trifluoromethoxy phenoxyacetate ester (Prodrug LXIV) |  | 608.65 |

Figure 1W

| 63 | Treprostinil SC phenoxyacetate ester (Prodrug LXV) | | 524.65 |
|---|---|---|---|
| 64 | Treprostinil SC 3,4 dihydroxy benzoic ester (Prodrug LXVI) | | 526.63 |
| 65 | Treprostinil isobutyric ester (Prodrug LXVII) | | 460.61 |

| 66 | Treprostinil SC p-hydroxy benzoic ester (Prodrug LXVIII) |  | 510.63 |
| --- | --- | --- | --- |
| 67 | Treprostinil SC adamantane ester (Prodrug LXIX) |  | 552.75 |
| 68 | Treprostinil diproprionic ester (Prodrug LXX) |  | 502.65 |

| | | |
|---|---|---|
| 69 | Treprostinil dicarbonate ester (Prodrug LXXI) |  506.59 |
| 70 | Treprostinil diacetate ester (Prodrug LXXII) |  474.59 |
| 71 | Treprostinil diphosphate ester (Prodrug LXXIII) |  550.48 |

Prodrug IV and treprostinil in Dogs and Rats

Treprostinil from Prodrug XVII in Dogs and Rats

* Prodrug XVII plasma levels below the quantitation limit.

Treprostinil from Prodrug VI in Dogs and Rats

* Prodrug VI plasma levels below the quantitation limit.

TREPROSTINIL PRODRUGS

PRIORITY

This application claims priority to U.S. provisional applications Nos. 62/890,839 fried Aug. 23, 2019 and 62/976,183 fried Feb. 13, 2020, each of which is incorporated herein by reference in its entirety.

FIELD

The present application generally relates to prostacyclins and more particularly, to prodrugs of treprostinil and to methods of making and using such prodrugs.

BACKGROUND

Pulmonary hypertension is a progressive and life-threatening disease characterized by increased pressure in the pulmonary vasculature that can lead to, inter alia, heart failure.

Pulmonary hypertension (PH) has been previously classified as primary (idiopathic) or secondary. The World Health Organization (WHO) has classified pulmonary hypertension into five groups:

Group 1: pulmonary arterial hypertension (PAH);

Group 1': Pulmonary veno-occlusive disease (PVOD) and/or pulmonary capillary haemangiomatosis (PCH)

Group 2: PH with left heart disease;

Group 3: PH with lung disease and/or hypoxemia;

Group 4: PH due to chronic thrombotic and/or embolic disease; and

Group 5: miscellaneous conditions; unclear multifactorial mechanisms (e.g., sarcoidosis, histiocytosis X, lymphangiomatosis and compression of pulmonary vessels).

There are currently a number of approved products for certain types of pulmonary hypertension, including Group 1 (PAH). Those products include products containing treprostinil as the active ingredient, such as Remodulin® (treprostinil) injection. Treprostinil, however, is commonly associated with site pain when administered subcutaneously. In some cases, patients must discontinue use of subcutaneous treprostinil because the site pain is too severe. Thus, a need exists for administering treprostinil without causing site pain.

Once treprostinil is absorbed, regardless of the route of administration, its half-life is short, about 1 hour. Therefore, a need exists to prolong the half-life of treprostinil.

Another challenge associated with oral delivery of treprostinil is the high first-pass effect for treprostinil. It has been measured in animal studies to be approximately 60%. Thus, there is a need to increase the bioavailability of treprostinil, such as by modifying the first pass effect.

SUMMARY

In one aspect, a compound having the following formula:

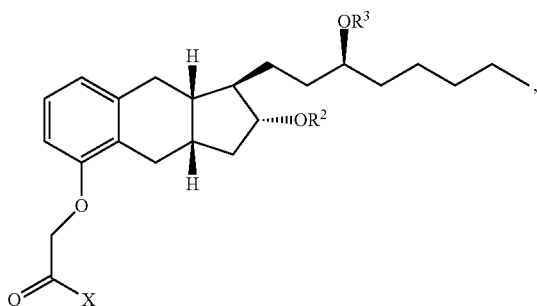

or pharmaceutically acceptable salt thereof, is provided wherein:

X is $OR^{14}$, $-NR^1SO_2R^1$, $-NR^1CO_2H$,

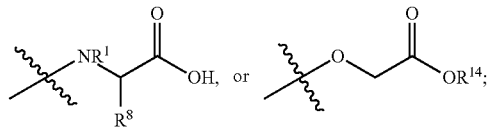

wherein:

each $R^1$ is independently H or $C_1$-$C_4$ alkyl and $R^8$ is optionally substituted $C_1$-$C_6$ falkyl or the side group of an amino acid, or $R^1$ and $R^8$ together form 4-7 membered heterocycle;

$R^{14}$ is a H, optionally substituted $C_1$-$C_6$ alkyl, a first drug moiety, or:

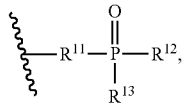

wherein $R^{11}$ is absent, an optionally substituted $C_1$-$C_6$ alkylene, or -$Q^1$-O— wherein $Q^1$ is optionally substituted $C_1$-$C_6$ alkylene; and each of $R^{12}$ and $R^{13}$ are independently selected from H, OH, optionally substituted $C_1$-$C_6$ alkoxy, optionally substituted $C_1$-$C_6$ alkyl, optionally substituted $C_1$-$C_6$ alkenyl, optionally substituted $C_1$-$C_8$ cycloalkyl, optionally substituted $C_1$-$C_{10}$ aryl;

each of $R^2$ and $R^3$ independently is a second drug moiety or a third drug moiety, H, a phosphorous containing group, —C(O)$R^6$, or an -A-B-C substituent, wherein:

A is optionally substituted $C_1$-$C_6$ alkylene, —$NR^6$—, —C(O)—, —C(O)O—, or —C(O)$NR^6$—;

B is a bond, optionally substituted $C_1$-$C_6$ alkylene, —C(O)—, —O—, —S—, heterocyclyl; and C is optionally substituted heterocyclyl, optionally substituted heteroaryl, optionally substituted aryl, optionally substituted cycloalkyl, —(OCH$_2$CH$_2$)$_q$—OR$^6$, —C(O)N(R$^6$)$_2$, —C(O)N(R$^{18}$)$_2$, —C(O)R$^6$, —CO$_2$H, —OR$^6$, —N(R$^{18}$)$_2$, —N(R$^6$)$_2$, or

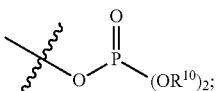

wherein:
both $R^{18}$ together form an optionally substituted 3-8 membered heterocyclyl;
each $R^6$ is independently H, optionally substituted $C_1$-$C_6$ alkyl, optionally substituted heteroaryl, optionally substituted aryl, or both of $R^6$ together form an 4 to 8 membered optionally substituted heterocyclyl or a 5 membered optionally substituted heteroaryl;
or $R^2$ and $R^3$ are joined together to form —C(O)—, —SO$_2$—,

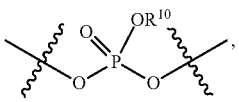

in an 8-12 membered heterocyclyl, wherein
each $R^{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl; and
q is 0, 1, 2, 3, 4, 5 or 6;
provided that:
when A is —C(O)—, B is not a bond and C is not —N($R^6$)$_2$;
when A is —C(O)—, B is not a bond and C is not —OR$^6$;
$R^{14}$, $R^2$ and $R^3$ are not H;
when X is OH, $R^2$ and $R^3$ are not H;
when $R^8$ is H, then at least one of $R^2$ and $R^3$ is not H In another aspect, a method of treating a disease or condition is provided, the method comprising administering to a subject a compound disclosed herein. In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma.

DETAILED DESCRIPTION

Figure 1C:
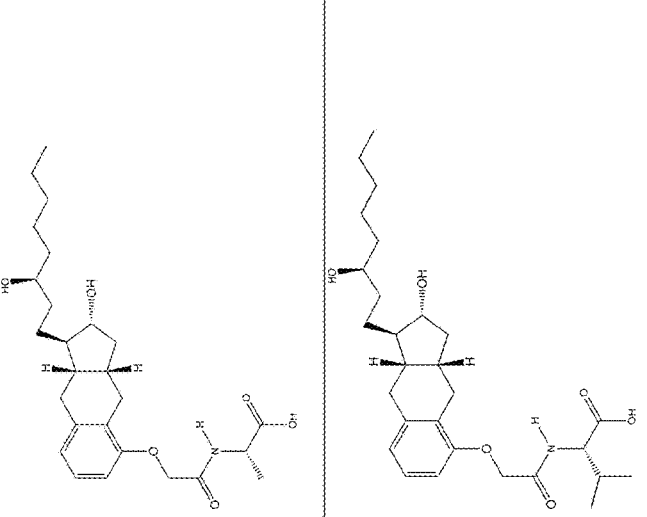
FIGS. 1A-Y show selected prodrugs.
Figure 1C:
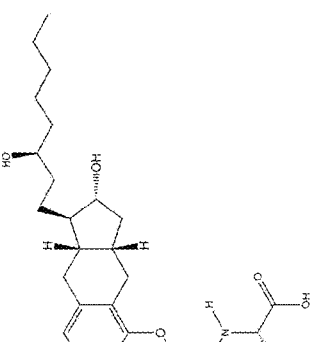
Figure 1C:
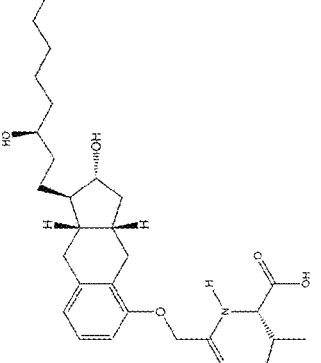
Figure 1H:
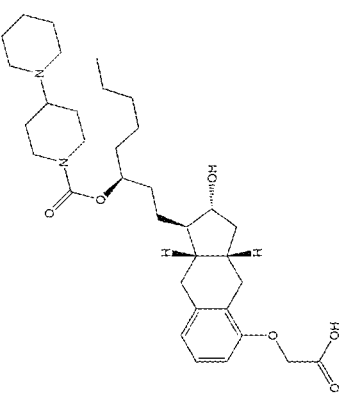
Figure 1H:
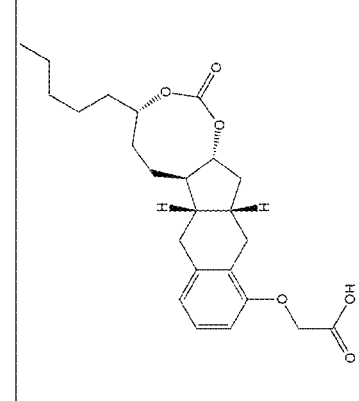
Figure 1H:
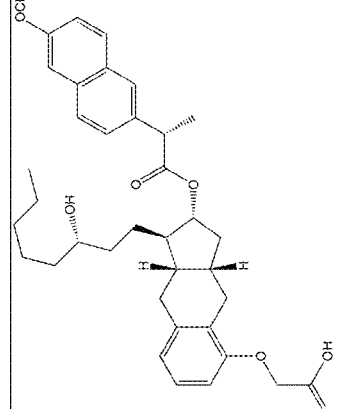
Figure 1I:
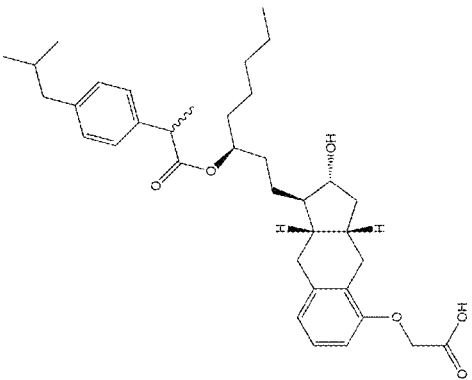
Figure 1I:
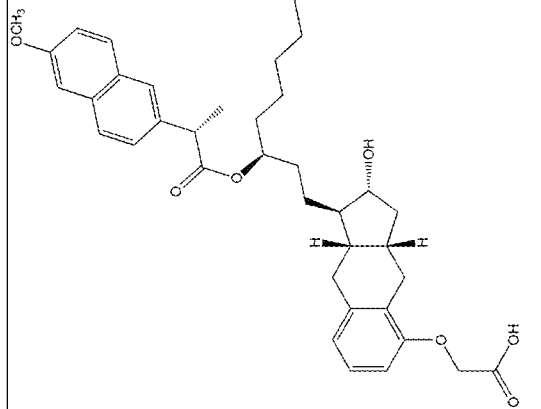
Figure 1K:
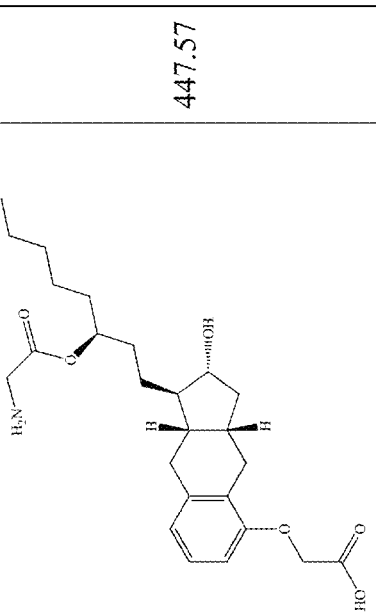
Figure 1K:
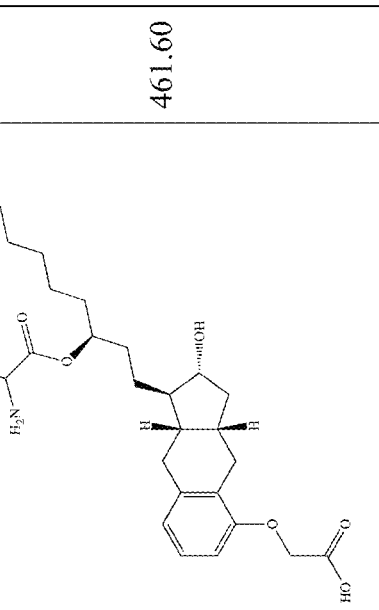
Figure 1L:
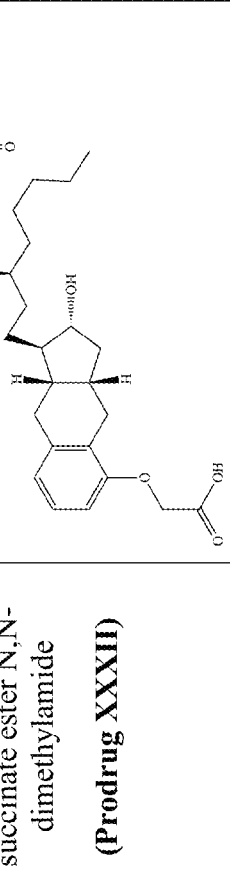
Figure 1L:
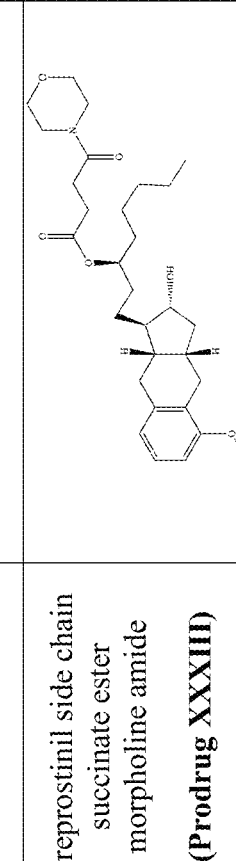
Figure 1L:
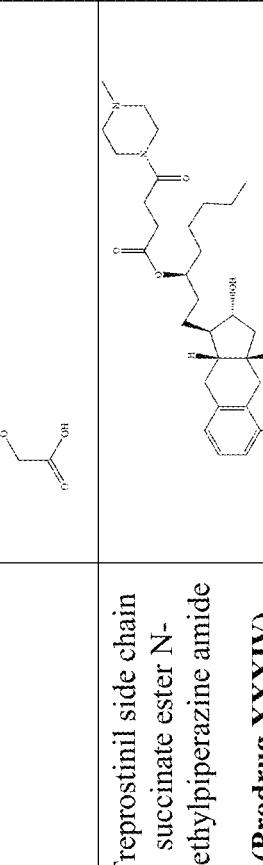

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about."

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only, and is not intended to limit the scope of the present invention, which is defined solely by the claims. In order that the present disclosure can be more readily understood, certain terms are first defined. Additional definitions are set forth throughout the detailed description.

All numerical designations, e.g., pH, temperature, time, concentration, and molecular weight, including ranges, are approximations which are varied (+) or (−) by increments of 0.05%, 1%, 2%, 5%, 10% or 20%. It is to be understood, although not always explicitly stated that all numerical designations are preceded by the term "about." It also is to be understood, although not always explicitly stated, that the reagents described herein are merely exemplary and that equivalents of such are known in the art.

"HPLC" refers to high-performance liquid chromatography.

"NMR" refers to nuclear magnetic resonance.

As used herein, $C_m$-$C_n$, such as $C_1$-$C_{12}$, $C_1$-$C_8$, or $C_1$-$C_6$ when used before a group refers to that group containing m to n carbon atoms.

"Optionally substituted" refers to a group selected from that group and a substituted form of that group. Substituents may include any of the groups defined below. In one embodiment, substituents are selected from $C_1$-$C_{10}$ or $C_1$-$C_6$, alkyl, substituted $C_1$-$C_{10}$ or $C_1$-$C_6$ alkyl, $C_2$-$C_6$ alkenyl, $C_2$-$C_6$ alkynyl, $C_6$-$C_{10}$ aryl, $C_3$-$C_8$ cycloalkyl, $C_2$-$C_{10}$ heterocyclyl, $C_1$-$C_{10}$ heteroaryl, substituted $C_2$-$C_6$ alkenyl, substituted $C_2$-$C_6$ alkynyl, substituted $C_6$-$C_{10}$ aryl, substituted $C_3$-$C_8$ cycloalkyl, substituted $C_2$-$C_{10}$ heterocyclyl, substituted $C_1$-$C_{10}$ heteroaryl, halo, nitro, cyano, —$CO_2H$ or a $C_1$-$C_6$ alkyl ester thereof.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl ((CH3)(CH3CH2)CH—), t-butyl ((CH3)3C—), n-pentyl ($CH_3CH_2CH_2CH_2CH_2$), and neopentyl (($CH_3)_3CCH_2$—).

"Alkenyl" refers to monovalent straight or branched hydrocarbyl groups having from 2 to 10 carbon atoms and preferably 2 to 6 carbon atoms or preferably 2 to 4 carbon atoms and having at least 1 and preferably from 1 to 2 sites of vinyl (>C=C<) unsaturation. Such groups are exemplified, for example, by vinyl, allyl, and but 3-en-1-yl. Included within this term are the cis and trans isomers or mixtures of these isomers.

"Alkynyl" refers to straight or branched monovalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—$CH_2C$≡CH).

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Heteroalkyl" refers to an alkyl group one or more carbons is replaced with —O—, —S—, $SO_2$, a P containing moiety as provided herein, —$NR^Q$—,

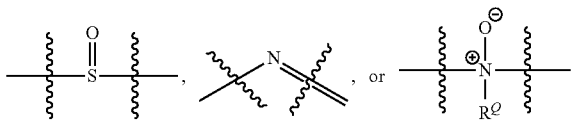

moieties where $R^Q$ is H or $C_1$-$C_6$ alkyl. Substituted heteroalkyl refers to a heteroalkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxyl, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein and with the proviso that any hydroxyl or thiol substitution is not attached to a vinyl (unsaturated) carbon atom.

"Heteroalkenyl" refers to an alkenyl group one or more carbons is replaced with —O—, —S—, $SO_2$, a P containing moiety as provided herein, —NRQ-,

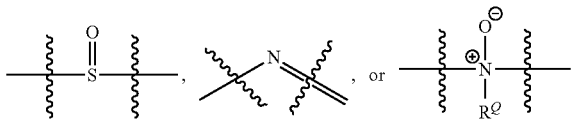

moieties where $R^Q$ is H or $C_1$-$C_6$ alkyl. Substituted heteroalkenyl refers to a heteroalkenyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO3H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkynyl" refers to an alkynyl group one or more carbons is replaced with —O—, —S—, SO$_2$, a P containing moiety as provided herein, —NRQ-,

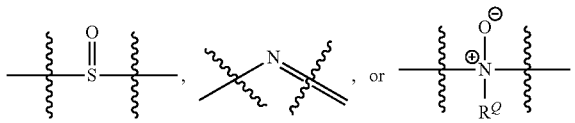

moieties where R$^Q$ is H or C$_1$-C$_6$ alkyl. Substituted heteroalkynyl refers to a heteroalkynyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonyl amino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Alkylene" refers to divalent saturated aliphatic hydrocarbyl groups having from 1 to 10 carbon atoms, preferably having from 1 to 6 and more preferably 1 to 3 carbon atoms that are either straight chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)— or —CH(CH$_3$)CH$_2$—), butylene (—CH$_2$CH$_2$CH$_2$CH$_2$—), isobutylene (—CH$_2$CH (CH$_3$—)CH$_2$—), sec-butylene (—CH$_2$CH$_2$(CH$_3$—)CH—), and the like. Similarly, "alkenylene" and "alkynylene" refer to an alkylene moiety containing respective 1 or 2 carbon carbon double bonds or a carbon carbon triple bond.

"Substituted alkylene" refers to an alkylene group having from 1 to 3 hydrogens replaced with substituents selected from the group consisting of alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, and oxo wherein said substituents are defined herein. In some embodiments, the alkylene has 1 to 2 of the aforementioned groups, or having from 1-3 carbon atoms replaced with —O—, —S—, or —NRQ-moieties where R$^Q$ is H or C$_1$-C$_6$ alkyl. It is to be noted that when the alkylene is substituted by an oxo group, 2 hydrogens attached to the same carbon of the alkylene group are replaced by "=O". "Substituted alkenylene" and "substituted alkynylene" refer to alkenylene and substituted alkynylene moieties substituted with substituents as described for substituted alkylene.

"Alkynylene" refers to straight or branched divalent hydrocarbyl groups having from 2 to 10 carbon atoms and preferably 2 to 6 carbon atoms or preferably 2 to 3 carbon atoms and having at least 1 and preferably from 1 to 2 sites of acetylenic (—C≡C—) unsaturation. Examples of such alkynylene groups include C≡C— and CH$_2$C≡C—.

"Substituted alkynylene" refers to alkynylene groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein and with the proviso that any hydroxyl or thiol substitution is not attached to an acetylenic carbon atom.

"Heteroalkylene" refers to an alkylene group wherein one or more carbons is replaced with —O—, —S—, SO$_2$, a P containing moiety as provided herein, —NR$^Q$—,

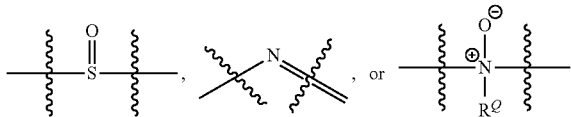

moieties where R$^Q$ is H or C$_1$-C$_6$ alkyl. "Substituted heteroalkylene" refers to heteroalkynylene groups having from 1 to 3 substituents, and preferably 1 to 2 substituents, selected from the substituents disclosed for substituted alkylene.

"Heteroalkenylene" refers to an alkenylene group wherein one or more carbons is replaced with —O—, —S—, SO$_2$, a P containing moiety as provided herein, —NR$^Q$—,

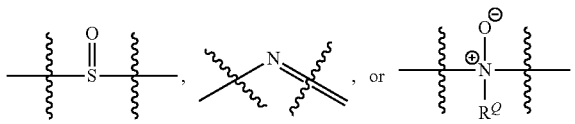

moieties where R$^Q$ is H or C$_1$-C$_6$ alkyl. "Substituted heteroalkenylene" refers to heteroalkynylene groups having from 1 to 3 substituents, and preferably 1 to 2 substituents, selected from the substituents disclosed for substituted alkenylene.

"Heteroalkynylene" refers to an alkynylene group wherein one or more carbons is replaced with —O—, —S—, SO$_2$, a P containing moiety as provided herein, —NR$^Q$—,

moieties where R$^Q$ is H or C$_1$-C$_6$ alkyl. "Substituted heteroalkynylene" refers to heteroalkynylene groups having from 1 to 3 substituents, and preferably 1 to 2 substituents, selected from the substituents disclosed for substituted alkynylene.

"Alkoxy" refers to the group O alkyl wherein alkyl is defined herein. Alkoxy includes, by way of example, methoxy, ethoxy, n propoxy, isopropoxy, n butoxy, t butoxy, sec butoxy, and n pentoxy.

"Substituted alkoxy" refers to the group O (substituted alkyl) wherein substituted alkyl is defined herein.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Acyl includes the "acetyl" group CH$_3$C(O)—.

"Acylamino" refers to the groups —NR$^{47}$C(O)alkyl, —NR$^{47}$C(O)substituted alkyl, —NR$^{47}$C(O)cycloalkyl, —NR$^{47}$C(O)substituted cycloalkyl, —NR$^{47}$C(O)cycloalkenyl, —NR$^{47}$C(O)substituted cycloalkenyl, —NR$^{47}$C(O)alkenyl, —NR$^{47}$C(O)substituted alkenyl, —NR$^{47}$C(O)alkynyl, —NR$^{47}$C(O)substituted alkynyl, —NR$^{47}$C(O)aryl, —NR$^{47}$C(O)substituted aryl, —NR$^{47}$C(O)heteroaryl, —NR$^{47}$C(O)substituted heteroaryl, —NR$^{47}$C(O)heterocyclic, and NR$^{47}$C(O)substituted heterocyclic wherein R$^{47}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, cycloalkenyl-C(O)O—, substituted cycloalkenyl-C(O)O—, heteroaryl-C(O)O—, substituted heteroaryl —C(O)O, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amino" refers to the group NH$_2$.

"Substituted amino" refers to the group —NR$^{48}$R$^{49}$ where R$^{48}$ and R$^{49}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic, SO$_2$ a-lkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic and wherein R$^{48}$ and R$^{49}$ are optionally joined, together with the nitrogen bound thereto to form a heterocyclic or substituted heterocyclic group, provided that R$^{48}$ and R$^{49}$ are both not hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. When R$^{48}$ is hydrogen and R$^{49}$ is alkyl, the substituted amino group is sometimes referred to herein as alkylamino. When R$^{48}$ and R$^{49}$ are alkyl, the substituted amino group is sometimes referred to herein as dialkylamino.

When referring to a monosubstituted amino, it is meant that either $R^{48}$ or $R^{49}$ is hydrogen but not both. When referring to a disubstituted amino, it is meant that neither $R^{48}$ nor $R^{49}$ are hydrogen.

"Aminocarbonyl" refers to the group —C(O)NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonyl" refers to the group —C(S)NR$^{50}$R51 where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{47}$C(O)NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic, and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^{47}$C(S)NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyloxy" refers to the group —O—C(O)NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyl" refers to the group —SO$_2$NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonyloxy" refers to the group —O—SO$_2$NR$^{50}$R$^{51}$ where $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminosulfonylamino" refers to the group —NR$^{47}$SO$_2$NR$^{50}$R$^{51}$ where $R^{47}$ is hydrogen or alkyl and $R^{50}$ and $R^{51}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Amidino" refers to the group —C(=NR$^{52}$)NR$^{50}$R$^{51}$ where $R^{50}$, $R^{51}$, and $R^{52}$ are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{50}$ and $R^{51}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2 benzoxazolinone, 2H 1,4 benzoxazin 3(4H) one 7 yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, substituted sulfonyloxy, thioacyl, thiol, alkylthio, and substituted alkylthio, wherein said substituents are as defined herein.

"Arylene" refers to a divalent aromatic carbocyclic group of from 6 to 14 carbon atoms having a single ring or multiple condensed rings. "Substituted arylene" refers to an arylene having from 1 to 5, preferably 1 to 3, or more preferably 1 to 2 substituents as defined for aryl groups.

"Heteroarylene" refers to a divalent aromatic group of from 1 to 10 carbon atoms and 1 to 4 heteroatoms selected from the group consisting of oxygen, nitrogen and sulfur within the ring. "Substituted heteroarylene" refers to heteroaryl ene groups that are substituted with from 1 to 5, preferably 1 to 3, or more preferably 1 to 2 substituents selected from the group consisting of the same group of substituents defined for substituted aryl.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group S (substituted aryl), where substituted aryl is as defined herein.

"Carbonyl" refers to the divalent group —C(O)— which is equivalent to —C(=O)—.

"Carboxyl" or "carboxy" refers to COOH or salts thereof.

"Carboxyl ester" or "carboxy ester" refers to the group —C(O)(O)-alkyl, —C(O)(O)-substituted alkyl, —C(O)O-alkenyl, —C(O)(O)-substituted alkenyl, —C(O)(O)-alkynyl, —C(O)(O)-substituted alkynyl, —C(O)(O)-aryl, —C(O)(O)-substituted-aryl, —C(O)(O)-cycloalkyl, —C(O)(O)-substituted cycloalkyl, —C(O)(O)-cycloalkenyl, —C(O)(O)-substituted cycloalkenyl, —C(O)(O)-heteroaryl, —C(O)(O)-substituted heteroaryl, —C(O)(O)-heterocyclic, and —C(O)(O)-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)amino refers to the group —$NR^{47}$C(O)(O)-alkyl, —$NR^{47}$C(O)(O)-substituted alkyl, —$NR^{47}$C(O)O-alkenyl, —$NR^{47}$C(O)(O)-substituted alkenyl, —$NR^{47}$C(O)(O)-alkynyl, —$NR^{47}$C(O)(O)-substituted alkynyl, —$NR^{47}$C(O)(O)-aryl, —$NR^{47}$C(O)(O)-substituted-aryl, —$NR^{47}$C(O)(O)-cycloalkyl, —$NR^{47}$C(O)(O)-substituted cycloalkyl, —$NR^{47}$C(O)(O)-cycloalkenyl, —$NR^{47}$C(O)(O)-substituted cycloalkenyl, —$NR^{47}$C(O)(O)-heteroaryl, —$NR^{47}$C(O)(O)-substituted heteroaryl, —$NR^{47}$C(O)(O)-heterocyclic, and —$NR^{47}$C(O)(O)-substituted heterocyclic wherein $R^{47}$ is alkyl or hydrogen, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)(O)-substituted alkynyl, —O—C(O)O-aryl, —O—C(O)O-substituted-aryl, —O—C(O)O-cycloalkyl, —O—C(O)O— substituted cycloalkyl, —O—C(O)O-cycloalkenyl, —O—C(O)O-substituted cycloalkenyl, —O—C(O)O— heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" refers to the group CN.

"Cycloalkyl" refers to cyclic alkyl groups of from 3 to 10 carbon atoms having single or multiple cyclic rings including fused, bridged, and spiro ring systems. The fused ring can be an aryl ring provided that the non aryl part is joined to the rest of the molecule. Examples of suitable cycloalkyl groups include, for instance, adamantyl, cyclopropyl, cyclobutyl, cyclopentyl, and cyclooctyl.

"Cycloalkenyl" refers to non aromatic cyclic alkyl groups of from 3 to 10 carbon atoms having single or multiple cyclic rings and having at least one >C=C< ring unsaturation and preferably from 1 to 2 sites of >C=C< ring unsaturation.

"Substituted cycloalkyl" and "substituted cycloalkenyl" refers to a cycloalkyl or cycloalkenyl group having from 1 to 5 or preferably 1 to 3 substituents selected from the group consisting of oxo, thioxo, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonyl amino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO₃H, substituted sulfonyl, substituted sulfonyloxy, thioacyl, thiol, alkylthio, and substituted alkylthio, wherein said substituents are as defined herein.

"Cyclopropane" refers to:

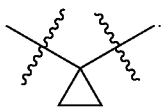 [SMILES: *C1(*)CC1]

"Cyclobutano" refers to:

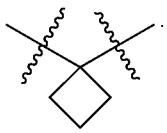 [SMILES: *C1(*)CCC1]

"Cycloalkyloxy" refers to —O-cycloalkyl.

"Substituted cycloalkyloxy refers to —O-(substituted cycloalkyl).

"Cycloalkylthio" refers to —S-cycloalkyl.

"Substituted cycloalkylthio" refers to —S-(substituted cycloalkyl).

"Cycloalkenyloxy" refers to —O-cycloalkenyl.

"Substituted cycloalkenyloxy" refers to —O-(substituted cycloalkenyl).

"Cycloalkenylthio" refers to —S-cycloalkenyl.

"Substituted cycloalkenylthio" refers to —S-(substituted cycloalkenyl).

"Guanidino" refers to the group —NHC(=NH)NH₂.

"Substituted guanidino" refers to —NR⁵³C(=NR⁵³)N(R⁵³)₂ where each R⁵³ is independently selected from the group consisting of hydrogen, alkyl, substituted alkyl, aryl, substituted aryl, heteroaryl, substituted heteroaryl, cycloalkyl, substituted cycloalkyl, heterocyclic, and substituted heterocyclic and two R⁵³ groups attached to a common guanidino nitrogen atom are optionally joined together with the nitrogen bound thereto to form a heterocyclic or substituted heterocyclic group, provided that at least one R⁵³ is not hydrogen, and wherein said substituents are as defined herein.

"Halo" or "halogen" refers to fluoro, chloro, bromo and iodo.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N oxide (N→O), sulfinyl, or sulfonyl moieties. Certain non-limiting examples include pyridinyl, pyrrolyl, indolyl, thiophenyl, oxazolyl, thizolyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryl oxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. Heterocycle encompasses single ring or multiple condensed rings, including fused bridged and spiro ring systems. In fused ring systems, one or more of the rings can be cycloalkyl, aryl, or heteroaryl provided that the point of attachment is through a non-aromatic ring. In one embodiment, the nitrogen and/or sulfur atom(s) of the heterocyclic group are optionally oxidized to provide for the N oxide, sulfinyl, or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryls include, but are not limited to, azetidine, pyrrole, furan, thiophene, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4 tetrahydroisoquinoline, 4,5,6,7 tetrahydrobenzo[b]thiophene, thiazole, thiazolidine, thiophene, benzo[b]thiophene, morpholinyl, thiomorpholinyl (also referred to as thiamorpholinyl), 1,1 dioxothiomorpholinyl, piperidinyl, pyrrolidine, and tetrahydrofuranyl.

"Nitro" refers to the group —NO₂.

"Oxo" refers to the atom (=O).

Phenylene refers to a divalent aryl ring, where the ring contains 6 carbon atoms.

Substituted phenylene refers to phenyl ene s which are substituted with 1 to 4, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, cycloalkenyl, substituted cycloalkenyl, cycloalkenyloxy, substituted cycloalkenyloxy, cycloalkenylthio, substituted cycloalkenylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, substituted sulfonyloxy, thioacyl, thiol, alkylthio, and substituted alkylthio, wherein said substituents are as defined herein.

"Spirocycloalkyl" and "spiro ring systems" refers to divalent cyclic groups from 3 to 10 carbon atoms having a cycloalkyl or heterocycloalkyl ring with a spiro union (the union formed by a single atom which is the only common member of the rings) as exemplified by the following structure:

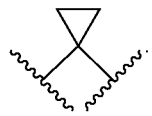 [SMILES: *C1(*)CC1]

"Sulfonyl" refers to the divalent group —S(O)$_2$—.

"Substituted sulfonyl" refers to the group —SO$_2$-alkyl, —SO$_2$-substituted alkyl, —SO$_2$-alkenyl, —SO$_2$-substituted alkenyl, SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Substituted sulfonyl includes groups such as methyl —SO$_2$—, phenyl —SO$_2$—, and 4-methylphenyl-SO$_2$—.

"Substituted sulfonyloxy" refers to the group —OSO$_2$-alkyl, —OSO$_2$-substituted alkyl, —OSO$_2$-alkenyl, —OSO$_2$-substituted alkenyl, OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, cycloalkenyl-C(S)—, substituted cycloalkenyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, cycloalkenyl, substituted cycloalk-enyl, aryl, substituted aryl, heteroaryl, substituted heteroaryl, heterocyclic, and substituted heterocyclic are as defined herein.

"Thiol" refers to the group SH.

"Thiocarbonyl" refers to the divalent group —C(S)— which is equivalent to —C(=S)—.

"Thioxo" refers to the atom (=S).

"Alkylthio" refers to the group S-alkyl wherein alkyl is as defined herein.

"Substituted alkylthio" refers to the group —S-(substituted alkyl) wherein substituted alkyl is as defined herein.

A substituted ring can be substituted with one or more fused and/or spiro cycles. Such fused cycles include a fused cycloalkyl, a fused heterocyclyl, a fused aryl, a fused heteroaryl ring, each of which rings can be unsubstituted or substituted. Such spiro cycles include a fused cycloalkyl and a fused heterocyclyl, each of which rings can be unsubstituted or substituted.

It is understood that the above definitions are not intended to include impermissible substitution patterns (e.g., methyl substituted with 5 fluoro groups). Such impermissible substitution patterns are well known to the skilled artisan.

It is understood that the above definitions are not intended to include impermissible substitution patterns (e.g., methyl substituted with 5 fluoro groups). Such impermissible substitution patterns are well known to the skilled artisan.

"Pharmaceutically acceptable salt" refers to salts of a compound, which salts are suitable for pharmaceutical use and are derived from a variety of organic and inorganic counter ions well known in the art and include, when the compound contains an acidic functionality, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate (see Stahl and Wermuth, eds., "Handbook of Pharmaceutically Acceptable Salts," (2002), Verlag Helvetica Chi mica Acta, Zurich, Switzerland), for a discussion of pharmaceutical salts, their selection, preparation, and use.

"Pulmonary hypertension" refers to all forms of pulmonary hypertension, WHO Groups 1-5. Pulmonary arterial hypertension, also referred to as PAH, refers to WHO Group 1 pulmonary hypertension. PAH includes idiopathic, heritable, drug- or toxin-induced, and persistent pulmonary hypertension of the newborn (PPHN).

Generally, pharmaceutically acceptable salts are those salts that retain substantially one or more of the desired pharmacological activities of the parent compound and which are suitable for in vivo administration. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydroiodic acid, etc.), sulfuric acid, nitric acid, phosphoric acid, and the like.

Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), aryl sulfonic acids (e.g., benzenesulfonic acid, 4 chlorobenzenesulfonic acid, 2-naphthalenesulfonic acid, 4-toluenesulfonic acid, camphorsulfonic acid, etc.), glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion, or an aluminum ion) or by an ammonium ion (e.g., an ammonium ion derived from an organic base, such as, ethanolamine, diethanolamine, triethanolamine, morpholine, piperidine, dimethylamine, diethylamine, triethylamine, and ammonia).

Treprostinil, the active ingredient in Remodulin® (treprostinil) Injection, Tyvaso® (treprostinil) Inhalation Solution, and Orenitram® (treprostinil) Extended Release Tablets, was described in U.S. Pat. No. 4,306,075. Methods of making treprostinil and other prostacyclin derivatives are described, for example, in Moriarty, et al., *J. Org. Chem.* 2004, 69, 1890-1902, *Drug of the Future*, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U S. Published Patent Application Nos. 2012-0197041, 2013-0331593, 2014-0024856, 2015-0299091, 2015-0376106, 2016-0107973, 2015-0315114, 2016-0152548, and 2016-0175319; PCT Publication No. WO2016/0055819 and WO2016/081658.

Various uses and/or various forms of treprostinil are disclosed, for examples, in U.S. Pat. Nos. 5,153,222, 5,234, 953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, 9,278,903, 9,758,465; 9,422,223; 9,878,972; 9,624,156; U S. Published Patent Application Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, 2016-0129087, 2017-0095432; 2018-0153847 and PCT Publications Nos. WO00/57701, WO20160105538, WO2016038532, WO2018/058124.

Treprostinil has the following chemical formula:

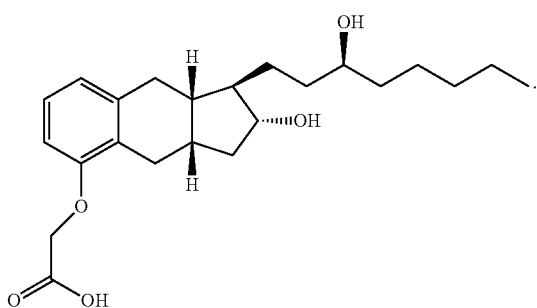 [SMILES: CCCCC[C@H](O)CC[C@@H]1[C@H]2Cc3cccc(OCC(=O)O)c3C[C@H]2C[C@H]1O]

The term "effective amount" may mean an amount of a treprostinil prodrug, which may be necessary to treat the disease or condition. In some embodiments, an effective amount of treprostinil prodrug may be the same or similar to an effective amount of treprostinil for treating the same disease or condition. In some embodiments, an effective amount of treprostinil prodrug may be different from an effective amount of treprostinil for treating the same disease or condition. A person of ordinary skill in the art would be able to determine and "effective amount" of the treprostinil prodrug based, for example, on the relevant disease or condition, the amount of treprostinil known to treat, ameliorate, or prevent the disease or condition, and the rate at which the prodrug converts to treprostinil in vivo.

In some embodiments, the prodrug may be a prodrug may be a prodrug disclosed in U.S. Pat. Nos. 7,384,978, 7,417, 070, 7,544,713, 8,252,839, 8,410,169, 8,536,363, 9,050,311, 9,199,908, 9,278,901, 9,422,223 and 9,624,156, which are incorporated herein by reference in their entirety.

In some embodiments, the prodrug may be a prodrug disclosed in U.S. Pat. Nos. 9,371,264, 9,394,227, 9,505,737, and 9,643,911, which are incorporated herein by reference in their entirety.

In some embodiments, the prodrug may be a prodrug disclosed in U.S. Patent Application Publication 2018-0153847.

In some embodiments, the prodrug may be one of prodrugs discussed below.

Prodrug Compounds

In one aspect, a compound having the following formula:

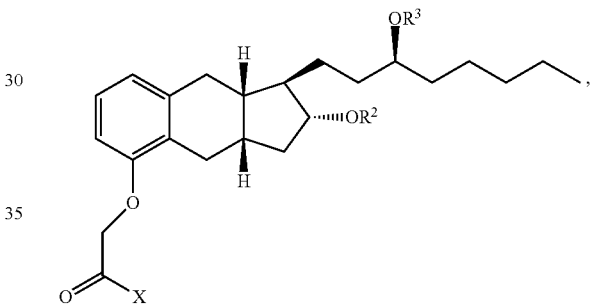

or pharmaceutically acceptable salt thereof, is provided wherein:

X is $OR^{14}$, $-NR^1SO_2R^1$, $-NR^1CO_2H$,

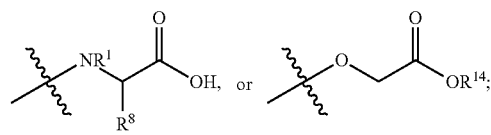

wherein:
each $R^1$ is independently H or $C_1$-$C_4$ alkyl and $R^8$ is optionally substituted $C_1$-$C_6$ alkyl or the side group of an amino acid, or $R^1$ and $R^8$ together form 4-7 membered heterocycle;

$R^{14}$ is a H, optionally substituted $C_1$-$C_6$ alkyl, a first drug moiety, or:

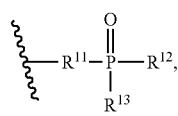

wherein $R^{11}$ is absent, an optionally substituted $C_1$-$C_6$ alkylene, or -$Q^1$-O— wherein $Q^1$ is optionally substituted $C_1$-$C_6$ alkylene; and each of $R^{12}$ and $R^{13}$ are independently selected from H, OH, optionally substituted $C_1$-$C_6$ alkoxy, optionally substituted $C_1$-$C_6$ alkyl, optionally substituted $C_1$-$C_6$ alkenyl, optionally substituted $C_1$-$C_8$ cycloalkyl, optionally substituted $C_1$-$C_{10}$ aryl;

each of $R^2$ and $R^3$ independently is a second drug moiety or a third drug moiety, H, a phosphorous containing group, —C(O)$R^6$, or an -A-B-C substituent, wherein:

A is optionally substituted $C_1$-$C_6$ alkylene, —$NR^6$—, —C(O)—, —C(O)O—, or —C(O)$NR^6$—;

B is a bond, optionally substituted $C_1$-$C_6$ alkylene, —C(O)—, —O—, —S—, heterocyclyl; and C is optionally substituted heterocyclyl, optionally substituted heteroaryl, optionally substituted aryl, optionally substituted cycloalkyl, —(OCH$_2$CH$_2$)$_q$—OR$^6$, —C(O)N(R$^6$)$_2$, —C(O)N(R$^{18}$)$_2$, —C(O)R$^6$, —CO$_2$H, —OR$^6$, —N(R$^{18}$)$_2$, —N(R$^6$)$_2$, or

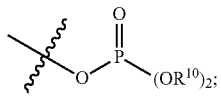

wherein:

both $R^{18}$ together form an optionally substituted 3-8 membered heterocyclyl;

each $R^6$ is independently H, optionally substituted $C_1$-$C_6$ alkyl, optionally substituted heteroaryl, optionally substituted aryl, or both of $R^6$ together form an 4 to 8 membered optionally substituted heterocyclyl or a 5 membered optionally substituted heteroaryl;

or R and R are joined together to form —C(O)—, —SO$_2$—,

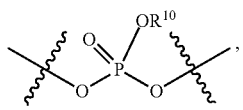

in an 8-12 membered heterocyclyl, wherein each $R^{10}$ is H, optionally substituted $C_1$-$C_6$ alkyl, optionally substituted $C_1$-$C_6$ alkenyl, optionally substituted cycloalkyl, optionally substituted heteroaryl, or optionally substituted aryl; and q is 0, 1, 2, 3, 4, 5 or 6;

provided that:

when A is —C(O)— B is not a bond and C is not —N(R$^6$)$_2$;

when A is —C(O)— B is not a bond and C is not —OR$^6$;

$R^{14}$, $R^2$ and $R^3$ are not H;

when X is OH, $R^2$ and $R^3$ are not H;

when $R^8$ is H then at least one of $R^2$ and $R^3$ is not H.

In one aspect, a compound having the following formula:

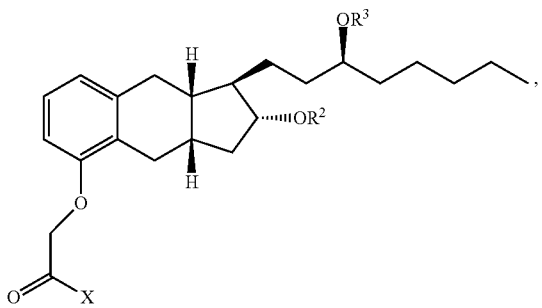

or pharmaceutically acceptable salt thereof, is provided wherein:

X is OR$^{14}$, —NR$^1$SO$_2$R$^1$, —NR$^1$CO$_2$H,

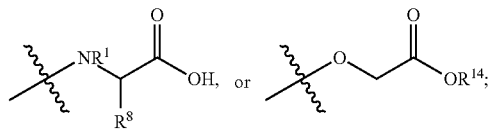

wherein:

each $R^1$ is independently H or $C_1$-$C_4$ alkyl and $R^8$ is $C_1$-$C_6$ alkyl or the side group of an amino acid, or $R^1$ and $R^8$ together form 4-7 membered heterocycle;

$R^{14}$ is a H, $C_1$-$C_6$ alkyl, a first drug moiety, or:

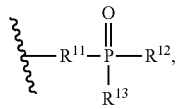

wherein $R^{11}$ is absent, a $C_1$-$C_6$ alkylene, or -Q$^1$-O— wherein $Q^1$ is $C_1$-$C_6$ alkylene; and each of $R^{12}$ and $R^{13}$ are independently selected from H, OH, $C_1$-$C_6$ alkoxy, $C_1$-$C_6$ alkyl, $C_1$-$C_6$ alkenyl, $C_1$-$C_8$ cycloalkyl, $C_1$-$C_{10}$ aryl;

each of $R^2$ and $R^3$ independently is a second drug moiety or a third drug moiety, H, a phosphorous containing group, —C(O)$R^6$, or an -A-B-C substituent, wherein:

A is $C_1$-$C_6$ alkylene, —$NR^6$—, —C(O)—, —C(O)O—, or —C(O)$NR^6$—;

B is a bond, $C_1$-$C_6$ alkylene, —C(O)—, —O—, —S—, heterocyclyl; and

C is heterocyclyl, heteroaryl, aryl, cycloalkyl, —(OCH$_2$CH$_2$)$_q$—OR$^6$, —C(O)N(R$^6$)$_2$, —C(O)N(R$^{18}$)$_2$, —C(O)R$^6$, —CO$_2$H, —OR$^6$, —N(R$^{18}$)$_2$, —N(R$^6$)$_2$,

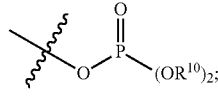

wherein:

both $R^{18}$ together form an 3-8 membered heterocyclyl;

each $R^6$ is independently H, $C_1$-$C_6$ alkyl, heteroaryl, aryl, or both of $R^6$ together form an 4 to 8 membered heterocyclyl or a 5 membered heteroaryl;

or R and R are joined together to form —C(O)—, —SO$_2$—,

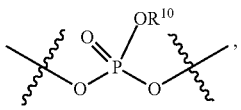

in an 8-12 membered heterocyclyl, wherein
each $R^{10}$ is H, $C_1$-$C_6$ alkyl, $C_1$-$C_6$ alkenyl, cycloalkyl, heteroaryl, or aryl; and
q is 0, 1, 2, 3, 4, 5 or 6;
provided that:
when A is —C(O)— B is not a bond and C is not —N($R^6$)$_2$;
when A is —C(O)— B is not a bond and C is not —$OR^6$;
$R^{14}$, $R^2$ and $R^3$ are not H;
when X is OH, $R^2$ and $R^3$ are not H;
when $R^8$ is H then at least one of $R^2$ and $R^3$ is not H.

In some embodiments, X is $OR^{14}$, $R^{14}$ is H or a first drug moiety, $R^2$ is H or a second drug moiety, and $R^3$ is H or a third drug moiety, with a proviso that each of $R^{14}$, $R^2$ and $R^3$ is not H. In some embodiments, $R^{14}$ is H, one of $R^2$ and $R^3$ is H and the other of $R^2$ and $R^3$ is a drug moiety. In some embodiments, $R^2$ is H and $R^3$ is a third drug moiety. In some embodiments, $R^2$ is a second drug moiety and $R^3$ is a third drug moiety. In some embodiments, each of $R^{12}$, $R^{13}$, $R^2$ and $R^3$ are each H, and $R^{11}$ is $C_1$-$C_4$ alkylene.

In some embodiments, $R^{14}$ is $C_1$-$C_4$ alkyl, which may be optionally substituted with a terminal hydroxyl or carboxy group. When $R^{14}$ is $C_1$-$C_4$ alkyl is substituted with a terminal carboxy group, $R^{14}$ may be carboxymethyl, carboxy ethyl, carboxypropyl, 4-carboxybutyl, 2-methyl-3-carboxy propyl.

Each drug moiety (first, second, and third) may be independently selected. In some embodiments, the drug moiety is a pain relief drug moiety. In some embodiments, the drug moiety is a nonsteroidal anti-inflammatory drug (NSAID) moiety. The drug moiety may be selected from any pain relief or NSAID drug known in the art conjugated to the compound. Conjugation may include direct covalent attachment or attachment by way of a linker group. Linkers may include optionally substituted alkylene groups, optionally substituted arylene or heteroarylene groups, peptides, or other linkers known in the art of drug conjugation. Exemplary pain relief drugs include, but are not limited to opioids (e.g. morphine, hydrocodone, oxycodone, oxymorphone, hydromorphone, fentanyl, thiofentanyl, tapentadol, methadone or meperidine); local anesthetics (e.g. lidocaine, prilocaine, tetracaine, articaine, benzocaine, chloroprocaine, cocaine, cyclomethycaine, dimethocaine, piperocaine, propoxycaine, proparacaine, saxitoxin, neosaxitoxin, tetrodotoxin, menthol, eugenol, and spilanthol); and acetaminophen. Non-limiting examples of non-steroidal anti-inflammatory drugs (NSAIDS) include aspirin, ibuprofen, celecoxib or any COX1 or COX2 inhibitor, or naproxen.

The second drug moiety may form an ester bond with a carboxylic group of treprostinil and/or one or both hydroxyl groups (e.g. $R^2$ or $R^3$ is H) of treprostinil. For example, when the second drug moiety comprises a hydroxyl group, it may form an ester bond with the carboxylic group of treprostinil. When the second drug moiety comprises a carboxylic group, it may form an ester bond with one of hydroxyl groups of treprostinil.

In some embodiments, only one of $R^2$ and $R^3$ is a phosphorous containing group. In some embodiments, both $R^2$ and $R^3$ are a phosphorous containing group. In some embodiments, each phosphorous containing group independently has the formula:

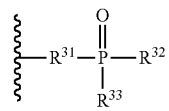

wherein $R^{31}$ is absent, optionally substituted $C_1$-$C_6$ alkylene, or -Q-O— wherein Q is optionally substituted $C_1$-$C_6$ alkylene; and
each of $R^{32}$ and $R^{33}$ are independently selected from H, optionally substituted $C_1$-$C_6$ alkoxy, optionally substituted $C_1$-$C_6$ alkenyloxy, optionally substituted $C_1$-$C_6$ cycloalkoxy, and optionally substituted aryloxy. In some embodiments, the phosphorous containing group has the formula

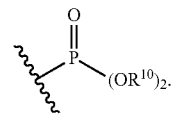

In some embodiments, $R^{31}$ is $C_1$-$C_6$ alkylene and each of $R^{32}$ and $R^{33}$ are H.

In some embodiments, X is OH, —$OCH_2OPO_3H_2$,

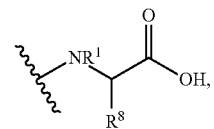

or —$NHSO_2CH_3$; wherein $R^8$ is $C_1$-$C_2$ alkyl optionally substituted with OH or —$CO_2H$. In some embodiments, X is

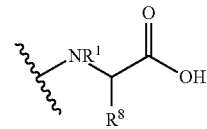

wherein $R^8$ is methyl. In some embodiments, $R^8$ is methyl substituted with OH. In some embodiments, $R^8$ is methyl substituted with —$CO_2H$. In some embodiments, $R^8$ is the side group of an amino acid as defined herein. In some embodiments, $R^1$ and $R^8$ together form a pyrrolidine, piperidine, aziridine, azepane, or azetidine. In some embodiments $R^1$ and $R^8$ together form a pyrrolidine.

In some embodiments, $R^2$ is —C(O)$R^{17}$, —$OPO_3H_2$ or -A-B-C wherein:
A is —C(O)—, —C(O)O—, $CH_2$, or —C(O)$NR^6$—;
B is —$CHR^{16}$— or —$(CH_2)_q$—; and
C is $C_1$-$C_3$ alkoxy, heterocyclyl, $OR^6$, $OPO_3H_2$, $CO_2H$, OH, $NH_2$, —C(O)$R^6$, —C(O)N($R^{18}$)$_2$, or —C(O)N($R^6$)$_2$; wherein:
$R^{16}$ is H or $C_1$-$C_3$ alkyl;
$R^{17}$ is $C_1$-$C_3$ alkyl, optionally substituted aryl or optionally substituted heteroaryl; and
q is 0, 1, or 2.

In some embodiments, $R^3$ is —C(O)$R^{17}$, —$OPO_3H_2$ or -A-B-C wherein:
A is —C(O)—, —C(O)O—, $CH_2$, or —C(O)$NR^6$—;
B is —$CHR^{16}$— or —$(CH_2)_q$—; and C is heterocyclyl, $OR^6$, $OPO_3H_2$, $CO_2H$, $OH$, $NH_2$, —$C(O)R^6$, —$C(O)N(R^{18})_2$, or —$C(O)N(R^6)_2$;
wherein:
$R^{16}$ is H or $C_1$-$C_3$ alkyl;
$R^{17}$ is $C_1$-$C_3$ alkyl, optionally substituted aryl or optionally substituted heteroaryl; and
q is 0, 1, or 2.

In some embodiments, $R^2$ and/or $R^3$ is —C(O)—$CHR^{19}$—$N(R^6)_2$, wherein each $R^{19}$ and $R^6$ are independently selected and $R^{19}$ is the side group of an amino acid or its enantiomer, for example, methyl (in the case of alanine), isopropyl, (in the case of valine), etc. Exemplary amino acids whose side groups may be employed include, arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan. In some embodiments, the amino acid is alanine, valine or glycine. In some embodiments, only one of $R^2$ and $R^3$ is —C(O)—$CHR^{19}$—$N(R^6)_2$ while the other one of $R^2$ and $R^3$ is H. In some embodiments $R^{19}$ is not H.

In some embodiments, $R^8$ is the side group of an amino acid or its enantiomer, for example, methyl (in the case of alanine), isopropyl, (in the case of valine), etc. Exemplary amino acids whose side groups may be employed include, arginine, histidine, lysine, aspartic acid, glutamic acid, serine, threonine, asparagine, glutamine, cysteine, glycine, proline, alanine, valine, isoleucine, leucine, methionine, phenylalanine, tyrosine, and tryptophan. In some embodiments, the amino acid is alanine, valine or glycine. In some embodiments $R^8$ is not H.

"Amino acid" may refer to a D-isomer amino acid or an L-isomer amino acid. In certain embodiments, an amino acid may be a naturally occurring amino acid. Yet, in some embodiments, an amino acid may be an artificial amino acid. Specific side groups of the above named amino acids include —$CH_3$ (alanine), —$(CH_2)_3HCNH_2NH$ (arginine), —$CH_2CONH_2$ (asparagine), —$CH_2COOH$ (aspartic acid), —$CH_3SH$ (cysteine), —$(CH_2)_2CONH_2$ (glutamine), —$(CH_2)_2COOH$ (glutamic acid), —H (glycine), —$CHCH_3CH_2CH_3$ (isoleucine), —$CH_2CH(CH_3)_2$ (leucine), —$(CH_2)_4NH_2$ (lysine), —$(CH_2)_2SCH_3$ (methionine), —$CH_2Ph$ (phenylalanine), —$CH_2OH$ (serine), —$CHOHCH_3$ (threonine), —$CH(CH_3)_2$ (valine),

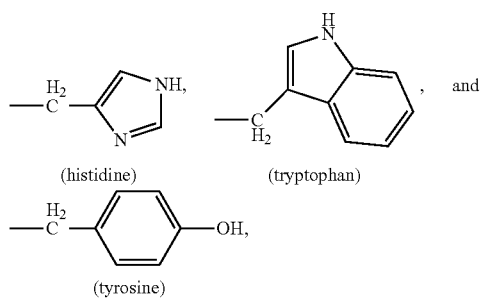

(histidine) (tryptophan)

(tyrosine)

—$(CH_2)_3NHCONH_2$ (citrulline) or —$(CH_2)_3NH_2$ (ornithine). Ph designates a phenyl group.

In some embodiments, $R^2$ is an A-B-C moiety wherein:
A and B are each $CH_2$; and
C is $CO_2H$, amino, $C(O)N(R^{18})_2$, or —$C(O)N(R^6)_2$.
In some embodiments, $R^3$ is an A-B-C moiety wherein:
A and B are each $CH_2$; and
C is $CO_2H$, amino, $C(O)N(R^{18})_2$, or —$C(O)N(R^6)_2$.

In some embodiments, $R^2$ is an A-B-C moiety of formula —C(O)—C wherein: C is optionally substituted aryl, or optionally substituted heteroaryl. In some embodiments, C is optionally substituted phenyl, optionally substituted piperidinyl, optionally substituted morpholino, optionally substituted azepanyl, optionally substituted aziridinyl, optionally substituted azetidinyl, optionally substituted pyrrolidinyl, or optionally substituted piperazinyl. In some embodiments, C is phenyl, piperidinyl, morpholino, azepanyl, aziridinyl, azetidinyl, pyrrolidinyl, or piperazinyl.

In some embodiments, $R^3$ is an A-B-C moiety of formula —C(O)—C wherein: C is optionally substituted aryl, or optionally substituted heteroaryl. In some embodiments, C is optionally substituted phenyl, optionally substituted piperidinyl, optionally substituted morpholino, optionally substituted azepanyl, optionally substituted aziridinyl, optionally substituted azetidinyl, optionally substituted pyrrolidinyl, or optionally substituted piperazinyl. In some embodiments, C is phenyl, piperidinyl, morpholino, azepanyl, aziridinyl, azetidinyl, pyrrolidinyl, or piperazinyl.

In some embodiments, $R^2$ is an A-B-C moiety of formula —C(O)—$CHCH_3$—C wherein C is optionally substituted aryl or optionally substituted heteroaryl. In some embodiments, C is optionally substituted phenyl or optionally substituted napthyl. In some embodiments, C is phenyl optionally substituted with $C_1$-$C_4$ alkyl or napthyl optionally substituted with methoxy.

In some embodiments, $R^3$ is an A-B-C moiety of formula —C(O)—$CHCH_3$—C wherein C is optionally substituted aryl or optionally substituted heteroaryl. In some embodiments, C is optionally substituted phenyl or optionally substituted napthyl. In some embodiments, C is phenyl optionally substituted with $C_1$-$C_4$ alkyl or napthyl optionally substituted with methoxy.

In some embodiments, $R^2$ is —C(O)—X—$CH_2CO_2H$, wherein X is O or $NR^1$. In some embodiments, $R^3$ is —C(O)—X—$CH_2CO_2H$, wherein X is O or $NR^1$. In some embodiments, $R^2$ is —C(O)—$(OCH_2CH_2)_q$—$OR^6$, wherein $R^6$ is a $C_1$-$C_6$ alkyl. In some embodiments $R^6$ is a methyl. In some embodiments, q is 1.

In some embodiments, $R^3$ is —C(O)—X—$CH_2CO_2H$, wherein X is O or $NR^1$. In some embodiments, $R^3$ is —C(O)—X—$CH_2CO_2H$, wherein X is O or $NR^1$. In some embodiments, $R^3$ is —C(O)—$(OCH_2CH_2)_q$—$OR^6$, wherein $R^6$ is a $C_1$-$C_6$ alkyl. In some embodiments $R^6$ is a methyl. In some embodiments, q is 1.

In some embodiments, $R^2$ is —C(O)—$(CH_2)_2CO_2H$ or —C(O)—$(CHCH_3)$—C, wherein C is optionally substituted aryl or optionally substituted heteroaryl. In some embodiments, $R^3$ is —C(O)—$(CH_2)_2CO_2H$ or C(O)—$(CHCH_3)$—C, wherein C is optionally substituted aryl or optionally substituted heteroaryl. In some embodiments, the optionally substituted aryl is phenyl or napthyl. In some embodiments, the optionally substituted phenyl or napthyl is substituted with $C_1$-$C_6$ alkyl or $C_1$-$C_6$ alkoxy. In some embodiments, the optionally substituted phenyl or napthyl is substituted with methoxy.

In some embodiments, X is OH, and $R^2$ and $R^3$ form together a carbonyl containing group or a phosphorous containing group. In some embodiments, $R^2$ and $R^3$ are joined together to form —C(O)—, —$SO_2$—,

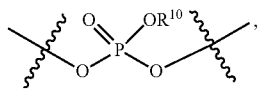

in an 8-12 membered heterocyclyl. In some embodiments, the compound is of formula:
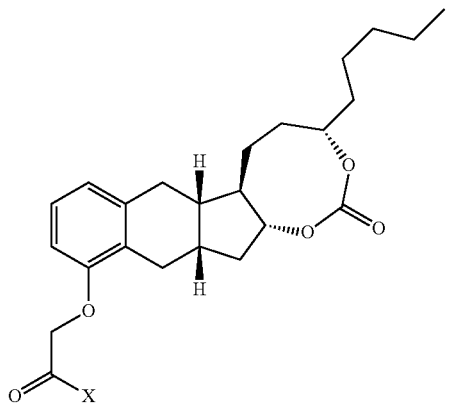
or
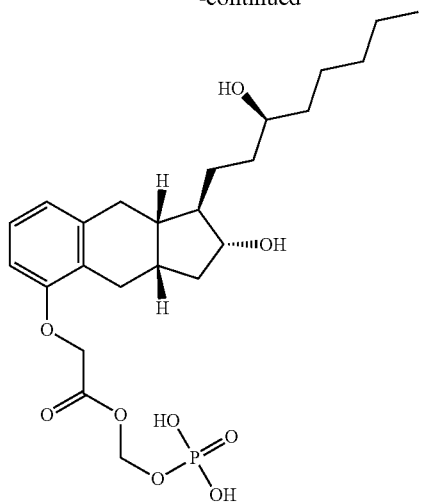
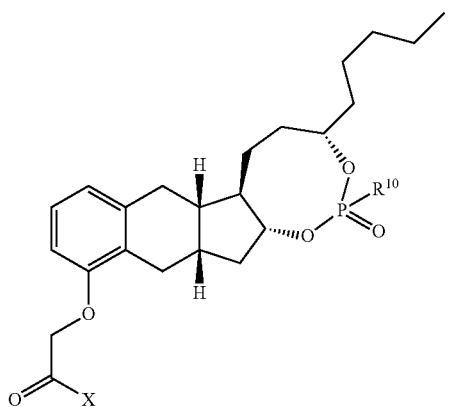
or a pharmaceutically acceptable salt thereof.
In another aspect, a compound of one of the following formulas is provided:
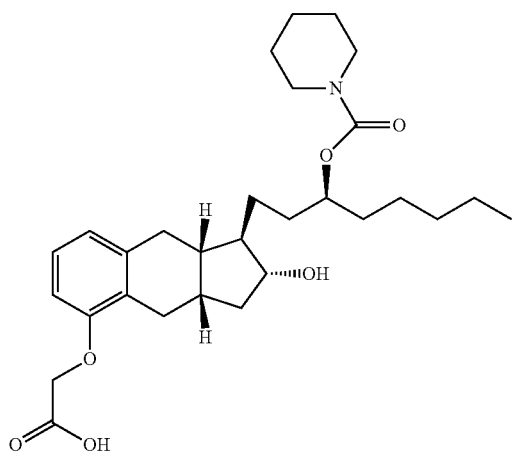
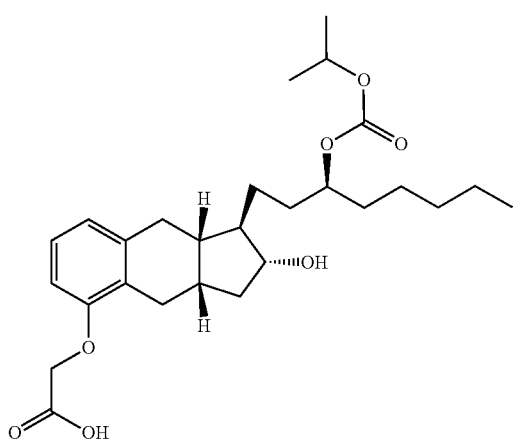
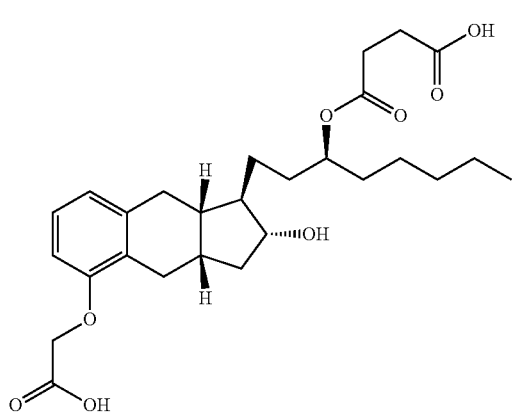

29
-continued
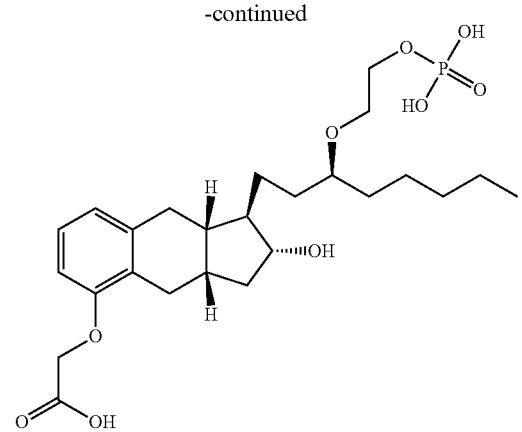
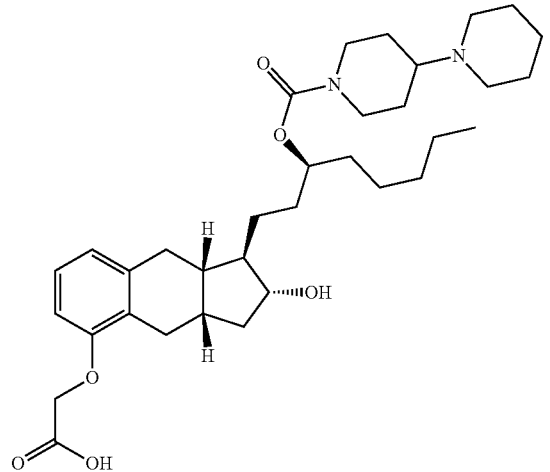
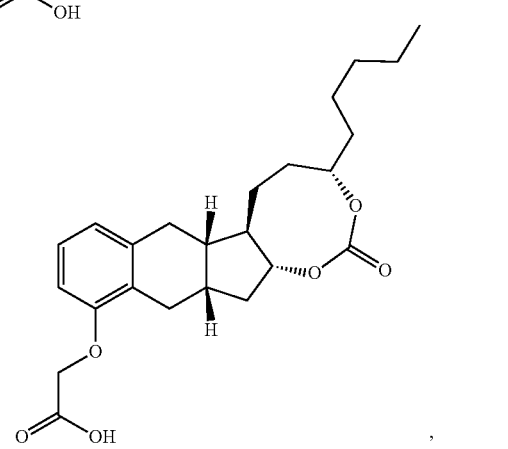
30
-continued
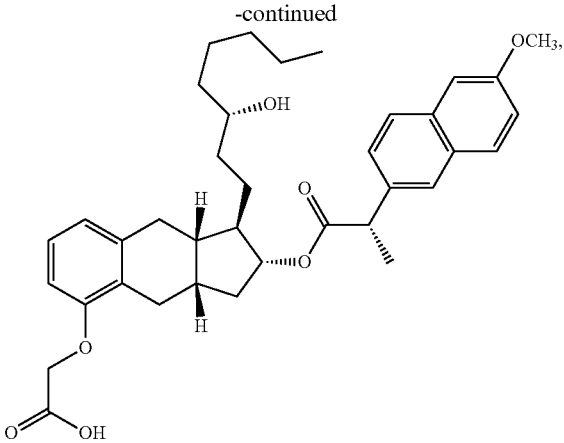
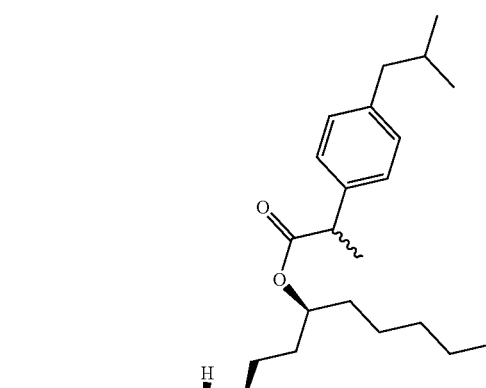

31
-continued
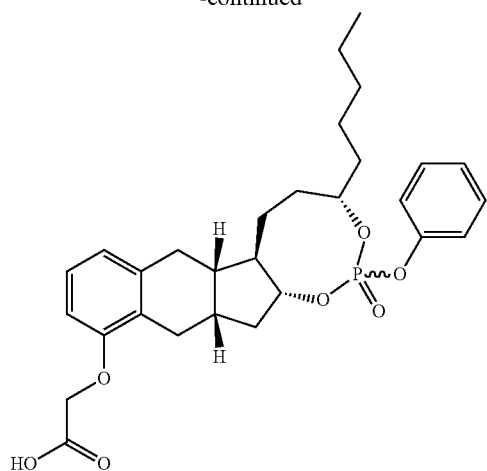
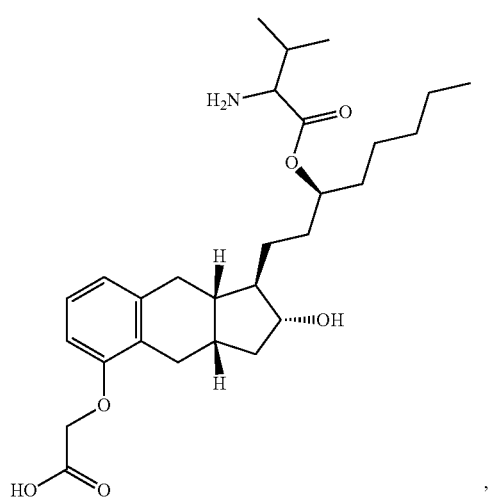
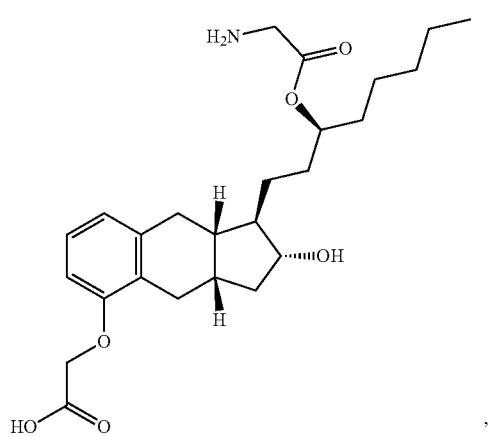
32
-continued
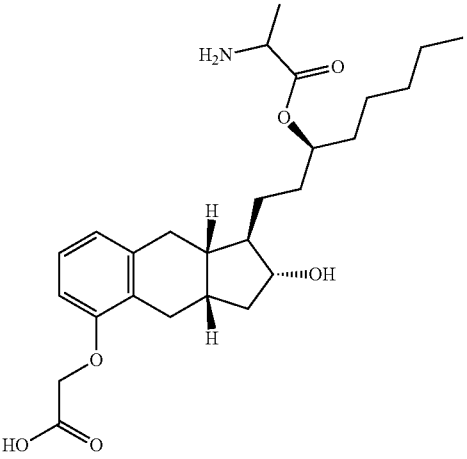
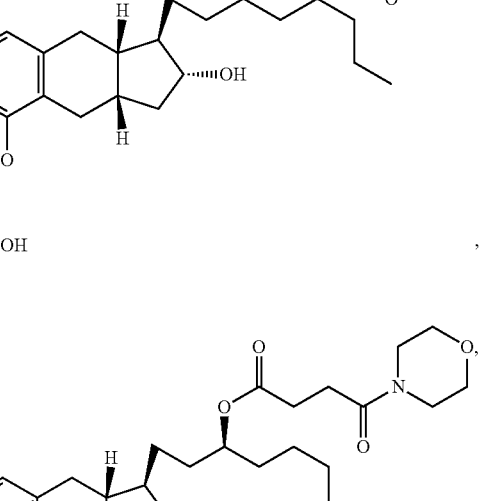
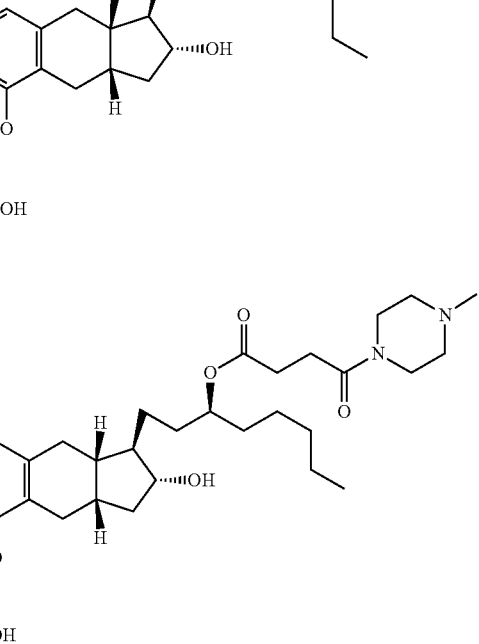

33
-continued
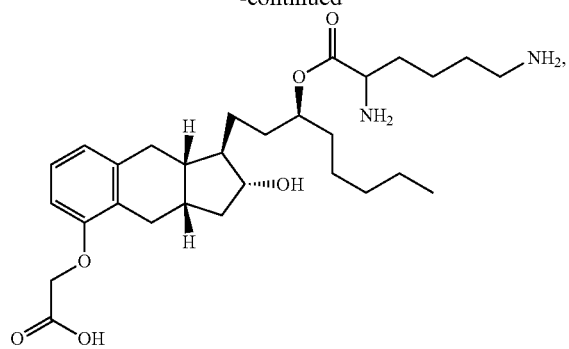
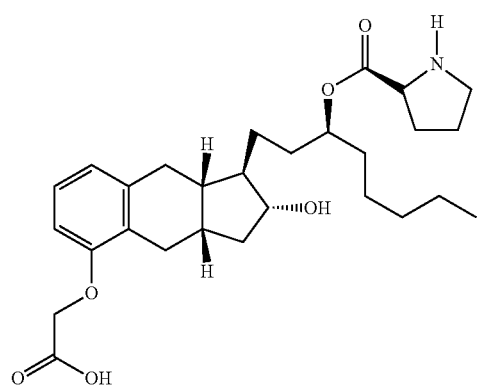
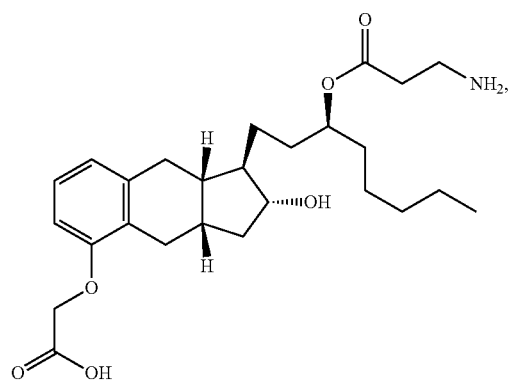
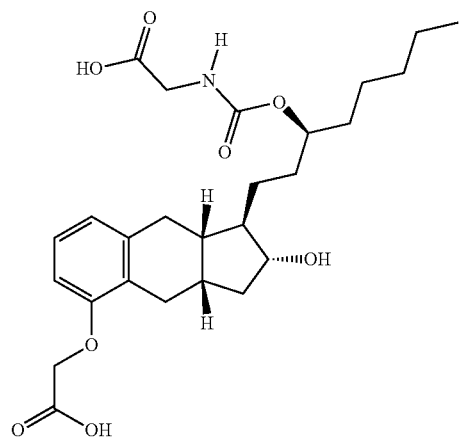
34
-continued
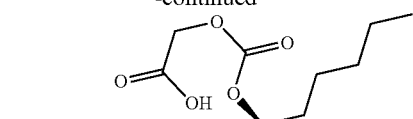
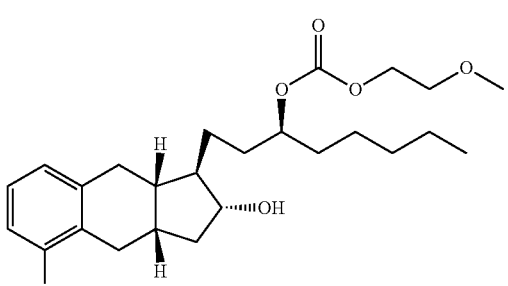
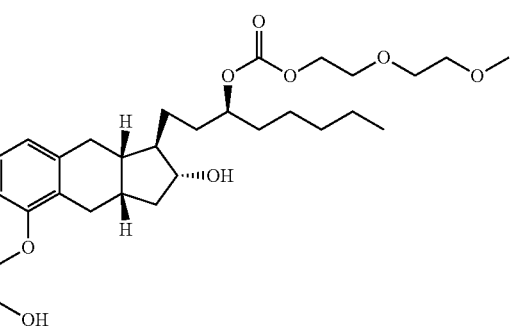
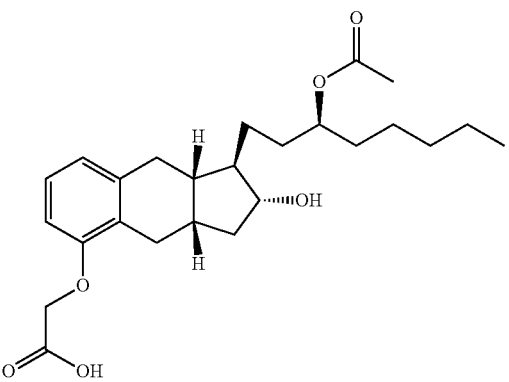

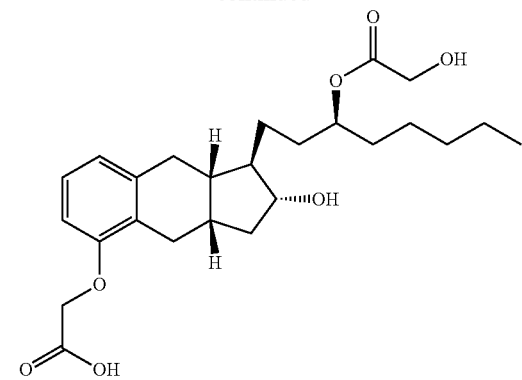
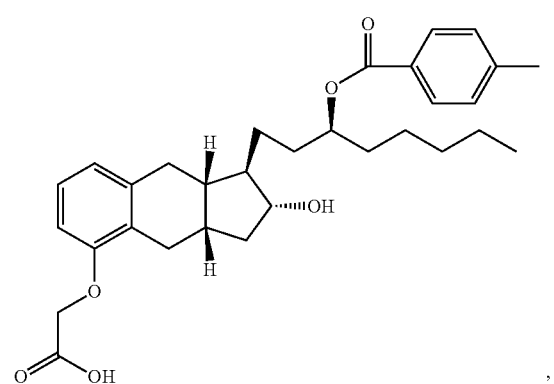
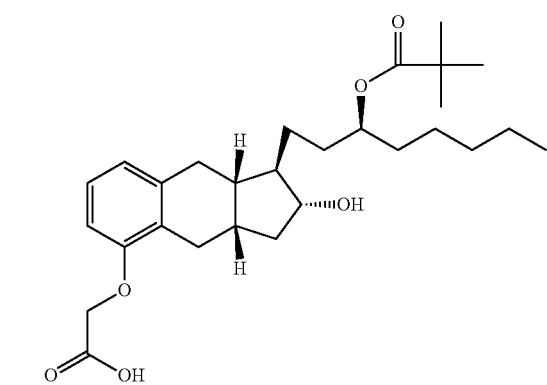
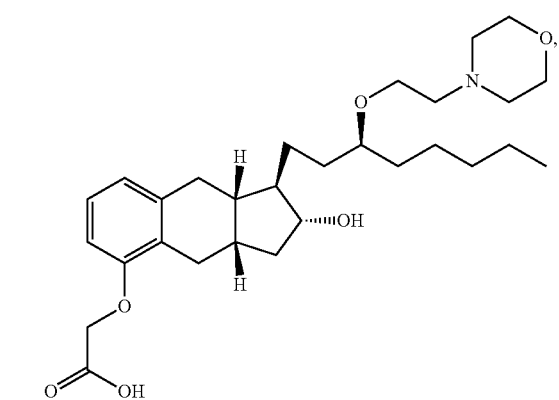
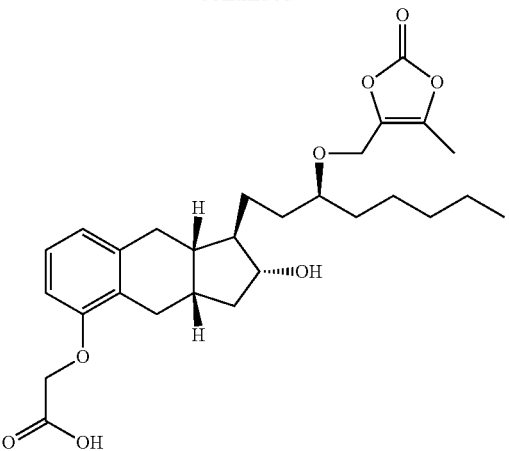

37
-continued
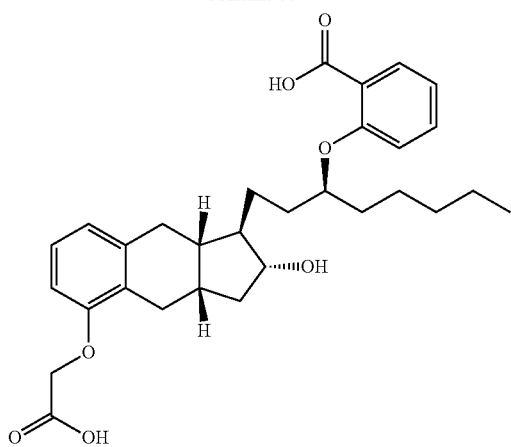
,
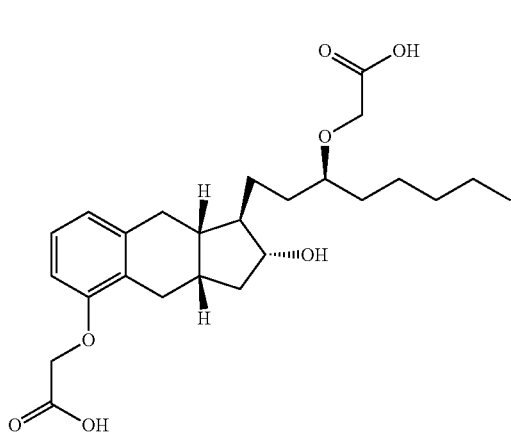
,
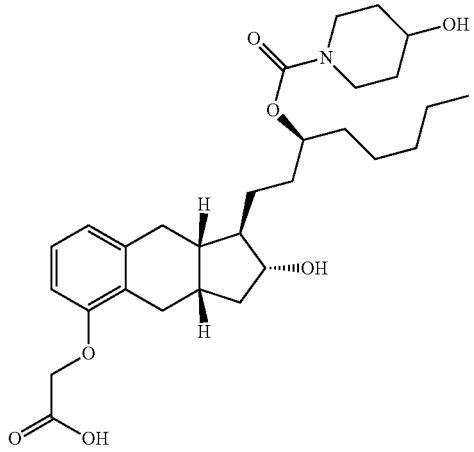
,
38
-continued
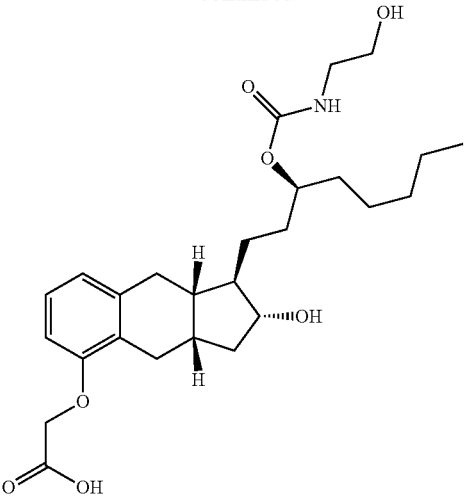
,
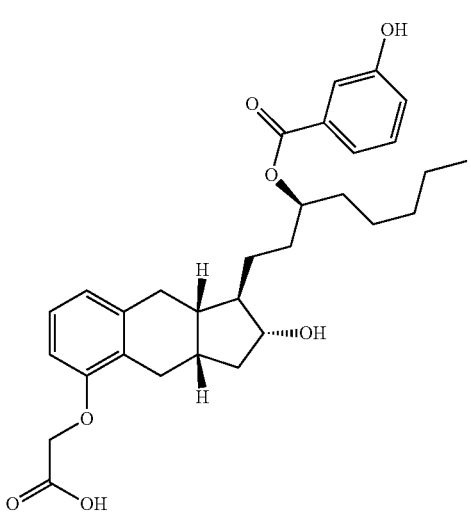
,
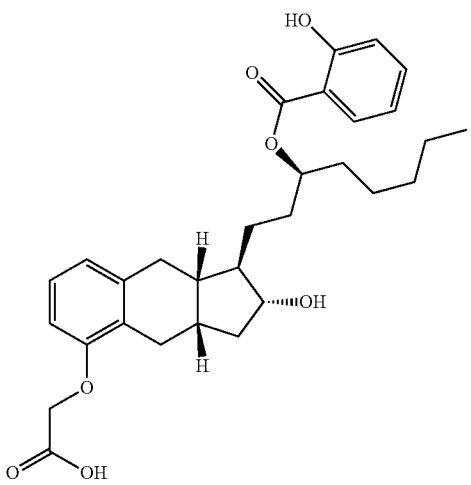
, 39
-continued
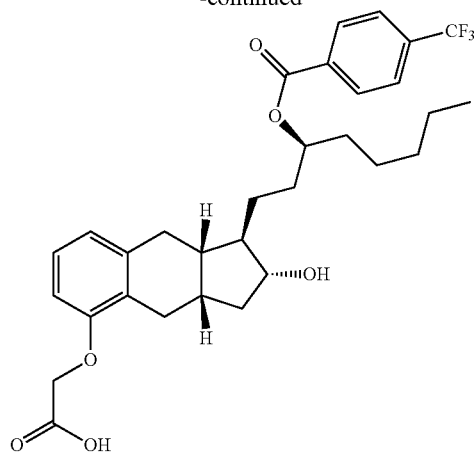
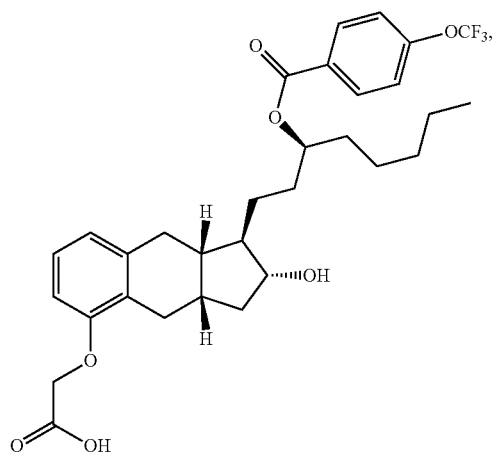
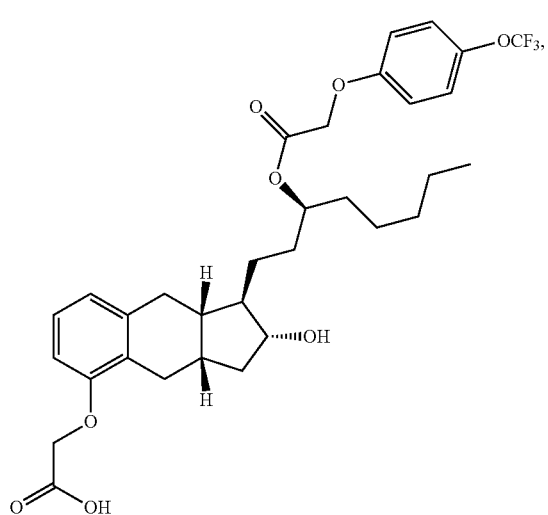
40
-continued
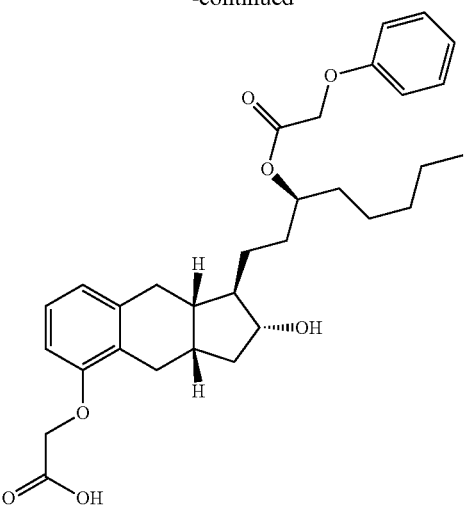
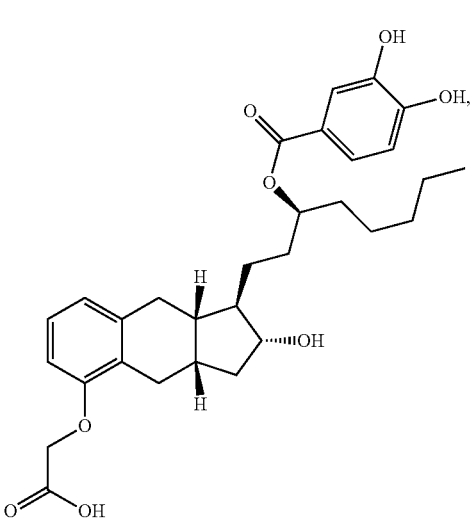
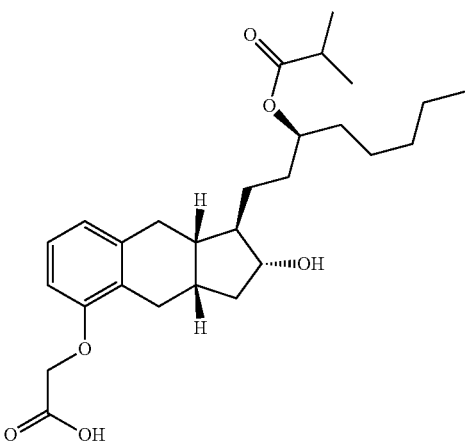

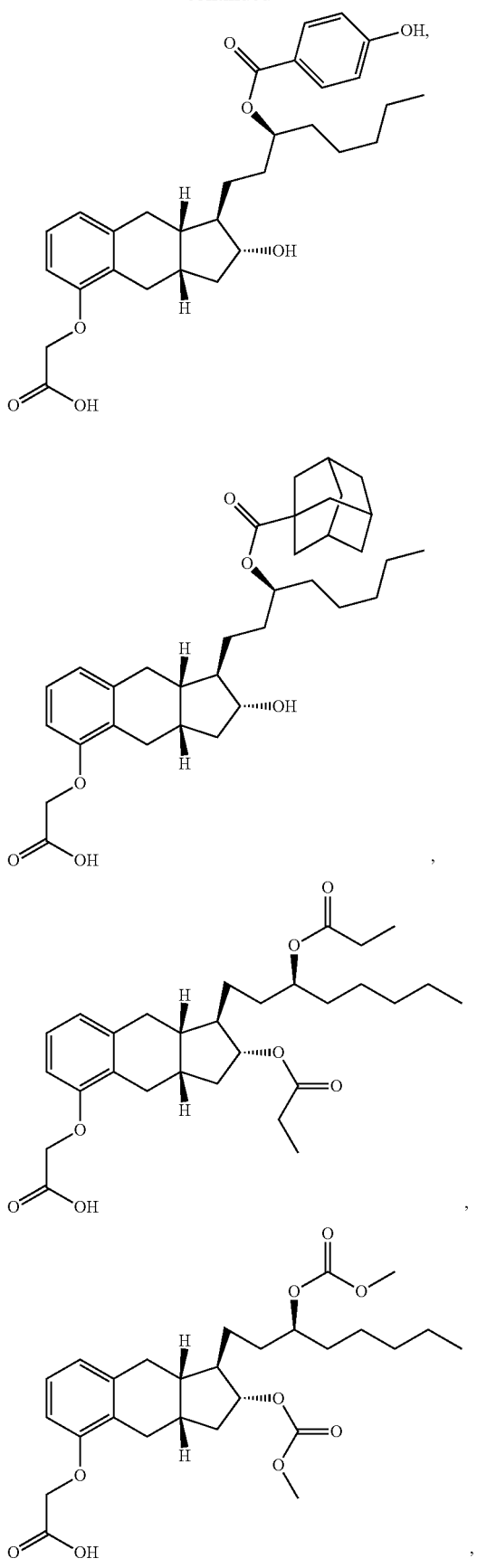

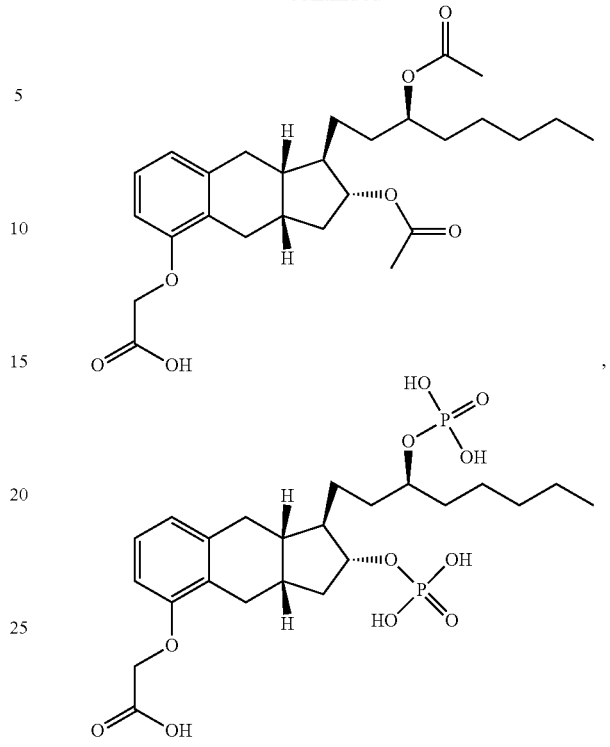

or a pharmaceutically acceptable salt thereof.

These prodrugs may have one or more advantages compared to treprostinil in addition to or alternative to reduction in site pain compared to administration of treprostinil or a salt thereof. For example, some of these prodrugs may have improved stability or greater tolerance in at least some patient populations.

At least some of these prodrugs may have half-life in human plasma of less than 150 minutes or less than 120 minutes or less than 90 minutes or less than 60 minutes or less than 50 minutes or less than 45 minutes or less than 40 minutes or less than 30 minutes or less than 20 minutes or less than 15 minutes or less than 12 minutes or about 10 minutes.

At least some of these prodrugs may have plasma half times upon oral administration of at least 3 hours or at least 3.5 hours or at least 4 hours or at least 4.5 hours or at least 5 hours or at least 6 hours or at least 7 hours or at least 8 hours or at least 9 hours or at least 10 hours or at least 11 hours or at least 12 hours or at least 13 hours or at least 14 hours or at least 15 hours or at least 16 hours or at least 17 hours or at least 18 hours or at least 19 hours or at least 20 hours or at least 21 hours or at least 22 hours or at least 23 hours or at least 24 hours.

At least some of these prodrugs may have oral bioavailability of at least 15% or at least 15% or at least 20% or at least 22% or at least 24% or at least 30% or at least 35% or at least 40% or at least 45% or at least 50% or at least 55% or at least 60% or at least 65% or at least 70% or at least 75% or at least 80%.

At least for some prodrugs, $C_{max}$ and $AUC_{0-24\ hrs}$ upon oral administration may increase in a dose proportional manner.

In some embodiments, the prodrug may be such that it does not convert to treprostinil before being administered to a subject, such as a human being. For example, the prodrug may be such that it does not convert to treprostinil during its storage. Furthermore, the prodrug may be such that it does not convert into treprostinil in a pharmaceutical formulation, such as an injection formulation, e.g. a subcutaneous formulation, prior to administering the formulation to the subject. The prodrug may be such that it does not convert to treprostinil when it contacts a subcutaneous tissue of the subject upon an injection, such as a subcutaneous injection, of a pharmaceutical formulation comprising the prodrug to the subject. The prodrug may be such that it converts to treprostinil only when it reaches blood and/or liver of the subject. For example, a prodrug formulation, such as a subcutaneous prodrug formulation, may contain essentially no treprostinil per se prior to administering. In other words, a concentration of treprostinil per se in a prodrug formulation, such as a parenteral prodrug formulation, which may be a subcutaneous prodrug formulation, prior to administering may be less than 0.5% or less than 0.3% or less than 0.2% or less than 0.1% or less than 0.05% or less than 0.03% or less than 0.02% or less than 0.01% or less than 0.005% or less than 0.003% or less than 0.002% or less than 0.001%. Preferably, a concentration of treprostinil per se in a prodrug formulation, such as a parenteral prodrug formulation, which may be a subcutaneous prodrug formulation, prior to administering is undetectable by High Performance Liquid Chromatography (HPLC).

In some embodiments, the prodrug may be such that it does not convert to treprostinil when stored at pH ranging from 5 to 9 or 5.5 to 8.5 or from 6 to 8 for at least 1 week or at least 2 weeks or at least 3 weeks or at least 4 weeks at a temperature from 30 C to 45 C or from 35 C to 45 C or 37 C to 43 C or about 40 C. For example, a prodrug formulation, such as a subcutaneous prodrug formulation, may contain essentially no treprostinil per se after said storage. In other words, a concentration of treprostinil per se in a prodrug formulation, such as a parenteral prodrug formulation, which may be a subcutaneous prodrug formulation, after the storage may be less than 0.5% or less than 0.3% or less than 0.2% or less than 0.1% or less than 0.05% or less than 0.03% or less than 0.02% or less than 0.01% or less than 0.005% or less than 0.003% or less than 0.002% or less than 0.001%. Preferably, a concentration of treprostinil per se in a prodrug formulation, such as a parenteral prodrug formulation, which may be a subcutaneous prodrug formulation, after the storage is undetectable by High Performance Liquid Chromatography (HPLC).

In some embodiments, the prodrug may be such that no prodrug may be detected in blood or plasma of the subject upon administering the prodrug to the subject, which may be, for example, oral administration or injection, such as, intravenous or subcutaneous injection. For example, a plasma concentration of the prodrug may be below 2 ng/ml or below 1 ng/ml or below 0.7 ng/ml or below 0.5 ng/ml or below 0.3 ng·ml or below 0.2 ng/ml or below 0.1 ng/ml at any time after administering the prodrug.

In certain embodiments, the prodrug may be such that a metabolic product of in vivo conversion of the prodrug consists essentially of treprostinil, which may mean that treprostinil constitutes at least 90% or at least 95% or at least 98% or at least 99% or at least 99.5% or at least 99.8% or at least 99.9% of the metabolic product. In certain embodiments, the prodrug may be such that no metabolic product of the in vivo conversion of the prodrug, other than treprostinil, may be detected in blood or plasma of the subject. For example, a plasma concentration of non-treprostinil product(s) of the in vivo conversion of the prodrug may be below 2 ng/ml or below 1 ng/ml or below 0.7 ng/ml or below 0.5 ng/ml or below 0.3 ng/ml or below 0.2 ng/ml or below 0.1 ng/ml at any time after administering the prodrug.

In some embodiments, the prodrug may be such that plasma concentration of treprostinil may me detectable at least 24 hours after orally administering the prodrug. For example, plasma concentration of treprostinil 24 hours after orally administering the prodrug may at 1 ng/ml or at least 1.5 ng/ml or at least 2 ng/ml or at least 3 ng/ml or at least 4 ng/ml or at least 5 ng/ml or at least 6 ng/ml or at least 7 ng/ml or at least 8 ng/ml or at least 9 ng/ml or at least 10 ng/ml.

In certain embodiments, a prodrug of treprostinil may have equilibrium water solubility of at least 1 mg/ml, or at least 2 mg/ml or at least 3 mg/ml, or at least 4 mg/ml, or at least 5 mg/ml, or at least 6 mg/ml. In certain embodiments, a prodrug of treprostinil may have equilibrium water solubility from 3 to 40 mg/ml or from 3 to 35 mg/ml or from 5 to 15 mg/ml or any value or subrange within these ranges. The solubility of the prodrug may be greater if pH is increased in a vehicle used in solubility measurement and/or if one or more salts are removed from the vehicle.

In certain embodiments, a prodrug may have equilibrium water solubility of at least 7 mg/ml, or at least 8 mg/ml, or at least 9 mg/ml, or at least 10 mg/ml, or at least 20 mg/ml, or at least 30 mg/ml, or at least 50 mg/ml, or at least 70 mg/ml, or at least 100 mg/ml, or at least 200 mg/ml, or at least 300 mg/ml. Higher solubility prodrugs may be preferred for oral administration.

In some embodiments, a prodrug may comprise a low water solubility prodrug having an equilibrium water solubility no more than 1 mg/ml or no more than 0.5 mg/ml or no more than 0.2 mg/ml or no more than 0.1 mg/ml or no more than 0.05 mg/ml or no more than 0.02 mg/ml or no more than 0.01 mg/ml or no more than 0.005 mg/ml or no more than 0.002 mg/ml or more than 0.001 mg/ml. In some embodiments, the low water solubility prodrug may be formulated by making a solid dispersion, such as an amorphous solid dispersion. Methods of making solid dispersions, such as amorphous solid dispersions, of low water solubility compounds are disclosed, for example, in Newman, Developing Solid Oral Dosage Forms (Second Edition), Pharmaceutical Theory and Practice, 2017, Pages 497-518 and Paudel et al, International Journal of Pharmaceutics 453 (2013) 253-284, each of which is incorporated herein by reference in its entirety. In some embodiments, the low water solubility prodrug may be used in a salt form, which may allow increasing of the water solubility.

Pharmaceutical Compositions

Treprostinil prodrugs may be provided in a form of a pharmaceutical composition, which may also comprise a pharmaceutically acceptable carrier, excipient, binder, diluent or the like. Such pharmaceutical composition may be manufactured by methods known in the art such as granulating, mixing, dissolving, encapsulating, lyophilizing, emulsifying or levigating processes, among others. The composition may be in the form of, for example, granules, powders, tablets, capsules, syrup, suppositories, injections, emulsions, elixirs, suspensions and solutions. The composition may be formulated for a number of different administration routes, such as, for oral administration, transmucosal administration, rectal administration, transdermal or subcutaneous administration, as well as intrathecal, intravenous, intramuscular, intraperitoneal, intranasal, intraocular or intraventricular injection. The treprostinil prodrug may be administered by any of the above routes, for example in a local rather than a systemic administration, including as an injection or as a sustained release formulation.

In one embodiment, the pharmaceutical composition can compromise a prodrug of treprostinil and a carrier, such as sterile water. In some embodiments, the prodrug of treprostinil is formulated for subcutaneous administration, and such formulation may or may not include m-cresol or another preservative.

The treprostinil prodrugs described herein can be used to treat pulmonary hypertension. In some embodiments, the treprostinil prodrugs can be used to treat PAH. In some embodiments, the treprostinil prodrugs can be used to treat one or more of WHO Groups 1-5 pulmonary hypertension. Likewise, the treprostinil prodrugs described herein can be used to treat any disease or condition for which treprostinil is indicated or useful. The treprostinil prodrugs can be administered as the sole therapeutic agent or in addition to other active agents, including treprostinil.

For oral, buccal, and sublingual administration, powders, suspensions, granules, tablets, pills, capsules, gel caps, and caplets may be acceptable as solid dosage forms. These can be prepared, for example, by mixing one or more treprostinil prodrugs, or pharmaceutically acceptable salts thereof, with at least one additive or excipient such as a starch or other additive. Suitable additives or excipients may be sucrose, lactose, cellulose sugar, mannitol, maltitol, dextran, sorbitol, starch, agar, alginates, chi tins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms may contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers. Besides those representative dosage forms described above, pharmaceutically acceptable excipients and carriers are generally known to those skilled in the art and can be employed. Such excipients and carriers are described, for example, in "Remingtons Pharmaceutical Sciences" Mack Pub. Co., New Jersey (1991), which is incorporated herein by reference.

A treprostinil prodrug may be formulated in a formulation suitable for parenteral administration that may comprise sterile aqueous preparations of a treprostinil prodrug, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations may contain from 0.1 to 5% w/v based on weight of treprostinil in the prodrug and may be administered at a rate of 0.1 ml/min/kg. Alternatively, the prodrug may be administered at a rate of 0.625 to 50 ng/kg/min based on weight of treprostinil in the prodrug. Alternatively, the prodrug may be administered at a rate of 10 to 15 ng/kg/min based on weight of treprostinil in the prodrug.

In some embodiments, a concentration of a treprostinil prodrug in a formulation for parenteral administration, such as intravenous infusion or subcutaneous infusion (including continuous subcutaneous infusion), may be from 0.0005 to 30 mg/mL or from 0.0007 to 50 mg/mL or from 0.001 to 15 mg/mL or any value or subrange within these ranges. Exemplary concentrations may include 0.1 mg/mL, 1 mg/mL, 2.5 mg/mL, 5 mg/mL or 10 mg/mL.

In some embodiments, a formulation of a treprostinil prodrug for parenteral administration, such as intravenous infusion or subcutaneous infusion (including continuous subcutaneous infusion), may be prepared by admixing the prodrug with a vehicle, such as a buffer. In certain embodiments, the vehicle may be a phosphate containing vehicle, i.e. at least one phosphate salt, which may be for example, dibasic phosphate, such as sodium dibasic phosphate or potassium dibasic phosphate, or tribasic phosphate, such as sodium tribasic phosphate or potassium phosphate. In certain embodiments, the vehicle may also contain a halogen salt, such as a chloride salt, which may be, for example, sodium chloride or potassium chloride. The halogen salt, such as sodium chloride may be used to adjust tonicity of the vehicle. In certain embodiments, it may be preferred that a phosphate and a halogen salt have the same cation. For example, when a phosphate is sodium phosphate, such as sodium tribasic phosphate or sodium tribasic phosphate, a halogen salt may a sodium halogen salt such as sodium chloride. Similarly, when a phosphate is potassium phosphate, such as potassium tribasic phosphate or potassium tribasic phosphate, a halogen salt may a potassium halogen salt such as potassium chloride. A solvent in the vehicle may contain water. In certain embodiments, water may be the only solvent in the vehicle. Yet in certain embodiments, the vehicle may contain one or more additional solvent in addition to water. In some embodiments, an additional solvent may be a preservative, such as m-cresol.

Preferably, the vehicle is isotonic with blood of a patient, such as a human being. The term isotonic may mean that the osmolarity and ion concentrations of the vehicle match those of the patient, such as human being. Non-limiting example of vehicles include phosphate-buffered saline, which is a water-based salt solution containing disodium hydrogen phosphate, sodium chloride and, in some formulations, potassium chloride and potassium dihydrogen phosphate. Other examples may include a vehicle containing 20 mM disbasic sodium phosphate with 125 mM sodium chloride and a vehicle containing 15 mM sodium phosphate tribasic, 125 mM sodium chloride and 0.3% w/w m-cresol.

Methods of Treatment

In some embodiments, a method of treating a disease or condition is provided, the method comprising administering to a subject a compound (e.g. a prodrug) or composition disclosed herein. In some embodiments, the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma. In some embodiments, the disease is pulmonary hypertension.

In some embodiments, the subject has detectable treprostinil plasma levels for at least 24 hours upon said administering. In some embodiments, the subject has detectable treprostinil plasma levels for at least 30 hours upon said administering. In some embodiments, the subject has detectable treprostinil plasma levels for at least 36 hours upon said administering. In some embodiments, the subject has detectable treprostinil plasma levels for at least 42 hours upon said administering. In some embodiments, the subject has detectable treprostinil plasma levels for at least 48 hours upon said administering.

Administration may be performed via a route described above, or, for example, orally, intravenously, intra-arterial, intramuscularly, intranasally, rectally, vaginally, or subcutaneously. In some embodiments, the composition is administered by an injection. In some embodiments, the administering is performed orally. In some embodiments, the administering is performed subcutaneously.

In some embodiments, said administering results in no or less pain at a site of the injection compared to administering treprostinil. Pain, or the reduction thereof, may be assessed by any medically recognized method known in the art, for example, numerical rating scale (MRS), visual analog scale (VAS, i.e. Wong-Baker Pain Scale), the FLACC scale, the CRIES Scale, the COMFORT Scale, the McGill Pain Scale, the Manoski Scale, or other categorical scales. In comparison to injection of treprostinil, the pain upon injection of the prodrug results in about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% less pain, as measured by a medically recognized method.

The subject treated may be a human, canine, feline, aves, non-human primate, bovine, or equine. In some embodiments, the subject is a human. In some embodiments, the subject is a human uncooperative or fearful of injections, for example, a pediatric or demented geriatric subject.

In some embodiments, a method of treating a disease or condition is provided, the method comprising administering to a subject a prodrug of treprostinil, wherein upon said administering said prodrug converts to a metabolic product, which consists essentially of treprostinil. The prodrug may be any of the compounds disclosed herein. In some embodiments, the metabolic product consists of treprostinil.

Embodiments described herein are further illustrated by, though in no way limited to, the following working examples.

EXAMPLES

Example 1: Synthesis of Prodrug XXI (10)

Treprostinil side chain phosphonooxyethyl prodrug was synthesized to study the stability and chemical feasibility of this prodrug. This prodrug was synthesized from side chain THP benzinndene triol (1) in 9 steps as shown in Scheme 1.

The side chain THP benzindene triol (1) was silylated with tert-butyldimethylsilyl trifluoromethanesulfonate in presence of 2,6-lutidine to obtain di-TBDMS THP benzindene triol (2) in 97.6% yield. The protected triol (2) was treated with magnesium bromide to remove the THP group to obtain di-TBDMS benzindene triol (3) in 89.6% yield. The di-TBDMS triol (3) was coupled with 2-benzyloxyethyl triflate in presence of sodium bis(trimethylsilyl)amide to obtain di-TBDMS benzindene triol benzyloxyethyl ether (4) in 49.1% yield. The phenolic TBDMS of ether (4) was selectively deprotected using lithium acetate dihydrate at 70° C. to obtain TBDMS benzindene triol benzyloxyethyl ether (5) in 74.6% yield. The benzyl ether of TBDMS benzindene triol benzyloxyethyl ether (5) was hydrogenolyzed using palladium on carbon and hydrogen gas to afford TBDMS benzindene triol side chain glycol ether (6) in 88.4% yield. The phenolic group of glycol ether (6) was O-alkylated using benzyl bromoacetate in presence of potassium carbonate to give TBDMS side chain glycol ether treprostinil benzyl ester (7) in 87.7% yield. The primary alcohol group of benzyl ester (7) was phosphitylated using dibenzyl N,N-diisopropylphosphoramidite in presence of 1H-tetrazole and was then oxidized in the same pot using 3-chloroperbenzoic acid to obtain TBDMS side chain dibenzyl phosphonooxyethyl treprostinil benzyl ester (8) in 92.5% yield. The phosphonooxyethyl treprostinil benzyl ester (8) was desilylated using hydrogen fluoride pyridine complex to get side chain dibenzyl phosphonooxyethyl treprostinil benzyl ester (9) in 88.9% yield. The side chain dibenzyl phosphonooxyethyl treprostinil benzyl ester (9) was hydrogenolyzed using palladium on carbon in presence of hydrogen gas to afford the treprostinil side chain phosphonooxyethyl prodrug (10) in 97.8% yield.

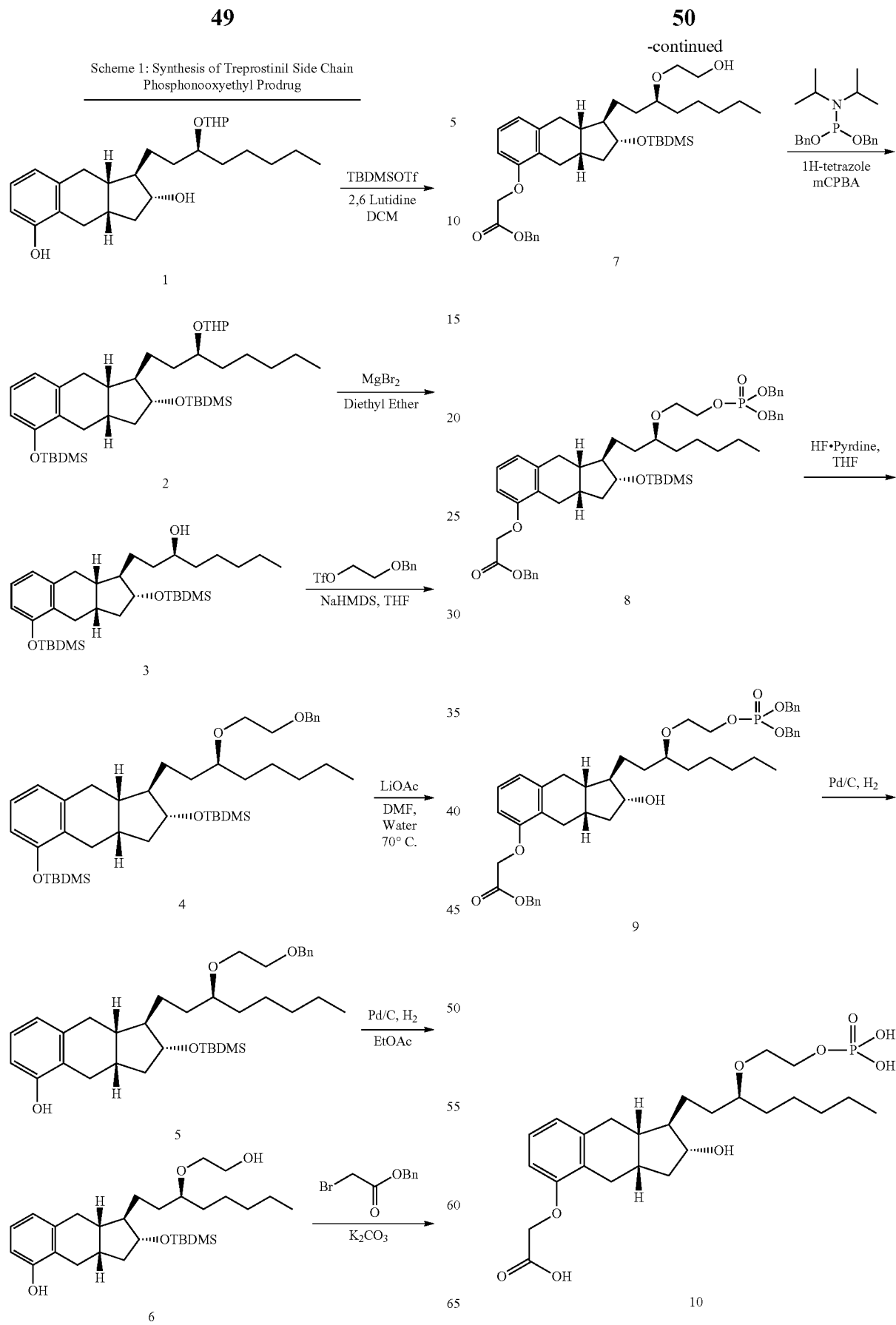
Scheme 1: Synthesis of Treprostinil Side Chain Phosphonooxyethyl Prodrug

EXPERIMENTAL

Synthesis of Di-TBDMS THP Benzindene Triol (2)

Reaction Scheme

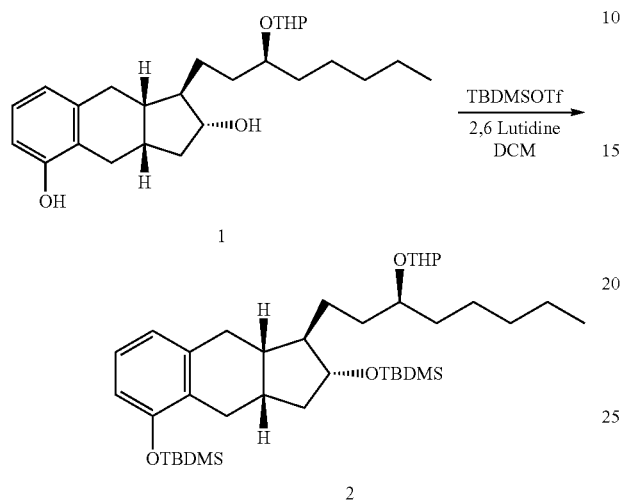

a. Bill of Materials

| Name | MW | Amount | mmol | Eq. |
|---|---|---|---|---|
| Side Chain THP benzindene triol (1) | 416.57 | 3.0 g | 7.20 | 1.0 |
| 2,6-Lutidine | 107.15 | 3.7 mL | 31.69 | 4.4 |
| tert-Butyldimethylsilyl trifluoromethanesulfonate | 264.34 | 3.6 mL | 15.84 | 2.2 |
| Dichloromethane (anhydrous) | NA | 40 mL | NA | NA |

Experimental Procedure

A solution of side chain THP benzindene triol (1) (3.0 g, 7.20 mmol) and 2,6-lutidine (3.7 mL, 31.69 mmol) in dichloromethane (30 mL) was cooled to 0° C. in an ice bath under argon. To this mixture, tert-butyldimethylsilyl trifluoromethanesulfonate (3.6 mL, 15.84 mmol) in dichloromethane (10 mL) was added dropwise over a period of 30 min. This mixture was stirred while allowing the temperature to rise to ambient temperature. After 3 h the reaction was found to be complete based on TLC (EtOAc/Hexanes 1:9). The reaction was quenched with water (30 mL) and the organic layer was separated, washed with brine, dried over sodium sulfate and evaporated in vacuo to obtain crude product (2). This was purified by silica gel column chromatography using ethyl acetate and hexanes (0 to 3%) to give pure di-TBDMS THP benzindene triol (2) (4.53 g) in 97.6% yield. This product was characterized by $^1$H NMR and $^{13}$C NMR.

Synthesis of Di-TBDMS Benzindene Triol (3)

Reaction Scheme

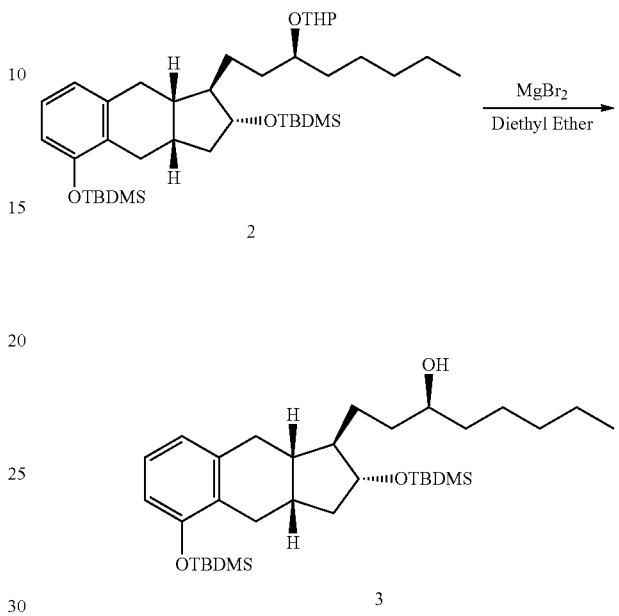

b. Bill of Materials

| Name | MW | Amount | mmol | Eq. |
|---|---|---|---|---|
| Di-TBDMS THP benzindene triol (2) | 645.09 | 4.43 g | 6.87 | 1.0 |
| Magnesium bromide | 184.13 | 7.6 g | 41.20 | 6.0 |
| Diethyl ether (anhydrous) | NA | 50 mL | NA | NA |

Experimental Procedure

To a solution of di-TBDMS THP benzindene triol (2) (4.43 g, 6.87 mmol) was added magnesium bromide (7.6 g, 41.20 mmol) and stirred under argon at ambient temperature. After 7 h the reaction was found to be complete based on TEC (EtOAc/Hexanes 1.5:5.5). The reaction was quenched carefully (exothermic) with water and the organic layer was separated. The aqueous layer was extracted with tert-butyl methyl ether (100 mL) and was separated. The combined organic layers were washed with brine, dried over sodium sulfate and evaporated in vacuo to obtain crude product (3). This was purified by silica gel column chromatography using ethyl acetate and hexanes (0 to 5%) to afford pure di-TBDMS benzindene triol (3) (3.45 g) in 89.6% yield. This product was characterized by $^3$H NMR and $^{13}$C NMR.

Synthesis of Di-TBDMS Benzindene Triol Benzyloxyethyl Ether (4)

Reaction Scheme

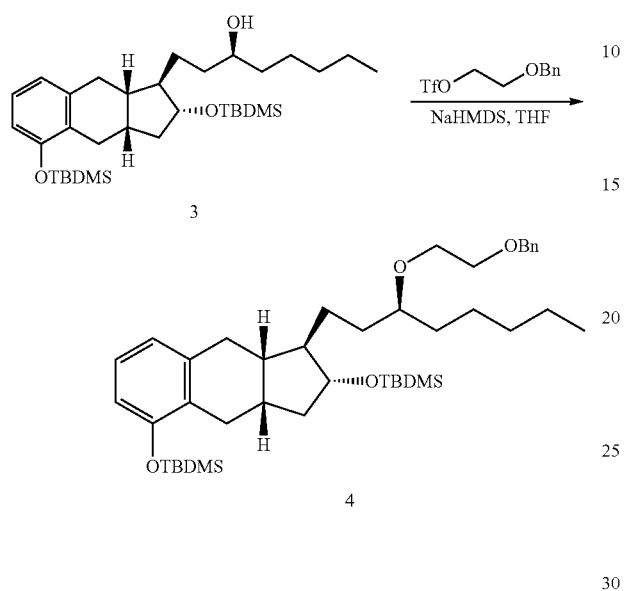

c. Bill of Materials

| Name | MW | Amount | mmol | Eq. |
|---|---|---|---|---|
| Di-TBDMS benzindene triol (3) | 561.02 | 0.94 g | 1.68 | 1.0 |
| 2-Benzyloxyethyl triflate (1 g/mL in tert-butyl methyl ether) | 283.86 | 1.43 g | 5.03 | 3.0 |
| Sodium bis(trimethylsilyl)amide 1.0M THF solution | 183.37 | 2.0 mL | 2.01 | 1.2 |
| Tetrahydrofuran (anhydrous) | NA | 15 mL | NA | NA |

Experimental Procedure

To a solution of di-TBDMS benzindene triol (3) (0.94 g, 1.68 mmol) in anhydrous tetrahydrofuran (15 mL) was added sodium bis(trimethylsilyl)amide solution (1.0 M THF solution) (2.0 mL, 2.01 mmol) under argon at −30° C. over 5 min. This solution was stirred at 30° C. for 1 h and then 2-benzyloxyethyl triflate solution (1.43 g in 1.43 mL) was added dropwise over a period of 10 min. The reaction mixture was allowed to warm to ambient temperature over 2 h and stirred overnight. The progress of the reaction was monitored by TLC (EtOAc/Hexanes 1:9). After 18 h, the reaction mixture was evaporated in vacuo and the residue was partitioned between ethyl acetate (30 mL) and water (20 mL). The organic layer was separated, washed with brine, dried over sodium sulfate and evaporated in vacuo to obtain crude product (3). This was purified by silica gel column chromatography using ethyl acetate and hexanes (0 to 6%) to give pure di-TBDMS benzindene triol benzyloxyethyl ether (4) (570 mg) in 49.1% yield. This product was characterized by $^1$H NMR and LC-MS.

Synthesis of TBDMS Benzindene Triol Benzyloxy Ethyl Ether (5)

Reaction Scheme

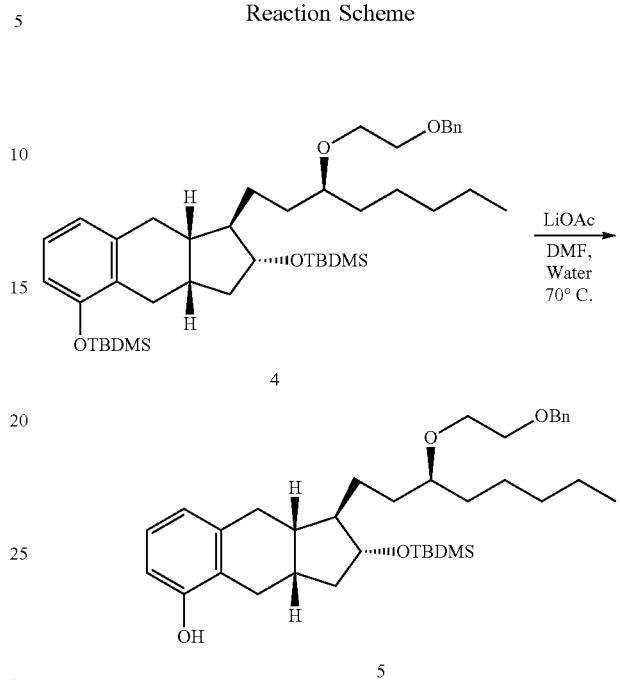

d. Bill of Materials

| Name | MW | Amount | mmol | Eq. |
|---|---|---|---|---|
| Di-TBDMS benzindene triol benzyloxyethyl ether (4) | 695.21 | 0.5 g | 0.719 | 1.0 |
| Lithium acetate dihydrate | 102.02 | 22 mg | 0.216 | 0.3 |
| N,N-Dimethylformamide | NA | 10 mL | NA | NA |
| Water | NA | 0.2 mL | NA | NA |

Experimental Procedure

To a solution of di-TBDMS benzindene triol benzyloxyethyl ether (4) (0.5 g, 0.719 mmol) in N,N-dimethylformamide (10 mL) and water (0.2 mL) was added lithium acetate dihydrate (22 mg, 0.216 mmol). The reaction mixture was heated to 70° C. and stirred under argon. The progress of the reaction was monitored by TLC (EtOAc/Hexanes 1:9) and the reaction was found to be complete after 7 h. The reaction mixture was quenched with saturated ammonium chloride solution (10 mL). This was extracted with ethyl acetate (3×15 mL). The combined organic layers were washed with brine, dried over sodium sulfate and evaporated in vacuo to obtain crude product (5). This was purified by silica gel column chromatography using ethyl acetate and hexanes (0 to 8%) to afford pure TBDMS benzindene triol benzyloxyethyl ether (5) (311 mg) in 74.6% yield. This product was characterized by $^1$H NMR.

Synthesis of TBDMS Benzindene Triol Side Chain Glycol Ether (6)

Reaction Scheme

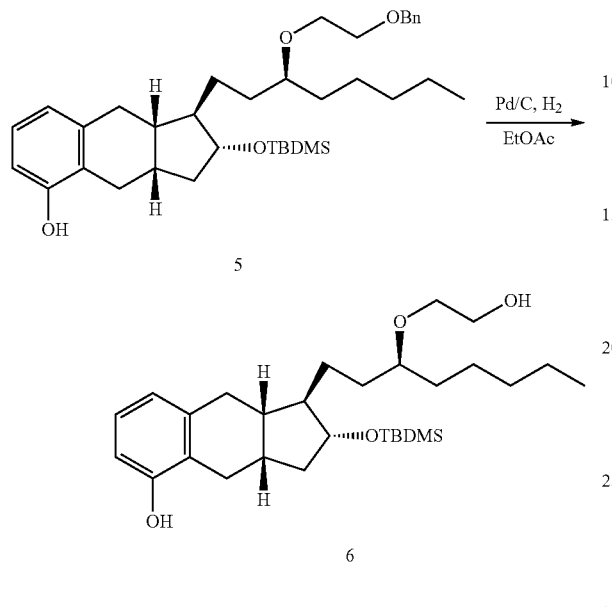

e. Bill of Materials

| Name | MW | Amount | mmol | Eq. |
|---|---|---|---|---|
| TBDMS benzindene triol benzyloxyethyl ether (5) | 580.92 | 0.25 g | 0.430 | NA |
| Palladium on carbon, 5 wt %, wet, Degussa type | NA | 50 mg | NA | NA |
| Ethyl acetate | NA | 5 mL | NA | NA |
| $H_2$ gas (Balloon Pressure) | NA | NA | NA | NA |

Experimental Procedure

To a solution of TBDMS benzindene triol benzyloxyethyl ether (5) (0.25 g, 0.430 mmol) in ethyl acetate (5 mL) was added palladium on carbon (50 mg). This was evacuated and replaced with hydrogen gas (three times). The mixture was stirred under hydrogen atmosphere at ambient temperature. The progress of the reaction was monitored by TEC (EtOAc/Hexanes 2:8) and the reaction was found to be complete after 4 h. The reaction mixture was filtered through Celite to remove palladium on carbon and the resulting filtrate was evaporated in vacuo to obtain crude product (6). This was combined with another batch and purified by silica gel column chromatography using ethyl acetate and hexanes (0 to 18%) to give pure TBDMS benzindene triol side chain glycol ether (6) (221 mg) in 88.4% yield. This product was characterized by $^1$H NMR.

Synthesis of TBDMS Side Chain Glycol Ether Treprostinil Benzyl Ester (7)

Reaction Scheme

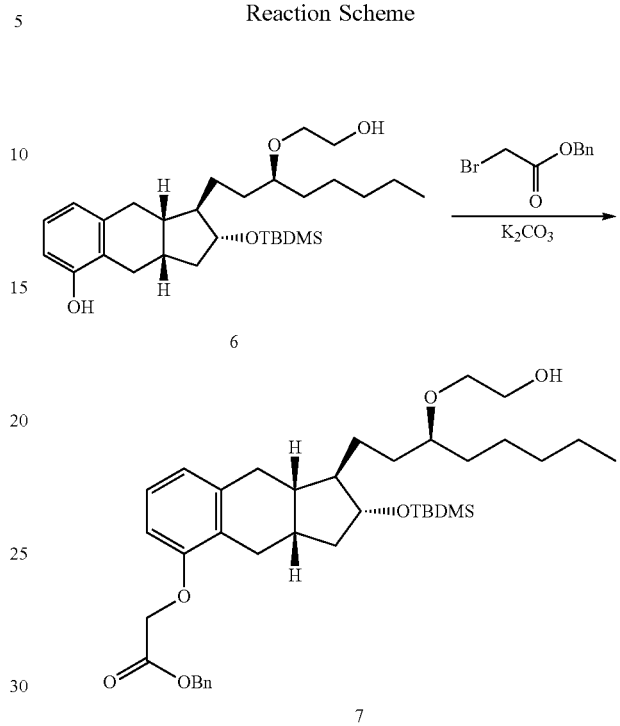

f. Bill of Materials

| Name | MW | Amount | mmol | Eq. |
|---|---|---|---|---|
| TBDMS benzindene triol side chain glycol ether (6) | 490.80 | 206 mg | 0.419 | 1.0 |
| Potassium carbonate (powder) | 138.21 | 145 mg | 1.049 | 2.5 |
| Benzyl bromoacetate | 229.08 | 86 µL | 0.545 | 1.3 |
| Acetone | NA | 4 mL | NA | NA |

Experimental Procedure

To a solution of TBDMS benzindene triol side chain glycol ether (6) (206 mg, 0.419 mmol) in acetone (4 mL) was added powdered potassium carbonate (145 mg, 1.049 mmol) and benzyl bromoacetate (86 µL, 0.545 mmol). The reaction mixture was stirred under argon at ambient temperature. The progress of the reaction was monitored by TEC (EtOAc/Hexanes 2:3). After 48 h the reaction was found to be complete based on TLC. The reaction mixture was filtered to remove potassium carbonate and the filtrate was evaporated in vacuo to obtain crude product (7). This was purified by silica gel column chromatography using ethyl acetate and hexanes (0 to 13%) to obtain pure TBDMS side chain glycol ether treprostinil benzyl ester (7) (235 mg) in 87.7% yield. The pure product was characterized by NMR.

Synthesis of TBDMS Side Chain Dibenzyl Phosphonooxyethyl Treprostinil Benzyl Ester (8)

Reaction Scheme:

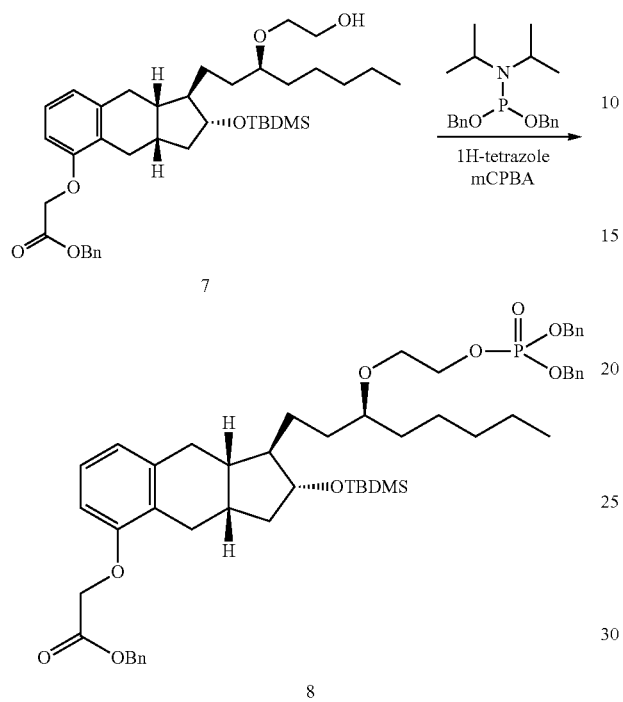

g. Bill of Materials

| Name | MW | Amount | mmol | Eq. |
|---|---|---|---|---|
| TBDMS side chain glycol ether treprostinil benzyl ester (7) | 638.91 | 200 mg | 0.313 | 1.0 |
| Tetrazole solution, ~0.45M in acetonitrile | 70.05 | 3.1 mL | 1.408 | 4.5 |
| Dibenzyl N,N-diisopropylphosphoramidite | 345.43 | 315 µL | 0.939 | 3.0 |
| 3-Chloroperbenzoic acid, ≤77% | 172.57 | 217 mg | 0.970 | 3.1 |
| Dichloromethane | NA | 4 mL | NA | NA |

Experimental Procedure

To a solution of TBDMS side chain glycol ether treprostinil benzyl ester (7) (0.2 g, 0.313 mmol) in dichloromethane (3 mL) was added tetrazole solution (~0.45 M in acetonitrile) (2.1 mL, 0.939 mmol) and dibenzyl N,N-diisopropylphosphoramidite (210 µL, 0.626 mmol). The reaction mixture was stirred at ambient temperature for 2 h. The progress of the reaction was monitored by TLC (EtOAc/Hexanes 3:7) and the reaction showed some starting material. Additional tetrazole solution (1.0 mL, 0.469 mmol) and dibenzyl N,N-diisopropylphosphoramidite (105 µL, 0.313 mmol) were added and the reaction was stirred for 1 h. At this stage the starting material was completely consumed. The reaction mixture was cooled to −78° C. and a solution of 3-chloroperbenzoic acid (217 mg, 0.970 mmol) in dichloromethane (1 mL) was added. The mixture was stirred for 1.5 h while allowing the temperature to raise. The reaction was found to be complete based on TLC (EtOAc/Hexanes 3:7). The reaction mixture was quenched with 10% aq. sodium sulfite solution (6 mL) and stirred for 15 min. The organic layer was separated, and the aqueous layer was extracted with dichloromethane (2×15 mL). The combined organic layers were washed with saturated aq. sodium bicarbonate solution, dried over sodium sulfate and evaporated in vacuo to obtain crude product (8). This was purified by silica gel column chromatography using ethyl acetate and hexanes (0 to 22%) to give pure TBDMS side chain dibenzyl phosphonooxyethyl treprostinil benzyl ester (8) (260 mg) in 92.5% yield. The pure product was characterized by $^1$H NMR and $^{31}$P NMR.

Synthesis of Side Chain Dibenzyl Phosphonooxy Ethyl Treprostinil Benzyl Ester (9)

Reaction Scheme

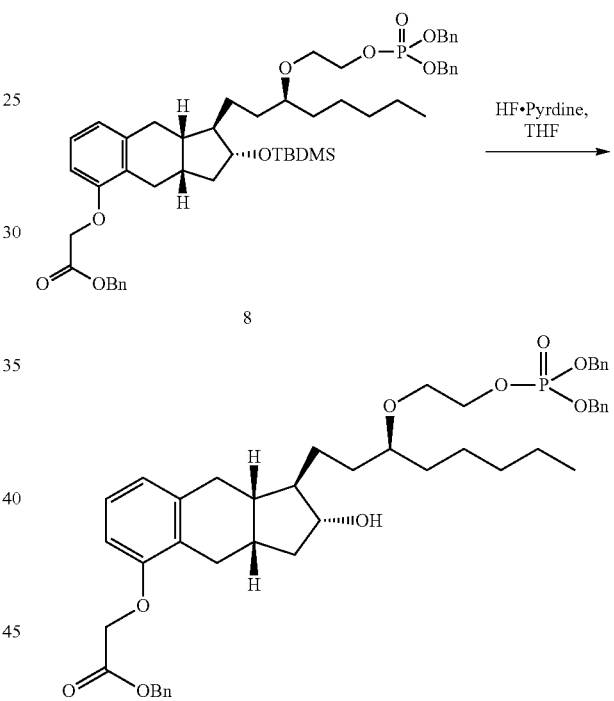

h. Bill of Materials

| Name | MW | Amount | mmol | Eq. |
|---|---|---|---|---|
| TBDMS side chain dibenzyl phosphonooxyethyl treprostinil benzyl ester (8) | 899.19 | 120 mg | 0.133 | NA |
| Hydrogen fluoride pyridine | NA | 0.9 mL | NA | NA |
| Tetrahydrofuran (anhydrous) | NA | 6 mL | NA | NA |

Experimental Procedure

To a solution of TBDMS side chain dibenzyl phosphonooxyethyl treprostinil benzyl ester (8) (120 mg, 0.133 mmol) in anhydrous tetrahydrofuran (6 mL) (in a Teflon tube) was added hydrogen fluoride pyridine (0.9 mL). The reaction mixture was stirred at ambient temperature. The progress of the reaction was monitored by TLC (EtOAc/Hexanes 4:1). After 3 h, the reaction was found to be complete based on TLC. The reaction mixture was quenched by dropwise addition of saturated aq. sodium bicarbonate solution (25 mL) and stirred for 15 min. This mixture was extracted with ethyl acetate (3×15 mL) and the organic layer was separated. The combined organic layers were dried over sodium sulfate and evaporated in vacuo to obtain crude product (9). This was combined with another 120 mg batch and purified by silica gel column chromatography using ethyl acetate and hexanes (0 to 52%) to obtain pure side chain dibenzyl phosphonooxyethyl treprostinil benzyl ester (9) (186 mg) in 88.9% yield. The pure product was characterized by $^1$H NMR, $^{13}$C NMR and $^{31}$P NMR.

Synthesis of Treprostinil Side Chain Phosphonooxyethyl Prodrug (10)

Reaction Scheme

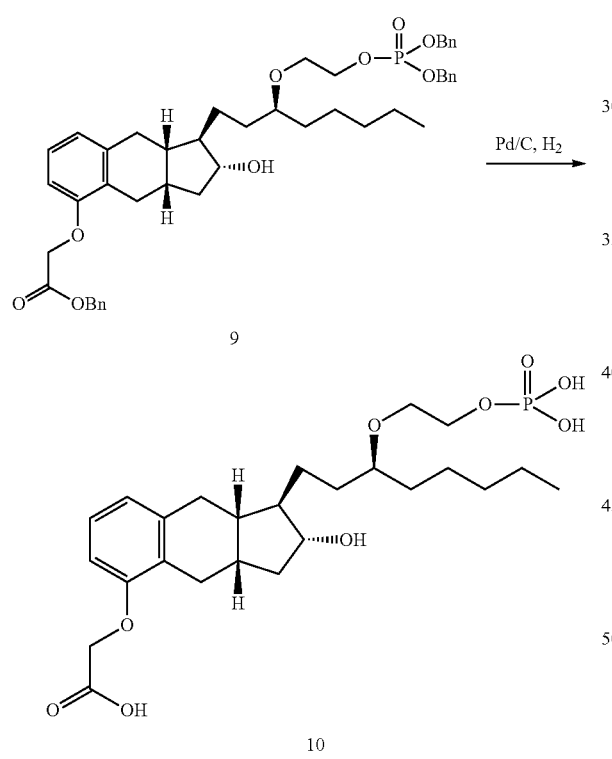

-continued

| Name | MW | Amount | mmol | Eq. |
|---|---|---|---|---|
| Ethyl acetate | NA | 8 mL | NA | NA |
| Water | NA | NA | NA | NA |
| H$_2$ gas (Balloon Pressure) | NA | NA | NA | NA |

Experimental Procedure

To a solution of side chain dibenzyl phosphonooxy ethyl treprostinil benzyl ester (9) (167 mg, 0.213 mmol) in ethyl acetate (8 mL) was added palladium on carbon (50 mg) and water (2 mL). The mixture was evacuated and replaced with hydrogen gas (three times). This was stirred under hydrogen atmosphere at ambient temperature. The progress of the reaction was monitored by TEC (EtOAc/Hexanes 3:7) and the reaction was found to be complete after 6 h. The reaction mixture was filtered through Celite (ethyl acetate (10 mL) and water (5 mL) were used for washing during filtration) and the resulting filtrate was evaporated in vacuo to obtain crude product (6). This was dissolved in tetrahydrofuran (5 mL) and filtered through cotton to remove haziness and to obtain pure treprostinil side chain phosphonooxyethyl prodrug (10) (106 mg) in 97.2% yield. The pure product was characterized by $^1$H NMR, $^{13}$C NMR, $^{31}$P NMR, LC-MS and IR. The HPLC purity of the compound was found to be 97.48%.

j. Summary of Analytical Data on Treprostinil Side Chain Phosphonooxy ethyl Prodrug

| Description | Results |
|---|---|
| Structure | 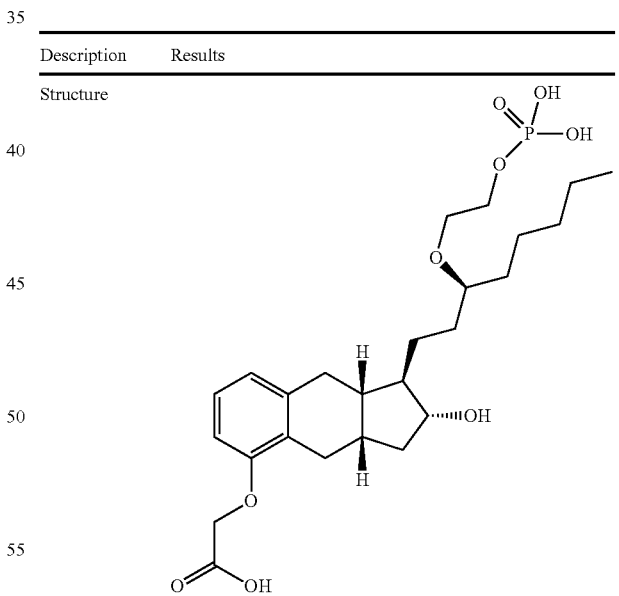 |
| Chemical Name | 2-(((1R,2R,3aS,9aS)-2-hydroxy-1-((S)-3-(2-(phosphonooxy)ethoxy)octyl)-2,3,3a,4,9,9a-hexahydro-1H-cyclopenta[b]naphthalen-5-yl)oxy)acetic acid |
| Physical Description | Viscous Liquid |
| Molecular Formula | C$_{29}$H$_{39}$O$_9$P |
| Molecular Weight | 514.55 | i. Bill of Materials

| Name | MW | Amount | mmol | Eq. |
|---|---|---|---|---|
| Side chain dibenzyl phosphonooxyethyl treprostinil benzyl ester (9) | 784.93 | 167 mg | 0.213 | NA |
| Palladium on carbon 5 wt %, wet, Degussa type | NA | 33 mg | NA | NA |

-continued

| Description | Results |
|---|---|
| MS | Conforms to the molecular weight |
| ¹H NMR | Conforms to the structure |
| ¹³C NMR | Conforms to the structure |
| IR | Conforms to the structure |
| Purity by UPLC | 97.48% |

Example 2: Synthesis of Treprostinil Side Chain Ethyl Carbonate (Prodrug XVI)

Scheme 2: Synthesis of Treprostinil Side Chain Ethyl Carbonate (Prodrug XVI)

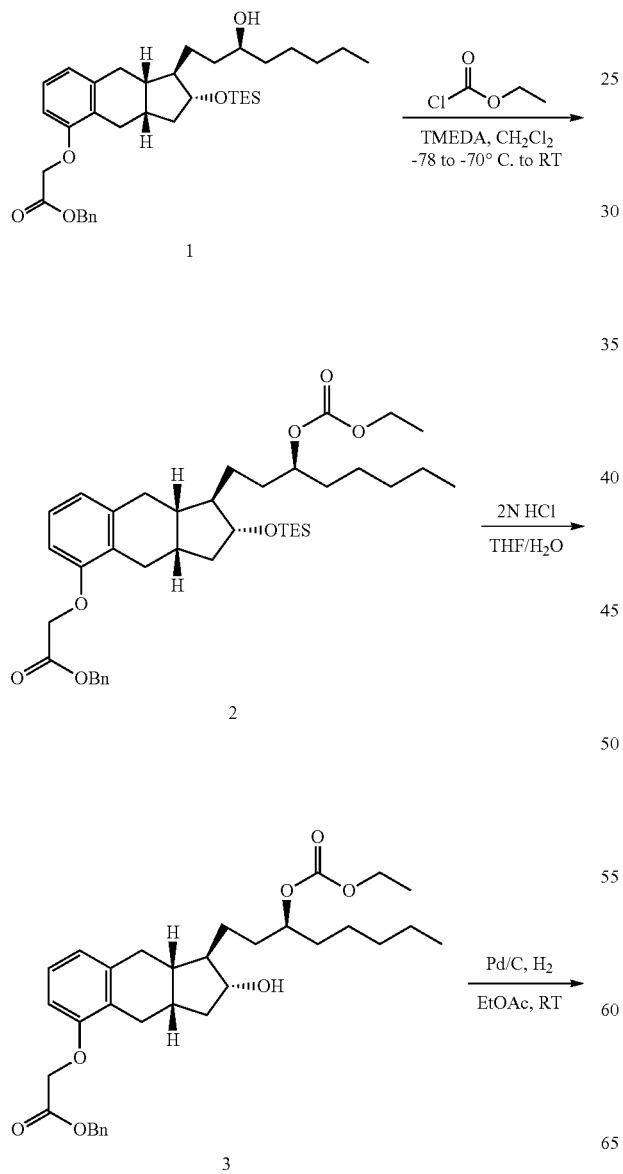

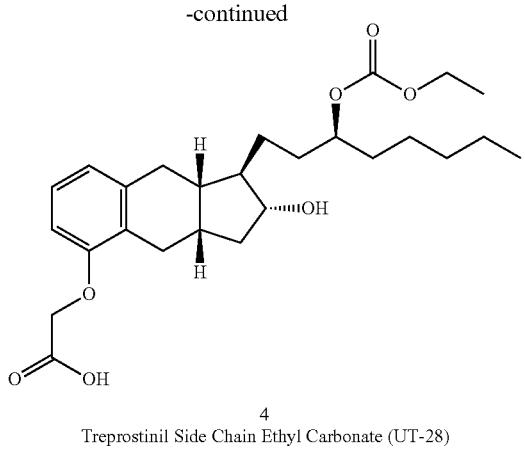

4
Treprostinil Side Chain Ethyl Carbonate (UT-28)

EXPERIMENTAL

Synthesis of TES-Treprostinil Benzyl Ester Ethyl Carbonate (2)

Reaction Scheme

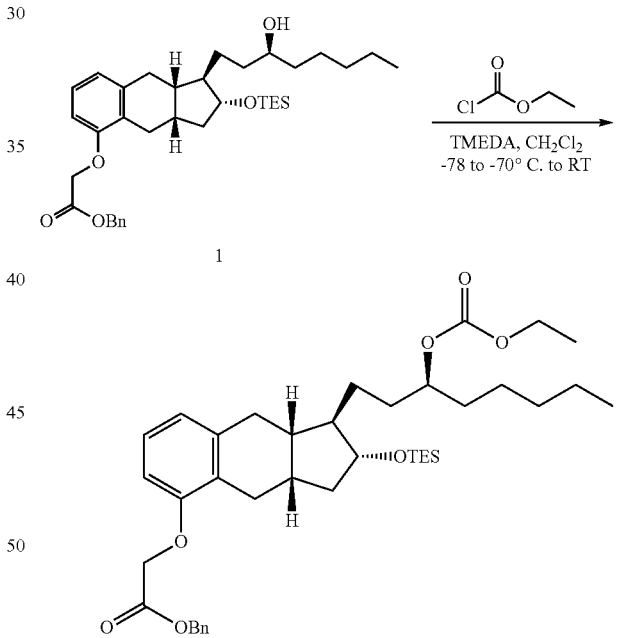

k. Bill of Materials

| Name | Mol Wt. | Amount | mmol | Eq. |
|---|---|---|---|---|
| Mono-TES-Treprostinil benzyl ester (1) | 594.88 | 2.4 g | 4.03 | 1.0 |
| N,N,N',N'-Tetramethylethylenediamine | 116.21 | 0.73 mL | 4.84 | 1.2 |

| Name | Mol Wt. | Amount | mmol | Eq. |
|---|---|---|---|---|
| Ethyl chloroformate | 108.52 | 0.77 mL | 8.07 | 2.0 |
| Dichloromethane (anhydrous) | NA | 35 mL | NA | NA |

Experimental Procedure

To a solution of mono-TES-treprostinil benzyl ester (1) (2.4 g, 4.03 mmol) in anhydrous dichloromethane (35 mL) was added N,N,N',N'-tetramethylethylenediamine (0.73 mL, 4.84 mmol). The clear solution was cooled to −78 to −70° C. and then added dr op wise ethyl chloroformate (0.77 mL, 8.07 mmol) over a period of 5 min under argon. After complete addition, the reaction mixture was stirred while allowing the temperature to rise to RT. After 4 h, the reaction was complete based on TLC (ethyl acetate/hexanes, 1:4). The reaction mixture was quenched with water (15 mL). The organic layer was separated and washed with brine (10 mL), dried over sodium sulfate and evaporated in vacuo to obtain crude product (3.1 g). The crude compound was purified by column chromatography on silica gel using 0 to 7% EtOAc/Hexane as mobile phase to afford pure TES-treprostinil benzyl ester ethyl carbonate (2) (2.79 g, in 103% yield with residual solvent). The pure compound (2) was characterized by $^1$H NMR.

Synthesis of Treprostinil Benzyl Ester Ethyl Carbonate (3)

Reaction Scheme

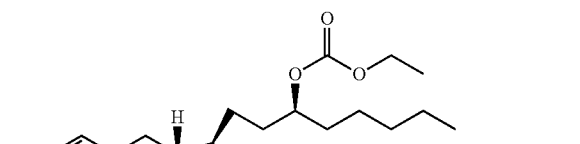

2

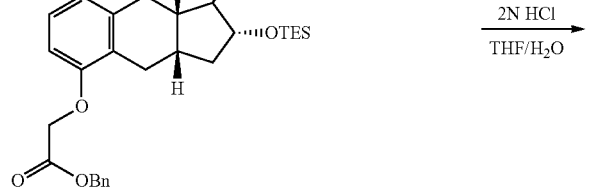

3

1. Bill of Materials

| Name | Mol Wt. | Amount | mmol | Eq. |
|---|---|---|---|---|
| TES-treprostinil benzyl ester ethyl carbonate (2) | 666.97 | 2.6 g | 3.89 | 1.0 |
| Hydrochloric acid solution (2N) | 36.50 | 3.9 mL | 3.89 | 1.0 |
| Tetrahydrofuran | NA | 30 mL | NA | NA |
| Water | NA | 1.1 mL | NA | NA |
| Triethylamine | 101.19 | 1.1 mL | 7.79 | 2.0 |

Experimental Procedure

To a solution of TES-treprostinil benzyl ester ethyl carbonate (2) (2.6 g, 3.89 mmol) in tetrahydrofuran (30 mL) was added hydrochloric acid solution (2 N) (3.9 mL, 3.89 mmol) (water (1.1 mL) used for rinsing). The reaction mixture was stirred at room temperature for 1 h. Based on TLC (ethyl acetate/hexanes, 2:3) the reaction was found to be complete. The reaction mixture was neutralized with triethylamine (1.1 mL, 7.79 mmol). The organic volatiles were evaporated in vacuo and the residue was partitioned between MTBE (20 mL) and water (10 mL). The organic layer was separated, washed with brine, dried (Na$_2$SO$_4$) and concentrated in vacuo to crude product (2.4 g). The crude product was purified by silica gel column chromatography using 0-25% EtOAc/Hexane as mobile phase to obtain pure treprostinil benzyl ester ethyl carbonate (3) (2.24 g, in 104% yield with residual solvent). The pure compound (3) was characterized by $^1$H NMR.

Synthesis of Treprostinil Side Chain Ethyl Carbonate (4)

Reaction Scheme

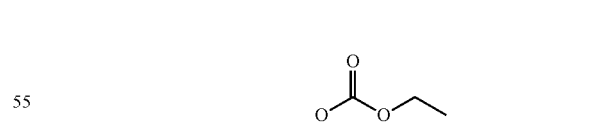

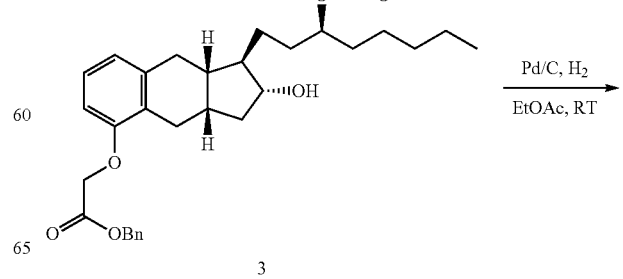

3

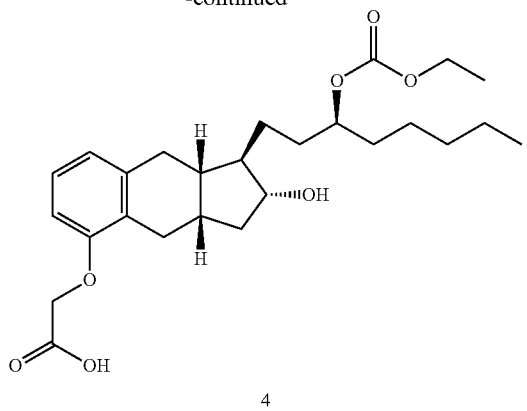

4 m. Bill of Materials

| Name | Mol Wt. | Amount | mmol | Eq |
|---|---|---|---|---|
| Treprostinil benzyl ester ethyl carbonate (3) | 552.71 | 2.0 g | 3.62 | 1.00 |
| Palladium on carbon, 5 wt % (dry basis), ~50 % water, (Degussa Type) | NA | 0.4 g | NA | NA |
| Hydrogen gas | 2.00 | filled in a balloon | NA | NA |
| Ethyl acetate | NA | 20 mL | NA | NA |

Experimental Procedure

To a solution of treprostinil benzyl ester ethyl carbonate (3) (2.0 g, 3.62 mmol) in ethyl acetate (20 mL) was added palladium on carbon (5 wt %, 50% water) (0.4 g). The mixture was stirred and evacuated under house vacuum and replaced by hydrogen (filled in a balloon). This process was repeated three times. The mixture was stirred at room temperature under the atmosphere of hydrogen for 3 h. Based on TEC (ethyl acetate/hexane, 2:3) the reaction was found to be complete. The reaction mixture was filtered through a pad of Celite. The filtrate was concentrated in vacuo to obtain treprostinil side chain ethyl carbonate (Prodrug XVI) (4) (1.58 g, in 94.6% yield). The compound was fully characterized by spectral data (IR, $^1$H NMR, $^{13}$C NMR and LC-MS) and purity of 99.63% by HPLC.

Scheme 3: Synthesis of Treprostinil Side Chain Isopropyl Carbonate (Prodrug XVII)

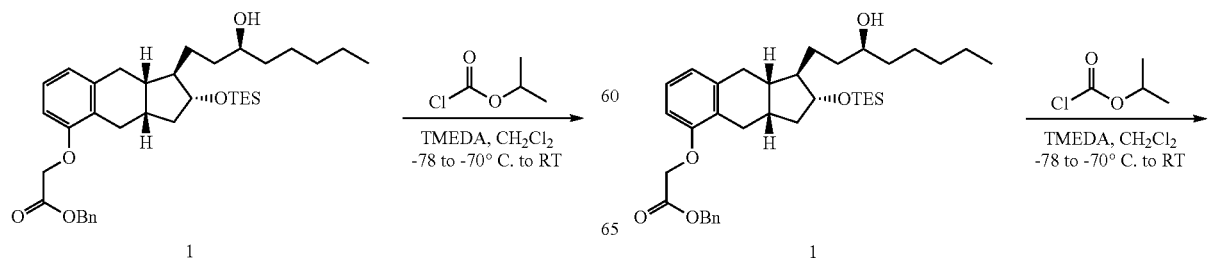

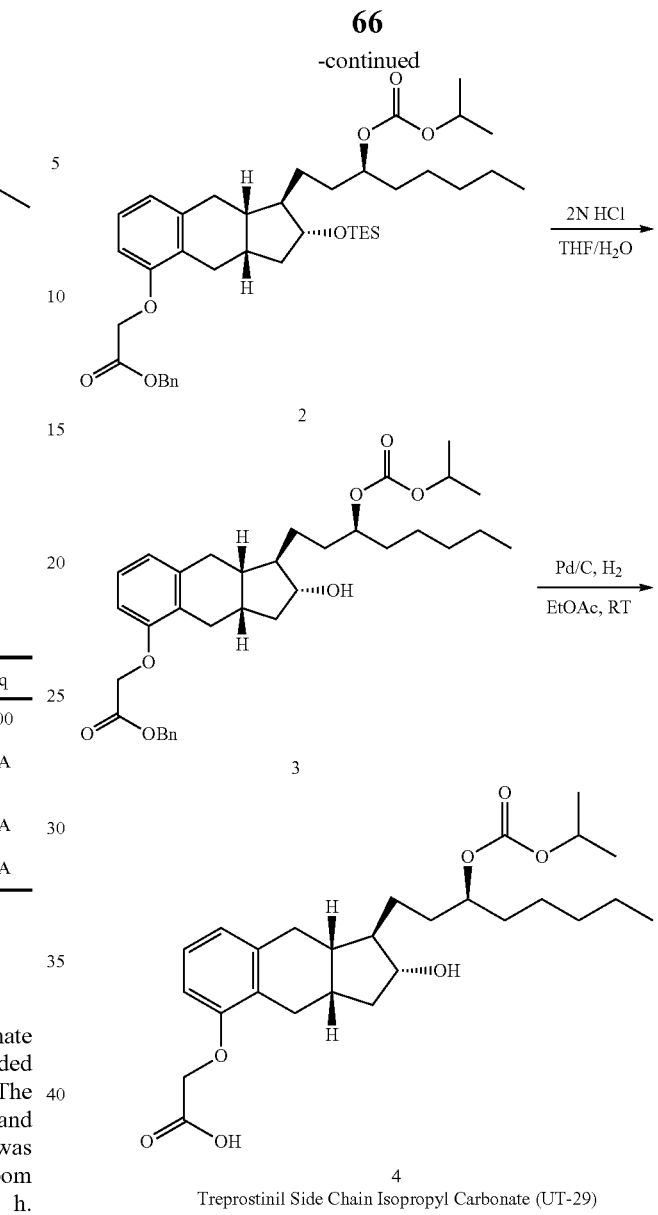

4
Treprostinil Side Chain Isopropyl Carbonate (UT-29)

EXPERIMENTAL

Synthesis of TES-Treprostinil Benzyl Ester Isopropyl Carbonate (2)

Reaction Scheme

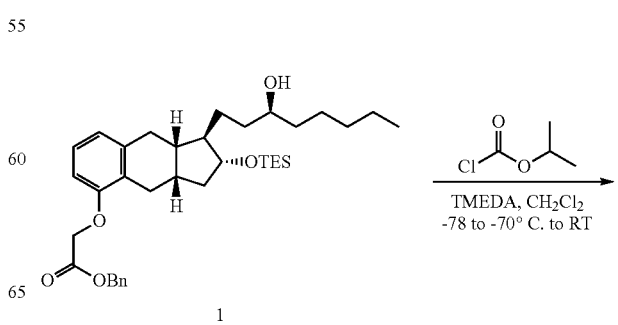

Synthesis of Treprostinil Benzyl Ester Isopropyl Carbonate (3)

Reaction Scheme

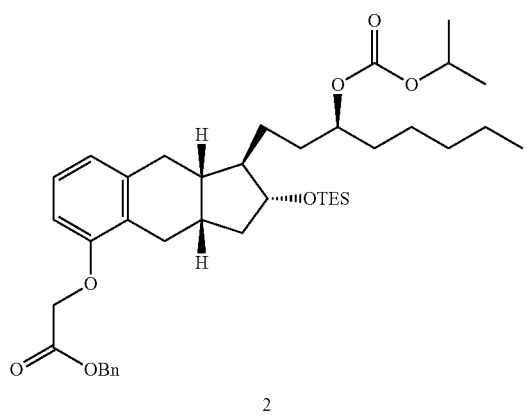

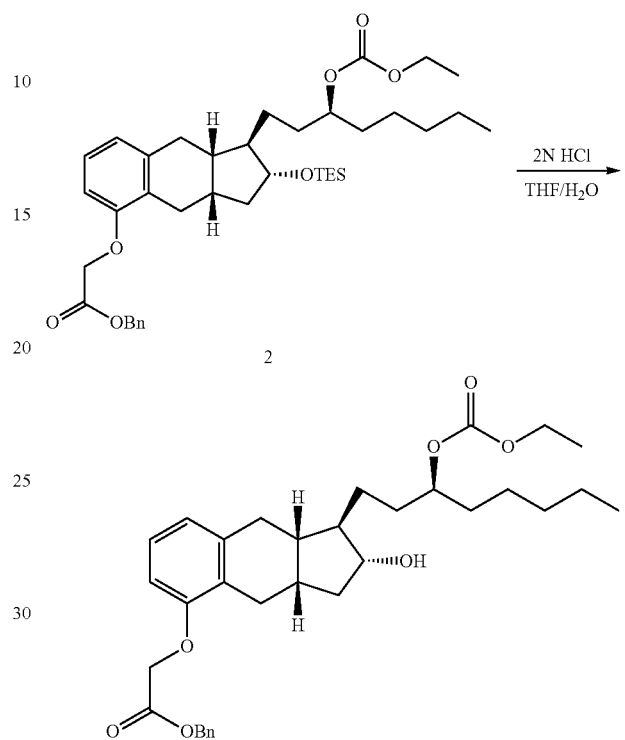

n. Bill of Materials

| Name | Mol Wt. | Amount | mmol | Eq. |
|---|---|---|---|---|
| Mono-TES-Treprostinil benzyl benzyl ester (1) | 594.88 | 3.57 g | 6.00 | 1.0 |
| N,N,N',N'-Tetramethylethylenediamine | 116.21 | 1.07 mL | 7.20 | 1.2 |
| Isopropyl chloroformate solution (1.0M in toluene) | 122.55 | 12 mL | 12.00 | 2.0 |
| Dichloromethane (anhydrous) | NA | 40 mL | NA | NA |

Experimental Procedure

To a solution of mono-TES-treprostinil benzyl ester (1) (3.57 g, 6.00 mmol) in anhydrous dichloromethane (40 mL) was added N,N,N',N'-tetramethylethylenediamine (1.07 mL, 7.20 mmol). The clear solution was cooled to −78 to −70° C. and then added dr op wise isopropyl chloroformate solution (1.0 M in toluene) (12 mL, 12.00 mmol) over a period of 10 min under argon. After complete addition, the reaction mixture was stirred while allowing the temperature to rise to RT. After 4 h, the reaction was complete based on TLC. The reaction mixture was quenched with water (20 mL). The organic layer was separated, washed with brine (10 mL), dried over sodium sulfate and evaporated in vacuo to obtain crude product (4.86 g). The crude compound was purified by column chromatography on silica gel using 0 to 8% EtOAc/Hexane as mobile phase to afford pure TES-treprostinil benzyl ester isopropyl carbonate (2) (3.88 g, in 95.1% yield). The pure compound (2) was characterized by $^1$H NMR.

o. Bill of Materials

| Name | MMol Wt. | Amount | mmol | Eq. |
|---|---|---|---|---|
| TES-treprostinil benzyl ester isopropyl carbonate (2) | 680.88 | 3.77 g | 5.54 | 1.0 |
| Hydrochloric acid solution (2N) | 36.50 | 5.6 mL | 5.54 | 1.0 |
| Tetrahydrofuran | NA | 40 mL | NA | NA |
| Water | NA | 1.5 mL | NA | NA |
| Triethylamine | 101.19 | 1.6 mL | 11.08 | 2.0 |

Experimental Procedure

To a solution of TES-treprostinil benzyl ester isopropyl carbonate (2) (3.77 g, 5.54 mmol) in tetrahydrofuran (40 mL) was added hydrochloric acid solution (2 N) (5.6 mL, 5.54 mmol) (water (1.5 mL) used for rinsing). The reaction mixture was stirred at room temperature for 1 h. Based on TEC (ethyl acetate/hexanes 2:3) the reaction was found to be complete. The reaction mixture was neutralized with triethylamine (1.6 mL, 11.08 mmol). The organic volatiles were evaporated in vacuo and the residue was partitioned between MTBE (30 mL) and water (15 mL). The organic layer was separated, washed with brine, dried over Na$_2$SO$_4$ and concentrated in vacuo to crude product (3.88 g). The crude product was purified by silica gel column chromatography using 0-26% EtOAc/Hexane to obtain pure treprostinil benzyl ester isopropyl carbonate (3) (3.0 g, in 95.5% yield). The pure compound (3) was characterized by ¹H NMR.

Synthesis of Treprostinil Side Chain Isopropyl Carbonate (4)

Reaction Scheme

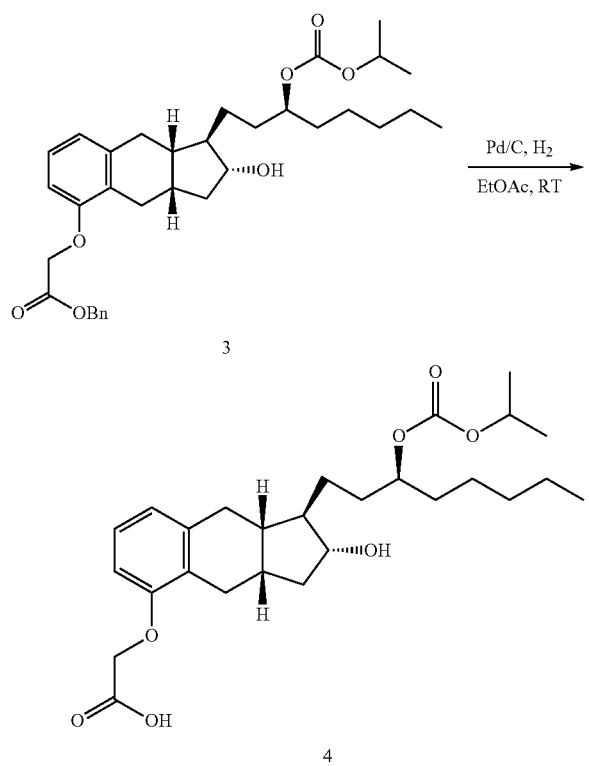

p. Bill of Materials

| Name | MMol Wt. | Amount | mmol | Eq |
|---|---|---|---|---|
| Treprostinil benzyl ester isopropyl carbonate (3) | 566.74 | 2.9 g | 5.12 | 1.00 |
| Palladium on carbon, 5 wt % (dry basis), ~50% water, (Degussa Type) | NA | 0.58 g | NA | NA |
| Hydrogen gas | 2.00 | filled in a balloon | NA | NA |
| Ethyl acetate | NA | 30 mL | NA | NA |

Experimental Procedure

To a solution of treprostinil benzyl ester isopropyl carbonate (3) (2.9 g, 5.12 mmol) in ethyl acetate (30 mL) was added palladium on carbon (5 wt %, 50% water) (0.58 g). The mixture was stirred and evacuated under house vacuum and replaced by hydrogen (filled in a balloon). This process was repeated three times. The mixture was stirred at room temperature under the atmosphere of hydrogen for 3 h. Based on TLC (ethyl acetate/hexane, 2:3) the reaction was found to be complete. The reaction mixture was filtered through a pad of Celite. The filtrate was concentrated in vacuo to obtain treprostinil side chain isopropyl carbonate (Prodrug XVII) (4) (2.38 g, in 97.5% yield). The compound was fully characterized by spectral data (IR, ¹H NMR, ¹³C NMR and LC-MS) and purity of 96.53% by HPLC.

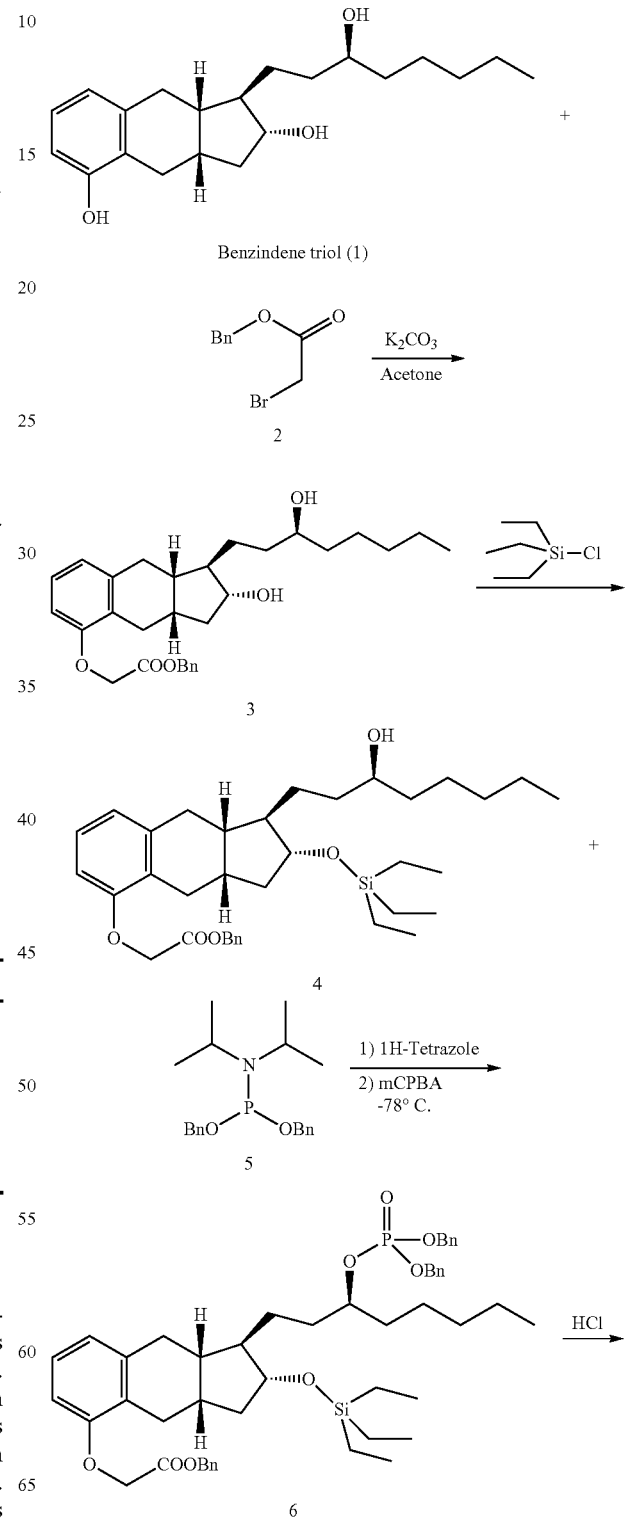

Scheme 4: Synthesis of Treprostinil Side Chain Phosphate (Prodrug VI)

-continued

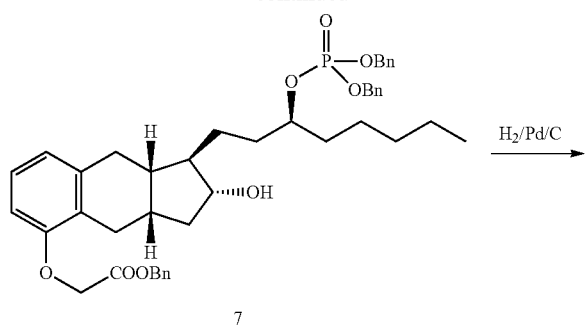

q. Bill of Materials

| Name | Mol. Wt. | Eq. | Amount | mmol |
|---|---|---|---|---|
| Benzindene triol (1) | 332.48 | 1.0 | 150.0 g | 451.1 |
| Benzyl bromoacetate (2) | 229.08 | 1.2 | 124.0 g | 541.3 |
| Potassium carbonate | 138.21 | 2.2 | 137.3 g | 992.4 |
| Acetone | 58.08 | NA | 1200 ml | NA |

Experimental Procedure

To a 2-L three necked, round-bottom flask equipped with an air-driven mechanic stirrer was added triol (1) (150 g) in acetone (800 ml), followed by benzyl bromoacetate (2) (124 g) in acetone (200 ml). To this stirring solution was added powder potassium carbonate (137.3 g) and the mixture was stirred at room temperature. The reaction was checked with TEC (MeOH/DCM, 1:10). After completion of reaction, the mixture was filtered, and washed with acetone (2×100 ml). The filtrate was concentrated in vacuo to give crude product (260.7 g). The product was dissolved in ethyl acetate (35 ml) and transferred into 5-L, three-necked flask equipped with air-driven mechanic stirrer. The mixture was stirred at 50° C. in water bath. Hexanes (1 L) was added to the solution while stirring. The mixture was stopped stirring at room temperature for 30 min and decanted out the supernatant liquid. Ethyl acetate (25 ml) was added and stirred at 50° C. in water bath and hexane was added (slowly, 750 ml). After stirring for 40 min, it was stopped stirring for 30 min at room temperature and decanted out the supernatant liquid. This process was repeated one more time to give white solid. It was filtered and the solid was washed with hexane (2×100 ml). The solid was air-dried overnight and weighed 209.7 g (96.7% yield) (96.70% HPLC purity). The compound was characterized by $^1$H NMR and MS.

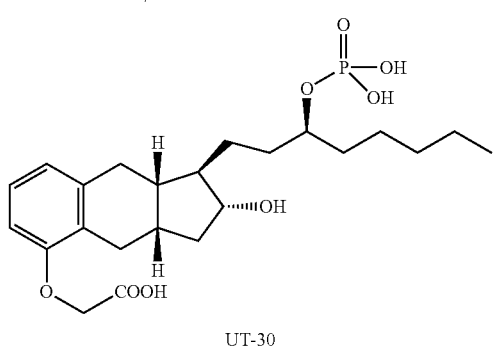

UT-30

EXPERIMENTAL

Synthesis of Treprostinil Benzyl Ester (3)

Reaction Scheme

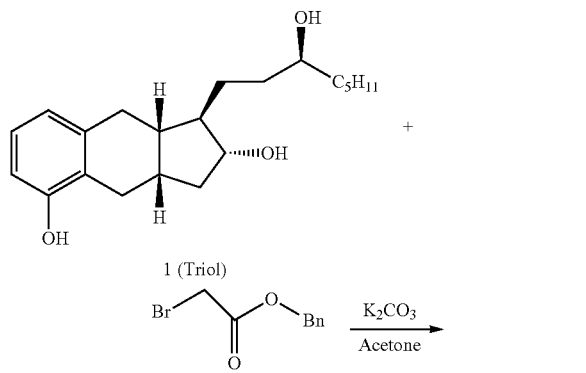

Synthesis of Treprostinil Mono-TES Benzyl Ester (4)

Reaction Scheme

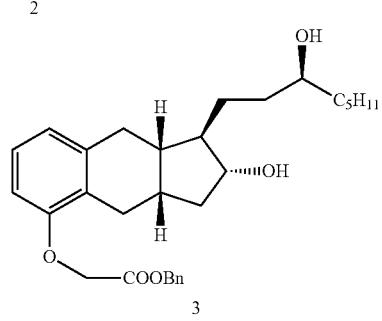

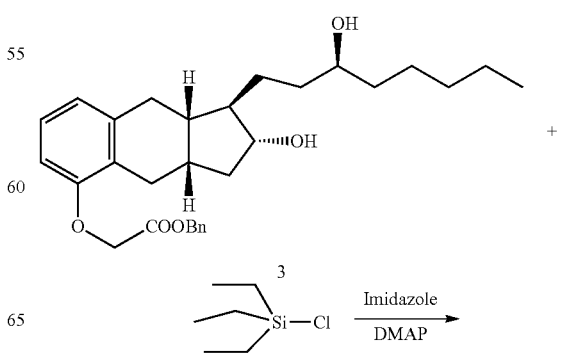

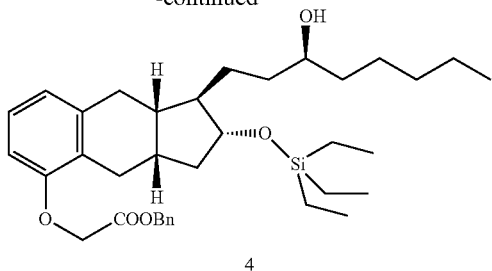

4 r. Bill of Materials

| Name | Mol. Wt. | Eq. | Amount | mmol |
|---|---|---|---|---|
| Treprostinil benzyl ester (3) | 480.62 | 1.0 | 10.0 g | 20.8 |
| Triethylsilylchloride (TES-Cl) | 150.72 | 1.0 | 3.5 ml | 20.8 |
| Imidazole | 68.08 | 1.0 | 1.41 g | 20.8 |
| 4-(Dimethylamino)-pyridine (DMAP) | 122.17 | 0.1 | 0.25 g | 2.08 |
| Dichloromethane (DCM) (anhydrous) | 84.93 | NA | 200 ml | NA |
| Silica gel (230-400 mesh) (Merck) | NA | NA | 300 g | NA |

Experimental Procedure

To a round-bottom flask equipped with a magnetic stir bar was charged with treprostinil benzyl ester (3) (10.0 g), imidazole (1.41 g), DMAP (0.25 g) and anhydrous DCM (200 ml). The mixture was stirred at room temperature under argon and TES-Cl (3.5 ml) was added. After stirring for 1 h and the reaction was checked by TLC (EtOAc/Hex, 1:4). The reaction was quenched with water (150 ml). The organic layer washed with brine and dried over sodium sulfate. It was filtered, and the solvent was removed in vacuo to give crude product which was purified on silica gel column chromatography using 0-11% ethyl acetate in hexanes to give desired pure treprostinil mono-TES benzyl ester (4) (6.68 g, 54% yield). It was characterized by $^1$H NMR.

Synthesis of Mono-TES Treprostinil Benzyl Ester Dibenzyl Phosphate (6)

Reaction Scheme

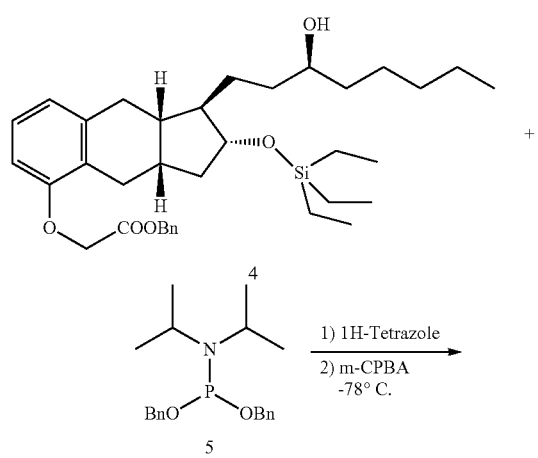

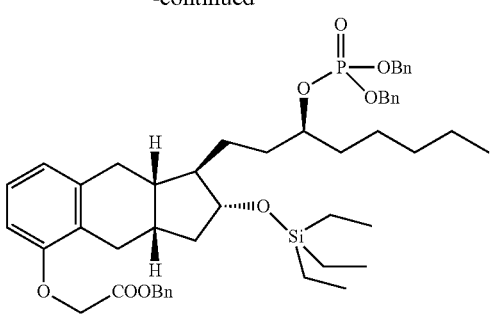

6 s. Bill of Materials

| Name | Mol. Wt. | Eq. | Amount | mmol |
|---|---|---|---|---|
| Treprostinil mono-TES benzyl ester (4) | 594.91 | 1.0 | 1.08 g | 1.82 |
| Dibenzyl diisopropyl-phosphoramidite (5) | 345.43 | 2.0 | 1.26 g | 3.64 |
| 1H-Tetrazole (0.45M in acetonitrile) | 70.05 | 3.0 | 12.1 ml | 5.46 |
| meta-Chloroperbenzoic acid (<77%) (m-CPBA) | 172.57 | 3.1 | 0.97 g | 5.64 |
| Dichloromethane (DCM) (anhydrous) | 84.93 | NA | 50 ml | NA |
| Silica gel (230-400 mesh) (Merck) | NA | NA | 40 g | NA |
| Sodium Sulfite | 126.04 | NA | 20 ml | NA |

Experimental Procedure

To a round-bottom flask equipped with a magnetic stir bar was charged with mono-TES treprostinil benzyl ester (4) (1.08 g), dibenzyl diisopropyl phosphoramidite (5) (1.26 g) and 1H-tetrazole (12.1 ml, 0.45 M in acetonitrile) in anhydrous DCM (50 ml). The mixture was stirred at room temperature under argon for 2 h and checked by TEC (EtOAc/Hex, 1:4). It was cooled to −78° C. and then m-CPBA (0.94 g, <77% purity) was added in one portion. The resulting suspension was stirred at that temperature for 2 h and checked by TEC (EtOAc/Hex, 1:4). After completion of the reaction, 10% $Na_2SO_3$ solution (20 ml) and DCM (20 ml) were added and stirred for 10 min. The DCM layer was tested with peroxide 100 test paper to make sure that there was no peroxide existed in the solution (washed more with $Na_2SO_3$ solution if peroxide existed). The DCM layer was washed with water (20 ml), sat. sodium bicarbonate (20 ml), brine (20 ml) and dried over sodium sulfate. It was filtered and the solvent was removed in vacuo to give crude product (6) (2.32 g). It was purified on silica gel column chromatography using 5-45% ethyl acetate in hexane to give pure treprostinil mono-TES benzyl ester dibenzyl phosphate (6) (1.42 g, 92% yield). It was characterized by $^1$H NMR and MS.

Synthesis of Treprostinil Benzyl Ester Dibenzyl Phosphate (7)

Reaction Scheme

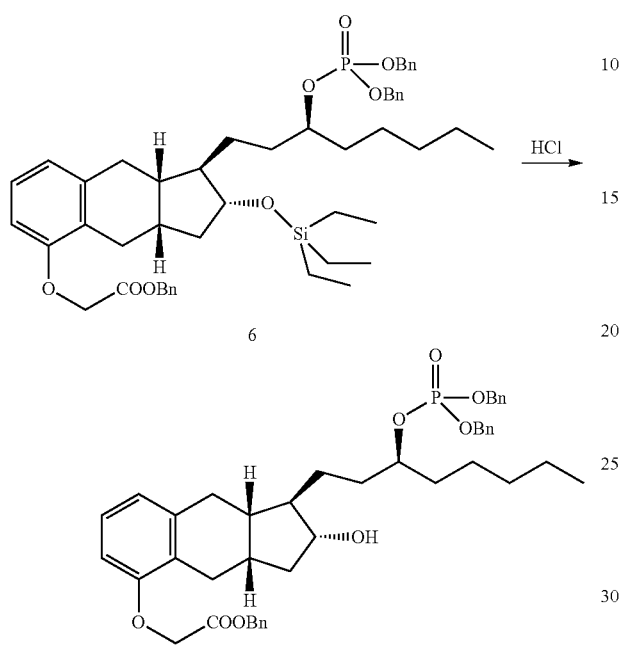

t. Bill of Materials

| Name | Mol. Wt. | Eq. | Amount | mmol |
|---|---|---|---|---|
| Treprostinil mono-TES benzyl ester dibenzyl phosphate (6) | 885.14 | 1.0 | 1.40 g | 1.63 |
| Hydrochloric acid (2M) | 36.46 | 1.5 | 1.22 ml | 2.45 |
| Tetrahydrofuran (THF) | 72.11 | NA | 20 ml | NA |
| Silica gel (230-400 mesh) (Merck) | NA | NA | 30 g | NA |

Experimental Procedure

To a round-bottom flask equipped with a magnetic stir bar was charged treprostinil mono-TES benzyl ester dibenzyl phosphate (6) (1.40 g) in THF (20 ml) and water (4 ml). To this stirring solution was added hydrochloric acid (2M) (1.22 ml) and the reaction mixture stirred at room temperature for 1 h and checked by TLC (EtOAc/Hex, 1:2). After completion of reaction, water (20 ml) and ethyl acetate (20 ml) were added and stirred for 10 min and separated the organic layer. The aqueous layer was extracted with ethyl acetate (2×20 ml). The combined organic extracts were washed with water (20 ml), sodium bicarbonate (20 ml), brine (20 ml) and dried over sodium sulfate (20 g). It was filtered, and the solvent was removed in vacuo to give crude product (1.53 g), which was purified on silica gel column chromatography using 5-70% ethyl acetate in hexanes to obtain pure treprostinil benzyl ester dibenzyl phosphate (7), (1.12 g, 92% yield) (96.16% HPLC purity). It was characterized by $^1$H NMR and MS.

Synthesis of Treprostinil Side Chain Phosphate (Prodrug VI)

Reaction Scheme

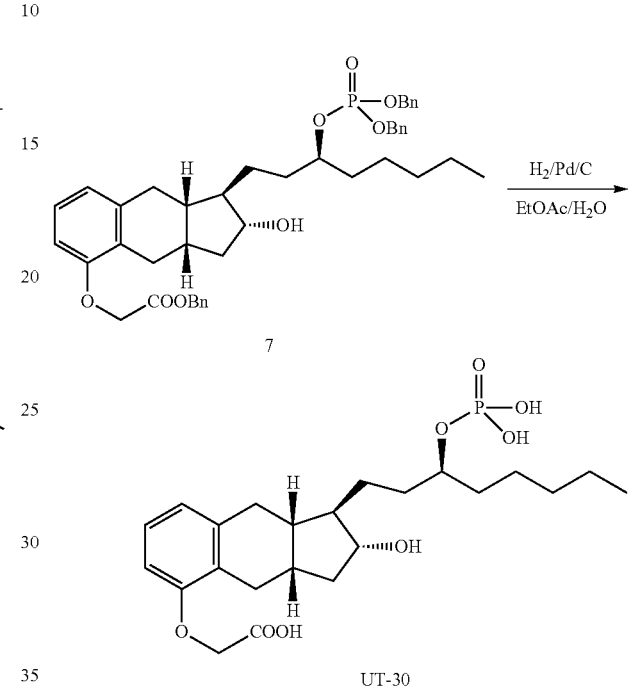

u. Bill of Materials

| Name | Mol. Wt. | Eq | Amount | mmol |
|---|---|---|---|---|
| Treprostinil benzyl ester dibenzyl phosphate (7) | 740.87 | 1.0 | 1.00 g | 1.34 |
| Palladium on carbon (5 wt %, ~50% water) | 106.42 | NA | 300 mg | NA |
| Ethyl acetate | 88.10 | NA | 50 ml | NA |
| Celite | NA | NA | 2 g | NA |

Experimental Procedure

To a 2-neck round-bottom flask equipped with a magnetic stir bar, equipped with a three-way connector to a hydrogen balloon was charged treprostinil benzyl ester dibenzyl phosphate (7) (1.00 g) in ethyl acetate (50 ml) and water (2.5 ml). To this stirring solution at room temperature was added palladium on carbon (5% wt.) (300 mg). The system was evacuated and replaced by hydrogen (repeated two more times) and then connected the flask to hydrogen balloon and stirred at room temperature for 4 h and checked by TEC (MeOH/DCM, 1:4). After completion of the reaction, the mixture was evacuated and replaced with air before it was filtered through a Celite (~2 g) pad. Ethyl acetate (3×10 ml) was used to wash the filter. The filtrate was concentrated in vacuo to give treprostinil side chain phosphate (Prodrug VI)

as a white solid (0.57 g, 90% yield) (99.93% HPLC purity). It was characterized by $^1H$, $^{13}C$, $^{31}P$ NMR, IR and MS.

Large Scale Synthesis of Treprostinil Side Chain Phosphate (Prodrug VI)

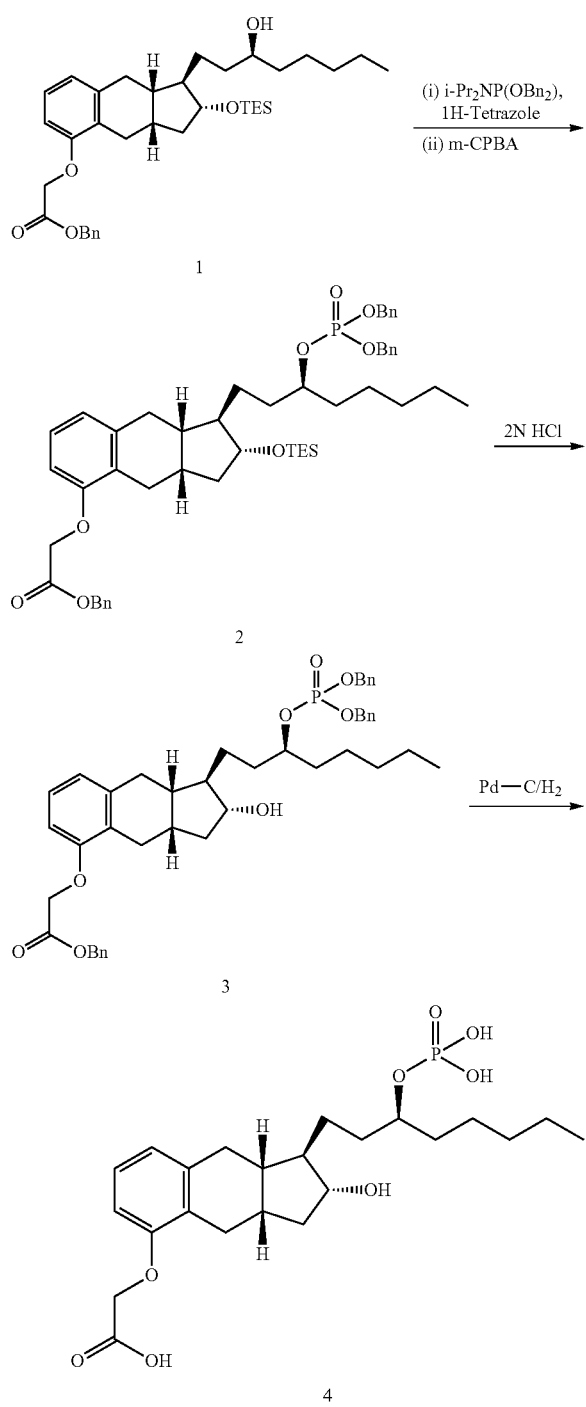

Scheme 4': Large Scale Synthesis of Treprostinil Side Chain Phosphate (Prodrug VI)

The treprostinil side chain phosphate (Prodrug VI) was synthesized from mono-TES-treprostinil benzyl ester (1) in three steps as shown in Scheme 4'. The phosphitylation of 1 with dibenzyl N,N-diisopropylphosphoramidite in the presence of 1H-tetrazole followed by oxidation with 3 chloroperbenzoic acid to give TES-treprostinil benzyl ester dibenzylphosphate (2). The desilylation of 2 with 2N hydrochloric acid in aqueous tetrahydrofuran gave treprostinil benzyl ester dibenzylphosphate (3). The pure compound (3) was hydrogenolyzed using 5% palladium on carbon and hydrogen to give treprostinil side chain phosphate (Prodrug VI) (4) as a white solid. The UT-30 was characterized by spectral data and purity by HPLC.

EXPERIMENTAL

Synthesis of TES-Treprostinil Benzyl Ester Dibenzylphosphate (2)

Experimental Procedure

To a solution of mono-TES-treprostinil benzyl ester (1) (46.33 g, 77.88 mmol) in anhydrous dichloromethane (800 mL) was added a solution of 1H-tetrazole (0.45 M in acetonitrile) (519 mL, 233.69 mmol) over a period of 15 min under argon at room temperature. The mixture was stirred at RT for 1 h and then added a solution of dibenzyl N,N-diisopropylphosphoramidite (53.80 g, 155.75 mmol) in anhydrous dichloromethane (120 mL). The reaction mixture was stirred at room temperature for 1 h and then cooled to −60±3° C. To this cold mixture was added 3-chloroperbenzoic acid (~77%) (54.11 g, 247.2 mmol) in portions. The reaction mixture was stirred at this temperature for 1 h and the reaction was complete (TEC, EtOAc/Hexane, 1:4). The reaction mixture was treated with 10% sodium sulfite in water (1250 mL) and stirred at room temperature overnight. The organic layer was separated from the mixture and the aqueous layer was extracted with dichloromethane (2×200 mL). The combined organic extracts were washed with saturated sodium bicarbonate solution (400 mL), dried ($Na_2SO_4$), filtered and concentrated in vacuo to give crude product. The chromatography of the crude product on silica gel using ethyl acetate in hexane gave TES-treprostinil benzyl ester dibenzylphosphate (2) as a viscous liquid (54.1 g). The product was characterized by 1H NMR and purity 97.43% by HPLC.

Synthesis of Treprostinil Benzyl Ester Dibenzylphosphate (3)

Experimental Procedure

To a solution of TES-treprostinil benzyl ester dibenzylphosphate (2) (53.8 g, 62.91 mmol) in a mixture of tetrahydrofuran (540 mL) and water (108 mL) was added a solution of 2N hydrochloric acid (48 mL) at room temperature. The reaction mixture was stirred at room temperature for 30 min and the reaction was complete (TEC, EtOAc/Hexane, 1:1). The reaction mixture was treated with ethyl acetate (100 mL) and separated the aqueous layer. The aqueous layer was extracted with ethyl acetate (2×200 mL). The combined organic extracts were washed with water (1×350 mL), saturated sodium bicarbonate (1×200 mL), brine (1×70 mL), dried ($Na_2SO_4$), filtered and concentrated in vacuo to give a crude product. The chromatography of the crude product on silica gel using ethyl acetate in hexane gave treprostinil benzyl ester dibenzylphosphate (3) as a viscous liquid (34.1 g) and purity 99.47% by HPLC.

Synthesis of Treprostinil Side Chain Phosphate (Prodrug VI) (4)

Experimental Procedure

To a solution of treprostinil benzyl ester dibenzylphosphate (3) (34.0 g, 45.89 mmol) in a mixture ethyl acetate (1500 mL) and water (75 mL) was added 5% palladium on carbon (50% water) (8.5 g). The mixture was evacuated under house vacuum at room temperature and replaced by hydrogen (filled in a balloon). This process was repeated two more times. Then the reaction mixture was stirred under the atmosphere of hydrogen at room temperature for 4 h. The reaction was complete (TLC, EtOAC/Hexane, 6:4). The reaction mixture was filtered through a pad of Celite and washed the pad with ethyl acetate and water. The filtrate was evaporated in vacuo to give white solid. The solid was treated with ethyl acetate (500 mL) and filtered through a Buchner funnel. The solid, treprostinil side chain phosphate (Prodrug VI) (4) was air dried overnight. The weight of the dried prodrug VI was 19.22 g and the purity 99.93% by HPLC.

Under similar reaction conditions, 40.79 g and 25.15 g of prodrug VI were also synthesized. These three lots were combined to give 85.15 g of prodrug VI. The prodrug VI was fully characterized by spectral data (IR, 1H, 13C & 31P NMR), melting point and purity 99.95% by HPLC.

The mono-TES-treprostinil benzyl ester (1) was prepared from benzindene triol by alkylation followed by silylation and chromatography as described above.

The synthesis process for preparing prodrug VI may be used for preparing prodrug VI in large quantity batches, while maintaining a high purity of prodrug VI in such batches. For example, prodrug VI may be prepared in a batch size of at least 20 g or at least 30 g or at least 40 g or at least 50 g or at least 60 g or at least 70 g or at least 80 g or at least 90 g or at least 100 g or at least 110 g or at least 120 g or at least 130 g or at least 140 g or at least 150 g or at least 160 g or at least 170 g or at least 180 g or at least 190 g or at least 200 g or at least 300 g or at least 500 g or at least 1000 g or at least 2000 g. Such batch may have a purity of at least 98.0%; at least 98.5%; at least 98.8%; at least 99%; at least 99.1%; at least 99.2%; at least 99.3%; at least 99.4%; at least 99.5%; at least 99.6%; at least 99.7%; at least 99.8%; or at least 99.9% or at least 99.95%.

In the synthesis process for prodrug VI as well in the processes from synthesizing other prodrugs, TES may be replaced, for example, with another silyl ester, such as trimethylsilyl, t-butyldimethylsilyl, t-butyldiphenylsilyl, phenyldimethylsilyl, while benzyl may be replaced, for example, with a substituted benzyl, i.e. a benzyl group substituted at one or more meta, ortho or para positions with one or more substituents, which may be independently selected from the group consisting of —$NO_2$, —CN, halogen (e.g., —F, —Cl, —Br or —I), ($C_1$-$C_3$)alkyl, halo($C_1$-$C_3$)alkyl, ($C_1$-$C_3$)alkoxy and halo($C_1$-$C_3$)alkoxy.

Scheme 5: Synthesis of Treprostinil Side Chain Piperidine Carbamate (Prodrug XIX)

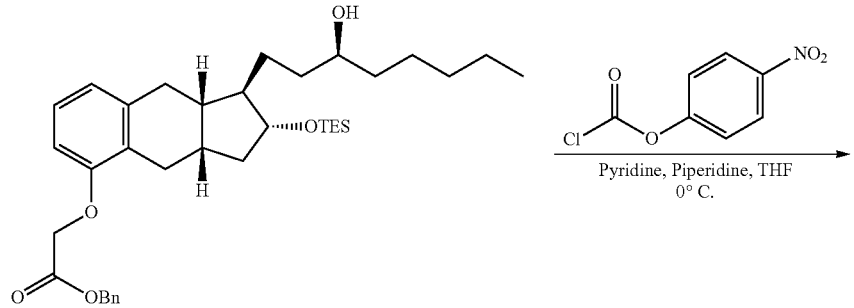

1

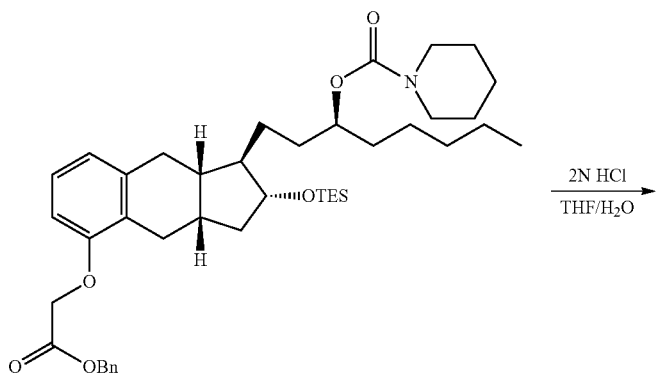

2

-continued
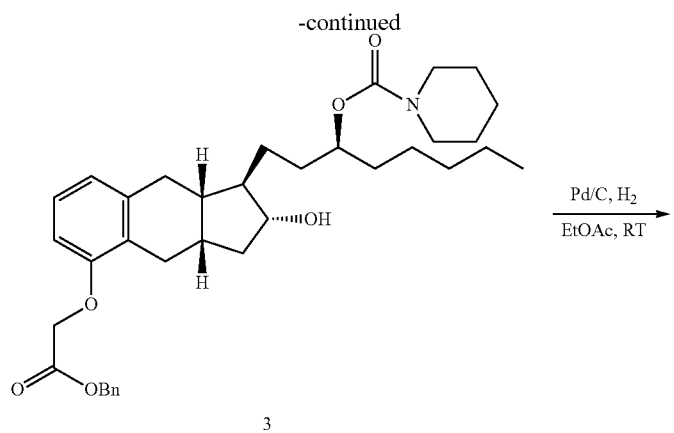
3
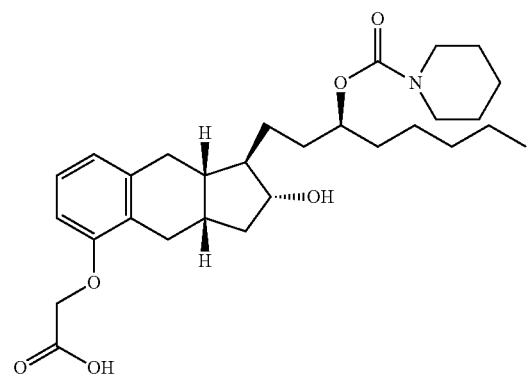
4
Treprostinil Side Chain Piperidine Carbamate (UT-32)
EXPERIMENTAL
Synthesis of TES-Treprostinil Benzyl Ester Piperidine Carbamate (2)
Reaction Scheme
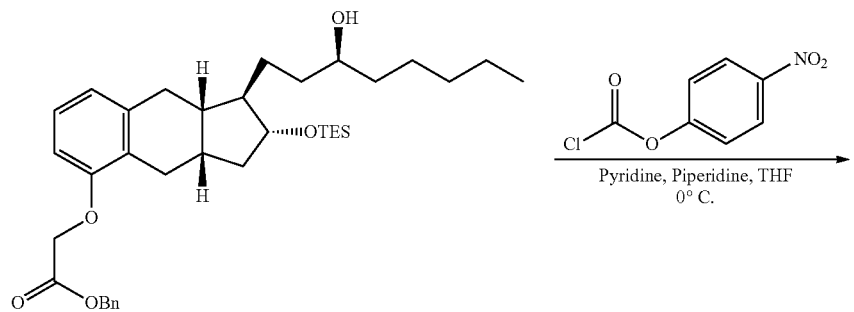
1

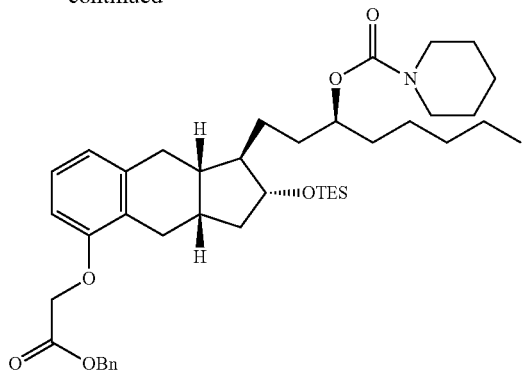

2 v. Bill of Materials

| Name | Mol Wt. | Amount | mmol | Eq. |
|---|---|---|---|---|
| Mono-TES-Treprostinil benzyl ester (1) | 594.88 | 1.5 g | 2.52 | 1.00 |
| Pyridine | 79.16 | 0.62 mL | 7.56 | 3.0 |
| 4-Nitrophenyl chloroformate | 201.57 | 0.76 g | 3.78 | 1.5 |
| Piperidine | 85.15 | 0.75 mL | 7.56 | 3.0 |
| Tetrahydrofuran (anhydrous) | NA | 25 mL | NA | NA |

Experimental Procedure

To a solution of mono-TES-treprostinil benzyl ester (1) (1.5 g, 2.52 mmol) in anhydrous tetrahydrofuran (15 mL) was added pyridine (0.62 mL, 7.56 mmol) at room temperature under argon. The clear solution was cooled to 0° C. (ice/water bath) and then added dropwise a solution of 4-nitrophenyl chloroformate (0.76 g, 3.78 mmol) in anhydrous tetrahydrofuran (5 mL) over a period of 15 min keeping the temperature below 5° C. under argon. After complete addition, the reaction mixture (white turbid) was stirred at 0° C. to room temperature for 5 h. The reaction was partially complete based on TLC (EtOAc/Hexane, 1:4) and this was stored at 2-8° C. overnight. Next day, a solution of piperidine (0.75 mL, 7.56 mmol) in tetrahydrofuran (5 mL) was added dropwise at 0° C. over 10 min. After 6 h, the reaction mixture was checked by TLC (EtOAc/Hexane, 1:4) and the reaction was complete. The reaction mixture was filtered to remove the precipitate and the resulting filtrate was concentrated in vacuo to give crude product (2.3 g). The crude compound was purified by silica gel column chromatography using 0-9% EtOAc/Hexane, which afforded pure TES-treprostinil benzyl ester piperidine carbamate (2) (1.49 g, 84.6% yield). The pure compound (2) was characterized by $^1$H NMR.

Synthesis of Treprostinil Benzyl Ester Piperidine Carbamate (3)

Reaction Scheme

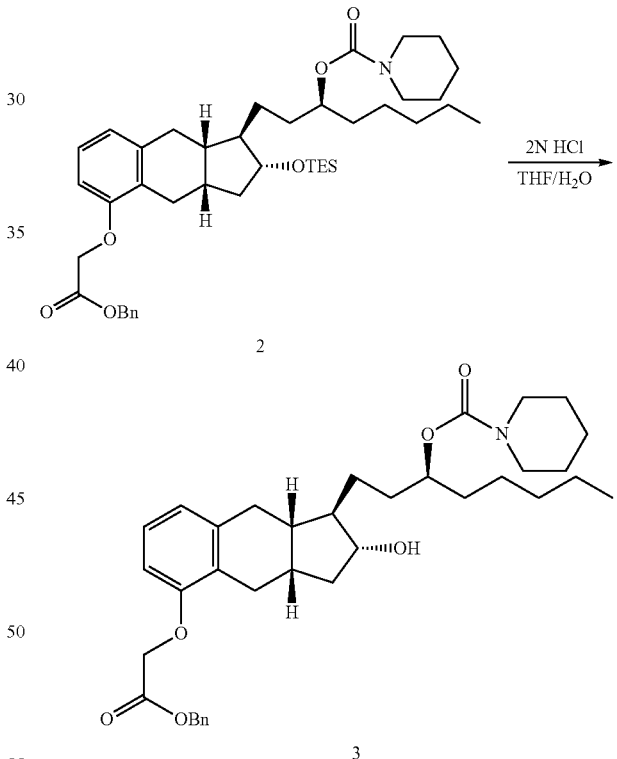

w. Bill of Materials

| Name | Mol Wt. | Amount | mmol | Eq. |
|---|---|---|---|---|
| TES-treprostinil benzyl ester piperidine carbamate (2) | 699.52 | 1.45 g | 2.07 | 1.0 |
| Hydrochloric acid solution (2N) | 36.50 | 1 mL | 2.07 | 1.0 |
| Tetrahydrofuran | NA | 12 mL | NA | NA |

| Name | Mol Wt. | Amount | mmol | Eq. |
|---|---|---|---|---|
| Water | NA | 1 mL | NA | NA |
| Triethylamine | 101.19 | 0.58 mL | 4.14 | 2.0 |

Experimental Procedure

To a solution of TES-treprostinil benzyl ester piperidine carbamate (2) (1.45 g, 2.07 mmol) in a mixture of tetrahydrofuran (12 mL) and water (1 mL) was added hydrochloric acid solution (2 N) (1.0 mL, 2.07 mmol) at room temperature. The reaction mixture was stirred at room temperature for 1.5 h and checked TLC (EtOAc/Hexane, 1:1). The reaction was found to be complete. The reaction mixture was neutralized with triethylamine (0.58 mL, 0.58 mmol) and then the organic volatiles were evaporated. The residue was dissolved in EtOAc (30 mL) and washed with water (20 mL), brine (20 mL), dried over $Na_2SO_4$ and concentrated in vacuo to give crude product (1.28 g). The crude product was chromatographed on silica gel column using 0-20% EtOAc/Hexane to give pure treprostinil benzyl ester piperidine carbamate (3) (1.15 g, 94.3% yield). The pure compound (3) was characterized by $^1$H NMR.

Synthesis of Treprostinil Side Chain Piperidine Carbamate (4)

Reaction Scheme x. Bill of Materials

| Name | Mol Wt. | Amount | mmol | Eq |
|---|---|---|---|---|
| Treprostinil benzyl ester piperidine carbamate (3) | 591.79 | 1.1 g | 1.86 | 1.00 |
| Palladium on carbon, 5 wt % (dry basis), ~50% water, (Degussa Type) | NA | 0.22 g | NA | NA |
| Hydrogen gas | 2.00 | filled in a balloon | NA | NA |
| Ethyl acetate | NA | 15 mL | NA | NA |

Experimental Procedure

To a solution of treprostinil benzyl ester piperidine carbamate (3) (1.1 g, 1.86 mmol) in ethyl acetate (15 mL) was added palladium on carbon (5 wt %, 50% water) (0.22 g). The mixture was stirred and evacuated under house vacuum and replaced by hydrogen (filled in a balloon). The process was repeated three times. The mixture was stirred at room temperature under the atmosphere of hydrogen for 4 h and checked TEC (EtOAc/Hexane, 2:3). The reaction was found to be complete. The reaction mixture was filtered through a pad of Celite and the filtrate was concentrated in vacuo to give treprostinil side chain piperidine carbamate (4) (0.86 g, 92.3% yield). The compound was fully characterized by spectral data (IR, $^1$H NMR, $^{13}$C NMR and MS) and purity of 99.06% by HPLC.

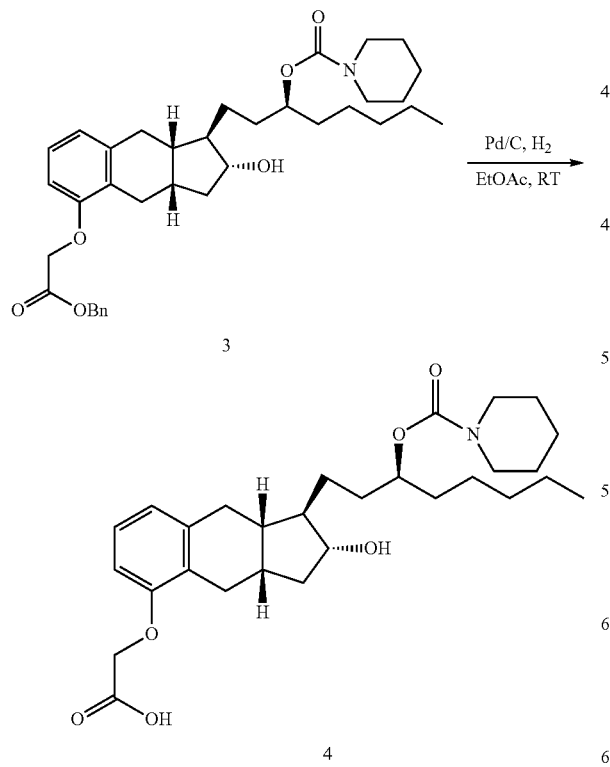

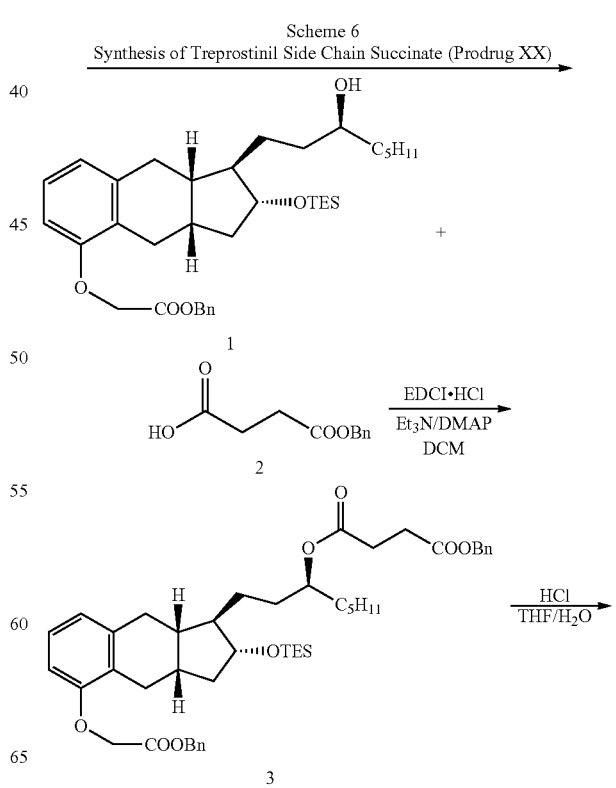

Scheme 6
Synthesis of Treprostinil Side Chain Succinate (Prodrug XX)

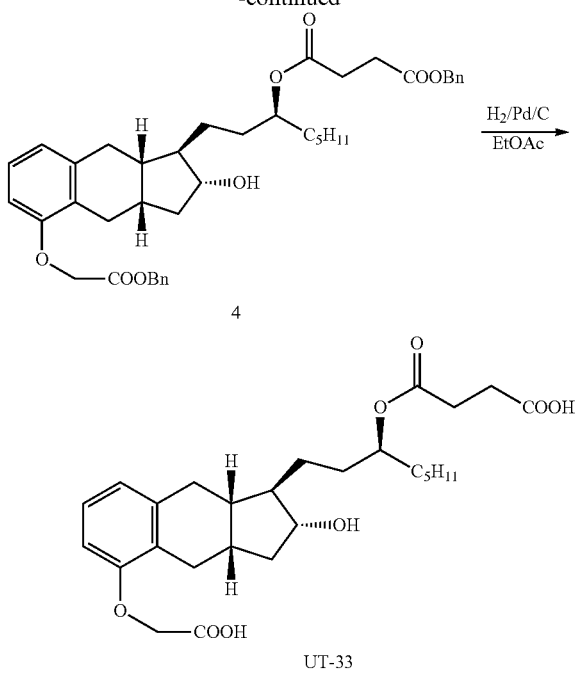

UT-33

Synthesis of Treprostinil Mono-TES Benzyl Ester Side Chain Succinate Benzyl Ester (3)

Reaction Scheme

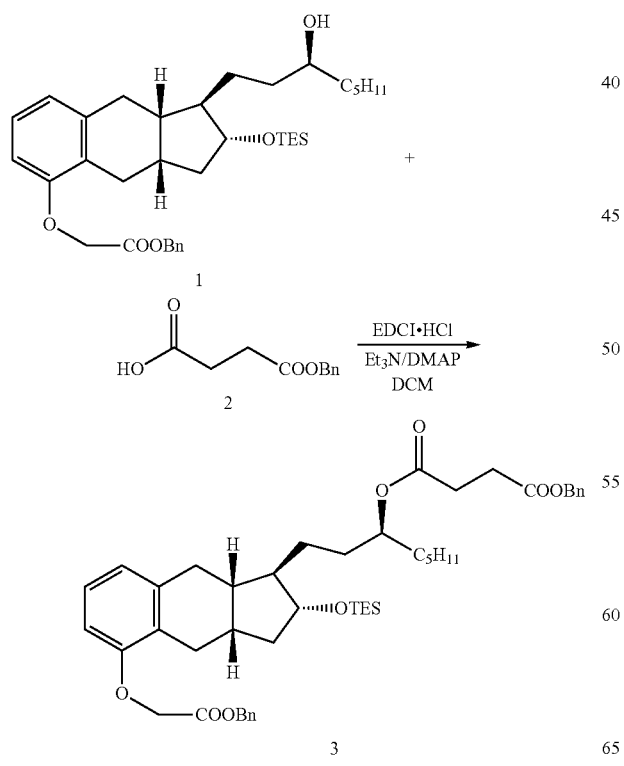

y. Bill of Materials

| Name | Mol. Wt. | Eq. | Amount | mmol |
|---|---|---|---|---|
| Treprostinil mono-TES benzyl ester (1) | 594.91 | 1.0 | 2.33 g | 3.92 |
| Succinic acid mono benzyl ester (2) | 208.21 | 1.1 | 0.90 g | 4.31 |
| EDCI•HCl | 191.75 | 1.1 | 0.82 g | 4.31 |
| Triethylamine | 101.29 | 1.2 | 655 μl | 4.70 |
| DMAP | 122.17 | 0.1 | 48 mg | 0.39 |
| Dichloromethane (DCM) (anhydrous) | 84.93 | NA | 50 ml | NA |
| Silica gel (230-400 mesh) (Merck) | NA | NA | 60 g | NA |

Experimental Procedure: A 250-ml, round-bottom flask, equipped with a stir bar was charged with anhydrous DCM (50 ml) and treprostinil mono-TES benzyl ester (1) (2.33 g). To this stirring solution at room temperature under argon, were added succinic acid mono benzyl ester (2) (0.90 g), triethylamine (655 μl) and DMAP (48 mg). After stirring for 10 min, EDCI.HCl (0.82 g) was added and the mixture stirred at room temperature under argon overnight and checked by TEC (EtOAc/Hex, 1:4). Water (20 ml) was added and the aqueous layer was extracted with DCM (2×20 ml). The combined organic extracts were washed with water (20 ml), brine (20 ml) and dried over sodium sulfate (10 g). It was filtered, and the solvent was removed in vacuo to give crude product (3.78 g). It was purified on silica gel column chromatography using 1-10% ethyl acetate in hexanes to afford the desired pure treprostinil mono-TES benzyl ester side chain succinic benzyl ester (3) (2.13 g, 69% yield) (96.94% HPLC purity). The compound was characterized by $^1$H NMR.

Synthesis of Treprostinil Benzyl Ester Side Chain Succinic Benzyl Ester (4)

Reaction Scheme

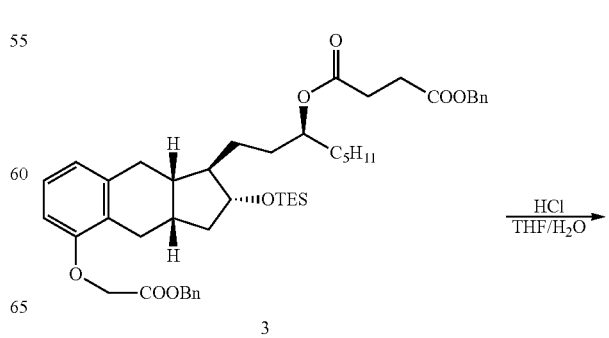

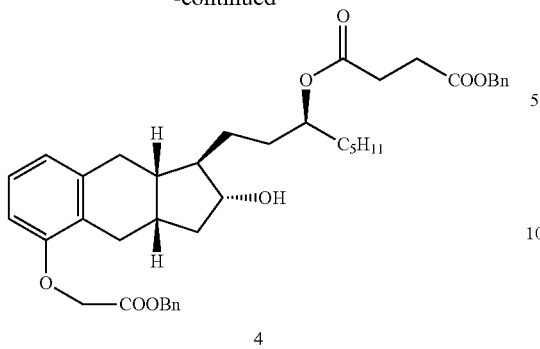

4 z. Bill of Materials

| Name | Mol. Wt. | Eq. | Amount | mmol |
|---|---|---|---|---|
| Treprostinil mono-TES benzyl ester side chain succinic benzyl ester (3) | 785.11 | 1.0 | 1.79 g | 2.28 |
| Hydrochloric acid (2M) | 36.46 | 1.0 | 1.14 ml | 2.28 |
| Tetrahydrofuran (THF) | 72.11 | NA | 40 ml | NA |
| Triethylamine | 101.29 | 1.2 | 0.5 ml | 4.70 |
| Silica gel (230-400 mesh) (Merck) | NA | NA | 30 g | NA |

Experimental Procedure: A 250 ml, round-bottom flask, equipped with a stir bar was charged with treprostinil mono-TES benzyl ester side chain succinic benzyl ester (3) (1.79 g) in THF (40 ml) and water (8 ml). To this stirring solution was added HCl solution (2M) (1.14 ml) and the mixture was stirred at room temperature for 30 min and checked by TEC (EtOAc/Hex, 1:4). Triethylamine (0.5 ml) was added and stirred for 10 min. Water (20 ml) and EtOAc (20 ml) were added. The aqueous layer was extracted with ethyl acetate (2×20 ml). The organic layers were washed with water (20 ml), brine (20 ml) and dried over sodium sulfate (~10 g). It was filtered, and the solvent was removed in vacuo to give crude product (2.29 g). It was purified on silica gel column chromatography using 1-25% ethyl acetate in hexanes to obtain desired pure treprostinil benzyl ester side chain succinic benzyl ester (4) (1.54 g, 92% yield) (99.60% HPLC purity). The compound was characterized by $^1$H NMR.

Synthesis of Treprostinil Side Chain Succinate (Prodrug XX)

Reaction Scheme

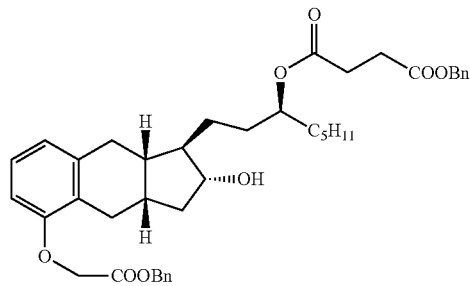

4

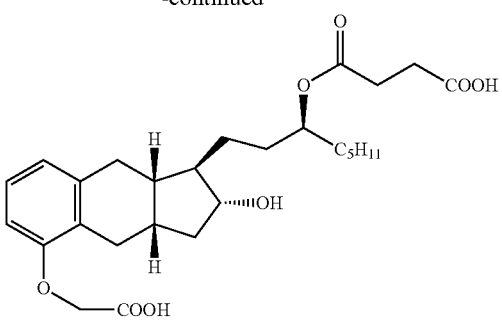

UT-33 aa. Bill of Materials

| Name | Mol. Wt. | Eq. | Amount | mmol |
|---|---|---|---|---|
| Treprostinil benzyl ester side chain succinic benzyl ester (4) | 670.84 | 1.0 | 1.25 g | 1.87 |
| Palladium on carbon (5% wt, 50% water) | 106.42 | NA | 0.25 g | NA |
| Ethyl acetate | 88.10 | NA | 50 ml | NA |
| Celite | NA | NA | 5 g | NA |

Experimental Procedure: A 250-ml, round-bottom flask, equipped with a stir bar was charged with ethyl acetate (50 ml) and treprostinil benzyl ester side chain succinic benzyl ester (4) (1.25 g). To this stirring solution at room temperature was added palladium on carbon (5% wt, 50% water, 0.25 g). The system was evacuated and replaced with hydrogen (repeated this process for two more times). The system was connected to hydrogen balloon and stirred at room temperature for 4 h and checked by TEC (EtOAc/Hex, 1:2). The system was evacuated and replaced with air. It was filtered through a Celite pad (5 g) and washed the filter with ethyl acetate (20 ml). The solvent was removed in vacuo to give treprostinil side chain succinate (UT-33) (0.77 g, 84% yield) (96.74% HPLC purity). The compound was characterized by $^1$H, $^{13}$C NMR, IR and LC-MS.

Scheme 7
Synthesis of Treprostinil Cyclopentyl Succinate (Prodrug XXII)

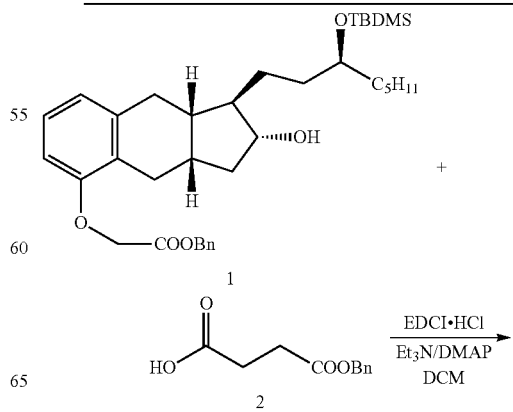

-continued

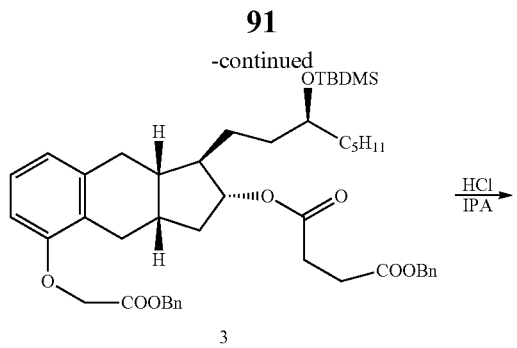

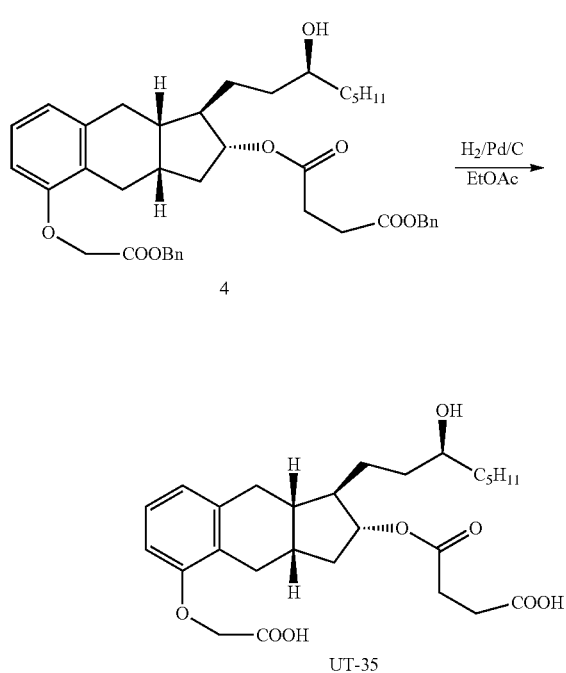

UT-35

Synthesis of Treprostinil Side Chain TBDMS
Benzyl Ester Succinic Benzyl Ester (3)

Reaction Scheme

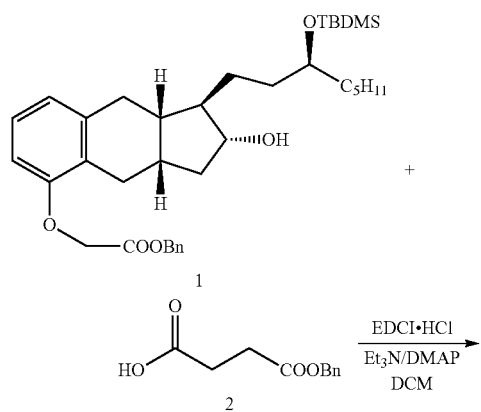

-continued

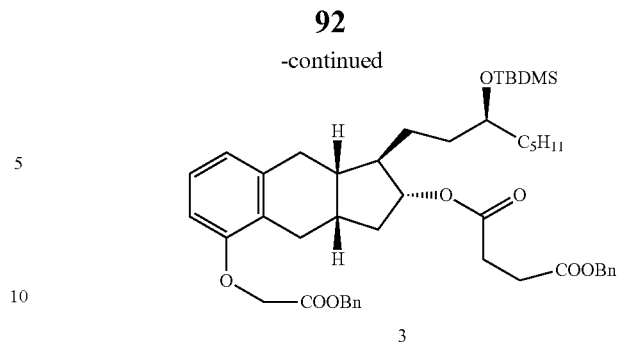

bb. Bill of Materials

| Name | Mol. Wt. | Eq. | Amount | mmol |
| --- | --- | --- | --- | --- |
| Treprostinil side chain TBDMS benzyl ester (1) | 594.91 | 1.0 | 0.82 g | 1.38 |
| Succinic acid mono benzyl ester (2) | 208.21 | 1.1 | 0.32 g | 1.52 |
| EDCI•HCl | 191.75 | 1.1 | 0.30 g | 1.52 |
| Triethylamine | 101.29 | 2.0 | 385 □l | 2.76 |
| DMAP | 122.17 | 0.2 | 34 mg | 0.39 |
| Dichloromethane (DCM) (anhydrous) | 84.93 | NA | 30 ml | NA |
| Silica gel (230-400 mesh) (Merck) | NA | NA | 30 g | NA |

Experimental Procedure: A 100-ml, round-bottom flask, equipped with a stir bar was charged with anhydrous DCM (30 ml) and treprostinil side chain TBDMS benzyl ester (1) (0.82 g). To this stirring solution at room temperature under argon, were added succinic acid mono benzyl ester (2) (0.32 g), triethylamine (385 □l) and DMAP (34 mg). After stirring for 10 min, EDCI.HCl (0.30 g) was added and the mixture stirred at room temperature under argon overnight and checked by TLC (EtOAc/Hex, 1:2). Water (20 ml) was added and the aqueous layer was extracted with DCM (2×10 ml). The combined organic extracts were washed with water (20 ml), brine (20 ml) and dried over sodium sulfate (10 g). It was filtered, and the solvent was removed in vacuo to give crude product (1.56 g). It was purified on silica gel column chromatography using 1-15% ethyl acetate in hexanes to afford treprostinil side chain TBDMS benzyl ester succinic benzyl ester (3) (0.81 g, 75% yield) (99.01% HPLC purity). The compound was characterized by $^1$H NMR.

Synthesis of Treprostinil Benzyl Ester Cyclopentyl Succinic Benzyl Ester (4)

Reaction Scheme

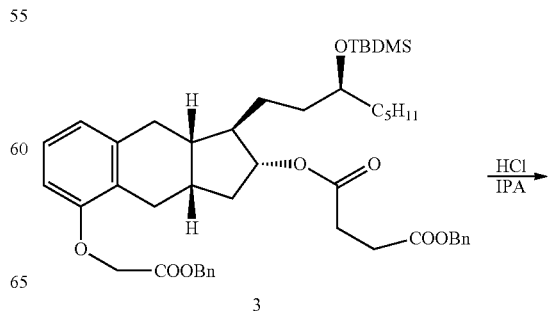

93
-continued

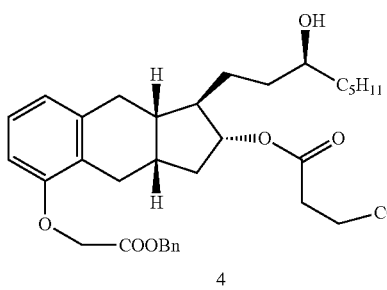

4

CC. Bill of Materials

| Name | Mol. Wt. | Eq. | Amount | mmol |
|---|---|---|---|---|
| Treprostinil benzyl ester side chain TBDMS succinic benzyl ester (3) | 785.11 | 1.0 | 0.77 g | 0.98 |
| Hydrochloric acid (2M) | 36.46 | 2.5 | 1.25 ml | 2.45 |
| iso Propyl alcohol (IPA) | 60.10 | NA | 20 ml | NA |
| Silica gel (230-400 mesh) (Merck) | NA | 30 g | NA | NA |
| Triethylamine | 101.29 | NA | 1 ml | NA |

Experimental Procedure: A 100 ml, round-bottom flask, equipped with a stir bar was charged with IPA (20 ml) and treprostinil benzyl ester side chain TBDMS succinic benzyl ester (3) (0.77 g). To this stirring solution was added HCl solution (2M) (1.25 ml) and the mixture was stirred at room temperature for 7 h and checked by TEC (EtOAc/Hex, 1:2). Triethylamine (1 ml) was added and stirred for 10 min. Water (10 ml) and EtOAc (20 ml) were added. The aqueous layer was extracted with ethyl acetate (2×10 ml). The combined organic layers were washed with water (20 ml), brine (20 ml) and dried over sodium sulfate (10 g). It was filtered, and the solvent was removed in vacuo to give crude product (1.05 g). It was purified on silica gel column chromatography using 1-40% ethyl acetate in hexanes to obtain treprostinil benzyl ester cyclopentyl succinic benzyl esters (4) (0.52 g, 79% yield) (99.51% HPLC purity). The compound was characterized by $^1$H NMR.

94

Synthesis of Treprostinil Cyclopentyl Succinate (Prodrug XXII)

Reaction Scheme

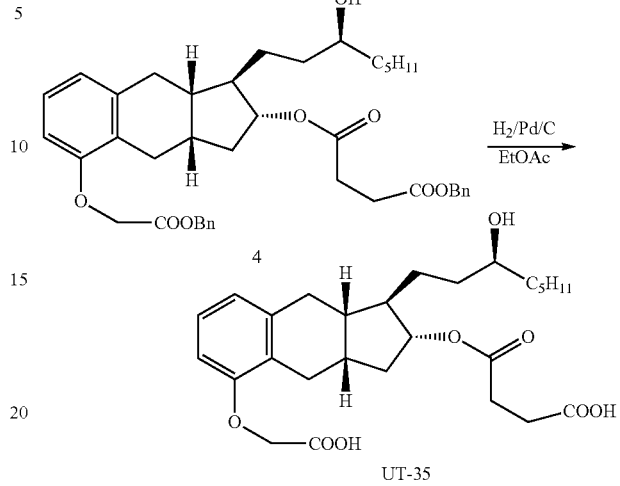

dd. Bill of Materials

| Name | Mol. Wt. | Eq. | Amount | mmol |
|---|---|---|---|---|
| Treprostinil benzyl ester cyclopentyl succinic benzyl ester (4) | 670.84 | 1.0 | 0.49 g | 0.73 |
| Palladium on carbon (5% wt., 50% water) | 106.42 | NA | 100 mg | NA |
| Ethyl acetate | 88.10 | NA | 20 ml | NA |
| Celite | NA | NA | 2 g | NA |

Experimental Procedure: A 100-ml, round-bottom flask, equipped with a stir bar was charged with ethyl acetate (20 ml) and treprostinil benzyl ester cyclopentyl succinic benzyl ester (4) (0.49 g). To this stirring solution at room temperature was added palladium on carbon (100 mg). The system was evacuated and replaced with hydrogen (repeated this process for two more times). The flask was connected to hydrogen balloon and stirred at room temperature for 4 h and checked by TEC (EtOAc/Hex, 1:2). The system was evacuated and replaced with air. It was filtered through a Celite pad (~2 g) and washed the filter with ethyl acetate (10 ml). The solvent was removed in vacuo to give treprostinil cyclopentyl succinate (Prodrug XXII) (0.35 g, 97% yield) (98.15% HPLC purity). The compound was characterized by $^1$H, $^{13}$C NMR, IR and LC-MS.

Scheme 8
Synthesis of Treprostinil Side Chain Bipiperidine Carbamate (Prodrug XXIII)

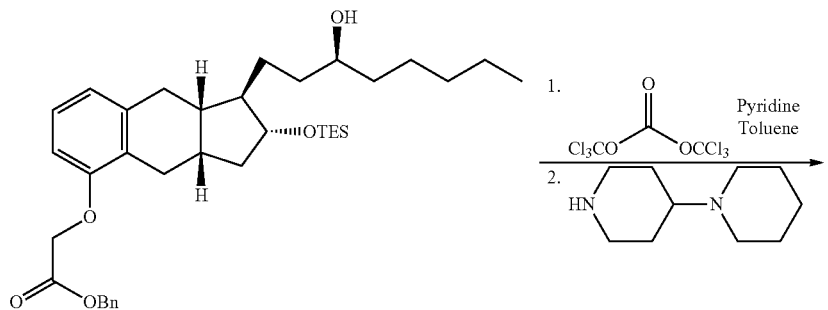

-continued
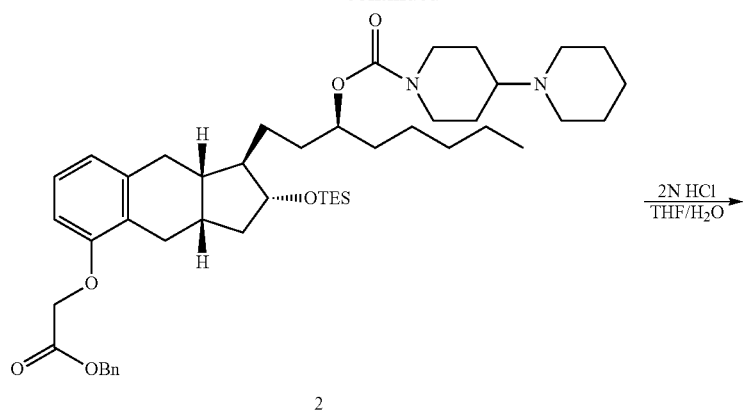
2
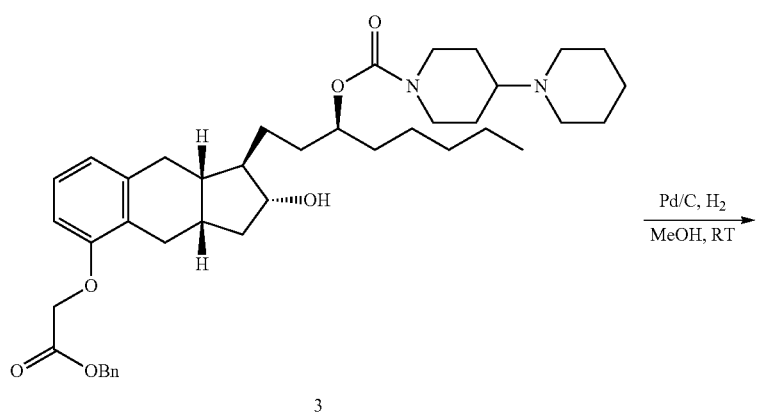
3
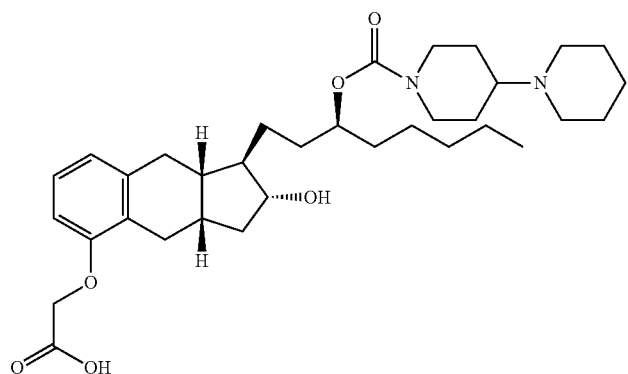
4
Treprostinil Side Chain Bipiperidine Carbamate (UT-36)

EXPERIMENTAL

Synthesis of TES-Treprostinil Benzyl Ester Bipiperidine Carbamate (2)

Reaction Scheme

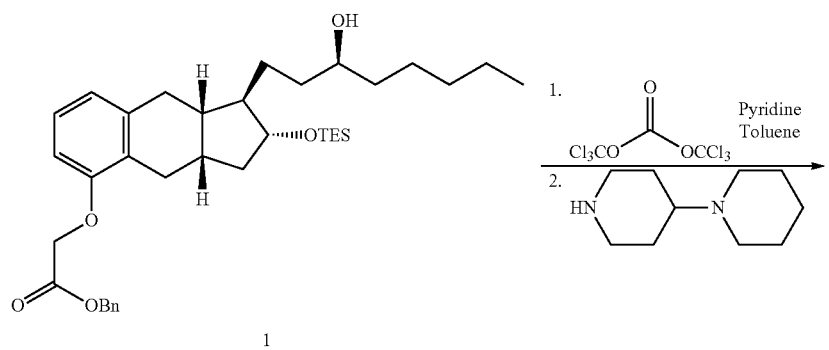

1

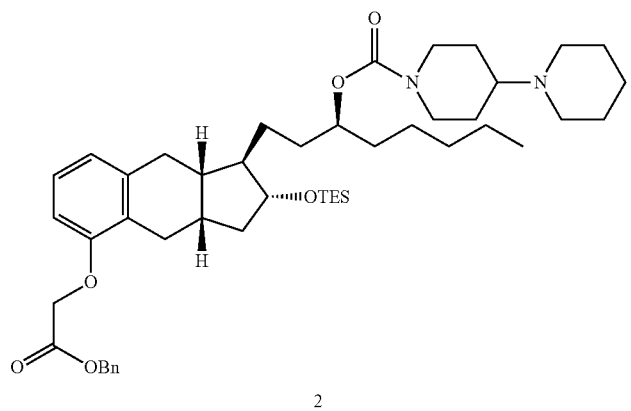

2 ee. Bill of Materials

| Name | Mol Wt. | Amount | mmol | Eq. |
|---|---|---|---|---|
| Mono-TES-Treprostinil benzyl ester (1) | 594.88 | 1.46 g | 2.46 | 1.00 |
| Pyridine | 79.16 | 0.6 mL | 7.37 | 3.0 |
| Triphosgene | 296.75 | 1.1 g | 3.68 | 1.5 |
| 4-Piperidinopiperidine | 168.28 | 0.62 g | 3.68 | 1.5 |
| Toluene (anhydrous) | NA | 35 mL | NA | NA |
| Dichloromethane (anhydrous) | NA | 18 mL | NA | NA |

Experimental Procedure: To a solution of mono-TES-treprostinil benzyl ester (1) (1.46 g, 2.46 mmol) in anhydrous toluene (20 mL) was added pyridine (0.6 mL, 7.37 mmol) at room temperature under argon. To this solution and ice-cold solution of triphosgene (1.1 g, 3.68 mmol) in toluene (10 mL) was added dropwise. After complete addition, the reaction mixture (white turbid) was stirred at room temperature for 1 h. The intermediate formation was complete based on TLC (EtOAc/Hexane, 1:4). To this a suspension of 4-piperidinopiperidine (0.62 g, 3.68 mmol) in toluene (5 mL) was added and dichloromethane (18 mL) was used for washings. After 3 h, the TLC (MeOH/DCM 1:9) indicated completion of the reaction. The reaction mixture was concentrated in vacuo and the residue was partitioned between ethyl acetate (30 mL) and water (30 mL). The organic layer was separated, and the aqueous layer was extracted with ethyl acetate (15 mL). The combined organic layers were washed with brine, dried over sodium sulfate and evaporated in vacuo to give crude product (1.8 g). The crude compound was purified by silica gel chromatography using 0-100% EtOAc/Hexane and 1-4% MeOH/DCM, to afford pure TES-treprostinil benzyl ester bipiperidine carbamate (2) (1.32 g, 68.0% yield). The pure compound (2) was characterized by $^1$H NMR.

Synthesis of Treprostinil Benzyl Ester Bipiperidine Carbamate (3)

Reaction Scheme

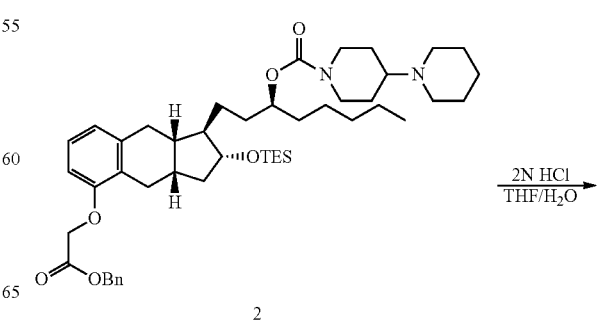

2

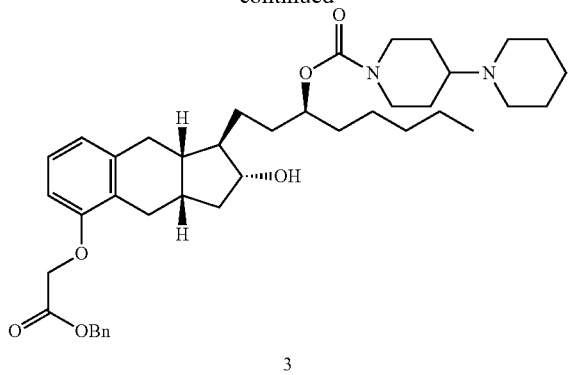

3

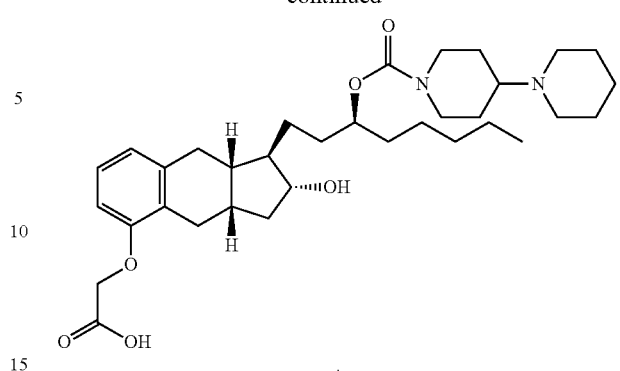

4 ff. Bill of Materials

| Name | Mol Wt. | Amount | mmol | Eq. |
|---|---|---|---|---|
| TES-treprostinil benzyl ester bipiperidine carbamate (2) | 789.18 | 1.26 g | 1.6 | 1.0 |
| Hydrochloric acid solution (2N) | 36.50 | 1.7 mL | 3.4 | 2.1 |
| Tetrahydrofuran | NA | 15 mL | NA | NA |
| Water | NA | 1 mL | NA | NA |
| Triethylamine | 101.19 | 0.94 mL | 6.7 | 4.2 |

Experimental Procedure: To a solution of TES-treprostinil benzyl ester bipiperidine carbamate (2) (1.26 g, 1.6 mmol) in a mixture of tetrahydrofuran (15 mL) and water (1 mL) was added hydrochloric acid solution (2 N) (1.7 mL, 3.4 mmol) at room temperature. The reaction mixture was stirred at room temperature for 1 h and checked TEC (EtOAc/Hexane, 1:1). The reaction was found to be complete. The reaction mixture was neutralized with tri ethyl amine (0.94 mL, 6.72 mmol) and then the organic volatiles were evaporated. The residue was dissolved in EtOAc (20 mL) and washed with water (10 mL), brine (20 mL), dried over $Na_2SO_4$ and concentrated in vacuo to give crude product (1.34 g). The crude product was chromatographed on silica gel column chromatography using 0-11% MeOH/DCM to give pure treprostinil benzyl ester bipiperidine carbamate (3) (0.61 g) and some impure compound (3) (0.34 g) with a total yield of 88.0%. The pure compound (3) was characterized by $^1$H NMR.

Synthesis of Treprostinil Side Chain Bipiperidine Carbamate (4)

Reaction Scheme gg. Bill of Materials

| Name | Mol Wt. | Amount | mmol | Eq |
|---|---|---|---|---|
| Treprostinil benzyl ester bipiperidine carbamate (3) | 674.92 | 0.49 g | 0.73 | 1.00 |
| Palladium on carbon, 5 wt % (dry basis), ~50% water, (Degussa Type) | NA | 0.1 g | NA | NA |
| Hydrogen gas | 2.00 | filled in a balloon | NA | NA |
| Methanol | NA | 15 mL | NA | NA |

Experimental Procedure: To a solution of treprostinil benzyl ester bipiperidine carbamate (3) (0.49 g, 0.73 mmol) in methanol (15 mL) was added palladium on carbon (5 wt %, 50% water) (0.1 g). The mixture was stirred and evacuated under house vacuum and replaced by hydrogen (filled in a balloon). The process was repeated three times. The mixture was stirred at room temperature under the atmosphere of hydrogen for 2 h and checked TEC (MeOH/EtOAc, 1:1). The reaction was found to be complete. The reaction mixture was filtered through a pad of Celite and the filtrate was concentrated in vacuo to give treprostinil side chain bipiperidine carbamate (4) (0.43 g, 102% yield with residual solvent). The compound was fully characterized by spectral data (IR, $^1$H NMR, $^{13}$C NMR and MS) and purity of 98.01% by HPLC.

Scheme 9
Synthesis of Treprostinil Cyclic Carbonate (Prodrug XXIV)

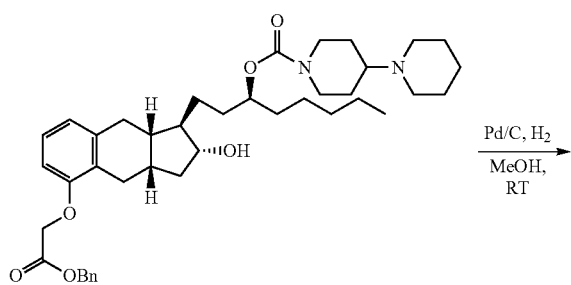

3

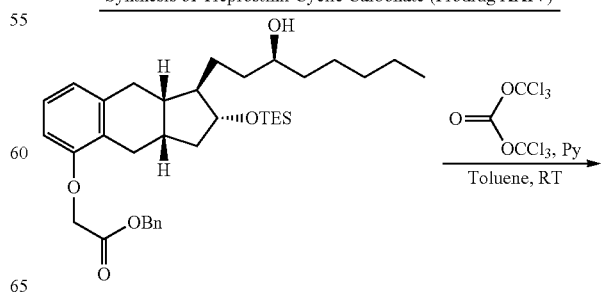

1

-continued
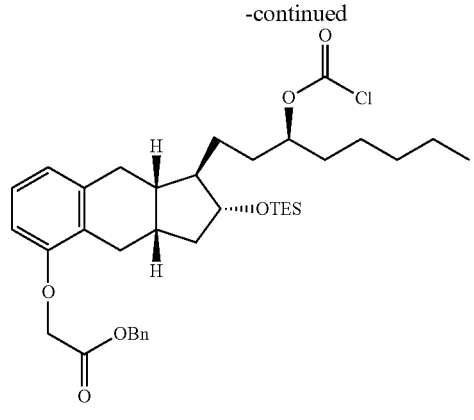
2
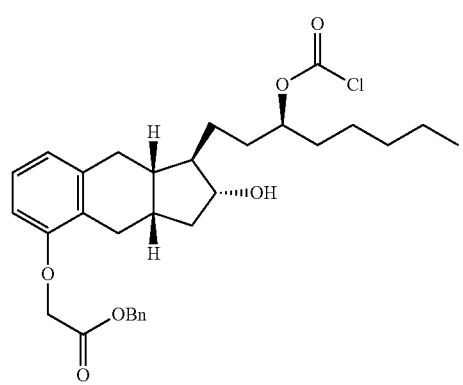
3
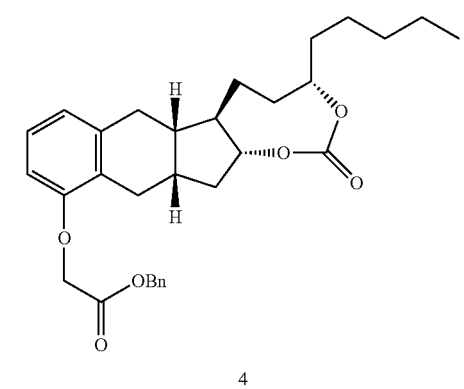
4
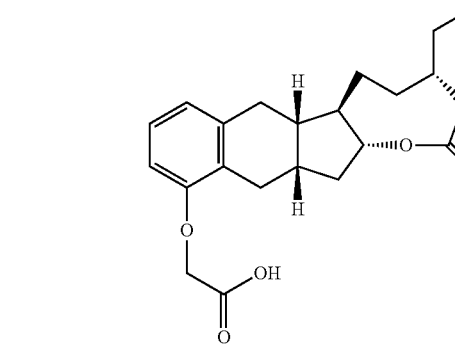
5
EXPERIMENTAL
Synthesis of Treprostinil Benzyl Ester Side Chain Chloroformate (3)
Reaction Scheme
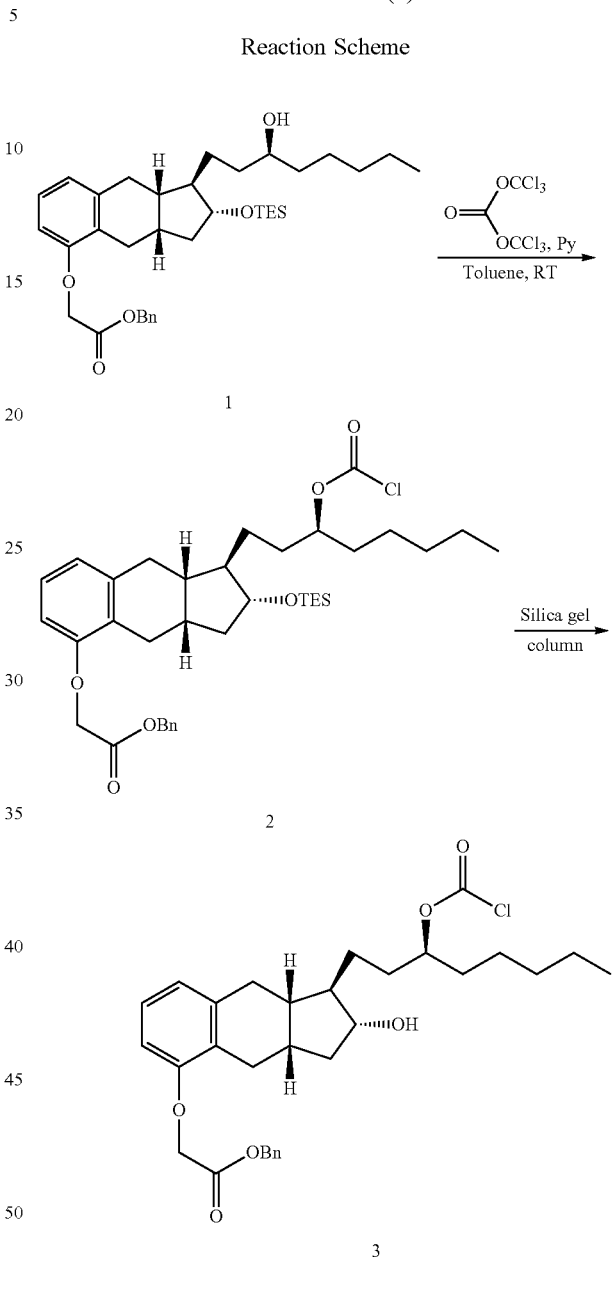
hh. Bill of Materials
| Name | MW | Amount | mmol | Eq. |
|---|---|---|---|---|
| Mono-TES treprostinil benzyl ester (1) | 594.91 | 1.15 g | 1.93 | 1.00 |
| Triphosgene | 296.75 | 0.60 g | 2.02 | 1.05 |
| Pyridine | 78.11 | 0.167 g (0.17 mL) | 2.14 | 1.11 |
| Toluene (anhydrous) | NA | 30 mL | NA | NA |
| Silica gel (230-400 mesh) | NA | 30.8 g | NA | NA |

Experimental Procedure: To a solution of mono-TES treprostinil benzyl ester (1.15 g, 1.93 mmol) in anhydrous toluene (15 mL) was added pyridine (0.167 g, 0.17 mL) at room temperature under argon. To this clear solution was added a cold solution of triphosgene (0.39 g, 1.31 g) in anhydrous toluene (15 mL) (pre-cooled at 0° C. before addition) at room temperature. The reaction mixture became turbid with white precipitate and it was stirred room temperature for 6 h and checked by TLC (EtOAc/Hexane, 1:4). The reaction was not complete, therefore, additional triphosgene (0.21 g, 0.71 mmol) (total, 0.60 g) was added to the mixture and stirred at room temperature overnight. After 17 h, the reaction was complete (TLC, EtOAc, 1:4) indicating TES-treprostinil benzyl ester side chain chloroformate (2) was formed along with some treprostinil benzyl ester side chain chloroformate (3) The reaction mixture was treated with hexane (60 mL) and stirred for 10 min and then passed through silica gel (30.8 g) column and eluted the compound using 5-40% ethyl acetate in hexane to give pure treprostinil benzyl ester side chain chloroformate (3) as a clear viscous liquid (1.06 g, 100%). The pure chloroformate (3) was fully characterized by spectral data (IR, $^1$H NMR, $^{13}$C NMR, DEPT, MS) and purity, 95.28% by HPLC.

Synthesis of Treprostinil Benzyl Ester Cyclic Carbonate (4)

Reaction Scheme

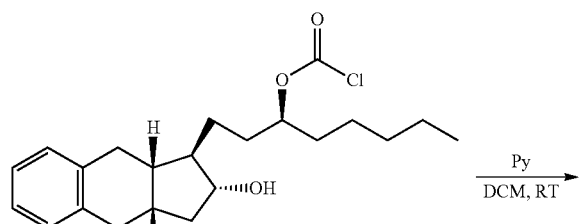

ii. Bill of Materials

| Name | MW | Amount | mmol | Eq. |
|---|---|---|---|---|
| Treprostinil benzyl ester side chain chloroformate (3) | 543.07 | 0.86 g | 1.58 | 1.00 |
| Pyridine | 79.11 | 10 mL (excess) | NA | excess |
| Dichloromethane (anhydrous) | NA | 10 mL | NA | NA |
| Silica gel (230-400 mesh) | NA | 35.4 g | NA | NA |

Experimental Procedure: To a clear solution treprostinil benzyl ester side chain chloroformate (3) (0.86 g, 1.58 mmol) in anhydrous dichloromethane (10 mL) was added anhydrous pyridine (10 mL) at room temperature under argon. The clear reaction mixture was stirred at room temperature for 45 min and checked by TLC (EtOAc/Hexane, 3:7) and the reaction was complete. The mixture was evaporated in vacuo to remove organic volatiles (DCM and pyridine) to give crude cyclic carbonate (4) along with pyridine hydrochloride as white solid (0.97 g). The crude product was chromatographed on silica gel (35.4 g) using 5-10% ethyl acetate in hexane to give pure treprostinil benzyl ester cyclic carbonate (4) as a white solid (0.59 g, 73.7%). The pure cyclic carbonate (4) was fully characterized by spectral data (IR, $^1$H NMR, $^{13}$C NMR, DEPT, MS) and purity, 99.54% by HPLC.

Synthesis of Treprostinil Cyclic Carbonate (Prodrug XXIV) (5)

Reaction Scheme

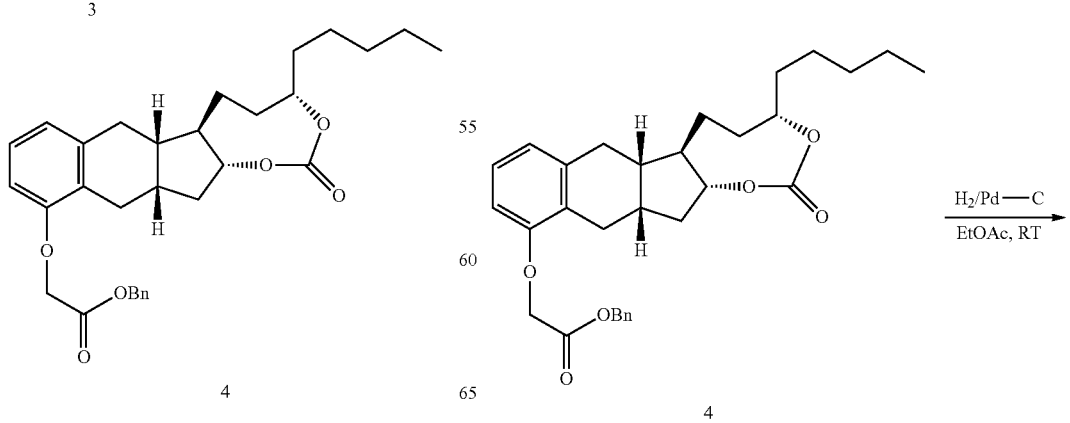

-continued

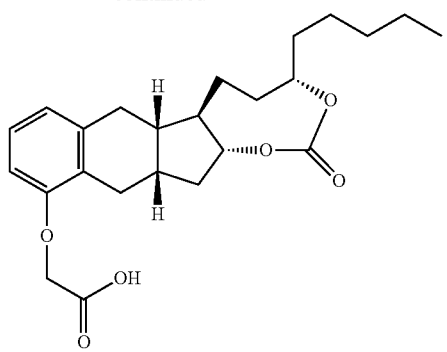

5 jj. Bill of Materials

| Name | MW | Amount | mmol | Eq. |
|---|---|---|---|---|
| Treprostinil benzyl ester cyclic carbonate (4) | 506.61 | 0.51 g | 1.01 | 1.00 |
| Palladium on carbon, extent of labelling: 5 wt % loading (dry basis), matrix activated carbon, wet support, Degussa type E101 NO/W (~50% water) | NA | 0.21 g | NA | cat |
| Hydrogen gas | 2.00 | filled in a balloon | NA | NA |
| Ethyl acetate | NA | 30 mL | NA | NA |
| Celite | NA | 4.25 g | NA | NA |

Experimental Procedure: To a solution of treprostinil benzyl ester cyclic carbonate (4) (0.51 g, 1.01 mmol) in ethyl acetate (30 mL) was added palladium on carbon, 5 wt %, ~50% water (0.21 g). The mixture was evacuated under house vacuum and replaced by hydrogen gas (filled in a balloon). This process was repeated three times. Then the reaction mixture was stirred under the atmosphere of hydrogen at room temperature for 2 h and checked TEC (EtOAc/Hexane, 3:7 and 7:3). The reaction was complete. The mixture was passed through a pad of Celite (4.25 g) in a disposable filter funnel and the solid was washed with ethyl acetate (3×30 mL). The filtrate was concentrated in vacuo to give jelly product which was dissolved in tetrahydrofuran (10 mL) and filtered (Note: the product was more soluble in tetrahydrofuran than in acetone, acetonitrile and ethyl acetate). The filtrate was concentrated in vacuo to give treprostinil cyclic carbonate (5) as a white solid (0.43 g, 100%). The treprostinil cyclic carbonate (Prodrug XXIV) (5) was fully characterized by spectral data (IR, $^1$H NMR, $^{13}$C NMR, DEPT, MS), melting point, 184-186° C., and purity, 99.05% by HPLC.

Scheme 10: Synthesis of Treprostinil Cyclopenyl Naproxen Ester (Prodrug XXV)

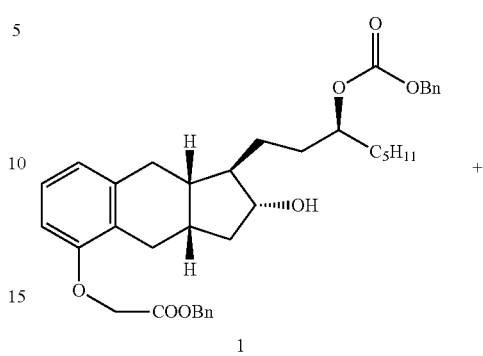

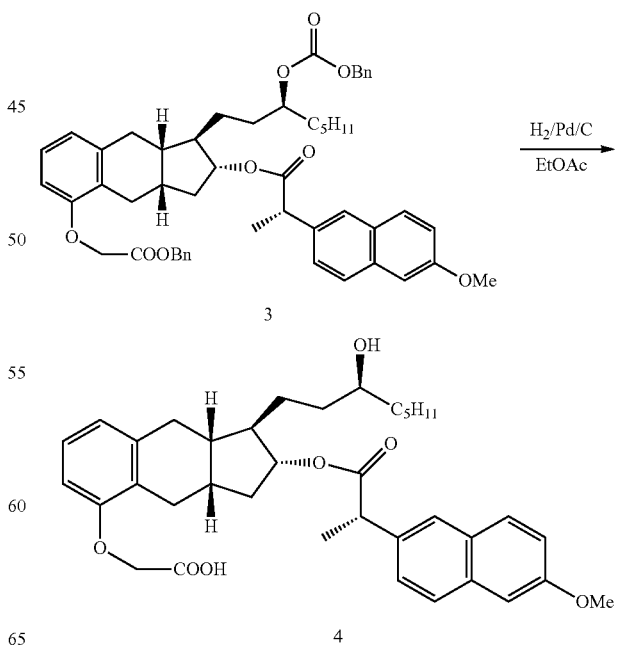

Synthesis of Treprostinil Side Chain CBZ Benzyl Ester Cyclopentyl Naproxen Ester (3)

Reaction Scheme

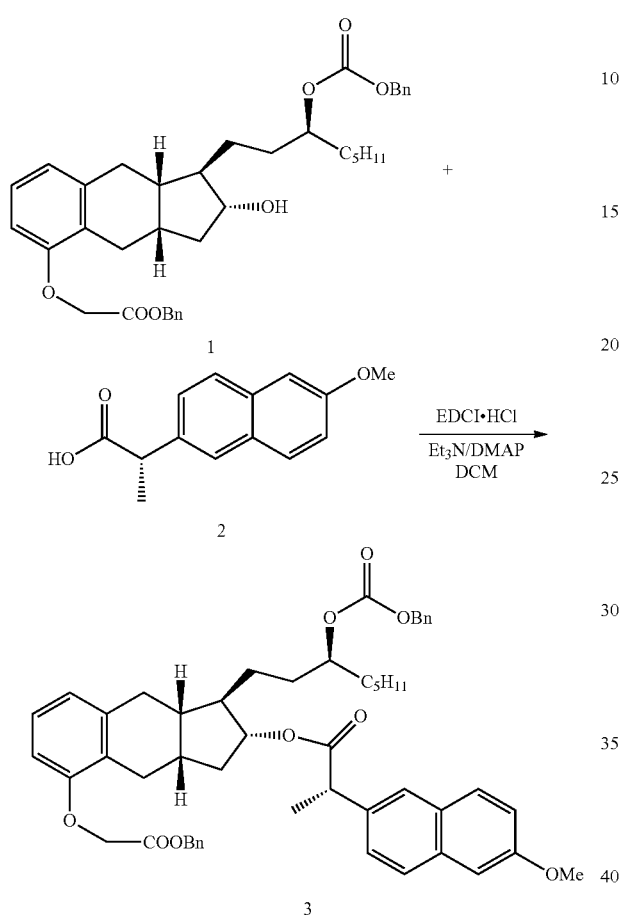

kk. Bill of Materials

| Name | Mol. Wt. | Eq. | Amount | mmol |
|---|---|---|---|---|
| Treprostinil side chain CBZ benzyl ester (1) | 614.78 | 1.0 | 0.53 g | 0.86 |
| Naproxen (2) | 230.26 | 1.2 | 0.24 g | 1.03 |
| EDCI•HCl | 191.75 | 1.2 | 0.20 g | 1.52 |
| Triethylamine | 101.19 | 2.0 | 230 □l | 1.72 |
| DMAP | 122.17 | 0.2 | 17 mg | 0.14 |
| Dichloromethane (DCM) (anhydrous) | 84.93 | NA | 20 ml | NA |
| Silica gel (230-400 mesh) (Merck) | NA | 30 g | NA | NA |

Experimental Procedure: A 100-ml, round-bottom flask, equipped with a stir bar was charged with anhydrous DCM (20 ml) and treprostinil side chain CBZ benzyl ester (1) (0.53 g). To this stirring solution at room temperature under argon, were added naproxen (2) (0.24 g), triethylamine (230 □l) and DMAP (17 mg). After stirring for 10 min, EDCI.HCl (0.20 g) was added and the mixture stirred at room temperature under argon overnight and checked by TEC (EtOAc/Hex, 1:4). Water (10 ml) was added and the aqueous layer was extracted with DCM (10 ml). The combined organic extracts were washed with water (20 ml), brine (20 ml) and dried over sodium sulfate (10 g). It was filtered, and the solvent was removed in vacuo to give crude product (1.18 g). It was purified on silica gel column chromatography using 1-30% ethyl acetate in hexanes to afford treprostinil side chain CBZ benzyl ester cyclopentyl naproxen ester (3) (0.33 g, 46% yield) (98.15% HPLC purity). The compound was characterized by $^1$H NMR.

Synthesis of Treprostinil Cyclopentyl Naproxen Ester (Prodrug XXV)

Reaction Scheme

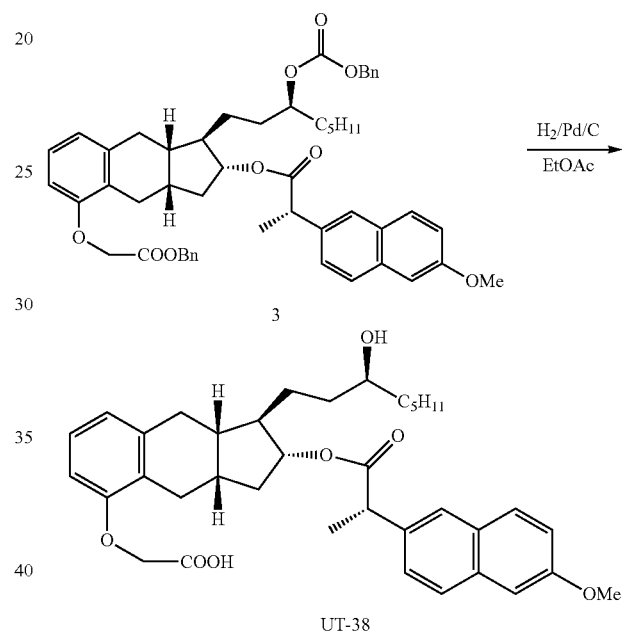

ll. Bill of Materials

| Name | Mol. Wt. | Eq. | Amount | mmol |
|---|---|---|---|---|
| Treprostinil benzyl ester side chain CBZ cyclopentyl naproxen ester (3) | 827.03 | 1.0 | 0.31 g | 0.37 |
| Palladium on carbon (5% wt. 50% water) | 106.42 | NA | 50 mg | NA |
| Ethyl acetate | 88.10 | NA | 10 ml | NA |
| Celite | NA | NA | 2 g | NA |

Experimental Procedure: A 100-ml, round-bottom flask, equipped with a stir bar was charged with ethyl acetate (10 ml) and treprostinil benzyl ester side chain CBZ cyclopentyl naproxen ester (3) (0.31 g). To this stirring solution at room temperature was added palladium on carbon (50 mg). The system was evacuated and replaced with hydrogen (repeated this process for two more times). Then, the flask was connected to hydrogen balloon and stirred at room temperature for 1 h and checked by TEC (EtOAc/Hex, 1:2). The system was evacuated and replaced with air. It was filtered through a Celite (~2 g) pad and washed with ethyl acetate (2×5 ml). The solvent was removed in vacuo to give treprostinil cyclopentyl naproxen ester (Prodrug XXV) (0.23 g, 99% yield) (97.08% HPLC purity). The compound was characterized by $^1$H, $^{13}$C NMR, IR and LC-MS.

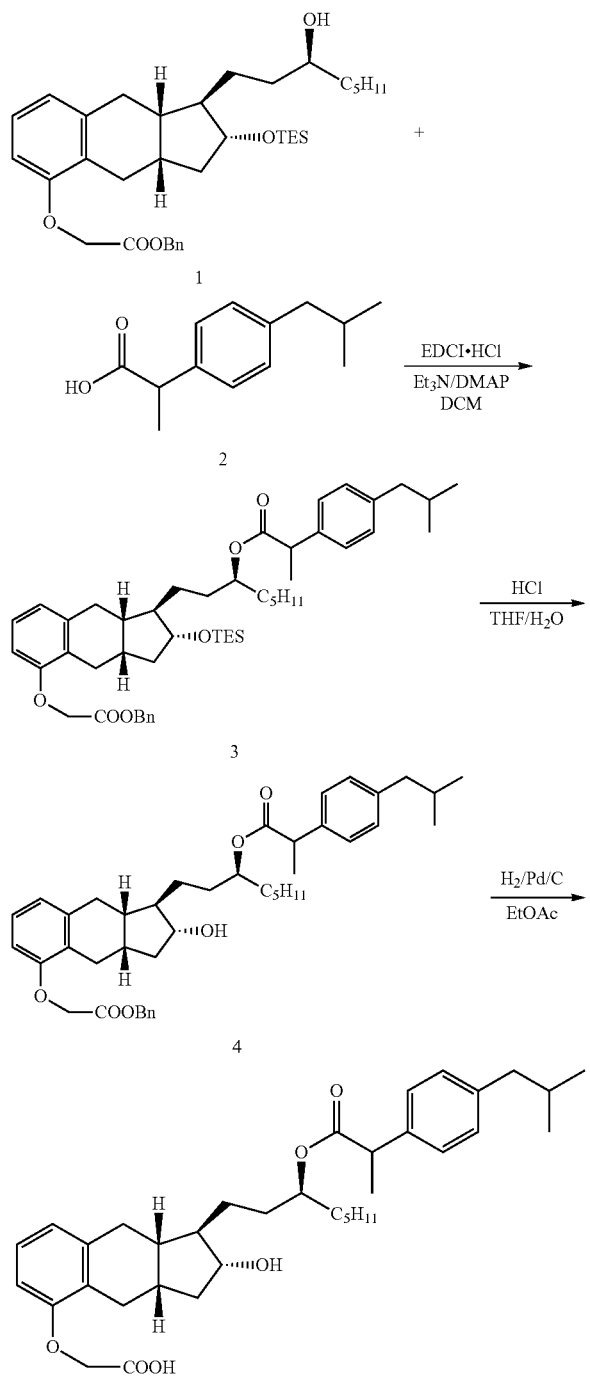

Synthesis of Treprostinil Mono-TES Benzyl Ester Side Chain Ibuprofen Benzyl Ester (3)

Reaction Scheme

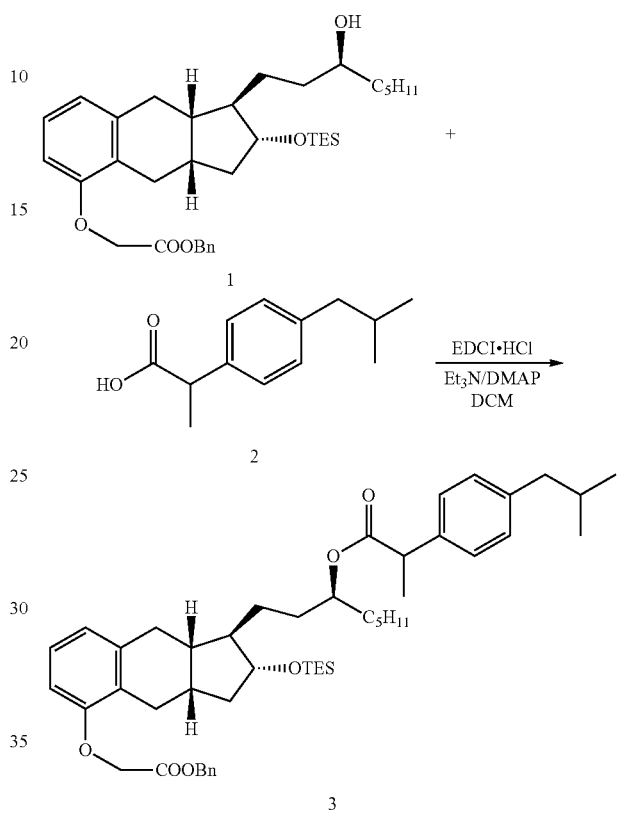

mm. Bill of Materials

| Name | Mol. Wt. | Amount | Eq. | mmol |
|---|---|---|---|---|
| Treprostinil mono-TES benzyl ester (1) | 594.91 | 3.60 g | 1.0 | 6.05 |
| Ibuprofen (2) | 206.29 | 1.50 g | 1.2 | 7.26 |
| EDCI•HCl | 191.75 | 1.40 g | 1.2 | 7.26 |
| Triethylamine | 101.29 | 1.7 ml | 2.0 | 12.1 |
| DMAP | 122.17 | 150 mg | 0.2 | 1.21 |
| Dichloromethane (DCM) (anhydrous) | 84.93 | 50 ml | NA | NA |
| Silica gel (230-400 mesh) (Merck) | NA | NA | 80 g | NA |

Experimental Procedure: A 250-ml, round-bottom flask, equipped with a stir bar was charged with anhydrous DCM (50 ml) and treprostinil mono-TES benzyl ester (1) (3.60 g). To this stirring solution at room temperature under argon, were added ibuprofen (2) (1.50 g), triethylamine (1.7 ml) and DMAP (150 mg). After stirring for 10 min, EDCI.HCl (1.40 g) was added and the mixture stirred at room temperature under argon for 6 h and checked by TLC (EtOAc/ Hex, 1:4). Water (50 ml) was added and the aqueous layer was extracted with DCM (2×20 ml). The combined organic extracts were washed with water (20 ml), brine (20 ml) and dried over sodium sulfate (10 g). It was filtered, and the solvent was removed in vacuo to give crude product (6.04 g). It was purified on silica gel column chromatography using 1-10% ethyl acetate in hexanes to give the desired pure treprostinil mono-TES benzyl ester side chain ibuprofen ester (3) (4.06 g, 85% yield) (97.65% HPLC purity). The compound was characterized by $^1$H NMR.

Synthesis of Treprostinil Benzyl Ester Side Chain Ibuprofen Ester (4)

Reaction Scheme

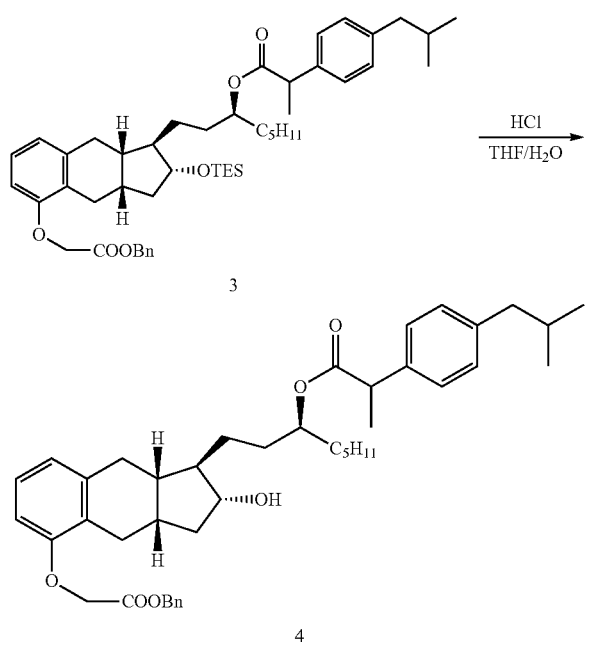

nn. Bill of Materials

| Name | Mol. Wt. | Eq. | Amount | mmol |
|---|---|---|---|---|
| Treprostinil mono-TES benzyl ester side chain ibuprofen esters (3) | 783.20 | 1.0 | 4.06 g | 5.18 |
| Hydrochloric acid (2M) | 36.46 | 1.0 | 2.60 ml | 5.18 |
| Tetrahydrofuran (THF) | 72.11 | NA | 80 ml | NA |
| Triethylamine | 101.29 | NA | 2 ml | NA |
| Silica gel (230-400 mesh) (Merck) | NA | NA | 80 g | NA |

Experimental Procedure: A 250 ml, round-bottom flask, equipped with a stir bar was charged with THF (80 ml), water (16 ml) and treprostinil mono-TES benzyl ester side chain ibuprofen esters (3) (4.06 g). To this stirring solution was added HCl solution (2.60 ml) (2M) and the mixture stirred at room temperature for 1 h and checked by TEC (EtOAc/Hex, 1:4). Triethylamine (2.0 ml) was added and stirred for 10 min. Water (20 ml) and EtOAc (20 ml) were added. The aqueous layer was extracted with ethyl acetate (2×20 ml). The combined organic layers were washed with water (20 ml), brine (20 ml) and dried over sodium sulfate (~30 g). It was filtered, and the solvent was removed in vacuo to give crude product (5.07 g). It was purified on silica gel column chromatography using 1-25% ethyl acetate in hexanes to obtain desired pure treprostinil benzyl ester side chain ibuprofen ester (4) (3.43 g, 98% yield) (99.76% HPLC purity). The compound was characterized by $^1$H NMR.

Synthesis of Treprostinil Side Chain Ibuprofen Ester (Prodrug XXVI)

Reaction Scheme

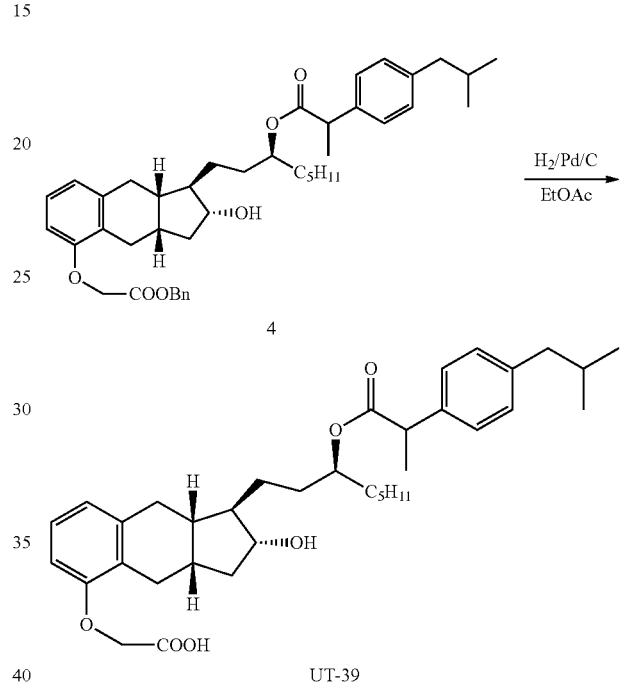

oo. Bill of Materials

| Name | Mol. Wt. | Eq. | Amount | mmol |
|---|---|---|---|---|
| Treprostinil benzyl ester side chain ibuprofen ester (4) | 668.91 | 1.0 | 2.48 g | 3.71 |
| Palladium on carbon (5% wt, 50% water) | 106.42 | NA | 0.50 g | NA |
| Ethyl acetate | 88.10 | NA | 100 ml | NA |
| Celite | NA | NA | 5 g | NA |

Experimental Procedure: A 250-ml, round-bottom flask, equipped with a stir bar was charged with ethyl acetate (100 ml) and treprostinil benzyl ester side chain ibuprofen ester (4) (2.48 g). To this stirring solution at room temperature was added palladium on carbon (0.50 g). The system was evacuated and replaced with hydrogen (repeated this process for two more times). The system was connected to hydrogen balloon and stirred at room temperature for 4 h and checked by TEC (EtOAc/Hex, 1:2). The system was evacuated and replaced with air. It was filtered through a Celite (~5 g) pad and washed with ethyl acetate (2×5 ml). The solvent was removed in vacuo to give treprostinil side chain ibuprofen ester (Prodrug XXVI) (2.01 g, 95% yield) (99.23% HPLC purity). The compound was characterized by $^1$H, $^{13}$C NMR, IR and LC-MS.

Synthesis of Treprostinil Mono-TES Benzyl Ester Side Chain Naproxen Ester (3)

Reaction Scheme

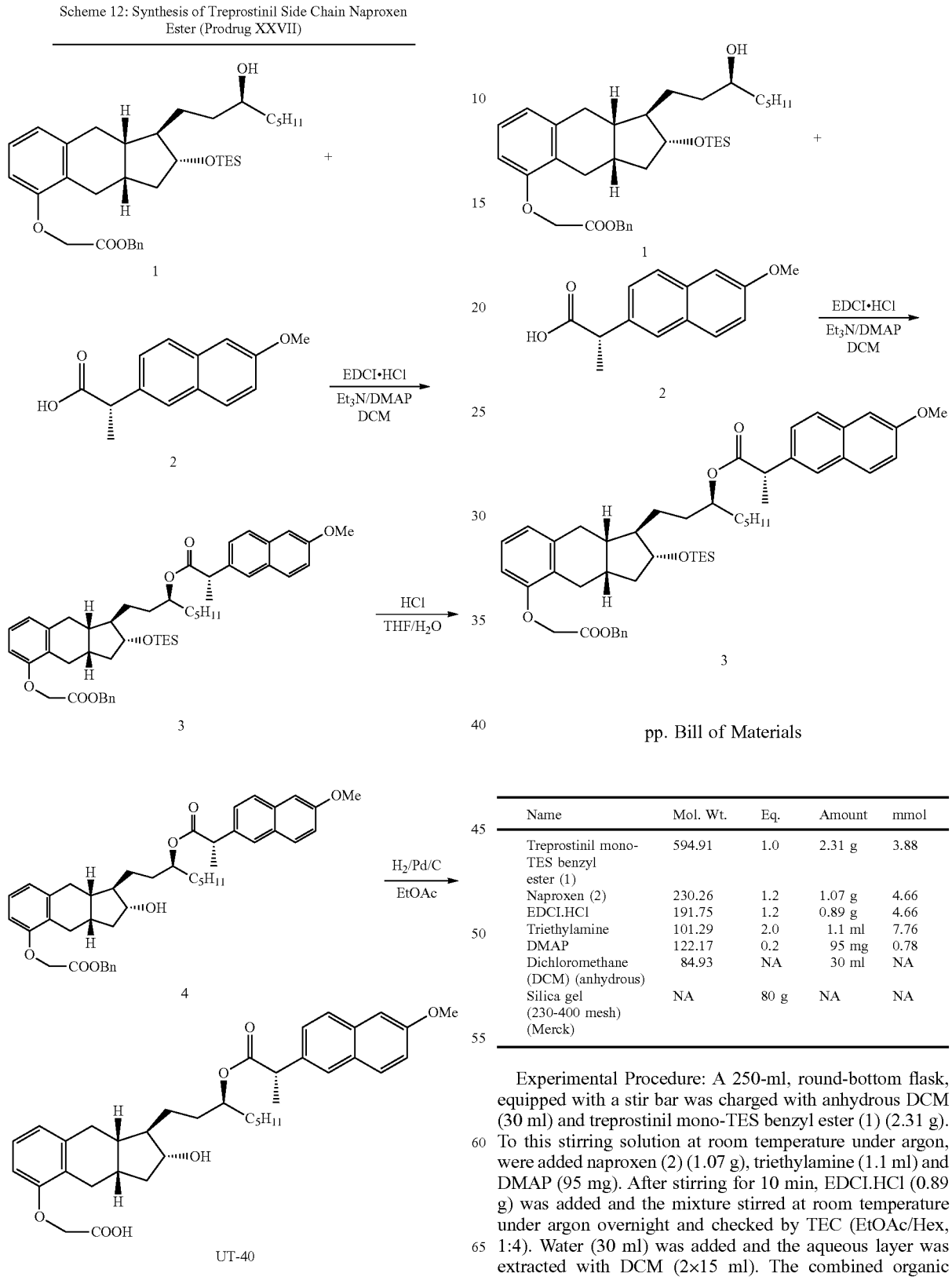

pp. Bill of Materials

| Name | Mol. Wt. | Eq. | Amount | mmol |
|---|---|---|---|---|
| Treprostinil mono-TES benzyl ester (1) | 594.91 | 1.0 | 2.31 g | 3.88 |
| Naproxen (2) | 230.26 | 1.2 | 1.07 g | 4.66 |
| EDCI.HCl | 191.75 | 1.2 | 0.89 g | 4.66 |
| Triethylamine | 101.29 | 2.0 | 1.1 ml | 7.76 |
| DMAP | 122.17 | 0.2 | 95 mg | 0.78 |
| Dichloromethane (DCM) (anhydrous) | 84.93 | NA | 30 ml | NA |
| Silica gel (230-400 mesh) (Merck) | NA | 80 g | NA | NA |

Experimental Procedure: A 250-ml, round-bottom flask, equipped with a stir bar was charged with anhydrous DCM (30 ml) and treprostinil mono-TES benzyl ester (1) (2.31 g). To this stirring solution at room temperature under argon, were added naproxen (2) (1.07 g), triethylamine (1.1 ml) and DMAP (95 mg). After stirring for 10 min, EDCI.HCl (0.89 g) was added and the mixture stirred at room temperature under argon overnight and checked by TEC (EtOAc/Hex, 1:4). Water (30 ml) was added and the aqueous layer was extracted with DCM (2×15 ml). The combined organic extracts were washed with water (20 ml), brine (20 ml) and dried over sodium sulfate (20 g). It was filtered, and the solvent was removed in vacuo to give crude product (4.93 g). It was purified on silica gel column chromatography using 1-20% ethyl acetate in hexanes to give the desired pure treprostinil mono-TES bezyl ester side chain naproxen ester (3) (2.63 g, 84% yield) (96.89% HPLC purity). The compound was characterized by $^1$H NMR.

Synthesis of Treprostinil Benzyl Ester Side Chain Naproxen Ester (4)

Reaction Scheme

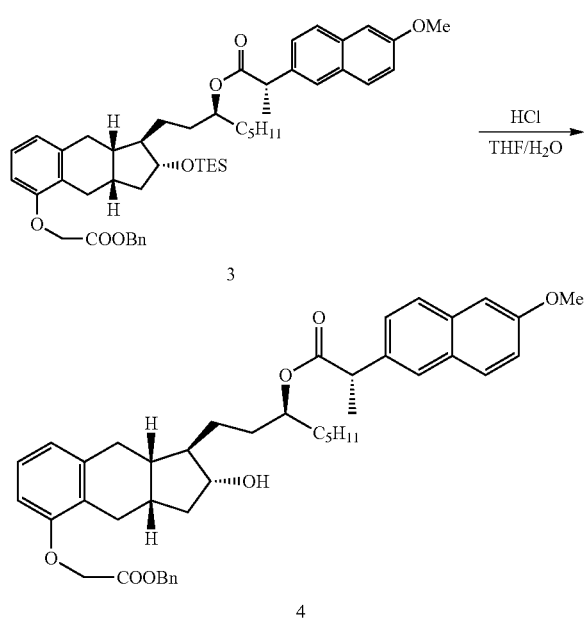

qq. Bill of Materials

| Name | Mol. Wt. | Eq. | Amount | mmol |
|---|---|---|---|---|
| Treprostinil mono-TES benzyl ester side chain naproxen ester (3) | 807.16 | 1.0 | 2.50 g | 3.10 |
| Hydrochloric acid (2M) | 36.46 | 1.0 | 1.60 ml | 3.10 |
| Tetrahydrofuran (THF) | 72.11 | NA | 50 ml | NA |
| Triethylamine | 101.29 | NA | 1.5 ml | NA |
| Silica gel (230-400 mesh) (Merck) | NA | 80 g | NA | NA |

Experimental Procedure: A 250 ml, round-bottom flask, equipped with a stir bar was charged with THF (80 ml), water (16 ml) and treprostinil mono-TES benzyl ester side chain naproxen ester (3) (2.50 g). To this stirring solution was added HCl solution (1.60 ml) (2M) and the mixture stirred at room temperature for 1 h and checked by TEC (EtOAc/Hex, 1:4). Triethylamine (1.5 ml) was added and stirred for 10 min. Water (50 ml) and EtOAc (50 ml) were added. The aqueous layer was extracted with ethyl acetate (2×15 ml). The combined organic layers were washed with water (20 ml), brine (20 ml) and dried over sodium sulfate (20 g). It was filtered, and the solvent was removed in vacuo to give crude product (4.51 g). It was purified on silica gel column chromatography using 1-25% ethyl acetate in hexanes to obtain desired pure treprostinil benzyl ester side chain naproxen esters (4) (2.09 g, 97% yield) (99.44% HPLC purity). The compound was characterized by $^1$H NMR.

Synthesis of Treprostinil Side Chain Naproxen Ester (Prodrug XXVII)

Reaction Scheme

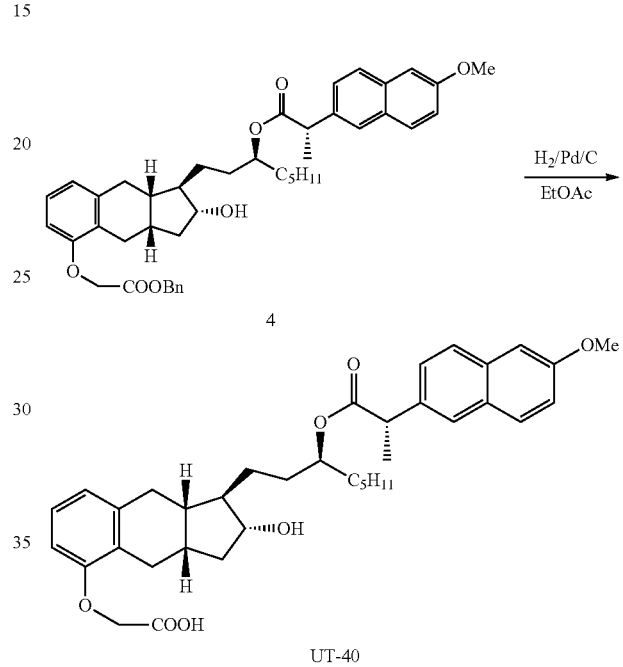

rr. Bill of Materials

| Name | Mol. Wt. | Eq. | Amount | mmol |
|---|---|---|---|---|
| Treprostinil benzyl ester side chain naproxen esters (4) | 692.89 | 1.0 | 0.55 g | 0.79 |
| Palladium on carbon (5% wt, 50% water) | 106.42 | NA | 100 mg | NA |
| Ethyl acetate | 88.10 | NA | 10 ml | NA |
| Celite | NA | NA | 2 g | NA |

Experimental Procedure: A 100-ml, round-bottom flask, equipped with a stir bar was charged with ethyl acetate (10 ml) and treprostinil benzyl ester side chain naproxen esters (4) (0.55 g). To this stirring solution at room temperature was added palladium on carbon (100 mg). The system was evacuated and replaced with hydrogen (repeated this process for two more times). The system was connected to hydrogen balloon and stirred at room temperature for 1 h and checked by TEC (EtOAc/Hex, 1:2). The system was evacuated and replaced with air. It was filtered through a Celite (~2 g) pad and washed with ethyl acetate (2×5 ml). The solvent was removed in vacuo to give treprostinil side chain naproxen ester (Prodrug XXVII) (0.44 g, 93% yield) (97.75% HPLC purity). The compound was characterized by $^1$H, $^{13}$C NMR, IR and LC-MS.

Scheme 13: Synthesis of Treprostinil Cyclic Phenyl Phosphate (Prodrug XXVIII)

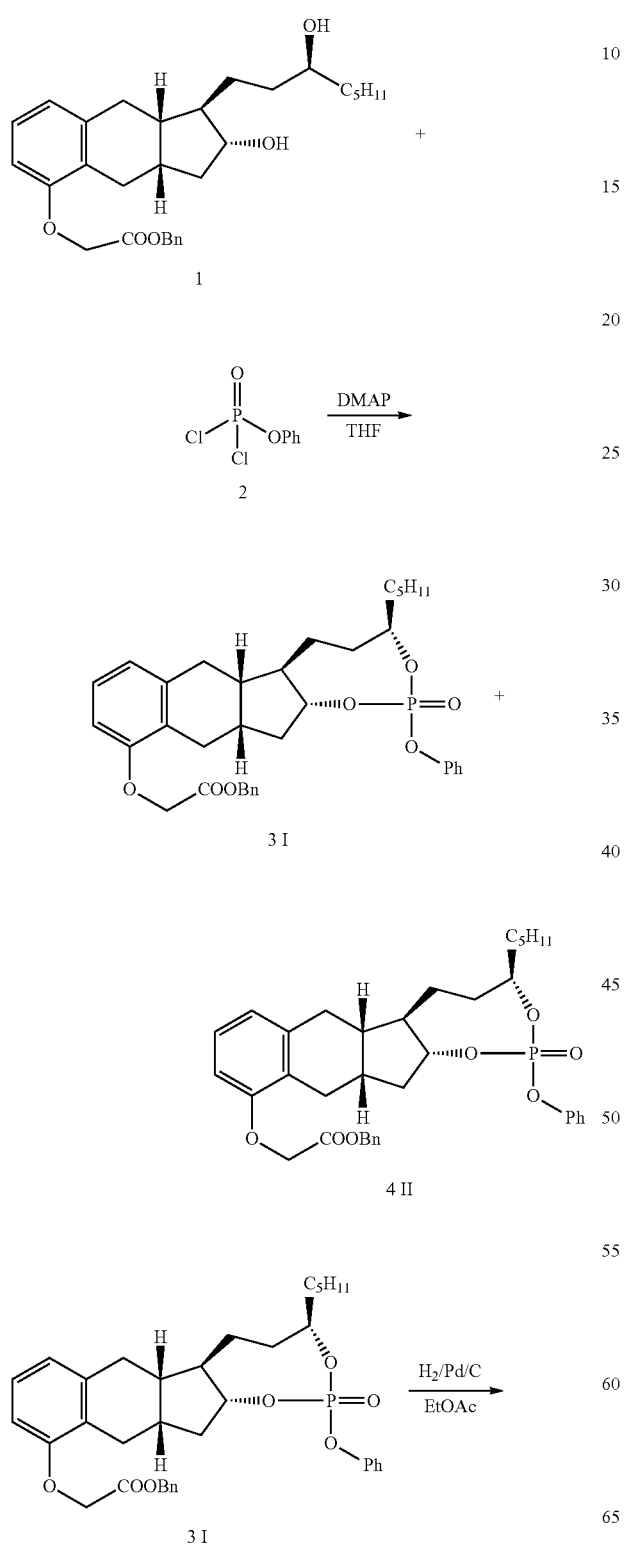

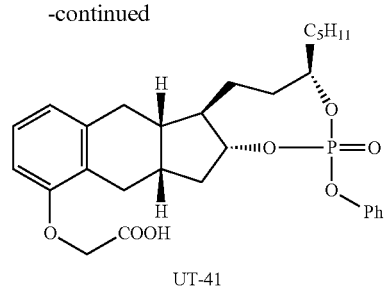

Synthesis of Treprostinil Benzyl Ester Cyclic Phenyl Phosphates I (3)

Reaction Scheme

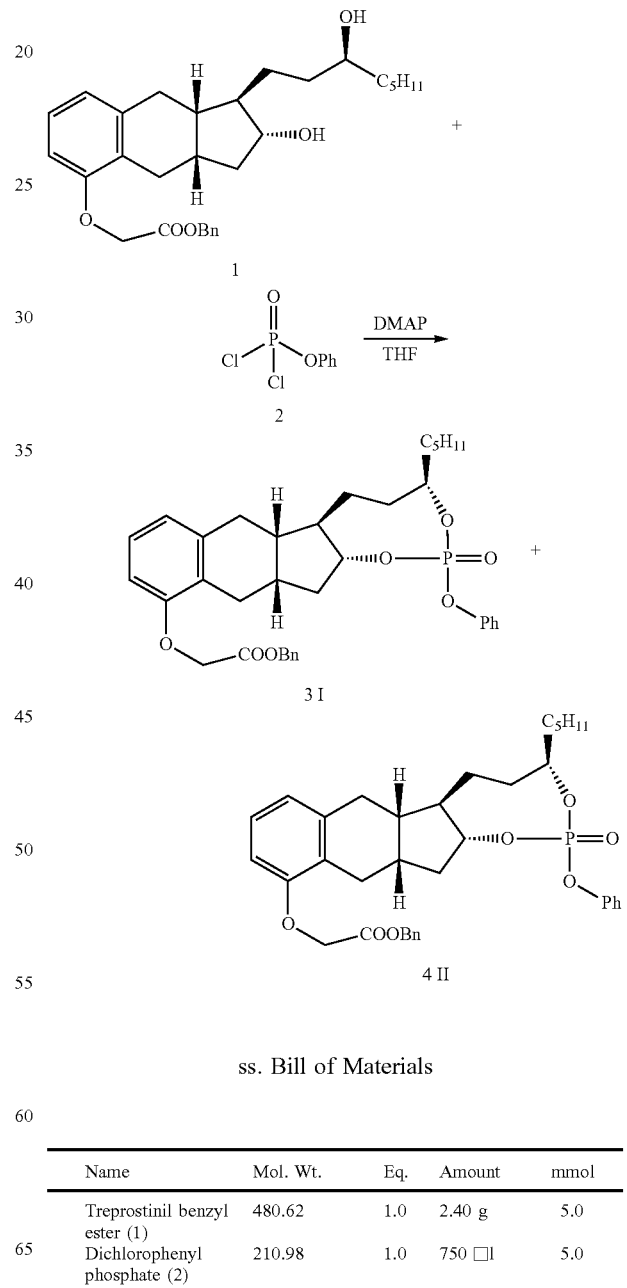

ss. Bill of Materials

| Name | Mol. Wt. | Eq. | Amount | mmol |
|---|---|---|---|---|
| Treprostinil benzyl ester (1) | 480.62 | 1.0 | 2.40 g | 5.0 |
| Dichlorophenyl phosphate (2) | 210.98 | 1.0 | 750 □l | 5.0 |

| Name | Mol. Wt. | Eq. | Amount | mmol |
|---|---|---|---|---|
| DMAP | 122.17 | 2.0 | 1.22 g | 10.0 |
| Tetrahydrofuran (THF) | 72.11 | NA | 50 ml | NA |
| Silica gel (230-400 mesh) (Merck) | NA | NA | 80 g | NA |

Experimental Procedure: A 250-ml, round-bottom flask, equipped with a stir bar was charged with THF (50 ml) and treprostinil benzyl ester (1) (2.4 g). To this stirring solution at room temperature under argon were added DMAP (1.22 g) and dichlorophenyl phosphate (2) (750 □l) and the mixture stirred overnight and checked by TEC (EtOAc/Hex, 1:2). It was filtered and washed with THF (2×5 ml). The solvent was removed in vacuo to give crude products 3.78 g. It was purified on silica gel column chromatography using 1-30% ethyl acetate in hexanes to give treprostinil benzyl ester cyclic phosphate I (3), a white solid, (1.02 g, 33% yield) (99.69% HPLC purity), treprostinil benzyl ester cyclic phosphate II (4), a liquid, (0.45 g, 15% yield) (HPLC purity: 96.02%) (I:II~1:6). The compounds were characterized by $^1$H NMR.

Synthesis of Treprostinil Cyclic Phenyl Phosphate I (Prodrug XXVIII)

Reaction Scheme

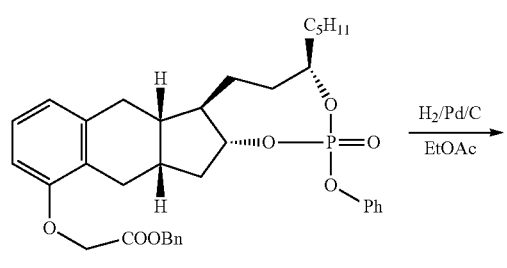

3 I

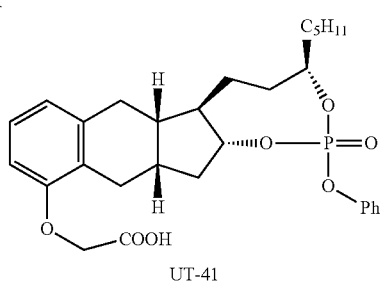

UT-41 tt. Bill of Materials

| Reagent Name | Mol. Weight | Eq. | Amount | mmol |
|---|---|---|---|---|
| Treprostinil benzyl ester cyclic phenyl phosphate I (3) | 618.71 | 1.0 | 0.31 g | 0.50 |

| Reagent Name | Mol. Weight | Eq. | Amount | mmol |
|---|---|---|---|---|
| Palladium on carbon (5% wt, 50% water) | 106.42 | NA | 50 mg | NA |
| Ethyl acetate | 88.10 | NA | 10 ml | NA |
| Celite | NA | NA | 2 g | NA |

Experimental Procedure: A 100-ml, round-bottom flask, equipped with a stir bar was charged with ethyl acetate (10 ml) and treprostinil benzyl ester cyclic phenyl phosphate I (3) (0.31 g). To this stirring solution at room temperature was added palladium on carbon (50 mg). The system was evacuated and replaced with hydrogen (repeated this process for two more times). Then, the flask was connected to hydrogen balloon and stirred at room temperature for 4 h and checked by TEC (EtOAc/Hex, 1:2). The system was evacuated and replaced with air. It was filtered through a Celite (~2 g) pad and washed with ethyl acetate (3×5 ml). The solvent was removed in vacuo to give treprostinil cyclic phenyl phosphate I (Prodrug XXVIII) (0.25 g, 96% yield) (99.47% HPLC purity). The compound was characterized by $^1$H, $^{13}$C, $^{31}$P NMR, IR and LC-MS.

Syntheses of Treprostinil Side Chain Acetate (Prodrug XLIII) and Hydroxy Acetate (Prodrug XLIV)

Treprostinil side chain acetate (Prodrug XLIII) and hydroxy acetate (Prodrug XLIV) were synthesized as shown in Scheme 14 and Scheme 15 respectively. The treprostinil side chain acetate (Prodrug XLIII) (4) was synthesized from mono-TES treprostinil benzyl ester (1) in three steps (Scheme 14). The mono-TES treprostinil benzyl ester (1) was acetylated with acetic anhydride in the presence of 4-(dimethylamino)pyridine (DMAP) to give acetate derivative (2).

Scheme 14: Synthesis of Treprostinil Side Chain Acetate (Prodrug XLIII) (4)

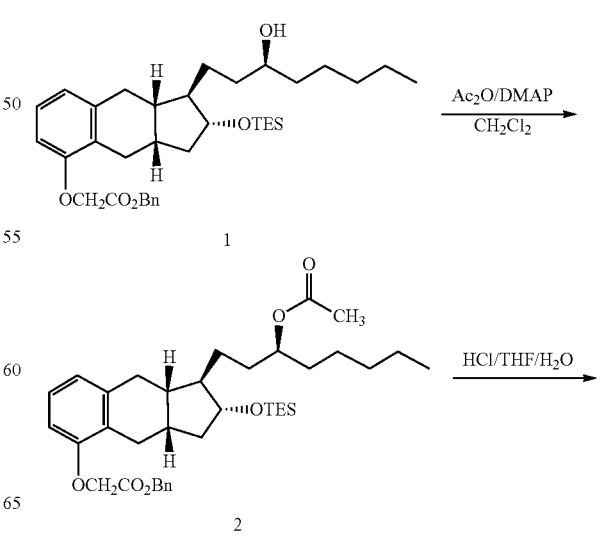

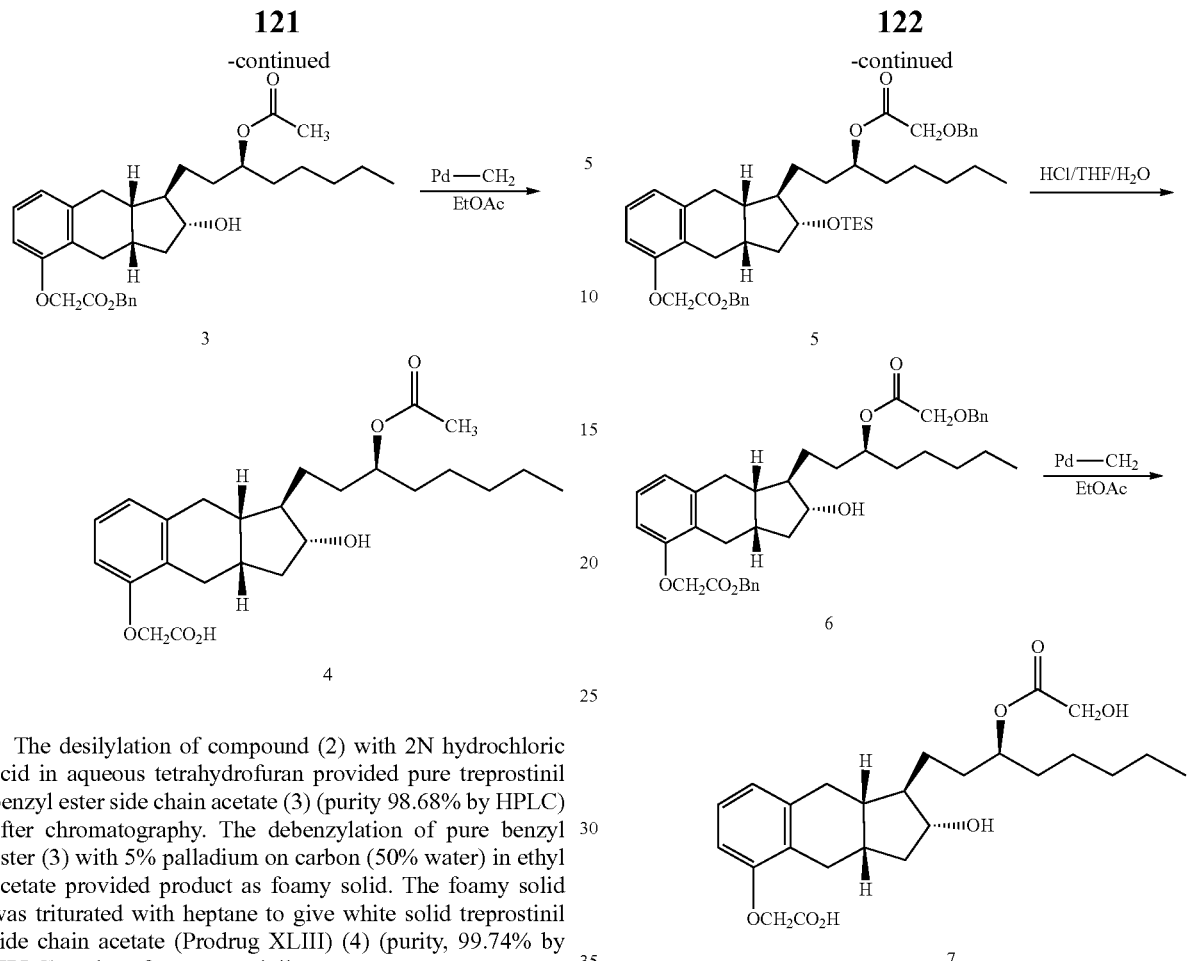

The desilylation of compound (2) with 2N hydrochloric acid in aqueous tetrahydrofuran provided pure treprostinil benzyl ester side chain acetate (3) (purity 98.68% by HPLC) after chromatography. The debenzylation of pure benzyl ester (3) with 5% palladium on carbon (50% water) in ethyl acetate provided product as foamy solid. The foamy solid was triturated with heptane to give white solid treprostinil side chain acetate (Prodrug XLIII) (4) (purity, 99.74% by HPLC) and no free treprostinil.

Similarly, the treprostinil side chain hydroxy acetate (Prodrug XLIV) (7) was synthesized from mono-TES treprostinil benzyl ester (1) in three steps (Scheme 15). The acylation of 1 with benzyloxyacetic acid in the presence of 1-(3-dimethylaminopropyl)-3-ethylcarbodiimide hydrochloride (EDCI.HCl), N-ethyldiisopropylamine (N,N-diisopropylethylamine) (DIEA) and 4-(dimethyl-amino)pyridine (DMAP) gave TES-treprostinil benzyl ester side chain benzyloxy acetate (5) after chromatography. The desilylation of compound (5) with 2N hydrochloric acid in aqueous tetrahydrofuran provided pure treprostinil benzyl ester side chain benzyloxy acetate (6) (purity 99.33% by HPLC) after chromatography. The debenzylation of pure benzyl ester (6) with 5% palladium on carbon (50% water) in ethyl acetate and water provided treprostinil side chain hydroxy acetate (Prodrug XLIV) (7) as foamy solid (purity, 97.57% by HPLC) and no free treprostinil.

Scheme 15: Synthesis of Treprostinil Side Chain Hydroxy Acetate (Prodrug XLIV) (7)

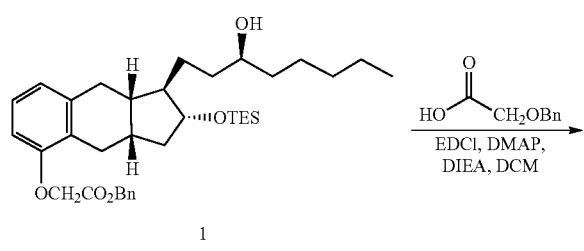

EXPERIMENTAL

Synthesis of TES-Treprostinil Benzyl Ester Side Chain Acetate (2)

Bill of Materials

| Name | MW | Source | Amount | mmol | Eq. |
|---|---|---|---|---|---|
| Mono-TES-treprostinil benzyl ester (1) | 594.91 | 4G Bio | 2.58 g | 4.34 | 1.00 |
| 4-(Dimethylamino)pyridine (DMAP) | 122.17 | Aldrich | 1.06 g | 8.68 | 2.00 |
| Acetic anhydride | 102.09 | Aldrich | 0.89 g (0.82 mL) | 8.72 | 2.01 |
| Dichloromethane (anhydrous) | NA | EMD) | 20 mL | NA | NA |
| Silica gel (230-400 mesh) | NA | Merck | 33 g | NA | NA |

Experimental Procedure

To a solution of mono-TES-treprostinil benzyl ester (2.58 g, 4.34 mmol) in anhydrous dichloromethane (20 mL) was added 4-(dimethylamino)pyridine (DMAP) (1.06 g, 8.68 mmol) at room temperature under argon. To this clear solution was added acetic anhydride (0.89 g, 0.82 mL, 8.72 mmol). The reaction mixture was stirred at room temperature for 2 h and checked TLC (EtOAc/Hexane, 1:4). The reaction was complete. The mixture was treated with hexane (40 mL) and then passed through silica gel (33 g) column and eluted the compound with ethyl acetate in hexane (5-15%) to give pure TES-treprostinil benzyl ester side chain acetate (2) as a clear viscous liquid (2.64 g, 95.6%) purity 98.68% by HPLC, and characterized by spectral data (IR, $^1$H NMR, $^{13}$C NMR, DEPT-NMR and LCMS).

Synthesis of Treprostinil Benzyl Ester Side Chain Acetate (3)

Reaction Scheme

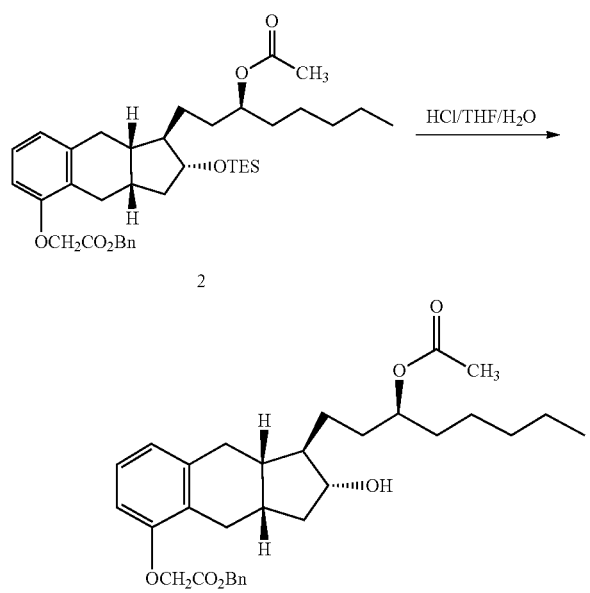

Bill of Materials

| Name | MW | Amount | mmol | Eq. |
|---|---|---|---|---|
| TES-treprostinil benzyl ester side chain acetate (2) | 636.92 | 1.40 g | 2.20 | 1.00 |
| Hydrochloric acid (2N) | 36.5 | 1.10 mL | 2.20 | 1.00 |
| Tetrahydrofuran | NA | 10 mL | NA | NA |
| Water | NA | 2 mL | NA | NA |
| Triethylamine | 101.19 | 0.5 mL | NA | NA |
| Silica gel (230-400 mesh) | NA | 32 g | NA | NA |

Experimental Procedure

To a solution of TES-treprostinil benzyl ester side chain acetate (2) (1.40 g, 2.20 mmol) in a mixture of tetrahydrofuran (10 mL) and water (2 mL) (5:1) was added hydrochloric acid (2N) (1.10 mL, 2.20 mmol). The reaction mixture (turbid) was stirred at room temperature for 30 min and checked TLC (EtOAc/Hexane, 1:4). The reaction was complete. The mixture was treated with triethylamine (0.5 mL) and then removed all organic volatiles in vacuo at 30° C. The residue was treated with water (20 mL) and then extracted with MTBE (2×30 mL). The combined MTBE extracts were washed with water (1×20 mL), brine (1×10 mL), dried (Na$_2$SO$_4$), filtered and concentrated in vacuo to give viscous liquid (1.36 g). The crude product was chromatographed on silica gel (32 g) using ethyl acetate in hexane (5-35%) to give pure treprostinil benzyl ester side chain acetate (3) a clear viscous liquid (0.18 g) and (0.95 g) (total, 1.13 g, 98.3%), purity 99.46% by HPLC, and characterized by spectral data (IR, $^1$H NMR, $^{13}$C NMR, DEPT-NMR and LCMS).

Synthesis of Treprostinil Side Chain Acetate (Prodrug XLIII) (4)

Reaction Scheme

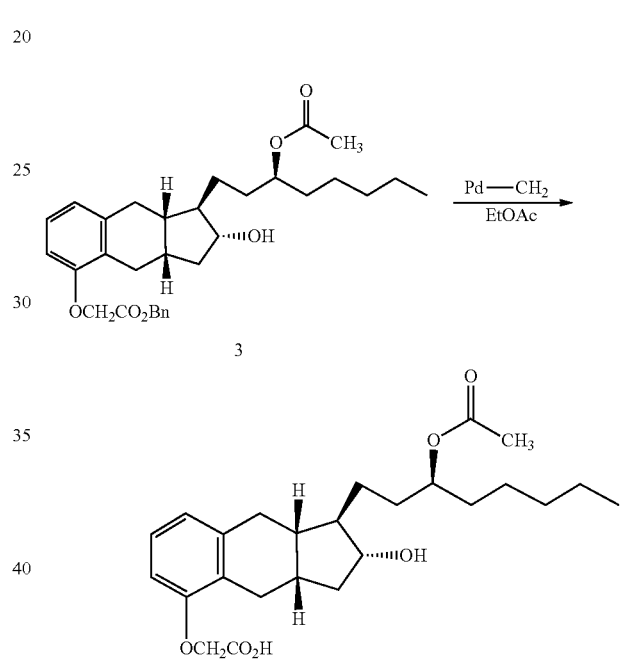

Bill of Materials

| Name | MW | Amount | mmol | Eq. |
|---|---|---|---|---|
| Treprostinil benzyl ester side chain acetate (3) | 522.66 | 0.91 g | 1.74 | 1.00 |
| Palladium on carbon, extent of labelling: 5 wt % loading (dry basis), matrix activated carbon, wet support, Degussa type E101 NO/W (~50% water) | NA | 0.24 g | cat | NA |
| Hydrogen gas | 2.00 | Filled in balloon | NA | NA |
| Ethyl acetate | NA | 30 mL | NA | NA |
| Celite | NA | 4.19 g | NA | NA |

Experimental Procedure

To a solution of treprostinil benzyl ester side chain acetate (3) (0.91 g, 1.74 mmol) in ethyl acetate (30 mL) was added palladium on carbon (5 wt %, ~50% water) (0.24 g) at room temperature. The mixture was stirred and evacuated under house vacuum and then replaced by hydrogen (filled in a balloon). This process was repeated three times. The reaction mixture was stirred under the atmosphere of hydrogen at room temperature for 3 h and checked TLC (EtOAc/Hexane, 4:6). The reaction was complete. The mixture was filtered through a pad of Celite (4.19 g) and washed the solid with ethyl acetate (3×15 mL). The filtrated was concentrated in vacuo to give foamy solid (0.74 g). The foamy solid was triturated with heptane (15 mL) and stirred at room temperature overnight. The white solid was collected in a Buchner funnel and washed the solid with hexane (3×20 mL). The solid was air-dried under house vacuum and transferred into a vial and further dried under high vacuum to give dry pure treprostinil side chain acetate (Prodrug XLIII) (4) as a white solid (0.65 g, 86.3%) purity 99.74% by HPLC and characterized by spectral data (IR, $^1$H NMR, $^{13}$C NMR, DEPT-NMR and LCMS), mp 81-84° C.

Synthesis of TES-Treprostinil Benzyl Ester Side

Reaction Scheme

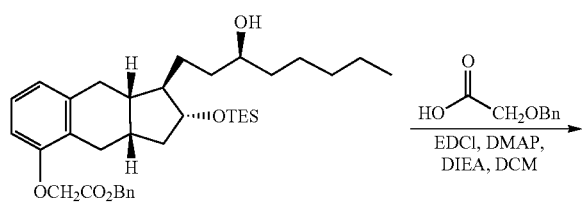

1

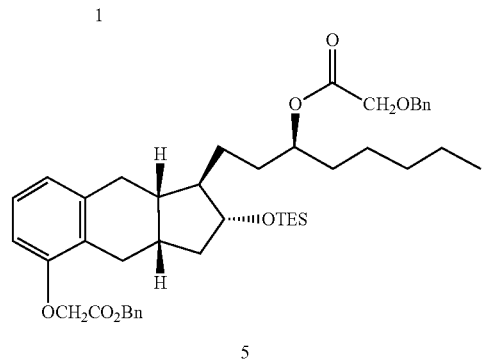

5

Bill of Materials

| Name | MW | Supplier | Amount | mmol | Eq. |
|---|---|---|---|---|---|
| Mono-TES-treprostinil benzyl ester (1) | 594.91 | 4G Bio | 1.83 g | 3.08 | 1.00 |
| Benzyloxyacetic acid | 166.17 | Aldrich | 0.49 mL | 3.39 | 1.10 |
| 1-(3-Dimethylaminopropyl)-3-ethylcarbodiimide hydrochloride (EDCI•HCl) | 191.70 | TCI | 1.48 g | 7.70 | 2.50 |
| N-Ethyldiisopropylamine (N,N-Diisopropylethylamine) (DIEA) | 129.24 | Aldrich | 1.34 mL | 7.70 | 2.50 |
| 4-(Dimethylamino)pyridine (DMAP) | 122.17 | Aldrich | 75 mg | 0.62 | 0.20 |
| Dichloromethane (anhydrous) | NA | EMD | 30 mL | NA | NA |
| Silica gel (230-400 mesh) | NA | Merck | 70 g | NA | NA |

Experimental Procedure

To a solution of mono-TES-treprostinil benzyl ester (1.83 g, 3.08 mmol) in anhydrous dichloromethane (30 mL) was added benzyloxyacetic acid (0.49 mL, 3.39 mmol) 1-(3-dimethylaminopropyl)-3-ethylcarbodiimide hydrochloride (EDCI.HCl) (1.48 g, 7.70 mmol), N-ethyldiisopropylamine (N, A-diisopropylethylamine) (DIEA) (1.34 mL, 7.70 mmol) and 4-(dimethylamino)pyridine (DMAP) (75 mg, 0.62 mmol) at room temperature under argon. The reaction mixture was stirred at room temperature for 4 h and checked TEC (EtOAc/Hexane, 1:4), the reaction was almost complete. The mixture was treated with water (10 mL) and extracted with dichloromethane (2×10 mL). The combined dichloromethane extracts were washed with brine (1×20 mL), dried (Na$_2$SO$_4$), filtered and concentrated in vacuo to give crude product (3.69 g). The crude product was chromatographed on silica gel (70 g) column using ethyl acetate in hexane (1-10%) to give pure TES-treprostinil benzyl ester side chain benzyloxy acetate (5) (1.87 g, 82%) purity 97.75% by HPLC, and characterized by spectral data (IR, $^1$H NMR, $^{13}$C NMR and LCMS)

Synthesis of Treprostinil Benzyl Ester Side Chain Benzyloxy Acetate (6)

Reaction Scheme

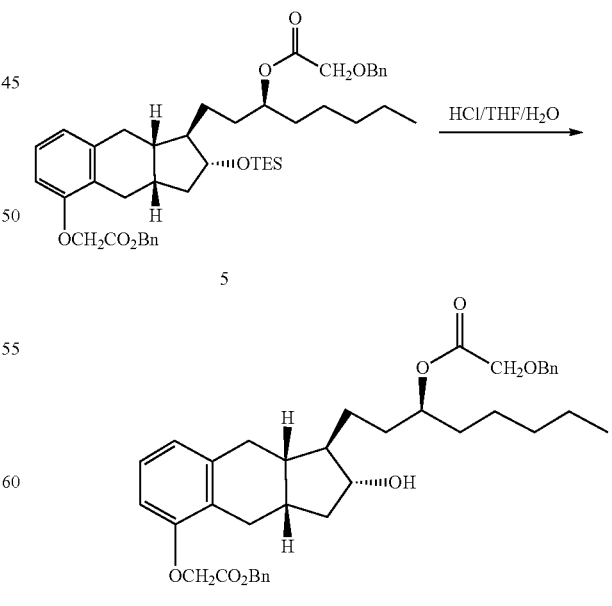

Bill of Materials

| Name | MW | Supplie. | Amount | mmol | Eq. |
|---|---|---|---|---|---|
| TES-treprostinil benzyl ester side chain benzyloxy acetate (5) | 743.07 | | 1.65 g | 2.22 | 1.00 |
| Hydrochloric acid (2N) | 36.5 | Aldrich | 1.10 mL | 2.20 | 1.00 |
| Tetrahydrofuran | NA | NA | 40 mL | NA | NA |
| Water | NA | NA | 8 mL | NA | NA |
| Triethylamine | 101.19 | NA | 1 mL | NA | NA |
| Silica gel (230-400 mesh) | NA | Merck | 50 g | NA | NA |

Experimental Procedure

To a solution of TES-treprostinil benzyl ester side chain benzyl oxy acetate (5) (1.65 g, 2.22 mmol) in a mixture of tetrahydrofuran (40 mL) and water (8 mL) (5:1) was added hydrochloric acid (2N) (1.10 mL, 2.20 mmol). The reaction mixture was stirred at room temperature for 1 h and checked TLC (EtOAc/Hexane, 1:2). The reaction was complete. The mixture was treated with triethylamine (1 mL), water (20 mL) and ethyl acetate (20 ml) and then separated layers. The aqueous layer was extracted with ethyl acetate (2×10 mL). The combined ethyl acetate extracts were washed with brine (1×20 mL), dried ($Na_2SO_4$), filtered and concentrated in vacuo to give crude product (2.30 g). The crude product was chromatographed on silica gel (50 g) column using ethyl acetate in hexane (2-30%) to give pure treprostinil benzyl ester side chain benzyloxy acetate (6) (1.42 g, 100%) purity 99.33% by HPLC, and characterized by spectral data (IR, $^1$H NMR, $^{13}$C NMR and LCMS)

Synthesis of Treprostinil Side Chain Hydroxy Acetate (Prodrug XLIV) (7)

Reaction Scheme

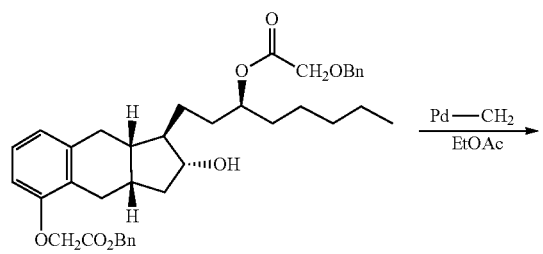

6

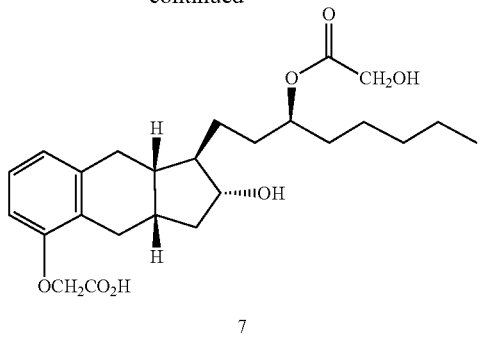

7

Bill of Materials

| Name | MW | Amount | mmol | Eq. |
|---|---|---|---|---|
| Treprostinil benzyl ester side chain benzyloxy acetate (6) | 628.81 | 1.25 g | 1.99 | 1.00 |
| Palladium on carbon, extent of labelling: 5 wt % loading (dry basis), matrix activated carbon, wet support, Degussa type E101 NO/W (~50% water) | NA | 0.30 g | cat | NA |
| Hydrogen gas | 2.00 | Filled in balloon | NA | NA |
| Ethyl acetate | NA | 40 mL | NA | NA |
| Water | NA | 2 mL | NA | NA |
| Celite | NA | 2 g | NA | NA |

Experimental Procedure

To a solution of treprostinil benzyl ester side chain benzyloxy acetate (6) (1.25 g, 1.99 mmol) in ethyl acetate (40 mL) and water (2 mL) was added palladium on carbon (5 wt %, ~50% water) (0.30 g) at room temperature. The mixture was stirred and evacuated under house vacuum and then replaced by hydrogen (filled in a balloon). This process was repeated three times. The reaction mixture was stirred under the atmosphere of hydrogen at room temperature for 3 h and checked TEC (EtOAc, 100%). The reaction was complete. The mixture was filtered through a pad of Celite (2.0 g) and washed the solid with ethyl acetate (2×10 mL) and a mixture of ethyl acetate (8 mL) and water (2 mL). The filtrate was concentrated in vacuo to give treprostinil side chain hydroxy acetate (Prodrug XLIV) (7) as a white solid (0.81 g, 92%), purity 97.57% by HPLC, and characterized by spectral data (IR, $^1$H NMR, $^{13}$C NMR and LCMS).

Analytical Data Sheet for Treprostinil Side Chain Acetate (Prodrug XLIII) (4)

| S. No. | Description | Results |
|---|---|---|
| 1. | Structure | |

| S. No. | Description | Results |
|---|---|---|
| 2. | Chemical Name | 2-(((1R,2R,3aS,9aS)-1-((S)-3-acetoxyoctyl)-2-hydroxy-2,3,3a,4,9,9a-hexahydro-1H-cyclopenta[b]naphthalen-5-yl)oxy)acetic acid |
| 4. | Molecular Formula | $C_{25}H_{36}O_6$ |
| 5. | Molecular Weight | 432.56 |
| 6. | MS | Practical Value: $[M + Na]^+$ = 455.34<br>Calculated Value: $[M + Na]^+$ = 455.25 |
| 7. | $^1H$ NMR | Conforms to structure |
| 8. | $^{13}C$ NMR | Conforms to structure |
| 9. | Purity by HPLC | 99.74% |
| 10. | IR | Conforms to structure |
| 11. | Appearance | White solid |

Analytical Data Sheet for Treprostinil Side Chain Hydroxy Acetate (XLIV) (7)

| S. No. | Description | Results |
|---|---|---|
| 1. | Structure | (structure image) |
| 2. | Chemical Name | 2-(((1R,2R,3aS,9aS)-2-hydroxy-1-(3-(2-hydroxyacetoxy)octyl)-2,3,3a,4,9,9a-hexahydro-1H-cyclopenta[b]naphthalen-5-yl)oxy)acetic acid |
| 4. | Molecular Formula | $C_{25}H_{36}O_7$ |
| 5. | Molecular Weight | 448.56 |
| 6. | MS | Practical Value: $[M + Na]^+$ = 471.31<br>Calculated Value: $[M + Na]^+$ = 471.25 |
| 7. | $^1H$ NMR | Conforms to structure |
| 8. | $^{13}C$ NMR | Conforms to structure |
| 9. | Purity by HPLC | 97.57% |
| 10. | IR | Conforms to structure |
| 11. | Appearance | White solid |

Example 3: Pharmacokinetic Studies

Prodrugs IV, XVI, XVII and VI: A Pharmacokinetic Evaluation following a Single Oral Gavage or Intravenous Administration in Sprague Dawley Rats Summary The objective of this study was to evaluate the pharmacokinetic profile of Prodrugs IV, XVI, XVII and VI when administered as a single oral (gavage) or intravenous injection (IV bolus) in male Sprague Dawley rats.

The study design was as follows:

uu. Experimental Design

| Group No. | Test Article [a] | Vehicle | Dose Route | Dose Level (mg/kg) | Conc. (mg/mL) | Dose Volume (mL/kg) | Number of Malesa |
|---|---|---|---|---|---|---|---|
| 1 | IV | 20 mM histidine, 125 mM NaCl | Oral | 1 [b] | 0.1 | 10 | 4 |
| 2 | IV | 20 mM histidine, 125 mM NaCl | Oral | 10 [b] | 1 | 10 | 4 |
| 3 | IV | 20 mM histidine, 125 mM NaCl | Oral | 50 [b] | 5 | 10 | 4 |

-continued

| Group No. | Test Article [a] | Vehicle | Dose Route | Level (mg/kg) | Conc. (mg/mL) | Dose Volume (mL/kg) | Number of Malesa |
|---|---|---|---|---|---|---|---|
| 4 | XVI | 20 mM histidine, 125 mM NaCl | Oral | 1 [c] | 0.1 | 10 | 4 |
| 5 | XVI | 20 mM histidine, 125 mM NaCl | Oral | 10 [c] | 1 | 10 | 4 |
| 6 | XVI | 20 mM histidine, 125 mM NaCl | Oral | 50 [c] | 5 | 10 | 4 |
| 7 | XVII | 20 mM histidine, 125 mM NaCl | Oral | 1 [d] | 0.1 | 10 | 4 |
| 8 | XVII | 20 mM histidine, 125 mM NaCl | Oral | 10 [d] | 1 | 10 | 4 |
| 9 | XVII | 20 mM histidine, 125 mM NaCl | Oral | 50 [d] | 5 | 10 | 4 |
| 10 | VI | 20 mM tribasic phosphate, 125 mM NaCl | Oral | 1 [e] | 0.1 | 10 | 4 |
| 11 | VI | 20 mM tribasic phosphate, 125 mM NaCl | Oral | 10 [e] | 1 | 10 | 4 |
| 12 | VI | 20 mM tribasic phosphate, 125 mM NaCl | Oral | 50 [e] | 5 | 10 | 4 |
| 13 | IV | 20 mM histidine, 125 mM NaCl | IV Bolus | 1 [b] | 1 | 1 | 4 |
| 14 | XVI | 20 mM histidine, 125 mM NaCl | IV Bolus | 1 [c] | 1 | 1 | 4 |
| 15 | XVII | 20 mM histidine, 125 mM NaCl | IV Bolus | 1 [d] | 1 | 1 | 4 |
| 16 | VI | 20 mM tribasic phosphate, 125 mM NaCl | IV Bolus | 1 [e] | 1 | 1 | 4 |

[a] Dose calculated from body weight.
[b] Corrected for salt, purity and water content. Correction factor for Prodrug IV: 1.016
[c] Corrected for salt, purity and water content. Correction factor for Prodrug XVI: 1.009
[d] Corrected for salt, purity and water content. Correction factor for Prodrug XVII: 1.013
[e] Corrected for salt, purity and water content. Correction factor for Prodrug VI: 1.002.

Animals received a single dose via oral gavage or intravenous (bolus) injection. The following parameters and end points were evaluated in this study: clinical signs and pharmacokinetic parameters. Single males in the oral 50 mg/kg prodrugs XVII and VI group were found dead on Day 2. No macroscopic findings were noted. All other animals survived to the scheduled euthanasia.

Test article-related clinical observations of decreased activity, cold to touch, red skin on the cranium/forelimbs/forepaws/hindlimbs/hindpaws, ungroomed fur, lying on side, and/or discharge from the eyes were noted for all oral 50 mg/kg groups (Groups 3, 6, 9, and 12) and all IV bolus 1 mg/kg groups (Groups 13, 14, 15, and 16).

Based on the results of this study, single oral or IV bolus administration of Prodrugs IV, XVI, XVII and VI to Crl: CD(SD) rats at dose levels of 1, 10, and 50 mg/kg resulted in lethality at oral 50 mg/kg Prodrug XVII and oral 50 mg/kg Prodrug VI and adverse clinical observations at IV bolus 1 mg/kg and oral 50 mg/kg for all 4 test articles.

Materials and Methods

Test Articles

Prodrug IV (side chain carbonate ester prodrug of treprostinil).
Physical Description: White powder.
Purity: 99.4%
Water Content: 0.97%
Correction Factor: 1.016
Storage Conditions: Kept in a refrigerator set to maintain 4° C., protected from light
Prodrug XVI (side chain ethyl carbonate of treprostinil)
Physical Description: White powder
Purity: 99.1%
Correction Factor: 1.009
Storage Conditions: Kept in a refrigerator set to maintain 4 C, protected from light
Prodrug XVII (side chain isopropyl carbonate of treprostinil)
Physical Description: White powder
Purity: 98.7%
Correction Factor: 1.013
Storage Conditions: Kept in a refrigerator set to maintain 4° C., protected from light
Prodrug VI (treprostinil side-chain phosphate ester)
Physical Description: White powder
Purity: 99.8%
Correction Factor: 1.002
Storage Conditions: Kept in a refrigerator set to maintain 4° C., protected from light Groups 1-9 and 13-15 Vehicle 20 mM histidine, 125 mM NaCl Vehicle Components Sterile water for injection
Physical Description: Clear, colorless liquid
Kept in a controlled temperature area set to maintain 18° C. to 24° C.
L-Histidine, USP
Storage Conditions: Kept in a controlled temperature area set to maintain 18° C. to 24° C.
Sodium chloride, USP
Physical Description: White crystalline powder Storage Conditions: Kept in a controlled temperature area set to maintain 18° C. to 24° C.

Groups 10-12 and 16 Vehicle 20 mM tribasic phosphate, 125 mM NaCl

Vehicle Components

Sterile water for injection
Physical Description: Clear, colorless liquid
Storage Conditions: Kept in a controlled temperature area set to maintain 18° C. to 24° C.
Sterile water for injection
Physical Description: Clear, colorless liquid
Kept in a controlled temperature area set to maintain 18° C. to 24° C.
Sodium phosphate tribasic anhydrous, FCC
Physical Description: White powder
Kept in a controlled temperature area set to maintain 18° C. to 24° C.
Sodium chloride, USP
Storage Conditions: Kept in a controlled temperature area set to maintain 18° C. to 24° C.

Dose Formulation

Preparation of Vehicle

The vehicles, 20 mM histidine, 125 mM NaCl (Groups 1-9 and 13-15) and 20 mM tribasic phosphate, 125 mM NaCl (Groups 10-12 and 16), were prepared on 27 and 31 Jul. 2018, respectively, and stored refrigerated (2° C. to 8° C.).

Preparation of Test Article

Test article dosing formulations were prepared at appropriate concentrations to meet dose level requirements. The dosing formulations were prepared on the day prior to each day of dosing and stored refrigerated (2° C. to 8° C.), protected from light (Groups 1-3, 13) or at room temperature (18° C. to 24° C.), protected from light (Groups 4-12, 14-16) until use. The dosing formulations for Groups 1-12 were stirred continuously during dosing.

Test System

Crl:CD(SD) rats were received from Charles River Laboratories, Inc., Raleigh, N.C. The animals were 9 weeks old and weighed between 296 and 350 g at the initiation of dosing.

The Crl:CD(SD) rat was chosen as the animal model for this study as it is an accepted rodent species for preclinical toxicity testing by regulatory agencies. The total number of animals used in this study was considered to be the minimum required to properly characterize the effects of the test articles. This study was designed such that it did not require an unnecessary number of animals to accomplish its objectives.

At this time, studies in laboratory animals provide the best available basis for extrapolation to humans and are required to support regulatory submissions. Acceptable models which do not use live animals currently do not exist.

Upon receipt, each animal was identified using a subcutaneously implanted electronic identification chip (BMDS system). After receipt at the Testing Facility, the Crl:CD(SD) rats were acclimated prior to initiation of dosing.

Animals were assigned to groups by a stratified randomization scheme designed to achieve similar group mean body weights. Animals were group housed (2 to 3 animals of the same dosing group together) in solid-bottom cages containing appropriate bedding equipped with an automatic watering valve. Animals were separated during designated procedures/activities. Each cage was clearly labeled with a color-coded cage card indicating study number, group number, dosage level, animal number(s), and sex. Cages were arranged on the racks in group order. Animals were maintained in accordance with the National Research Council. Guide for the Care and Use of Laboratory Animals, Committee for the Update of the Guide for the Care and Use of Laboratory Animals, Institute for Laboratory Animal Research, Division on Earth and Life Sciences; The National Academies Press: Washington, D.C., 2011. The animal facilities at Charles River Ashland are accredited by AAALAC International.

Environmental Conditions

Target temperatures of 68° F. to 78° F. (20° C. to 26° C.) with a relative target humidity of 30% to 70% were maintained. A 12 hour light/12 hour dark cycle was maintained, except when interrupted for designated procedures. Ten or greater air changes per hour with 100% fresh air (no air recirculation) were maintained in the animal rooms.

Food

PMI Nutrition International, LLC Certified Rodent Chow LabDiet® 5CR4 (meal) was provided ad libitum throughout the study. The feed was analyzed by the supplier for nutritional components and environmental contaminants. Results of the analysis are provided by the supplier and are on file at the Testing Facility. It was considered that there were no known contaminants in the feed that would interfere with the objectives of the study.

Water

Municipal tap water after treatment by reverse osmosis was freely available to each animal via an automatic watering system. Periodic analysis of the water was performed, and results of these analyses are on file at the Testing Facility. It was considered that there were no known contaminants in the water that could interfere with the outcome of the study.

Animal Enrichment

Animals were socially housed for psychological/environmental enrichment and were provided with environmental enrichment as appropriate to aid in maintaining the animals' oral health.

Veterinary Care

Veterinary care was available throughout the course of the study; however, no examinations or treatments were required.

vv. Experimental Design

| Group Number | Test Article[a] | Vehicle | Route | Dose Level (mg/kg) | Dose Volume (mL/kg) | Concentration (mg/mL) | Male Numbers[a] |
|---|---|---|---|---|---|---|---|
| 1 | IV | 20 mM histidine, 125 mM NaCl | Oral | 1 [b] | 10 | 0.1 | 1001-1004 |
| 2 | IV | 20 mM histidine, 125 mM NaCl | Oral | 10 [b] | 10 | 1 | 2001-2004 |
| 3 | IV | 20 mM histidine, 125 mM NaCl | Oral | 50 [b] | 10 | 5 | 3001-3004 |
| 4 | XVI | 20 mM histidine, 125 mM NaCl | Oral | 1 [c] | 10 | 0.1 | 4001-4004 |
| 5 | XVI | 20 mM histidine, 125 mM NaCl | Oral | 10 [c] | 10 | 1 | 5001-5004 |
| 6 | XVI | 20 mM histidine, 125 mM NaCl | Oral | 50 [c] | 10 | 5 | 6001-6004 |
| 7 | XVIII | 20 mM histidine, 125 mM NaCl | Oral | 1 [d] | 10 | 0.1 | 7001-7004 |
| 8 | XVII | 20 mM histidine, 125 mM NaCl | Oral | 10 [d] | 10 | 1 | 8001-8004 |
| 9 | XVII | 20 mM histidine, 125 mM NaCl | Oral | 50 [d] | 10 | 5 | 9001-9004 |
| 10 | XVII | 20 mM tribasic phosphate, 125 mM NaCl | Oral | 1 [e] | 10 | 0.1 | 10001-10004 |
| 11 | XVII | 20 mM tribasic phosphate, 125 mM NaCl | Oral | 10 [e] | 10 | 1 | 11001-11004 |
| 12 | XVII | 20 mM tribasic phosphate, 125 mM NaCl | Oral | 50 [e] | 10 | 5 | 12001-12004 |
| 13 | IV | 20 mM histidine, 125 mM NaCl | IV Bolus | 1 [b] | 1 | 1 | 13001-13004 |
| 14 | XVI | 20 mM histidine, 125 mM NaCl | IV Bolus | 1 [c] | 1 | 1 | 14001-14004 |
| 15 | XVII | 20 mM histidine, 125 mM NaCl | IV Bolus | 1 [d] | 1 | 1 | 15001-15004 |
| 16 | VI | 20 mM tribasic phosphate, 125 mM NaCl | IV Bolus | 1 [e] | 1 | 1 | 16001-16004 |

[a] Dose calculated from body weight.
[b] Corrected for salt, purity and water content. Correction factor for Prodrug IV: 1.016
[c] Corrected for salt, purity and water content. Correction factor for Prodrug XVI: 1.009
[d] Corrected for salt, purity and water content. Correction factor for Prodrug XVII 1.013
[e] Corrected for salt, purity and water content. Correction factor for Prodrug VI: 1.002.

Test article formulations were administered as a single dose via oral gavage or intravenous bolus injection. The route of administration was oral (gavage) or intravenous injection (IV bolus) to assess bioavailability of each test article.

The dose levels for this study were exploratory. Prodrugs XVI, XVII and VI have not been administered to animals. Prodrug IV has not been administered by the oral or IV routes of administration to rats. These test articles are prodrugs of the active metabolite treprostinil. Treprostinil is a tricyclic benzindene analogue of the naturally occurring prostacyclin. Prostacyclin is endogenously produced by the vascular endothelium and has potent vasodilatory, antiplatelet, and anti-proliferative activity, especially on the cardiovascular system and smooth muscle. Dose levels were selected based on previous concentrations from treprostinil to provide quantifiable plasma concentrations of the parent compound and active metabolite treprostinil in each group without causing undo duress to the animals.

Throughout the study, animals were observed for general health/mortality and moribundity twice daily, once in the morning and once in the afternoon. Animals were not removed from the cage during observations, unless necessary for identification or confirmation of possible findings.

Observations

The animals were removed from the cage, and a detailed clinical observation was performed on the day of animal selection. Cage side observations were performed at 1 to 2 hours post dose. Animals were weighed individually following receipt, on the day of randomization, and on each day of dosing (prior to dosing). Individual body weights are presented below.

Bioanalysis and Pharmacokinetic Evaluation

Blood was collected via a jugular vein into chilled tubes containing NaF/KOx.

Samples were collected according to Table ww below.

Ww. Pharmacokinetic Sample Collection Schedule

| | Sample Collection Time Points (Time Post Dose) on Day 1 | | | | | | | | |
|---|---|---|---|---|---|---|---|---|---|
| Group No. | 0.083 hr | 0.25 hr | 0.5 hr | 1 hr | 2 hr | 4 hr[a] | 8 hr | 12 hr | 24 hr |
| 1  | — | — | X | X | X | X | X | X | X |
| 2  | — | — | X | X | X | X | X | X | X |
| 3  | — | — | X | X | X | X | X | X | X |
| 4  | — | — | X | X | X | X | X | X | X |
| 5  | — | — | X | X | X | X | X | X | X |
| 6  | — | — | X | X | X | X | X | X | X |
| 7  | — | — | X | X | X | X | X | X | X |
| 8  | — | — | X | X | X | X | X | X | X |
| 9  | — | — | X | X | X | X | X | X | X |
| 10 | — | — | X | X | X | X | X | X | X |
| 11 | — | — | X | X | X | X | X | X | X |
| 12 | — | — | X | X | X | X | X | X | X |
| 13 | X | X | X | X | X | — | X | X | — |
| 14 | X | X | X | X | X | — | X | X | — |
| 15 | X | X | X | X | X | — | X | X | — |
| 16 | X | X | X | X | X | — | X | X | — |

X = Sample collected; — = not applicable.
[a] = See Appendix 1—Study Protocol and Deviations Blood samples were maintained on wet ice during collection and processing. Plasma was isolated in a refrigerated centrifuge and stored in a freezer set to maintain −70° C. The plasma samples to be analyzed were shipped on dry ice via overnight courier.

Bioanalysis of plasma samples to determine prodrug (parent) and treprostinil (metabolite) concentrations were conducted using a qualified analytical procedure. Watson Laboratory Information Management System (LIMS) and Microsoft Excel were used for the collection and analysis of data.

Pharmacokinetic parameters were estimated using Phoenix pharmacokinetic software (Certara, USA) using a non-compartmental approach consistent with the route of administration. All parameters were generated from individual concentrations in plasma from all sample days. Parameters were estimated using nominal sampling times relative to each dose administration and nominal doses unless otherwise specified. Plasma concentration values obtained at the predose time point were used to estimate the concentration at time zero whenever possible. Concentration values reported as not quantifiable (BQL) were assigned a value of zero.

The area under the concentration vs. time curve (AUC) was calculated using the linear trapezoidal method with linear interpolation. The AUC was not calculated for pharmacokinetic profiles with less than 3 quantifiable concentrations of test article at separate time points. When practical, the terminal elimination phase of each concentration versus time curve was identified using at least the final three observed concentration values not including $C_{max}$. The slope of the terminal elimination phase was determined using log linear regression on the unweighted concentration data. Parameters relying on the determination of the terminal elimination phase were not reported if the coefficient of determination is less than 0.800, or if the extrapolation of the AUC to infinity represented more than 20% of the total area xx. Pharmacokinetic Parameters Estimated

| Parameter | Description of Parameter |
|---|---|
| $T_{max}$ | The time after dosing at which the maximum observed concentration is observed. |
| $C_{max}$ | The maximum observed concentration measured after dosing. |
| $C_{max}/D$ | The $C_{max}$ divided by the dose administered. |
| $AUC_{(0-t)}$ | The area under the concentration versus time curve from the start of dose administration to the time after dosing at which the last quantifiable concentration is observed, using the linear trapezoidal method. |
| $AUC_{(0-t)}/D$ | The $AUC_{(0-t)}$ divided by the dose administered. |
| $T_{1/2}$ | The apparent terminal elimination half life. |
| CL | The apparent clearance rate of the analyte from the analyzed matrix. |
| Vss | The apparent volume of distribution of the analyte in the test system. |

Terminal Procedures

All surviving animals were euthanized and discarded. A necropsy was conducted for animals that died on study, and specified tissues were saved.

Results

Male No. 9004 in the 50 mg/kg Prodrug XVI group and Male No. 12003 in the 50 mg/kg Prodrug XVII group were found dead on Day 2. No macroscopic findings were noted. All other animals survived to the scheduled euthanasia.

Test article-related clinical observations of decreased activity, cold to touch, red skin on the cranium/forelimbs/forepaws/hindlimbs/hindpaws, ungroomed fur, lying on side, and/or discharge from the eyes were noted for all oral 50 mg/kg groups (Groups 3, 6, 9, and 12) and all IV bolus 1 mg/kg groups (Groups 13, 14, 15, and 16). These findings were considered to be exaggerated pharmacology and were consistent with the pharmacodynamic response (vasodilation) of the test articles.

Pharmacokinetic Evaluations yy. Summary of Pharmacokinetic Parameters

| Dose | Route | $AUC_{all}$ (ng·hr/mL) Day 1 | $C_{max}$ (ng/mL) Day 1 | $T_{max}$ (hr) Day 1 |
|---|---|---|---|---|
| Prodrug IV | | | | |
| 1 mg/kg | Oral | N/A | 0.00 | N/A |
| 10 mg/kg | Oral | N/A | 2.68 | 0.5 |
| 50 mg/kg | Oral | 49.2 | 12.2 | 0.5 |
| 1 mg/kg | IV Bolus | 94.4 | 179 | N/A |
| Prodrug VI | | | | |
| 1 mg/kg | Oral | N/A | 0.00 | N/A |
| 10 mg/kg | Oral | N/A | 0.00 | N/A |
| 50 mg/kg | Oral | 242 | 12.4 | N/A |
| 1 mg/kg | IV Bolus | N/A | 0.00 | N/A |
| Treprostinil | | | | |
| 1 mg/kg | Oral | 16.2 | 2.86 | 2 |
| 10 mg/kg | Oral | 111 | 24.1 | 0.5 |
| 50 mg/kg | Oral | 357 | 66.7 | 0.5 |
| 1 mg/kg | Oral | 11.4 | 1.97 | 0.5 |
| 10 mg/kg | Oral | 122 | 15.5 | 24 |
| 50 mg/kg | Oral | 396 | 50.0 | N/A |
| 1 mg/kg | Oral | 21.2 | 3.86 | 2 |
| 10 mg/kg | Oral | 86.8 | 9.63 | 0.5 |
| 50 mg/kg | Oral | 508 | 83.5 | 0.5 |
| 1 mg/kg | Oral | 36.7 | 2.65 | 24 |
| 10 mg/kg | Oral | 313 | 25.9 | 1 |
| 50 mg/kg | Oral | 2230 | 170 | 24 |
| 1 mg/kg | IV Bolus | 240 | 363 | N/A |
| 1 mg/kg | IV Bolus | 192 | 263 | 0.083 |
| 1 mg/kg | IV Bolus | 274 | 466 | 0.083 |
| 1 mg/kg | IV Bolus | 129 | 179 | 0.083 |

Prodrug IV—PO Administration (Groups 1, 2, and 3)

All Prodrug IV plasma concentrations were BLQ at 1 mg/kg Prodrug IV; therefore, the following discussion of Prodrug IV is based on the data for the 10 and 50 mg/kg dose groups only.

The variability in mean Prodrug IV plasma concentrations, as measured by CV values, ranged from 40.1% to 200% following a single PO administration of Prodrug IV to animals in Groups 2 and 3. The higher variability observed was the result of BLQ values converted to zero for parameter estimates and averaged with quantifiable results. The variability in mean Prodrug IV plasma concentrations without these values ranged from 40.1% to 51.3% following a single PO administration of Prodrug IV to animals in Groups 2 and 3. Prodrug IV was quantifiable up to 1 hour postdose at 10 mg/kg and up to 1, 2, 8, or 12 hours postdose at 50 mg/kg. Individual peak Prodrug IV plasma concentrations were observed by 0.5 hours postdose at 10 mg/kg and by 0.5 or 1 hour postdose at 50 mg/kg.

Following a single PO administration of Prodrug IV to animals in Groups 2 and 3, mean $C_{max}$ values for Prodrug IV increased with increasing dose from 10 to 50 mg/kg. A 5-fold increase in prodrug IV dose (10 to 50 mg/kg) resulted in an approximate 4.6-fold increase in mean Prodrug IV $C_{max}$ values. $AUC_{0-24hr}$ for Prodrug IV could only be reported for a single animal at 50 mg/kg (Animal No. 3003) and was 49.2 hr*ng/mL.

$AUC_{INF}$, $T_{1/2}$, Cl/F, and $V_z$/F values for Prodrug IV could only be reported for a single animal at 50 mg/kg (Animal No. 3001) and were 65.4 hr*ng/mL, 4.27 hours, 764000 mL/hr/kg, and 4710000 mL/kg, respectively.

Prodrug IV—IV Bolus Injection (Group 13)

The variability in mean Prodrug IV plasma concentrations, as measured by CV values, ranged from 53.0% to 120% following a single IV bolus injection of Prodrug IV to animals in Group 13. Prodrug IV was quantifiable up to 1 or 2 hours postdose and the estimated concentration at time zero ($C_0$) was determined; however, both $C_{max}$ and $T_{max}$ values were reported due to increases observed in Prodrug IV concentrations between the 0.083 and 0.5 hour collection intervals for two males (Animal No. 13002 and 13004). Individual peak Prodrug IV plasma concentrations were observed by 0.083 or 0.5 hours postdose.

Following a single IV bolus injection of Prodrug IV to animals in Group 13, mean $C_0$, $C_{max}$, and $AUC_{0-12hr}$ values for Prodrug IV were 324 ng/mL, 179 ng/mL, and 94.4 hr*ng/mL, respectively. Individual $C_0$ values ranged from 65.6 to 759 ng/mL, individual $C_{max}$ values ranged from 150 to 209 ng/mL, and individual $AUC_{0-12hr}$ values ranged from 42.3 to 155 hr*ng/mL.

Mean $AUC_{INF}$, $T_{1/2}$, Cl, and $V_z$ values for Prodrug IV following a single IV bolus injection of Prodrug IV were 98.7 hr*ng/mL, 0.212 hours, 13400 mL/hr/kg, and 3150 mL/kg, respectively. Individual $AUC_{INF}$ values ranged from 41.5 to 144 hr*ng/mL, individual $T_{1/2}$ values ranged from 0.0910 to 0.276 hours, individual Cl values ranged from 6940 to 24100 mL/hr/kg, and individual $V_z$ values ranged from 2690 to 3610 mL/kg.

Prodrug IV Bioavailability

Dose normalized systemic exposure ($AUC_{all}$/Dose) to Prodrug IV was lower following a single PO administration of Prodrug IV at 50 mg/kg when compared to a single IV bolus injection of 1 mg/kg Prodrug IV. The PO bioavailability (% F) value, based on mean $AUC_{all}$/Dose, was 1.04% at 50 mg/kg Prodrug IV.

Treprostinil—PO Administration of Prodrug IV (Groups 1, 2, and 3)

The variability in mean treprostinil plasma concentrations, as measured by CV values, ranged from 25.4% to 89.9% following a single PO administration of Prodrug IV to animals in Groups 1 through 3. Treprostinil was quantifiable up to 4 or 8 hours postdose at 1 mg/kg Prodrug IV, and up to 24 hours postdose at 10 and 50 mg/kg Prodrug IV. Individual peak treprostinil plasma concentrations were observed by 0.5 or 2 hours postdose at 1 mg/kg Prodrug IV and by 0.5 hours postdose at 10 and 50 mg/kg Prodrug IV.

Following a single PO administration of Prodrug IV to animals in Groups 1 through 3, mean $C_{max}$ and $AUC_{0-24hr}$ values for treprostinil increased with increasing dose. A 1:10:50-fold increase in Prodrug IV dose resulted in an approximate 1:8.4:23.3-fold increase in mean treprostinil $C_{max}$ values and an approximate 1:6.9:22.0-fold increase in mean treprostinil $AUC_{0-24hr}$ values.

Systemic exposure ($AUC_{0-24hr}$) to treprostinil was greater than systemic exposure to Prodrug IV following a single PO administration of 50 mg/kg Prodrug IV to Animal No. 3003 and the individual M:P $AUC_{0-24hr}$ ratio was 7.60 (only a single M:P $AUC_{0-24hr}$ ratio was reported due to limited data available for Prodrug IV).

Secondary parameters ($AUC_{INF}$, $T_{1/2}$, Cl/F, and $V_z/F$) for treprostinil could not be reported for any animal in Groups 1 through 3 due to an adjusted $R^2$ value less than 0.9 or insufficient plasma concentration-time data.

Treprostinil—IV Bolus Injection of Prodrug IV
(Group 13)

The variability in mean treprostinil plasma concentrations, as measured by CV values, ranged from 27.4% to 102% following a single IV bolus injection of Prodrug IV to animals in Group 13. Treprostinil was quantifiable up to 2 hours postdose and the estimated concentration at time zero ($C_0$) was determined; however, both $C_{max}$ and $T_{max}$ values were reported due to increases observed in treprostinil concentrations between the 0.083 and 0.5 hour collection intervals for two males (Animal No. 13002 and 13004). Individual peak treprostinil plasma concentrations were observed by 0.083 or 0.5 hours postdose.

Following a single IV bolus injection of Prodrug IV to animals in Group 13, mean $C_0$, $C_{max}$, and $AUC_{0-12hr}$ values for treprostinil were 538 ng/mL, 363 ng/mL, and 240 hr*ng/mL, respectively. Individual $C_0$ values ranged from 208 to 1000 ng/mL, individual $C_{max}$ values ranged from 199 to 581 ng/mL, and individual $AUC_{0-12hr}$ values ranged from 153 to 367 hr*ng/mL.

Systemic exposure ($AUC_{0-12hr}$) to treprostinil was greater than systemic exposure to Prodrug IV following a single IV bolus injection of 1 mg/kg Prodrug IV. The mean M:P $AUC_{0-12hr}$ ratio was 2.94 and individual M:P $AUC_{0-12hr}$ ratios ranged from 1.40 to 3.64.

Mean $AUC_{INF}$, $T_{1/2}$, Cl, and $V_z$ values for treprostinil following a single IV bolus injection of Prodrug IV were 217 hr*ng/mL, 0.332 hours, 4980 mL/hr/kg, and 2350 mL/kg, respectively. Individual $AUC_{INF}$ values ranged from 144 to 312 hr*ng/mL, individual $T_{1/2}$ values ranged from 0.234 to 0.408 hours, individual Cl values ranged from 3200 to 6930 mL/hr/kg, and individual $V_z$ values ranged from 1530 to 3300 mL/kg.

Treprostinil Bioavailability Following
Administration of Prodrug IV

Dose normalized systemic exposure ($AUC_{all}$/Dose) to treprostinil was lower following a single PO administration of IV when compared to a single IV bolus injection of Prodrug IV. The PO bioavailability (% F) values, based on mean $AUC_{all}$/Dose, were 6.75%, 4.63%, and 2.98% at 1, 10, and 50 mg/kg Prodrug IV, respectively.

Treprostinil—PO Administration of Prodrug XVI
(Groups 4, 5, and 6)

The variability in mean treprostinil plasma concentrations, as measured by CV values, ranged from 15.7% to 200% following a single PO administration of Prodrug XVI to animals in Groups 4 through 6. The higher variability observed was the result of BLQ values converted to zero for parameter estimates and averaged with quantifiable results. The variability in mean treprostinil plasma concentrations without these values ranged from 15.7% to 120% following a single PO administration of Prodrug XVI to animals in Groups 4 through 6. Treprostinil was quantifiable up to 1, 8, or 12 hours postdose at 1 mg/kg Prodrug XVI, and up to 24 hours postdose at 10 and 50 mg/kg Prodrug XV. Individual peak treprostinil plasma concentrations were observed at 0.5 or 4 hours postdose at 1 mg/kg Prodrug XVI, at 0.5, 1, or 4 hours postdose at 10 mg/kg Prodrug XV, and at 0.5 or 1 hour postdose at 50 mg/kg Prodrug XVI.

Following a single PO administration of Prodrug XVI to animals in Groups 4 through 6, mean $C_{max}$ and $AUC_{0-24hr}$ values for treprostinil increased with increasing dose. A 1:10:50-fold increase in Prodrug XV dose resulted in an approximate 1:7.9:25.4-fold increase in mean treprostinil $C_{max}$ values and an approximate 1:10.7:34.7-fold increase in mean treprostinil $AUC_{0-24hr}$ values. M:P ratios could not be determined due to insufficient data available for Prodrug XVI (all Prodrug XVI plasma concentrations were BLQ). Secondary parameters ($AUC_{INF}$, $T_{1/2}$, Cl/F, and $V_z/F$) for treprostinil could not be reported for any animal in Groups 4 through 6 due to an adjusted $R^2$ value less than 0.9 or insufficient plasma concentration-time data.

Treprostinil—IV Bolus Injection of Prodrug XVI
(Group 14)

The variability in mean treprostinil plasma concentrations, as measured by CV values, ranged from 15.2% to 92.8% following a single IV bolus injection of Prodrug XVI to animals in Group 14. Treprostinil was quantifiable up to 2 hours postdose and the estimated concentration at time zero ($C_0$) was determined; however, both $C_{max}$ and $T_{max}$ values were reported due to increases observed in treprostinil concentrations between the 0.083 and 0.5 hour collection intervals for a single male (Animal No. 14003). Individual peak treprostinil plasma concentrations were observed by 0.083 or 0.5 hours postdose.

Following a single IV bolus injection of Prodrug XVI to animals in Group 14, mean $C_0$, $C_{max}$, and $AUC_{0-12hr}$ values for treprostinil were 549 ng/mL, 263 ng/mL, and 192 hr*ng/mL, respectively. Individual $C_0$ values ranged from 21.4 to 1170 ng/mL, individual $C_{max}$ values ranged from 63.7 to 504 ng/mL, and individual $AUC_{0-12hr}$ values were 171 and 214 hr*ng/mL. M:P ratios could not be determined due to insufficient data available for Prodrug XVI (all Prodrug XVI plasma concentrations were BLQ). $AUC_{INF}$, Cl, and $V_z$ values for treprostinil could only be estimated for a single animal following a single PO administration of Prodrug XVI (Animal No. 14001) and were 183 hr*ng/mL, 5470 mL/hr/kg, and 5700 mL/kg, respectively. The mean $T_{1/2}$ value for treprostinil was hours (individual $T_{1/2}$ values were 0.722 and 1.10 hours).

Treprostinil Bioavailability Following
Administration of Prodrug XVI

Dose normalized systemic exposure ($AUC_{all}$/Dose) to treprostinil was lower following a single PO administration of Prodrug XVI when compared to a single IV bolus injection of Prodrug XVI. The PO bioavailability (% F) values, based on mean $AUC_{all}$/Dose, were 5.94%, 6.35%, and 4.13% at 1, 10, and 50 mg/kg, respectively.

Treprostinil—PO Administration of Prodrug XVII (Groups 7, 8, and 9)

The variability in mean treprostinil plasma concentrations, as measured by CV values, ranged from 4.98% to 174% following a single PO administration of Prodrug XVII to animals in Groups 7 through 9. Treprostinil was quantifiable up to 8 hours postdose at 1 mg/kg Prodrug XVI, up to 24 hours postdose at 10 mg/kg Prodrug XVI, and up to 12 or 24 hours postdose at 50 mg/kg Prodrug XVII. Individual peak treprostinil plasma concentrations were observed by 0.5 or 2 hours postdose at mg/kg Prodrug XVII, by 0.5 or 24 hours postdose at 10 mg/kg Prodrug XVII, and by 0.5 or 8 hours postdose at 50 mg/kg Prodrug XVI.

Following a single PO administration of Prodrug XVII to animals in Groups 7 through 9, mean $C_{max}$ and $AUC_{0-24hr}$ values for treprostinil increased with increasing dose. A 1:10:50-fold increase in Prodrug XVII dose resulted in an approximate 1:2.5:21.6-fold increase in mean treprostinil $C_{max}$ values and an approximate 1:4.1:24.0-fold increase in mean treprostinil $AUC_{0-24hr}$ values. M:P ratios could not be determined due to insufficient data available for Prodrug XVII (all Prodrug XVII plasma concentrations were BLQ). Secondary parameters ($AUC_{INF}$, $T_{1/2}$, Cl/F, and $V_z/F$) for treprostinil could not be reported for any animal in Groups 7 through 9 due to an adjusted $R^2$ value less than 0.9 or insufficient plasma concentration-time data.

Treprostinil—IV Bolus Injection of Prodrug XVII (Group 15)

The variability in mean treprostinil plasma concentrations, as measured by CV values, ranged from 42.1% to 200% following a single IV bolus injection of Prodrug XVII to animals in Group 15. The higher variability observed was the result of BLQ values converted to zero for parameter estimates and averaged with quantifiable results. The variability in mean treprostnil plasma concentrations without these values ranged from 42.1% to 81.1% following a single IV bolus injection of Prodrug XVII to animals in Group 15. Treprostinil was quantifiable up to 2 or 8 hours postdose and the estimated concentration at time zero ($C_0$) was determined; however, both $C_{max}$ and $T_{max}$ values were reported due to increases observed in treprostinil concentrations between the 0.083 and 0.5-hour collection intervals for a single male (Animal No. 15002). Individual peak treprostinil plasma concentrations were observed by 0.083 or 0.5 hours postdose.

Following a single IV bolus injection of Prodrug XVII to animals in Group 15, mean $C_0$, $C_{max}$, and $AUC_{0-12hr}$ values for treprostinil were 1350 ng/mL, 466 ng/mL, and 274 hr*ng/mL, respectively. Individual $C_0$ values ranged from 227 to 3320 ng/mL, individual $C_{max}$ values ranged from 254 to 917 ng/mL, and individual $AUC_{0-12hr}$ values ranged from 167 to 413 hr*ng/mL. M:P ratios could not be determined due to insufficient data available for Prodrug XVII (all Prodrug XVII plasma concentrations were BLQ). Secondary parameters ($AUC_{INF}$, $T_{1/2}$, Cl, and $V_z$) for treprostinil could not be reported for any animal in Group 15 due to adjusted $R^2$ values less than 0.9.

Treprostinil Bioavailability Following Administration of Prodrug XVII

Dose normalized systemic exposure ($AUC_{all}$/Dose) to treprostinil was lower following a single PO administration of Prodrug XVII when compared to a single IV bolus injection of Prodrug XVII. The PO bioavailability (% F) values, based on $AUC_{all}$/Dose, were 7.74%, 3.17%, and 3.72% at 1, 10, and 50 mg/kg Prodrug XVI, respectively.

Prodrug VI—PO Administration (Groups 10, 11, and 12)

All Prodrug VI plasma concentrations were BLQ at 1 and 10 mg/kg Prodrug VI; therefore, the following discussion of Prodrug VI is based on the data for the 50 mg/kg Prodrug VI dose group only. The variability in mean Prodrug VI plasma concentrations, as measured by CV values, ranged from 38.4% to 173% following a single PO administration of Prodrug VI to animals in Group 12. The higher variability observed was the result of BLQ values converted to zero for parameter estimates and averaged with quantifiable results. The variability in mean Prodrug VI plasma concentrations without these values ranged from 38.4% to 69.8% following a single PO administration of Prodrug XVII to animals in Group 12. Prodrug VI was quantifiable up to 2, 4, 8, or 24 hours postdose at 50 mg/kg Prodrug VI. Individual peak Prodrug VI plasma concentrations were observed by 0.5, 8, or 24 hours postdose at 50 mg/kg Prodrug VI.

Following a single PO administration of 50 mg/kg Prodrug VI to animals in Group 12, mean $C_{max}$ and $AUC_{0-24hr}$ values for Prodrug VI were 12.4 ng/mL and 242 hr*ng/mL, respectively. Individual $C_{max}$ values ranged from 4.14 to 32.8 ng/mL at 50 mg/kg Prodrug VI and individual $AUC_{0-24hr}$ values were 26.5 and 457 hr*ng/mL at 50 mg/kg Prodrug VI.

$AUC_{INF}$, $T_{1/2}$, Cl/F, and $V_z/F$ values for Prodrug VI could only be reported for a single animal at 50 mg/kg (Animal No. 12004) and were 28.2 hr*ng/mL, 1.76 hours, 1780000 mL/hr/kg, and 4520000 mL/kg, respectively.

Treprostinil—PO Administration of Prodrug VI (Groups 10, 11, and 12)

The variability in mean treprostinil plasma concentrations, as measured by CV values, ranged from 13.8% to 150% following a single PO administration of Prodrug VI to animals in Groups 10 through 12. Treprostinil was quantifiable up to 24 hours postdose at 1 and 10 mg/kg Prodrug VI, and up to 8 or 24 hours postdose at 50 mg/kg Prodrug VI. Individual peak treprostinil plasma concentrations were observed by 1, 2 or 4 hours postdose at 1 mg/kg Prodrug VI, by 1 or 2 hours postdose at 10 mg/kg Prodrug XVII, and by 2, 8, or 12 hours postdose at 50 mg/kg Prodrug VI.

Following a single PO administration of Prodrug VI to animals in Groups 10 through 12, mean $C_{max}$ and $AUC_{0-24hr}$ values for treprostinil increased with increasing dose. A 1:10:50-fold increase in Prodrug VI dose resulted in an approximate 1:9.8:64.2-fold increase in mean treprostinil $C_{max}$ values and an approximate 1:8.5:60.8-fold increase in mean treprostinil $AUC_{0-24hr}$ values.

Systemic exposure ($AUC_{0-24hr}$) to treprostinil was greater than the systemic exposure to Prodrug VI following a single PO administration of 50 mg/kg Prodrug VI to Animal No. 12002 and 12004 and the M:P ratios were 12.1 and 30.0, respectively (only two M:P $AUC_{0-24hr}$ ratios could be reported due to limited data available for Prodrug VI). The mean M:P ratio was 21.0.

Secondary parameters ($AUC_{INF}$, $T_{1/2}$, Cl/F, and $V_z/F$) for treprostinil could not be reported at 10 or 50 mg/kg Prodrug VI due to adjusted $R^2$ values less than 0.9, insufficient plasma concentration—time data, or % $AUC_{Extrap}$ values for $AUC_{INF}$ greater than 25%. Mean $AUC_{INF}$, $T_{1/2}$, Cl/F, and $V_z/F$ values for treprostinil were 38.4 hr*ng/mL, 14.0 hours, 26900 mL/hr/kg, and 243000 mL/kg, respectively at 1 mg/kg Prodrug VI. Individual $AUC_{INF}$ values ranged from 31.7 to 48.4 hr*ng/mL, individual $T_{1/2}$ values ranged from 4.71 to 36.9 hours (the $T_{1/2}$ value of 36.9 hours was estimated from less than three half-lives of data and should be viewed with caution, individual $T_{1/2}$ values ranged from 4.71 to 7.35 hours, otherwise), individual Cl/F values ranged from 20700 to 31600 mL/hr/kg, and individual $V_z/F$ values ranged from 194000 to 316000 mL/kg.

Treprostinil—IV Bolus Injection of Prodrug VI
(Group 16)

The variability in mean treprostinil plasma concentrations, as measured by CV values, ranged from 17.6% to 71.2% following a single IV bolus injection of Prodrug VI to animals in Group 16. The higher variability observed was the result of BLQ values converted to zero for parameter estimates and averaged with quantifiable results. The variability in mean treprostinil plasma concentrations without these values ranged from 17.6% to 48.4% following a single IV bolus injection of Prodrug VI to animals in Group 16. Treprostinil was quantifiable up to 8 or 12 hours postdose and the estimated concentration at time zero ($C_0$) was determined.

Following a single IV bolus injection of Prodrug VI to animals in Group 16, mean $C_0$ and $AUC_{0-12hr}$ values for treprostinil were 277 ng/mL and 129 hr*ng/mL, respectively. Individual $C_0$ values ranged from 207 to 454 ng/mL and individual $AUC_{0-12hr}$ values ranged from 97.4 to 158 hr*ng/mL. M:P ratios could not be determined due to insufficient data available for (all Prodrug VI plasma concentration were BLQ).

Mean $AUC_{INF}$, $T_{1/2}$, Cl, and $V_z$ values for treprostinil following a single IV bolus administration injection of Prodrug VI were 130 hr*ng/mL, 1.90 hours, 7920 mL/hr/kg, and 22000 mL/kg, respectively. Individual $AUC_{INF}$ values ranged from 99.0 to 159 hr*ng/mL, individual $T_{1/2}$ values ranged from 1.60 to 2.28 hours, individual Cl values ranged from 6290 to 10100 mL/hr/kg, and individual $V_z$ values ranged from 16800 to 33200 mL/kg.

Treprostinil Bioavailability Following
Administration of Prodrug VI

Dose normalized systemic exposure ($AUC_{all}$/Dose) to treprostinil was lower following a single PO administration of Prodrug VI when compared to a single IV bolus injection of Prodrug VI. The PO bioavailability (% F) values, based on $AUC_{all}$/Dose, were 28.4%, 24.3%, and 34.7% at 1, 10, and 50 mg/kg Prodrug XVII, respectively.

CONCLUSIONS

Based on the results of this study, single oral or IV bolus administration of Prodrugs IV, XVI, XVII and VI to Crl: CD(SD) rats at dose levels of 1, 10, and 50 mg/kg resulted in lethality at oral 50 mg/kg Prodrug XVII and oral 50 mg/kg Prodrug VI and adverse clinical observations at IV bolus 1 mg/kg and oral 50 mg/kg for all 4 test articles.

Example 4: Prodrugs IV, XVI, XVII and VI: A
Pharmacokinetic Evaluation Following a Single
Oral Gavage or Intravenous Administration in
Sprague Dawley Rats List of Abbreviations Adjusted Rsq ($R^2$) Goodness of fit statistic for the terminal elimination phase % $AUC_{Extrap}$ The percent of $AUC_{0-24hr}$ extrapolated from $T_{last}$ to 12 and/or 24 hours and/or the percent of $AUC_{INF}$ extrapolated from $T_{last}$ to infinity $AUC_{all}$ Area under the plasma concentration-time curve from time zero to 12 hours (IV Bolus injection only) or 24 hours (Oral administration only)

$AUC_{all}$/Dose Area under the plasma concentration-time curve from time zero to 12 hours (IV Bolus injection only) or 24 hours (Oral administration only) normalized for dose $AUC_{0-12hr}$ Area under the plasma concentration-time curve from time zero to 12 hours $AUC_{0-24hr}$ Area under the plasma concentration-time curve from time zero to 24 hours $AUC_{INF}$ Area under the plasma concentration-time curve from time zero extrapolated to infinity $AUC_{INF}$/Dose Area under the plasma concentration-time curve from time zero extrapolated to infinity based on the last predicted concentration normalized for dose $AUC_{Tlast}$ Area under the plasma concentration-time curve from time zero to the time of the final quantifiable sample BLQ, BQL Below the limit of quantitation $C_0$ Estimated concentration at time zero $C_0$/Dose Estimated concentration at time zero normalized for dose $C_{max}$ Maximum observed plasma concentration $C_{max}$/Dose Maximum observed plasma concentration normalized for dose Cl Total body clearance Cl/F Total body clearance divided by the fraction of dose absorbed CV Coefficient of variation, expressed as a percent F Bioavailability, fraction of dose absorbed relative to IV dosing, expressed as a percent hr Interval of collection, hours postdose IV Intravenous LLOQ Lower limit of quantitation M:P Metabolite to parent exposure ratio N Number of values used to calculate statistics NA Not applicable PO Oral SD Standard deviation $T_{1/2}$ Terminal half-life=$\ln(2)/\lambda_z$ $T_{last}$ Time of final quantifiable sample $T_{max}$ Time of maximum observed plasma concentration $V_z$ Volume of distribution based on terminal elimination phase $V_z/F$ Volume of distribution based on terminal elimination phase divided by the fraction of dose absorbed $\lambda_z$ Terminal elimination rate constant

TABLE 1

| Study Description | |
|---|---|
| Objective: | The pharmacokinetic objective of this study was to assess the exposure to Prodrugs IV, XV, XVI and XVII, and metabolite, treprostinil, following oral gavage administration or intravenous (IV) bolus |

TABLE 1-continued

| | |
|---|---|
| Compliance: | injection of Prodrugs IV, XV, XVI and XVII, and to male rats during a pharmacokinetic evaluation study. This study phase was conducted in accordance with MPI Research Standard Operating Procedures (SOPs) and the protocol as approved. This study phase was not intended to be conducted in accordance with the United States Food and Drug Administration (FDA) Good Laboratory Practice (GLP) Regulations, 21 Code of Federal Regulations (CFR) Part 58. |

Study Design

| | |
|---|---|
| Vehicles: | Prodrug IV: 20 mM Histidine, 125 mM NaCl<br>Prodrug XVI: 20 mM Histidine, 125 mM NaCl<br>Prodrug XVII 20 mM Histidine, 125 mM NaCl<br>Prodrug VI 20 mM Tribasic Phosphate, 125 mM NaCl |
| Test Article Formulations: | Prodrug IV (side chain carbonate ester prodrug of treprostinil) in 20 mM Histidine, 125 mM NaCl<br>Prodrug XVI (side chain ethyl carbonate of treprostinil) in 20 mM Histidine, 125 mM NaCl<br>Prodrug XVII (side chain isopropyl carbonate of treprostinil) in 20 mM Histidine, 125 mM NaCl<br>Prodrug VI (treprostinil side-chain phosphate ester) in 20 mM Tribasic Phosphate, 125 mM NaCl |
| Frequency and Routes of Exposure: | Once on Day 1 by oral (PO) gavage administration or IV bolus injection |
| Doses: | Oral: 1, 10, and 50 mg/kg Prodrugs IV, XVI, XVII or VI<br>IV Bolus: 1 mg/kg Prodrugs IV, XVI, XVII or VI |
| Test System: | CD ® [Crl: CD ®(SD)] rat |

Group Assignments

| Group | Prodrug[a] | Route | Dose Level (mg/kg) | Dose Volume (mL/kg) | Dose Concentration (mg/mL) | Animal Nos. Males |
|---|---|---|---|---|---|---|
| 1 | IV | Oral | 1[b] | 10 | 0.1 | 1001, 1002, 1003, 1004 |
| 2 | IV | Oral | 10[b] | 10 | 1 | 2001, 2002, 2003, 2004 |
| 3 | IV | Oral | 50[b] | 10 | 5 | 3001, 3002, 3003, 3004 |
| 4 | XVI | Oral | 1[c] | 10 | 0.1 | 4001, 4002, 4003, 4004 |
| 5 | XVI | Oral | 10[c] | 10 | 1 | 5001, 5002, 5003, 5004 |
| 6 | XVI | Oral | 50[c] | 10 | 5 | 6001, 6002, 6003, 6004 |
| 7 | XVII | Oral | 1[d] | 10 | 0.1 | 7001, 7002, 7003, 7004 |
| 8 | XVII | Oral | 10[d] | 10 | 1 | 8001, 8002, 8003, 8004 |
| 9 | XVII | Oral | 50[d] | 10 | 5 | 9001, 9002, 9003, 9004 |
| 10 | VI | Oral | 1[e] | 10 | 0.1 | 10001, 10002, 10003, 10004 |
| 11 | VI | Oral | 10[e] | 10 | 1 | 11001, 11002, 11003, 11004 |
| 12 | VI | Oral | 50[e] | 10 | 5 | 12001, 12002, 12003, 12004 |
| 13 | IV | IV Bolus | 1[b] | 1 | 1 | 13001, 13002, 13003, 13004 |
| 14 | XVI | IV Bolus | 1[c] | 1 | 1 | 14001, 14002, 14003, 14004 |
| 15 | XVII | IV Bolus | 1[d] | 1 | 1 | 15001, 15002, 15003, 15004 |
| 16 | VI | IV Bolus | 1[e] | 1 | 1 | 16001, 16002, 16003, 16004 |

Sample Collection and Analysis

| | |
|---|---|
| Samples: | Oral gavage administration: Blood (plasma) collection at approximately 0.5, 1, 2, 4, 8, 12, and 24 hours postdose.<br>IV bolus injection: Blood (plasma) collection at approximately 0.083, 0.25, 0.5, 1, 2, 8, and 12 hours postdose. |
| Sample Analysis: | Plasma samples were analyzed for concentrations by Covance, Salt Lake City, Utah. |

TABLE 1-continued

| Computer Software | |
|---|---|
| Program | Version/Release |
| Pharsight ® Knowledgebase | 04.0.3 |
| Server ™ Phoenix | 6.3 |
| WinNonlin ® | 3.0 |
| MPI Research ExyLIMS | 7.4 |
| Watson ™ LIMS | |

[a]Dose calculated from body weight.
[b]Corrected for salt, purity, and water content. Correction factor for Prodrug IV 1.016.
[c]Corrected for salt, purity, and water content. Correction factor for Prodrug XVI 1.009.
[d]Corrected for salt, purity, and water content. Correction factor for Prodrug XVII 1.013.
[e]Corrected for salt, purity, and water content. Correction factor for VI 1.002.

Study Method

Individual Prodrugs IV, XVI, XVII and VI, and treprostinil plasma concentration-time profiles from Prodrugs IV, XVI, XVII or VI-treated animals were analyzed using model-independent methods. The IV bolus model was used for the pharmacokinetic data analysis of the IV bolus dose groups for both prodrug and treprostinil due to the rapid conversion of prodrug to treprostinil. Pharmacokinetic parameters were obtained for each animal following a single PO or IV bolus dose of Prodrugs IV, XVI, XVII or VI Concentrations less than the lower limit of quantitation (LLOQ<2 ng/mL for Prodrugs IV and VI and <1.00 ng/mL for Prodrugs XVI and XVII, and <0.2 ng/mL or <1.00 ng/mL for treprostinil) were set to 0 for pharmacokinetic analysis.

For each animal, the following pharmacokinetic parameters were determined: estimated concentration at time 0. ($C_0$, IV bolus dose groups only), maximum observed plasma concentration ($C_{max}$), time of maximum observed plasma concentration ($T_{max}$), and area under the plasma concentration-time curve (AUC). The AUC from time 0 to 12 hours ($AUC_{0-12hr}$, IV bolus dose groups only), the AUC from time 0 to 24 hours ($AUC_{0-24hr}$, PO dose groups only), the AUC from time 0 to the time of the final quantifiable sample ($AUC_{Tlast}$), and the AUC from time 0 to infinity ($AUC_{INF}$) were calculated by the linear trapezoidal method for all animals with at least 3 consecutive quantifiable concentrations. For Day 1, 0 was used as an estimate of the 0-hour concentration for the PO dose groups. Half-life values ($T_{1/2}$) were reported for each plasma concentration-time profile that had sufficient plasma concentrations in the terminal elimination phase (at least 3 samples not including $T_{max}$) and an adjusted $R^2$ of ≥0.9. Additional pharmacokinetic parameters calculated were clearance (Cl, IV bolus dose groups only), clearance divided by fraction of dose absorbed (Cl/F, PO dose groups only), volume of distribution ($V_z$, IV bolus dose groups only), and volume of distribution divided by the fraction of dose absorbed ($V_z/F$, PO dose groups only). Secondary parameters for PO dose groups ($V_z/F$ or Cl/F) were not normalized for the fraction of dose absorbed.

The metabolite to parent ratio (M:P) were calculated for each animal, if appropriate, using the following formula:

IV Bolus Groups: M:P=$AUC_{0-12hr}$
Treprostinil÷$AUC_{0-12hr}$ Prodrugs IV, XVI, XVII or VI PO Groups: M:P=$AUC_{0-24hr}$ Treprostinil÷$AUC_{0-24hr}$
Prodrugs IV, XVI, XVII or VI When $T_{last}$ did not equal the last collection interval, the percent of AUC extrapolated (% $AUC_{Extrap}$) for $AUC_{0-12}$ hr (IV bolus dose groups) or $AUC_{0-24hr}$ (PO dose groups) was calculated as:

$$\% \ AUC_{Extrap} \text{ for } AUC_{0-12 \ hr} = [(AUC_{0-12 \ hr} - AUC_{Tlast})/AUC_{0-12 \ hr}] \times 100\% \ AUC_{Extrap} \text{ for}$$

$$AUC_{0-24 \ hr} = [(AUC_{0-24 \ hr} - AUC_{Tlast})/AUC_{0-24 \ hr}] \times 100$$

The percent of AUC extrapolated (% $AUC_{Extrap}$) for $AUC_{INF}$ was calculated as:

$$\% \ AUC_{Extrap} = [(AUC_{INF} - AUC_{Tlast})/AUC_{INF}] \times 100$$

AUC values calculated with greater than 25% extrapolation and % $AUC_{Extrap}$ values were not reported but are maintained in the study file.

Data Exclusions

No data exclusions were performed for pharmacokinetic data analysis.

Information

Following a single IV bolus injection Prodrugs XVI, XVII and VI. All Prodrug XVI, XVII or VI plasma concentrations were BQL (<1.00 ng/mL); therefore mean plasma concentrations and pharmacokinetic parameters for Prodrugs XVI, XVII and VI were not reported or discussed for Groups 14, 15, and 16.

Following a single oral administration of Prodrug XVI or XVII, all Prodrug XVI or XVII plasma concentrations were BQL (<1.00 ng/mL); therefore, mean plasma concentrations and pharmacokinetic parameters for Prodrugs XVI and XVII were not reported or discussed for Groups 4 through 9.

Following a single IV bolus injection of Prodrug IV or oral administration of Prodrug IV or VI, the majority of Prodrug IV or VI plasma concentrations were BQL (<2.00 ng/mL); therefore mean plasma concentrations and pharmacokinetic parameters were reported, where applicable, for informational purposes and the following discussion for Groups 1 through 3 (Prodrug IV), Groups 10 through 12 (Prodrug VI), and Group 13 (Prodrug IV) was limited to the available data and general trends observed.

The Prodrug IV and treprostinil plasma concentration-time profiles for two males at 1 mg/kg Prodrug IV (Animal No. 13002 and 13004) and the treprostinil plasma concentration-time profiles for one male at 1 mg/kg Prodrug XV (Animal No. 14003) and one male at 1 mg/kg Prodrug XVII (Animal No. 15002) had an increase in Prodrug IV or treprostinil plasma concentrations between the 0.083- and the 0.5-hour collection interval. Due to the increase observed in the aforementioned animals, both $C_0$ $C_{max}$, and $T_{max}$ were reported.

One male at 50 mg/kg Prodrug XVII (Animal No. 9003) was found dead prior to the 24 hour collection; therefore, a sample was not collected.

A sample was not obtained for one male at 50 mg/kg Prodrug XVII (Animal No. 12003) at 4 hours postdose due to the animal struggling during blood collection. Animal No. 12003 was found dead prior to the 12-hour collection; therefore, samples were not collected at 12 or 24 hours postdose.

The following samples collected at 12 hours postdose were not analyzed due to the sample clotting:

Group 3 (50 mg/kg prodrug IV): male Animal No. 3001
Group 5 (10 mg/kg Prodrug XVI): male Animal No. 5002
Group 10 (1 mg/kg Prodrug XVII): male Animal No. 10003
Group 11 (10 mg/kg Prodrug VI): male Animal No. 11004

Results

Figure 2:
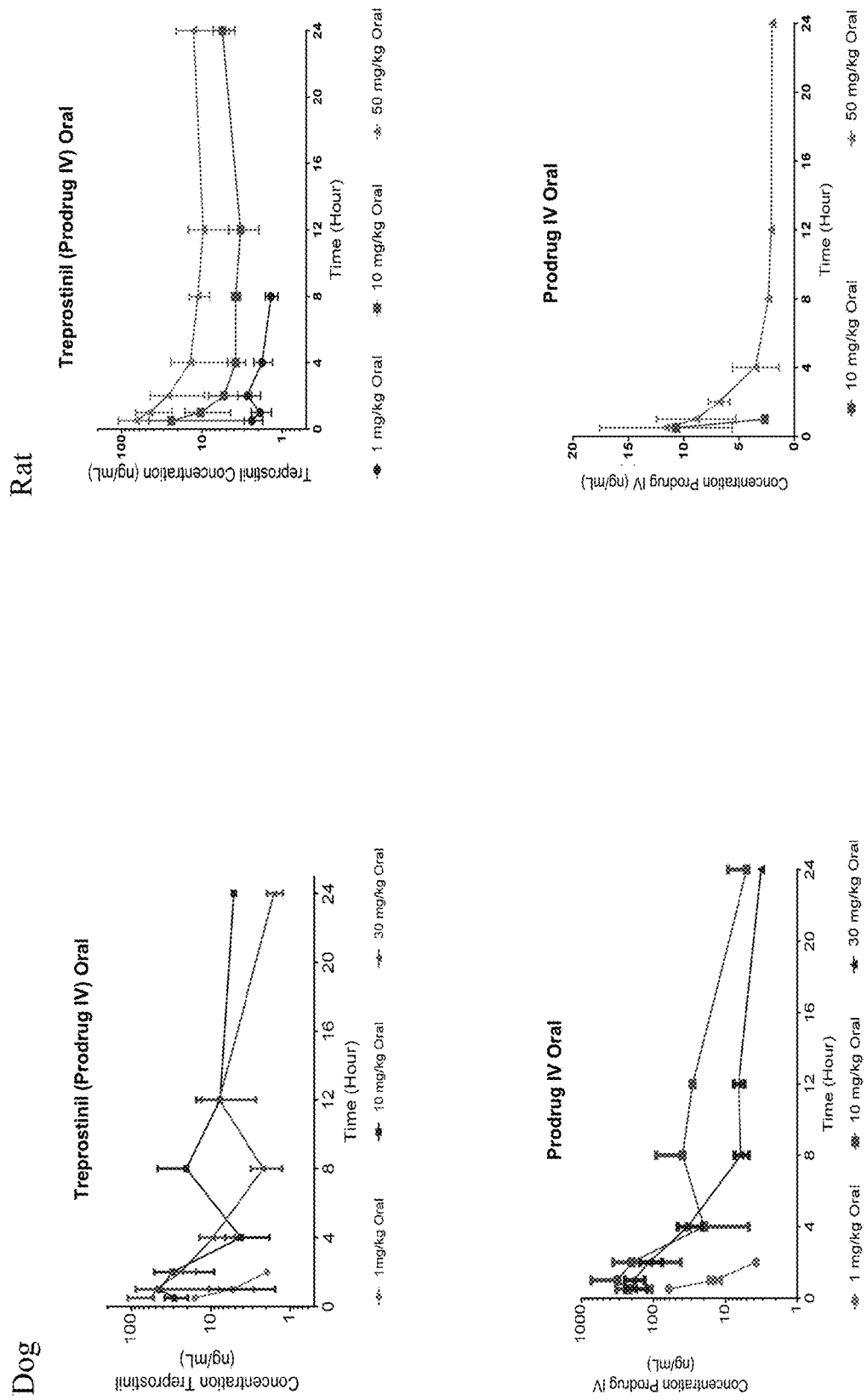
FIG. 2: Mean (±SD) Prodrug IV (bottom two graphs) and Treprostinil (top two graphs) Plasma Concentration-Time Profiles Following a Single Oral Gavage Administration of 1, 10, and 30 mg/kg (dogs)/50 mg/kg (rats) Prodrug IV to dogs (left graphs) and rats (right graphs).
Figure 3:
FIG. 3: Mean (±SD) Treprostinil Plasma Concentration-Time Profiles Following a Single Oral Gavage Administration of 1, 10, and 50 mg/kg Prodrug XVII to rats or 10 or 30 mg/kg Prodrug XVII to dogs.
Figure 4:
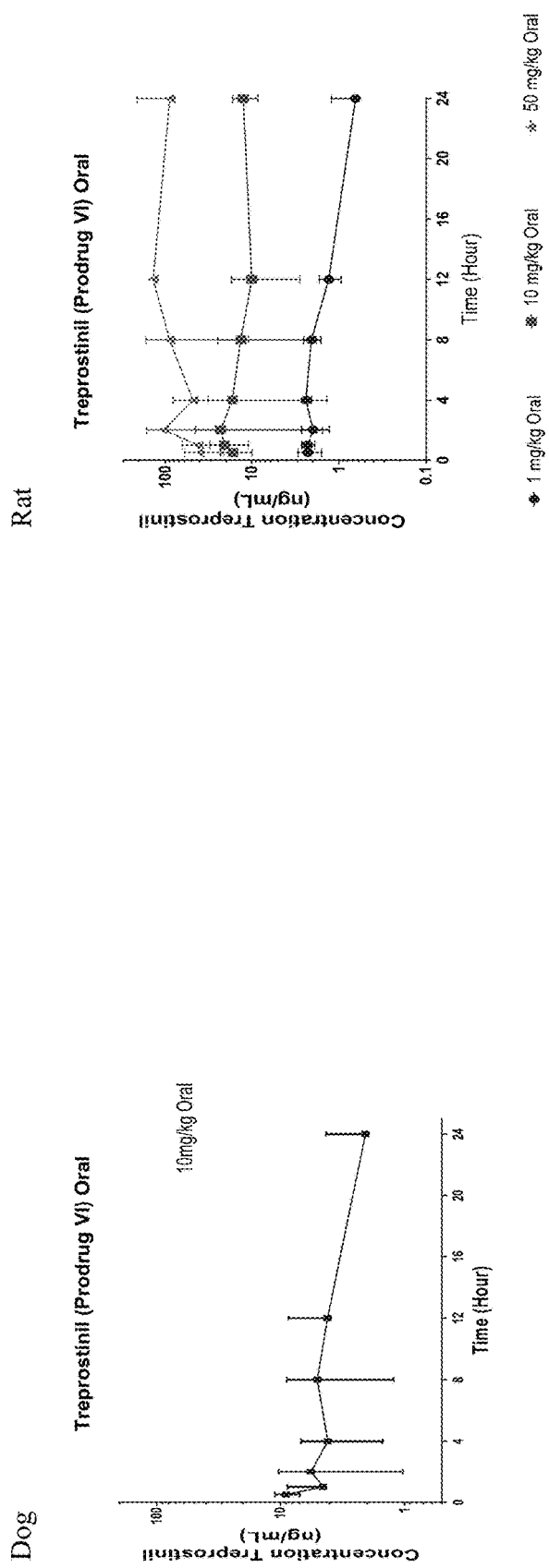
FIG. 4 Mean (±SD) Treprostinil Plasma Concentration-Time Profiles Following a Single Oral Gavage Administration of 1, 10, and 50 mg/kg Prodrug VI to rats or 10 mg/kg Prodrug VI to dogs.
Figure 5A:
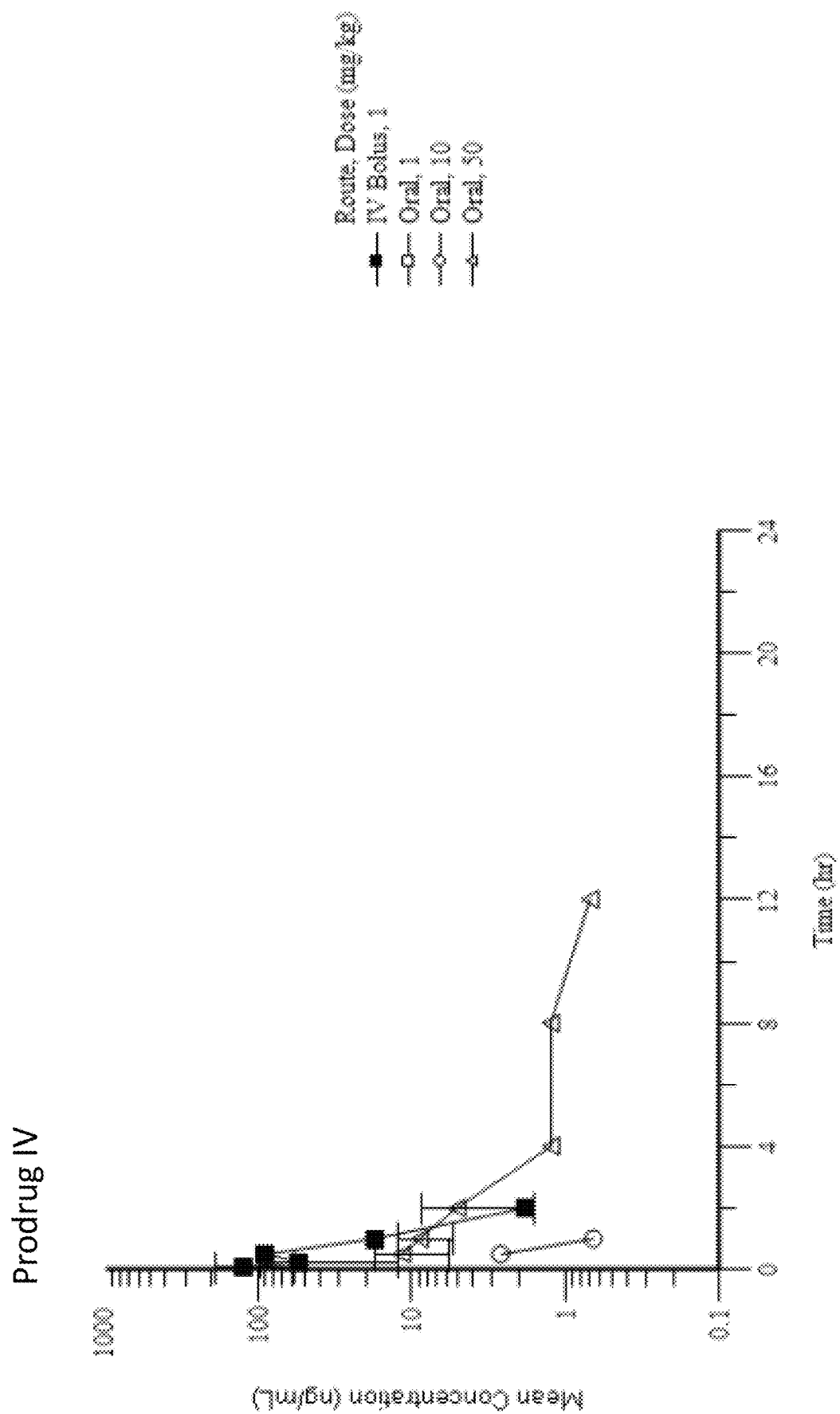
FIGS. 5A-B: Mean (±SD) Prodrug IV (5A) and Treprostinil (5B) Plasma Concentration-Time Profiles Following a Single Oral Gavage Administration of 1, 10, and 50 mg/kg Prodrug IV or a Single IV Bolus Injection of 1 mg/kg Prodrug IV to Male Rats.
Figure 5B:
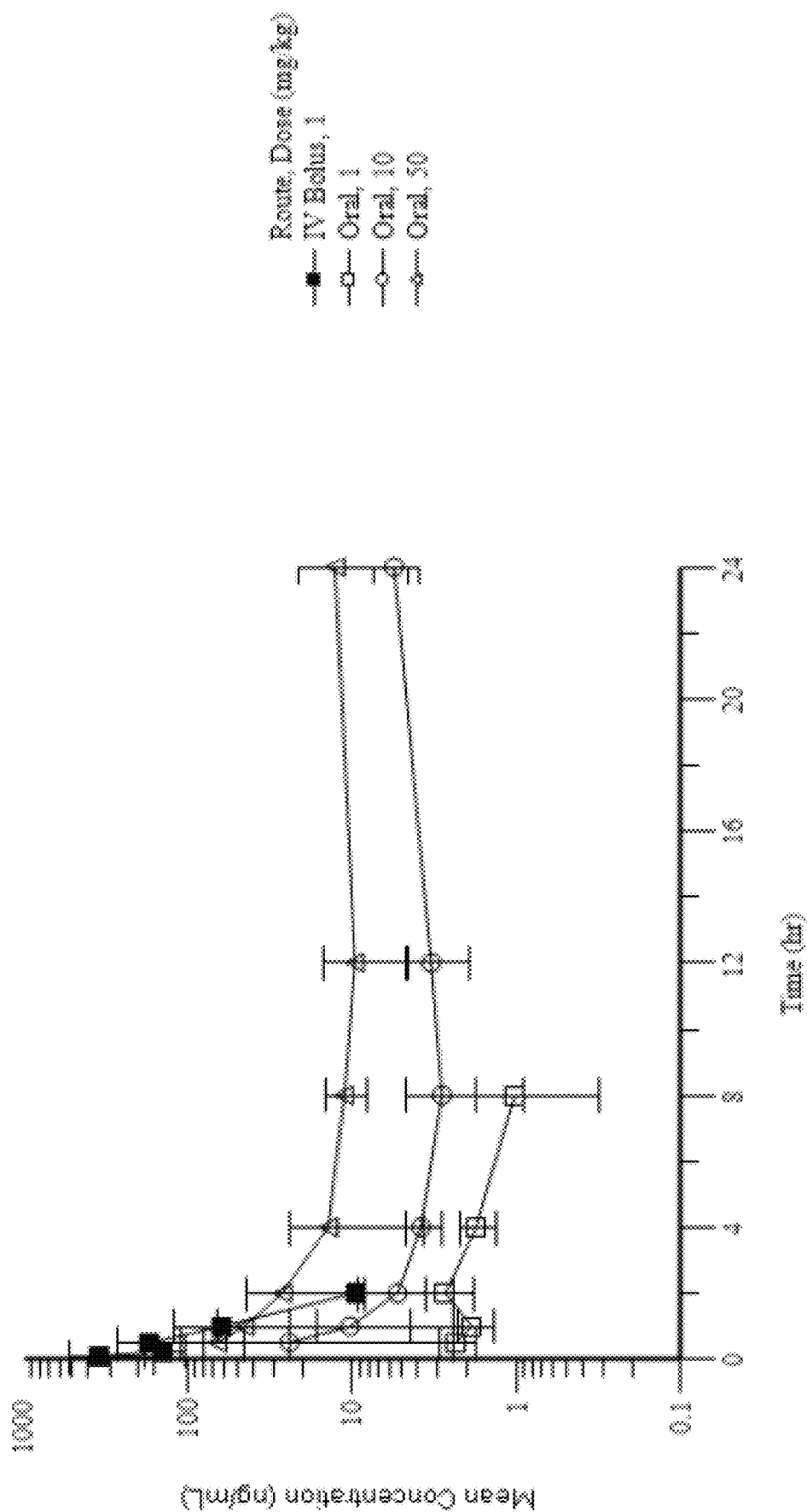
Figure 6:
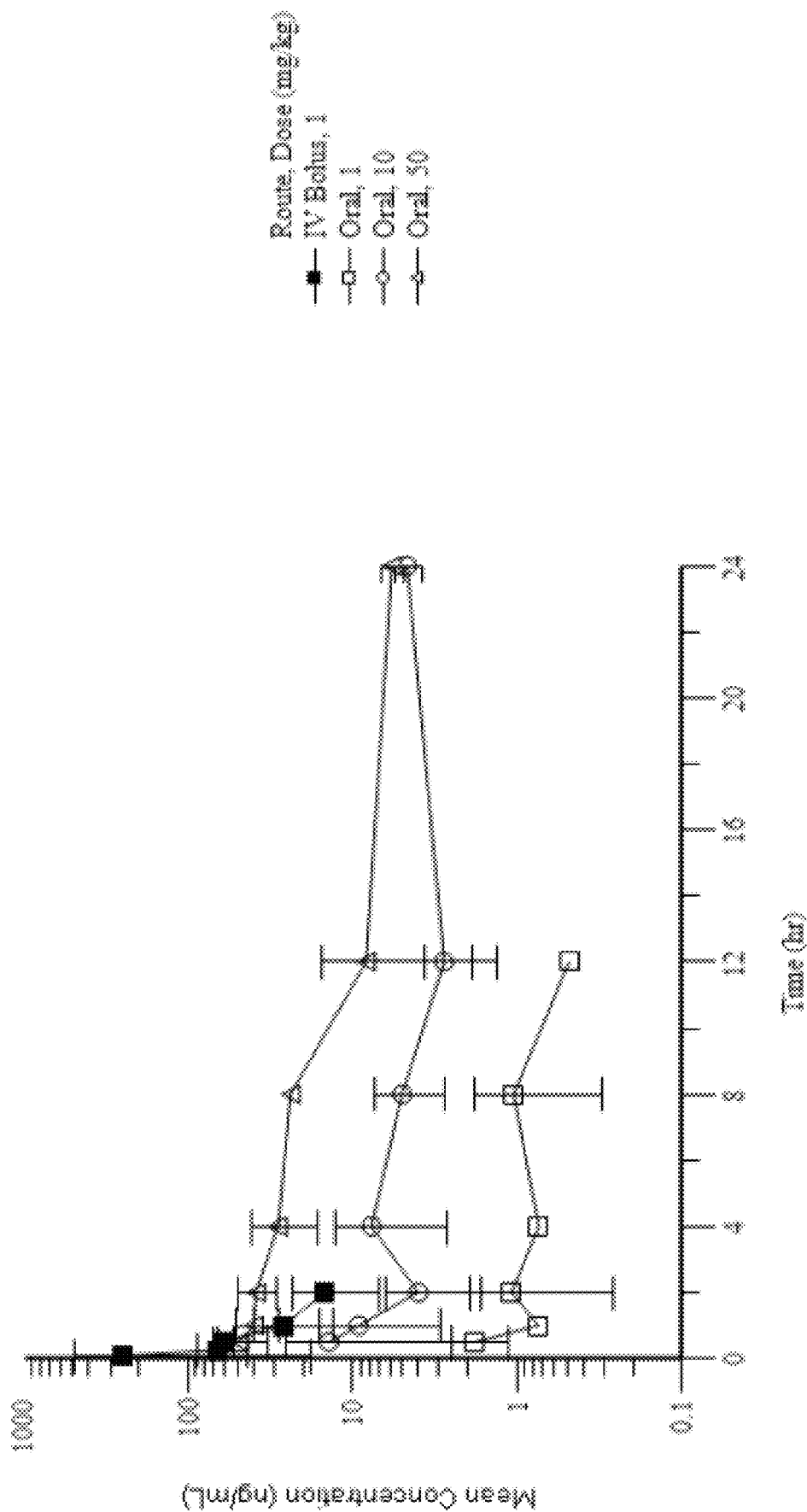
FIG. 6: Mean (±SD) Treprostinil Plasma Concentration-Time Profiles Following a Single Oral Gavage Administration of 1, 10, and 50 mg/kg Prodrug XVI or a Single IV Bolus Injection of 1 mg/kg Prodrug XVI to Male Rats.
Figure 7:
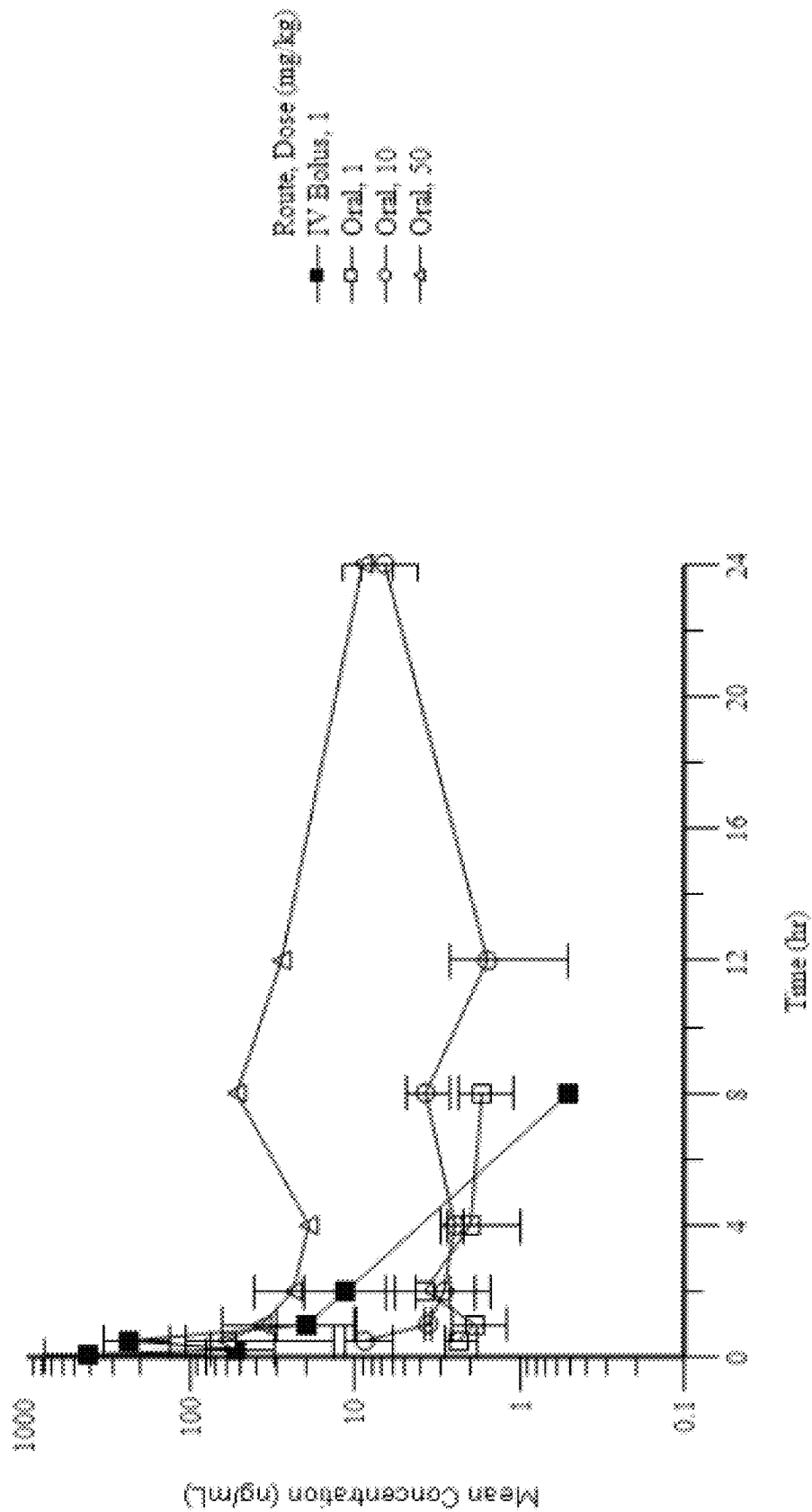
FIG. 7: Mean (±SD) Treprostinil Plasma Concentration-Time Profiles Following a Single Oral Gavage Administration of 1, 10, and 50 mg/kg Prodrug XVII or a Single IV Bolus Injection of 1 mg/kg Prodrug XVII to Male Rats.
Figure 8A:
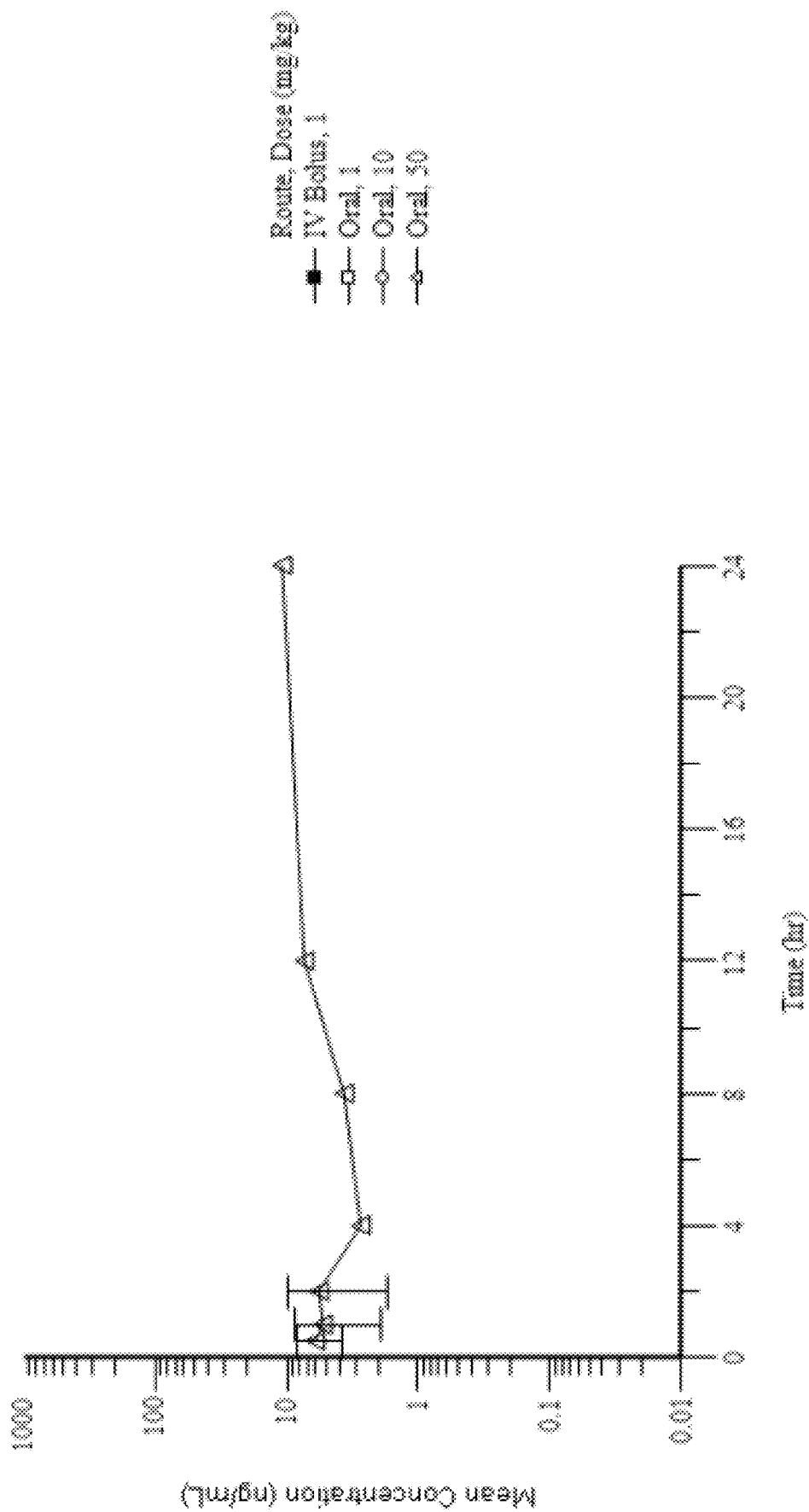
FIGS. 8A-B: Mean (±SD) Prodrug VI (8A) and Treprostinil (8B) Plasma Concentration-Time Profiles Following a Single Oral Gavage Administration of 1, 10, and 50 mg/kg Prodrug VI or a Single IV Bolus Injection of 1 mg/kg Prodrug VI to Male Rat.
Figure 8B:
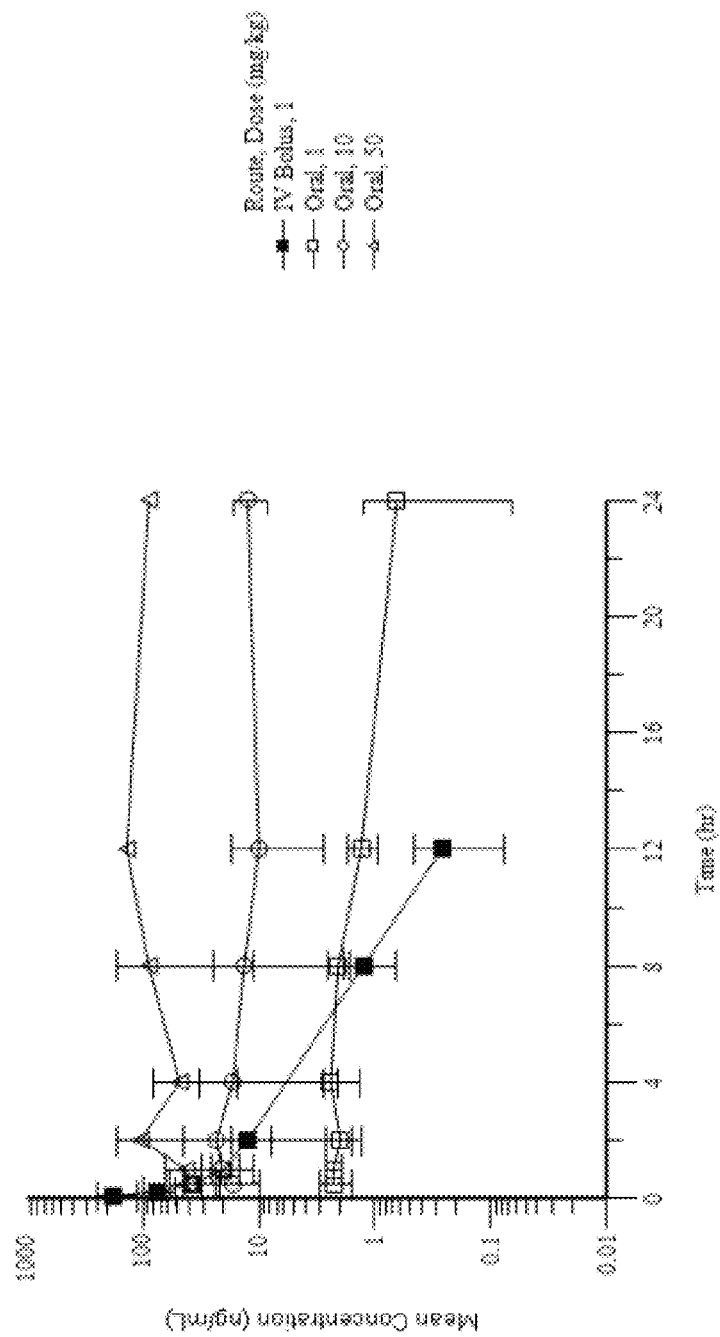

Mean Prodrug IV and treprostinil plasma concentration-time profiles are illustrated in FIGS. 2 and 5A-B. Mean treprostinil plasma concentration-time profiles are illustrated in FIGS. 6 (prodrug XVI) and 3/7 (prodrug XVII). Mean Prodrug VI and treprostinil plasma concentration-time profiles are illustrated in FIGS. 8A-B as well as in FIG. 4.

Discussion

Prodrug IV—PO Administration (Groups 1, 2, and 3)

All Prodrug IV plasma concentrations were BLQ at 1 mg/kg Prodrug IV; therefore, the following discussion of Prodrug IV is based on the data for the 10 and 50 mg/kg dose groups only.

The variability in mean Prodrug IV plasma concentrations, as measured by CV values, ranged from 40.1% to 200% following a single PO administration of Prodrug IV to animals in Groups 2 and 3. The higher variability observed was the result of BLQ values converted to zero for parameter estimates and averaged with quantifiable results. The variability in mean Prodrug IV plasma concentrations without these values ranged from 40.1% to 51.3% following a single PO administration of Prodrug IV to animals in Groups 2 and 3. Prodrug IV was quantifiable up to 1 hour postdose at 10 mg/kg and up to 1, 2, 8, or 12 hours postdose at 50 mg/kg. Individual peak Prodrug IV plasma concentrations were observed by 0.5 hours postdose at 10 mg/kg and by 0.5 or 1 hour postdose at 50 mg/kg.

Following a single PO administration of Prodrug IV to animals in Groups 2 and 3, mean $C_{max}$ values for Prodrug IV increased with increasing dose from 10 to 50 mg/kg. A 5-fold increase in Prodrug IV dose (10 to 50 mg/kg) resulted in an approximate 4.6-fold increase in mean Prodrug IV $C_{max}$ values. $AUC_{0-24hr}$ for Prodrug IV could only be reported for a single animal at 50 mg/kg (Animal No. 3003) and was 49.2 hr*ng/mL.

$AUC_{INF}$, $T_{1/2}$, Cl/F, and $V_z$/F values for Prodrug IV could only be reported for a single animal at 50 mg/kg (Animal No. 3001) and were 65.4 hr*ng/mL, 4.27 hours, 764000 mL/hr/kg, and 4710000 mL/kg, respectively.

Prodrug IV—IV Bolus Injection (Group 13)

The variability in mean Prodrug IV plasma concentrations, as measured by CV values, ranged from 53.0% to 120% following a single IV bolus injection of Prodrug IV to animals in Group 13. Prodrug IV was quantifiable up to 1 or 2 hours postdose and the estimated concentration at time zero ($C_0$) was determined; however, both $C_{max}$ and $T_{max}$ values were reported due to increases observed in Prodrug IV concentrations between the 0.083 and 0.5 hour collection intervals for two males (Animal No. 13002 and 13004). Individual peak Prodrug IV plasma concentrations were observed by 0.083 or 0.5 hours postdose.

Following a single IV bolus injection of Prodrug IV to animals in Group 13, mean $C_0$, $C_{max}$, and $AUC_{0-12hr}$ values for Prodrug IV were 324 ng/mL, 179 ng/mL, and 94.4 hr*ng/mL, respectively. Individual $C_0$ values ranged from 65.6 to 759 ng/mL, individual $C_{max}$ values ranged from 150 to 209 ng/mL, and individual $AUC_{0-12hr}$ values ranged from 42.3 to 155 hr*ng/mL.

Mean $AUC_{INF}$, $T_{1/2}$, Cl, and $V_z$ values for Prodrug IV following a single IV bolus injection of Prodrug IV were 98.7 hr*ng/mL, 0.212 hours, 13400 mL/hr/kg, and 3150 mL/kg, respectively. Individual $AUC_{INF}$ values ranged from 41.5 to 144 hr*ng/mL, individual $T_{1/2}$ values ranged from 0.0910 to 0.276 hours, individual Cl values ranged from 6940 to 24100 mL/hr/kg, and individual $V_z$ values ranged from 2690 to 3610 mL/kg.

Prodrug IV Bioavailability

Dose normalized systemic exposure ($AUC_{all}$/Dose) to Prodrug IV was lower following a single PO administration of Prodrug IV at 50 mg/kg when compared to a single IV bolus injection of 1 mg/kg Prodrug IV. The PO bioavailability (% F) value, based on mean $AUC_{all}$/Dose, was 1.04% at 50 mg/kg Prodrug IV.

Treprostinil—PO Administration of Prodrug IV (Groups 1, 2, and 3)

The variability in mean treprostinil plasma concentrations, as measured by CV values, ranged from 25.4% to 89.9% following a single PO administration of Prodrug IV to animals in Groups 1 through 3. Treprostinil was quantifiable up to 4 or 8 hours postdose at 1 mg/kg Prodrug IV, and up to 24 hours postdose at 10 and 50 mg/kg Prodrug IV. Individual peak treprostinil plasma concentrations were observed by 0.5 or 2 hours postdose at 1 mg/kg Prodrug IV and by 0.5 hours postdose at 10 and 50 mg/kg Prodrug IV.

Following a single PO administration of Prodrug IV to animals in Groups 1 through 3, mean $C_{max}$ and $AUC_{0-24hr}$ values for treprostinil increased with increasing dose. A 1:10:50-fold increase in Prodrug IV dose resulted in an approximate 1:8.4:23.3-fold increase in mean treprostinil $C_{max}$ values and an approximate 1:6.9:22.0-fold increase in mean treprostinil $AUC_{0-24hr}$ values.

Systemic exposure ($AUC_{0-24hr}$) to treprostinil was greater than systemic exposure to Prodrug IV following a single PO administration of 50 mg/kg Prodrug IV to Animal No. 3003 and the individual M:P $AUC_{0-24hr}$ ratio was 7.60 (only a single M:P $AUC_{0-24hr}$ ratio was reported due to limited data available for Prodrug IV).

Secondary parameters ($AUC_{INF}$, $T_{1/2}$, Cl/F, and $V_z$/F) for treprostinil could not be reported for any animal in Groups Treprostinil—IV Bolus Injection of Prodrug IV
(Group 13)

The variability in mean treprostinil plasma concentrations, as measured by CV values, ranged from 27.4% to 102% following a single IV bolus injection of Prodrug IV to animals in Group 13. Treprostinil was quantifiable up to 2 hours postdose and the estimated concentration at time zero ($C_0$) was determined; however, both $C_{max}$ and $T_{max}$ values were reported due to increases observed in treprostinil concentrations between the 0.083 and 0.5 hour collection intervals for two males (Animal No. 13002 and 13004). Individual peak treprostinil plasma concentrations were observed by 0.083 or 0.5 hours postdose.

Following a single IV bolus injection of Prodrug IV to animals in Group 13, mean $C_0$, $C_{max}$, and $AUC_{0-12hr}$ values for treprostinil were 538 ng/mL, 363 ng/mL, and 240 hr*ng/mL, respectively. Individual $C_0$ values ranged from 208 to 1000 ng/mL, individual $C_{max}$ values ranged from 199 to 581 ng/mL, and individual $AUC_{0-12hr}$ values ranged from 153 to 367 hr*ng/mL.

Systemic exposure ($AUC_{0-12hr}$) to treprostinil was greater than systemic exposure to Prodrug IV following a single IV bolus injection of 1 mg/kg Prodrug IV. The mean M:P $AUC_{0-12hr}$ ratio was 2.94 and individual M:P $AUC_{0-12hr}$ ratios ranged from 1.40 to 3.64.

Mean $AUC_{INF}$, $T_{1/2}$, Cl, and $V_z$ values for treprostinil following a single IV bolus injection of Prodrug IV were 217 hr*ng/mL, 0.332 hours, 4980 mL/hr/kg, and 2350 mL/kg, respectively. Individual $AUC_{INF}$ values ranged from 144 to 312 hr*ng/mL, individual $T_{1/2}$ values ranged from 0.234 to 0.408 hours, individual Cl values ranged from 3200 to 6930 mL/hr/kg, and individual $V_z$ values ranged from 1530 to 3300 mL/kg.

Treprostinil Bioavailability Following
Administration of Prodrug IV

Dose normalized systemic exposure ($AUC_{all}$/Dose) to treprostinil was lower following a single PO administration of Prodrug IV when compared to a single IV bolus injection of Prodrug IV. The PO bioavailability (% F) values, based on mean $AUC_{all}$/Dose, were 6.75%, 4.63%, and 2.98% at 1, 10, and 50 mg/kg Prodrug IV, respectively.

Treprostinil—PO Administration of Prodrug XVI
(Groups 4, 5, and 6)

The variability in mean treprostinil plasma concentrations, as measured by CV values, ranged from 15.7% to 200% following a single PO administration of Prodrug XVI to animals in Groups 4 through 6. The higher variability observed was the result of BLQ values converted to zero for parameter estimates and averaged with quantifiable results. The variability in mean treprostinil plasma concentrations without these values ranged from 15.7% to 120% following a single PO administration of Prodrug XVI to animals in Groups 4 through 6. Treprostinil was quantifiable up to 1, 8, or 12 hours postdose at 1 mg/kg Prodrug XVI, and up to 24 hours postdose at 10 and 50 mg/kg Prodrug XVI. Individual peak treprostinil plasma concentrations were observed at 0.5 or 4 hours postdose at 1 mg/kg Prodrug VI, at 0.5, 1, or 4 hours postdose at 10 mg/kg Prodrug XVI, and at 0.5 or 1 hour postdose at 50 mg/kg Prodrug XVI.

Following a single PO administration of Prodrug XVI to animals in Groups 4 through 6, mean $C_{max}$ and $AUC_{0-24hr}$ values for treprostinil increased with increasing dose. A 1:10:50-fold increase in Prodrug XVI dose resulted in an approximate 1:7.9:25.4-fold increase in mean treprostinil $C_{max}$ values and an approximate 1:10.7:34.7-fold increase in mean treprostinil $AUC_{0-24hr}$ values.

M:P ratios could not be determined due to insufficient data available for Prodrug XVI (all Prodrug XVI plasma concentrations were BLQ).

Secondary parameters ($AUC_{INF}$, $T_{1/2}$, Cl/F, and $V_z$/F) for treprostinil could not be reported for any animal in Groups 4 through 6 due to an adjusted $R^2$ value less than 0.9 or insufficient plasma concentration-time data.

Treprostinil—IV Bolus Injection of Prodrug XVI
(Group 14)

The variability in mean treprostinil plasma concentrations, as measured by CV values, ranged from 15.2% to 92.8% following a single IV bolus injection of Prodrug XVI to animals in Group 14. Treprostinil was quantifiable up to 2 hours postdose and the estimated concentration at time zero ($C_0$) was determined; however, both $C_{max}$ and $T_{max}$ values were reported due to increases observed in treprostinil concentrations between the 0.083 and 0.5 hour collection intervals for a single male (Animal No. 14003). Individual peak treprostinil plasma concentrations were observed by 0.083 or 0.5 hours postdose.

Following a single IV bolus injection of Prodrug XVI to animals in Group 14, mean $C_0$, $C_{max}$, and $AUC_{0-12hr}$ values for treprostinil were 549 ng/mL, 263 ng/mL, and 192 hr*ng/mL, respectively. Individual $C_0$ values ranged from 21.4 to 1170 ng/mL, individual $C_{max}$ values ranged from 63.7 to 504 ng/mL, and individual $AUC_{0-12hr}$ values were 171 and 214 hr*ng/mL.

M:P ratios could not be determined due to insufficient data available for Prodrug XV (all Prodrug XVI plasma concentrations were BLQ).

$AUC_{INF}$, Cl, and $V_z$ values for treprostinil could only be estimated for a single animal following a single PO administration of Prodrug XVI (Animal No. 14001) and were 183 hr*ng/mL, 5470 mL/hr/kg, and 5700 mL/kg, respectively. The mean $T_{1/2}$ value for treprostinil was 0.912 hours (individual $T_{1/2}$ values were 0.722 and 1.10 hours).

Treprostinil Bioavailability Following
Administration of Prodrug XVI

Dose normalized systemic exposure ($AUC_{all}$/Dose) to treprostinil was lower following a single PO administration of Prodrug XVI when compared to a single IV bolus injection of Prodrug XVI. The PO bioavailability (% F) values, based on mean $AUC_{all}$/Dose, were 5.94%, 6.35%, and 4.13% at 1, 10, and 50 mg/kg Prodrug XVI, respectively.

Treprostinil—PO Administration of Prodrug XVII
(Groups 7, 8, and 9)

The variability in mean treprostinil plasma concentrations, as measured by CV values, ranged from 4.98% to 174% following a single PO administration of Prodrug XVII to animals in Groups 7 through 9. Treprostinil was quantifiable up to 8 hours postdose at 1 mg/kg Prodrug XVII, up to 24 hours postdose at 10 mg/kg Prodrug XVII, and up to 12 or 24 hours postdose at 50 mg/kg Prodrug XVII. Individual peak treprostinil plasma concentrations were observed by 0.5 or 2 hours postdose at 1 mg/kg Prodrug XVII, by 0.5 or 24 hours postdose at 10 mg/kg Prodrug XVII and by 0.5 or 8 hours postdose at 50 mg/Prodrug XVII.

Following a single PO administration of Prodrug XVII to animals in Groups 7 through 9, mean $C_{max}$ and $AUC_{0-24hr}$ values for treprostinil increased with increasing dose. A 1:10:50-fold increase in Prodrug XVII dose resulted in an approximate 1:2.5:21.6-fold increase in mean treprostinil $C_{max}$ values and an approximate 1:4.1:24.0-fold increase in mean treprostinil $AUC_{0-24hr}$ values.

M:P ratios could not be determined due to insufficient data available for Prodrug XVII (all Prodrug XVII plasma concentrations were BLQ).

Secondary parameters ($AUC_{INF}$, $T_{1/2}$, Cl/F, and $V_z/F$) for treprostinil could not be reported for any animal in Groups 7 through 9 due to an adjusted $R^2$ value less than 0.9 or insufficient plasma concentration-time data.

Treprostinil—IV Bolus Injection of Prodrug XVII
(Group 15)

The variability in mean treprostinil plasma concentrations, as measured by CV values, ranged from 42.1% to 200% following a single IV bolus injection of Prodrug XVII to animals in Group 15. The higher variability observed was the result of BLQ values converted to zero for parameter estimates and averaged with quantifiable results. The variability in mean treprostnil plasma concentrations without these values ranged from 42.1% to 81.1% following a single IV bolus injection of Prodrug XVII to animals in Group 15. Treprostinil was quantifiable up to 2 or 8 hours postdose and the estimated concentration at time zero ($C_0$) was determined; however, both $C_{max}$ and $T_{max}$ values were reported due to increases observed in treprostinil concentrations between the 0.083 and 0.5-hour collection intervals for a single male (Animal No. 15002). Individual peak treprostinil plasma concentrations were observed by 0.083 or 0.5 hours postdose. Following a single IV bolus injection of Prodrug XVII to animals in Group 15, mean $C_0$, $C_{max}$, and $AUC_{0-12hr}$ values for treprostinil were 1350 ng/mL, 466 ng/mL, and 274 hr*ng/mL, respectively. Individual $C_0$ values ranged from 227 to 3320 ng/mL, individual $C_{max}$ values ranged from 254 to 917 ng/mL, and individual $AUC_{0-12hr}$ values ranged from 167 to 413 hr*ng/mL.

M:P ratios could not be determined due to insufficient data available for Prodrug XVII (all Prodrug XVII plasma concentrations were BLQ).

Secondary parameters ($AUC_{INF}$, $T_{1/2}$, Cl, and $V_z$) for treprostinil could not be reported for any animal in Group 15 due to adjusted $R^2$ values less than 0.9.

Treprostinil Bioavailability Following
Administration of Prodrug XVII

Dose normalized systemic exposure ($AUC_{all}$/Dose) to treprostinil was lower following a single PO administration of Prodrug XVII when compared to a single IV bolus injection of prodrug XVI. The PO bioavailability (% F) values, based on $AUC_{all}$/Dose, were 7.74%, 3.17%, and 3.72% at 1, 10, and 50 mg/kg Prodrug XVII, respectively.

Prodrug VI—PO Administration (Groups 10, 11, and 12)

All Prodrug VI plasma concentrations were BLQ at 1 and 10 mg/kg Prodrug XVII; therefore, the following discussion of Prodrug VI is based on the data for the 50 mg/kg Prodrug VI dose group only.

The variability in mean Prodrug VI plasma concentrations, as measured by CV values, ranged from 38.4% to 173% following a single PO administration of Prodrug VI to animals in Group 12. The higher variability observed was the result of BLQ values converted to zero for parameter estimates and averaged with quantifiable results. The variability in mean Prodrug VI plasma concentrations without these values ranged from 38.4% to 69.8% following a single PO administration of Prodrug VI to animals in Group 12. Prodrug VI was quantifiable up to 2, 4, 8, or 24 hours postdose at 50 mg/kg Prodrug VI. Individual peak Prodrug VI plasma concentrations were observed by 0.5, 8, or 24 hours postdose at 50 mg/kg Prodrug VI.

Following a single PO administration of 50 mg/kg Prodrug VI to animals in Group 12, mean $C_{max}$ and $AUC_{0-24hr}$ values for Prodrug VI were 12.4 ng/mL and 242 hr*ng/mL, respectively. Individual $C_{max}$ values ranged from 4.14 to 32.8 ng/mL at 50 mg/kg Prodrug VI and individual $AUC_{0-24hr}$ values were 26.5 and 457 hr*ng/mL at 50 mg/kg Prodrug VI.

$AUC_{INF}$, $T_{1/2}$, Cl/F, and $V_z/F$ values for Prodrug VI could only be reported for a single animal at 50 mg/kg (Animal No. 12004) and were 28.2 hr*ng/mL, 1.76 hours, 1780000 mL/hr/kg, and 4520000 mL/kg, respectively.

Treprostinil—PO Administration of Prodrug VI
(Groups 10, 11, and 12)

The variability in mean treprostinil plasma concentrations, as measured by CV values, ranged from 13.8% to 150% following a single PO administration of Prodrug VI to animals in Groups 10 through 12. Treprostinil was quantifiable up to 24 hours postdose at 1 and 10 mg/kg Prodrug XVII, and up to 8 or 24 hours postdose at 50 mg/kg Prodrug VI. Individual peak treprostinil plasma concentrations were observed by 1, 2 or 4 hours postdose at 1 mg/kg Prodrug XVII, by 1 or 2 hours postdose at 10 mg/kg Prodrug VI, and by 2, 8, or 12 hours postdose at 50 mg/kg Prodrug VI.

Following a single PO administration of Prodrug VI to animals in Groups 10 through 12, mean $C_{max}$ and $AUC_{0-24hr}$ values for treprostinil increased with increasing dose. A 1:10:50-fold increase in Prodrug VI dose resulted in an approximate 1:9.8:64.2-fold increase in mean treprostinil $C_{max}$ values and an approximate 1:8.5:60.8-fold increase in mean treprostinil $AUC_{0-24hr}$ values.

Systemic exposure ($AUC_{0-24hr}$) to treprostinil was greater than the systemic exposure to Prodrug VI following a single PO administration of 50 mg/kg Prodrug VI to Animal No. 12002 and 12004 and the M:P ratios were 12.1 and 30.0, respectively (only two M:P $AUC_{0-24hr}$ ratios could be reported due to limited data available for Prodrug VI). The mean M:P ratio was 21.0.

Secondary parameters ($AUC_{INF}$, $T_{1/2}$, Cl/F, and $V_z/F$) for treprostinil could not be reported at 10 or 50 mg/kg Prodrug VI due to adjusted $R^2$ values less than 0.9, insufficient plasma concentration-time data, or % $AUC_{Extrap}$ values for $AUC_{INF}$ greater than 25%. Mean $AUC_{INF}$, $T_{1/2}$, Cl/F, and $V_z/F$ values for treprostinil were 38.4 hr*ng/mL, 14.0 hours, 26900 mL/hr/kg, and 243000 mL/kg, respectively at 1 mg/kg Prodrug VI. Individual $AUC_{INF}$ values ranged from 31.7 to 48.4 hr*ng/mL, individual $T_{1/2}$ values ranged from 4.71 to 36.9 hours (the $T_{1/2}$ value of 36.9 hours was estimated from less than three half-lives of data and should be viewed with caution, individual $T_{1/2}$ values ranged from 4.71 to 7.35 hours, otherwise), individual Cl/F values ranged from 20700 to 31600 mL/hr/kg, and individual $V_z/F$ values ranged from 194000 to 316000 mL/kg.

Treprostinil—IV Bolus Injection of Prodrug VI (Group 16)

The variability in mean treprostinil plasma concentrations, as measured by CV values, ranged from 17.6% to 71.2% following a single IV bolus injection of Prodrug VI to animals in Group 16. The higher variability observed was the result of BLQ values converted to zero for parameter estimates and averaged with quantifiable results.

The variability in mean treprostinil plasma concentrations without these values ranged from 17.6% to 48.4% following a single IV bolus injection of Prodrug VI to animals in Group 16. Treprostinil was quantifiable up to 8 or 12 hours postdose and the estimated concentration at time zero ($C_0$) was determined.

Following a single IV bolus injection of Prodrug VI to animals in Group 16, mean $C_0$ and $AUC_{0-12hr}$ values for treprostinil were 277 ng/mL and 129 hr*ng/mL, respectively. Individual $C_0$ values ranged from 207 to 454 ng/mL and individual $AUC_{0-12hr}$ values ranged from 97.4 to 158 hr*ng/mL.

M:P ratios could not be determined due to insufficient data available for Prodrug VI (all Prodrug VI plasma concentration were BLQ).

Mean $AUC_{INF}$, $T_{1/2}$, Cl, and $V_z$ values for treprostinil following a single IV bolus administration injection of Prodrug VI were 130 hr*ng/mL, 1.90 hours, 7920 mL/hr/kg, and 22000 mL/kg, respectively. Individual $AUC_{INF}$ values ranged from 99.0 to 159 hr*ng/mL, individual $T_{1/2}$ values ranged from 1.60 to 2.28 hours, individual Cl values ranged from 6290 to 10100 mL/hr/kg, and individual $V_z$ values ranged from 16800 to 33200 mL/kg.

Treprostinil Bioavailability Following Administration of Prodrug VI

Dose normalized systemic exposure ($AUC_{all}$/Dose) to treprostinil was lower following a single PO administration of Prodrug VI when compared to a single IV bolus injection of Prodrug VI. The PO bioavailability (% F) values, based on $AUC_{all}$/Dose, were 28.4%, 24.3%, and 34.7% at 1, 10, and 50 mg/kg Prodrug VI, respectively.

CONCLUSION

Prodrug IV (Groups 1, 2, 3, and 13)

Following a single PO administration of Prodrug IV, mean $C_{max}$ values for Prodrug IV appeared to increase with increasing dose in an approximately dose proportional manner from 10 to 50 mg/kg. PO bioavailability for Prodrug IV was 1.04% at 50 mg/kg Prodrug IV.

Treprostinil (Groups 1, 2, 3, and 13)

Following a single PO administration of Prodrug IV to animals in Groups 1 through 3, mean $C_{max}$ and $AUC_{0-24hr}$ values for treprostinil increased with increasing dose in a less than dose proportional manner from 1 to 50 mg/kg. Systemic exposure ($AUC_{0-24hr}$) to treprostinil was approximately 8-fold greater than systemic exposure to Prodrug IV following a single PO administration of 50 mg/kg Prodrug IV to Animal No 3003. Systemic exposure ($AUC_{0-12hr}$) to treprostinil was approximately 3-fold greater than the systemic exposure to Prodrug IV following a single IV bolus injection of Prodrug IV. PO bioavailability for treprostinil ranged from 2.98% to 6.75% following administration of Prodrug IV.

Prodrug XVI (Groups 4, 5, 6, and 14)

Following a single PO or IV bolus injection Prodrug XVI, all Prodrug XVI plasma concentrations were BQL (<1.00 ng/mL).

Treprostinil (Groups 4, 5, 6, and 14)

Following a single PO administration of Prodrug XVI to animals in Groups 4 through 6, mean $C_{max}$ and $AUC_{0-24hr}$ values for treprostinil increased with increasing dose in a less than dose proportional manner from 1 to 50 mg/kg Prodrug XVI. PO bioavailability for treprostinil ranged from 4.13% to 6.35% following administration of Prodrug XVI.

Prodrug XVII (Groups 7, 8, 9, and 15)

Following a single PO or IV bolus injection Prodrug XVII, all Prodrug XVII plasma concentrations were BQL (<1.00 ng/mL).

Treprostinil (Groups 7, 8, 9, and 15)

Following a single PO administration of Prodrug XVII, mean $C_{max}$ and $AUC_{0-24hr}$ values for treprostinil increased with increasing dose in a less than dose proportional manner. PO bioavailability for treprostinil ranged from 3.17% to 7.74% following administration of Prodrug XVII.

Prodrug VI (Groups 10, 11, 12, and 16)

Following a single IV bolus injection Prodrug VI, all Prodrug VI plasma concentrations were BQL (<1.00 ng/mL).

Treprostinil (Groups 10, 11, 12, and 16)

Following a single PO administration of Prodrug VI, mean $C_{max}$ and $AUC_{0-24hr}$ values for treprostinil increased with increasing dose in an approximately dose proportional manner.

Systemic exposure ($AUC_{0-24hr}$) to treprostinil was approximately 21-fold greater than the systemic exposure to Prodrug VI following a single PO administration of Prodrug VI at 50 mg/kg Prodrug XVII.

PO bioavailability for treprostinil ranged from 24.3% to 34.7% following a single administration of Prodrug VI.

Example 5: Calculation of Solubility and pKa of Compounds

TABLE 2

Calculated Solubility and pKa for Select Compounds

| Compound | Structure | MW | Solubility and pKa | Patent Name |
|---|---|---|---|---|
| Treprostinil side chain ethyl carbonate<br>Chemical Formula: $C_{26}H_{38}O_7$<br>Molecular Weight: 462.58 | 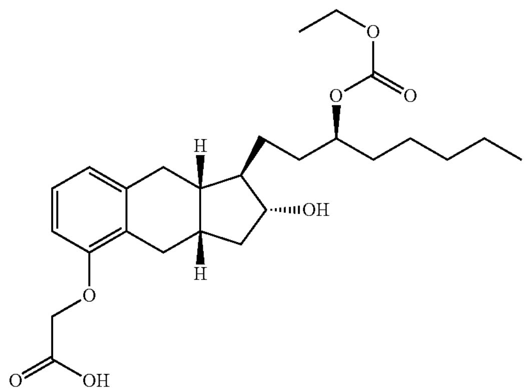 [SMILES: CCCCC[C@@H](CC[C@@H]1[C@H]2Cc3cccc(OCC(=O)O)c3C[C@H]2C[C@H]1O)OC(=O)OCC] | 462.58 | In Silico pKa = 3.2<br>Sol at pH 7.0 = 6.25 mg/mL<br>Measured Sol = 10 mg/mL at pH 6.5 | XVI |
| Side Chain Isopropyl Carbonate of Treprostinil<br>Chemical Formula: $C_{27}H_{40}O_7$<br>Molecular Weight: 476.61 | 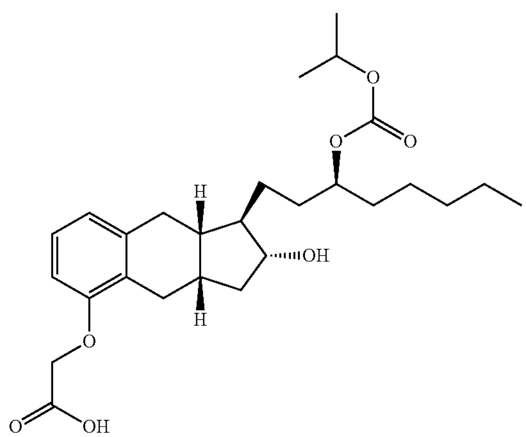 [SMILES: CCCCC[C@@H](CC[C@@H]1[C@H]2Cc3cccc(OCC(=O)O)c3C[C@H]2C[C@H]1O)OC(=O)OC(C)C] | 476.61 | In Silico pKa = 3.2<br>Sol at pH 7.0 = 3.55 mg/mL<br>Measured Sol = 10 mg/mL at pH 6.5 | XVII |
| Treprostinil side-chain phosphate ester<br>Chemical Formula: $C_{23}H_{35}O_8P$<br>Molecular Weight: 470.50 | 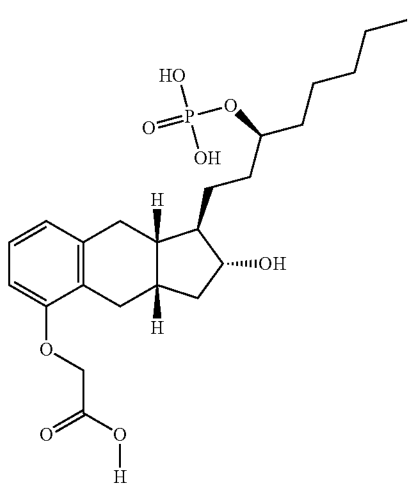 [SMILES: CCCCC[C@@H](CC[C@@H]1[C@H]2Cc3cccc(OCC(=O)O)c3C[C@H]2C[C@H]1O)OP(=O)(O)O] | 470.50 | In Silico pKa = 1.91, 3.2, 6.42<br>Sol at pH 7.0 = 1 g/mL<br>Measured Sol >10 mg/mL at pH 6.5 | VI |

TABLE 2-continued

Calculated Solubility and pKa for Select Compounds

| Compound | Structure | MW | Solubility and pKa | Patent Name |
|---|---|---|---|---|
| Phosphonooxy methyl ether of treprostinil<br>Chemical Formula: $C_{24}H_{37}O_9P$<br>Molecular Weight: 500.52 | | 500.52 | In Silico pKa = 1.54, 5.99<br>Sol at pH 7.0 = 227 mg/mL | XVIII |
| Treprostinil piperidine ester<br>Chemical Formula: $C_{29}H_{43}NO_6$<br>Molecular Weight: 501.66 | | 501.66 | In Silico pKa = 3.2<br>Sol at pH 7.0 = 2.04 mg/mL | XIX |
| Treprostinil hemi-succinate ester<br>Chemical Formula: $C_{27}H_{38}O_8$<br>Molecular Weight: 490.59 | | 490.59 | In Silico pKa = 3.2, 4.4<br>Sol at pH 7.0 = 278 mg/mL | XX |

TABLE 2-continued

Calculated Solubility and pKa for Select Compounds

| Compound | Structure | MW | Solubility and pKa | Patent Name |
|---|---|---|---|---|
| Treprostinil phosphonooxyy ethyl ether<br>Chemical Formula: $C_{25}H_{39}O_9P$<br>Molecular Weight: 514.55 | | 514.55 | In Silico pKa = 1.85, 3.2, 6.4<br>Sol at pH 7.0 = 1 g/mL | XXI |
| Treprostinil Cyclopentyl Succinate<br>Chemical Formula: $C_{27}H_{38}O_8$<br>Molecular Weight: 490.6 | | 490.59 | In Silico pKa = 3.2, 4.4<br>Sol at pH 7.0 = 303 mg/mL | XXII |
| Treprostinil Side Chain Bi-piperidine Carbamate<br>Chemical Formula: $C_{34}H_{52}N_2O_6$<br>Molecular Weight: 584.8 | | 584.80 | In Silico pKa = 3.2, 9.5<br>Sol at pH 7.0 = 0.00005 mg/mL | XXIII |

TABLE 2-continued

Calculated Solubility and pKa for Select Compounds

| Compound | Structure | MW | Solubility and pKa | Patent Name |
|---|---|---|---|---|
| Treprostinil Cyclopentyl Naproxen Ester | 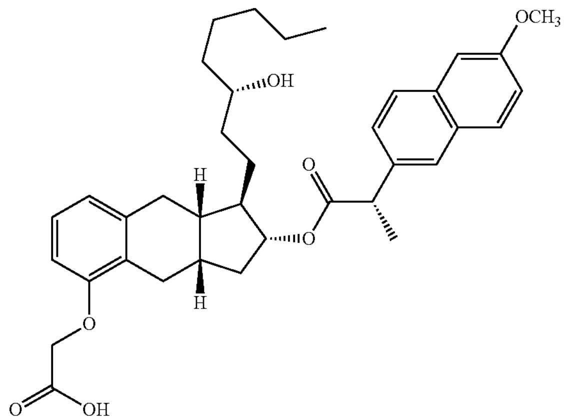 [SMILES: CCCCC[C@H](O)CC[C@@H]1[C@H]2Cc3cccc(OCC(=O)O)c3C[C@H]2C[C@H]1OC(=O)[C@@H](C)c1ccc2cc(OC)ccc2c1] | 602.77 | In Silico pKa = 3.2 Sol at pH 7.0 = 0.02 mg/mL | XXV |
| Treprostinil Side Chain isobutylphenylpropionic acid Ester (Mix of diastereomers ~1:1) Chemical Formula: $C_{36}H_{50}O_6$ Molecular Weight: 578.79 | 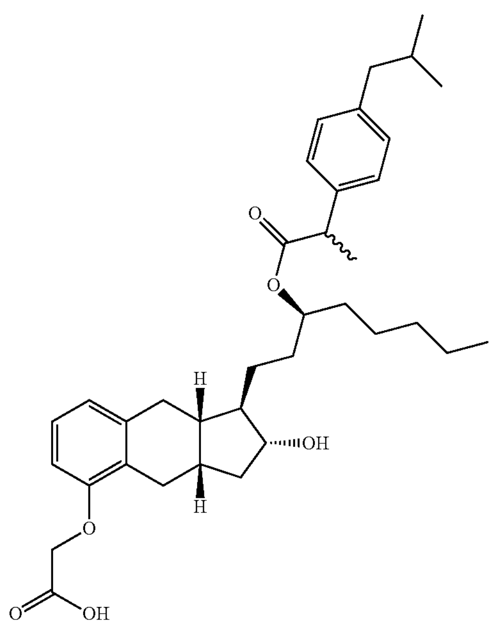 [SMILES: CCCCC[C@@H](CC[C@@H]1[C@H]2Cc3cccc(OCC(=O)O)c3C[C@H]2C[C@H]1O)OC(=O)C(C)c1ccc(CC(C)C)cc1] | 578.79 | In Silico pKa = 3.2 Sol at pH 7.0 = 0.03 mg/mL | XXVI |

TABLE 2-continued

Calculated Solubility and pKa for Select Compounds

| Compound | Structure | MW | Solubility and pKa | Patent Name |
|---|---|---|---|---|
| Treprostinil Side Chain (6-methoxynaphthalen-2-yl)propanoic acid Ester<br>Chemical Formula: $C_{37}H_{46}O_7$<br>Molecular Weight: 602.77 | | 602.77 | In Silico pKa = 3.2 Sol at pH 7.0 = 0.02 mg/mL | XXVII |
| Treprostinil Side Chain L-Valine Ester<br>Chemical Formula: $C_{28}H_{43}NO_6$ | | 489.65 | pKa = 3.2, 7.8, 15.1 Solubility at pH 7.0 = 0.0007, at pH 8.0 = 0.001 mg/mL | XXIX |
| Treprostinil Side Chain Glycine Ester<br>Chemical Formula: $C_{25}H_{37}NO_6$ | | 447.57 | pKa =3.2, 7.3, 15.1 Solubility at pH 7.0 = 0.005 mg/mL, at pH = 8.0 = 0.02 mg/mL | XXX |

TABLE 2-continued

Calculated Solubility and pKa for Select Compounds

| Compound | Structure | MW | Solubility and pKa | Patent Name |
|---|---|---|---|---|
| Treprostinil Side Chain L-Alanine Ester Chemical Formula: $C_{26}H_{39}NO_6$ | 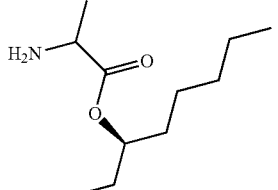 | 461.60 | pKa =3.2, 7.8, 15.1 Solubility at pH 7.0 = 0.002 mg/mL, at pH = 8.0 = 0.006 mg/mL | XXXI |
| Treprostinil mono-mer PEG carbonate | 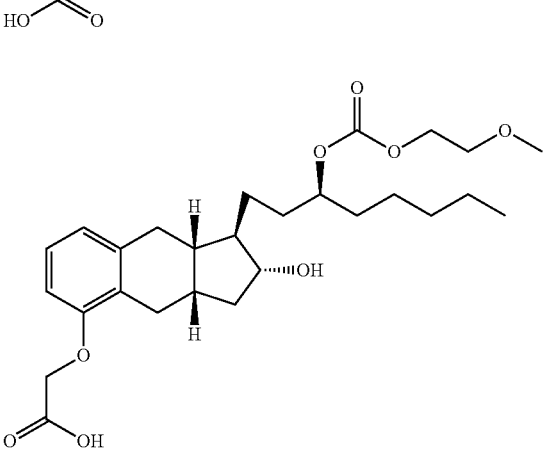 | 492.6 | Highly water soluble | XL |
| Treprostinil di-mer PEG carbonate | 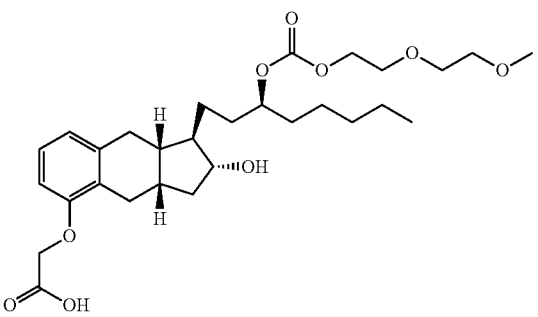 [SMILES: CCCCC[C@@H](CC[C@@H]1[C@H]2Cc3cccc(OCC(=O)O)c3C[C@H]2C[C@H]1O)OC(=O)OCCOCCOC] | 536.7 | Highly water soluble | XLI |

6.1. Plasma Stability

6.1.1. Experimental Procedure

Studies were carried out in mixed-gender human plasma male Sprague-Dawley rat plasma, and male Beagle dog plasma. All plasma was obtained from Bioreclamation and collected on K2EDTA. Plasma was adjusted to pH 7.4 prior to initiating the experiments. DMSO stocks were first prepared for the test articles. Aliquots of the DMSO solutions were dosed into 1.5 mL of plasma, which had been pre-warmed to 37° C., at a final test article concentration of 1 µM. The vials were kept in a benchtop Thermomixer® for the duration of the experiment. Aliquots (200 µL) were taken at each time point (0, 15, 30, 60, and 120 minutes) and added to 96-well plates which had been pre-filled with 400 µL of acetonitrile (ACN). Samples were stored at 4° C. until the end of the experiment. After the final time point was sampled, the plate was mixed and then centrifuged at 3000 rpm for 10 minutes. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives were calculated using GraphPad software, fitting to a single-phase exponential decay equation.

6.1.2. Experimental Results

TABLE 3

Stability of Prodrugs in Plasma

| Test Article | Species | Percent Remaining | | | | | Half-Life[a] |
| --- | --- | --- | --- | --- | --- | --- | --- |
| | | 0 min | 15 min | 30 min | 60 min | 120 min | (min) |
| Prodrug LXX | Human | 100 | 92.4 | 102 | 93.3 | 103 | >120 |
| | Rat | 100 | 98.3 | 80.3 | 69.3 | 45.0 | 102 |
| | Dog | 100 | 103 | 116 | 97.4 | 91.4 | >120 |
| Prodrug LXXI | Human | 100 | 114 | 108 | 99.1 | 95.3 | >120 |
| | Rat | 100 | 0 | 0 | 0 | 0 | <15 |
| | Dog | 100 | 102 | 92.0 | 97.6 | 81.6 | >120 |
| Prodrug LXXII | Human | 100 | 106 | 106 | 102 | 86.5 | >120 |
| | Rat | 100 | 107 | 107 | 83.6 | 79.7 | >120 |
| | Dog | 100 | 96.7 | 102 | 107 | 82.9 | >120 |

[a]When the calculated half-life is longer than the duration of the experiment, the half-life is expressed as > the longest incubation time. Then, if the calculated half-life is < 2x the duration of the experiment, the calculated half-life is listed in parentheses. Similarly, when the calculated half-life is < the first non-zero timepoint, the half-life is listed as <15, with the calculated half-life also listed in parentheses, if applicable

TABLE 4

Formation of Treprostinil in Plasma

| Test Article Dosed | Species | Concentration (μM) | | | | |
| --- | --- | --- | --- | --- | --- | --- |
| | | 0 min | 15 min | 30 min | 60 mm | 120 min |
| Prodrug LXX | Human | 0 | 0 | 0 | 0 | 0 |
| | Rat | 0 | 0.00392 | 0.0101 | 0.0331 | 0.0768 |
| | Dog | 0 | 0 | 0 | 0 | 0 |
| Prodrug LXXI | Human | 0 | 0 | 0 | 0 | 0 |
| | Rat | 0 | 0.860 | 1.04 | 1.14 | 1.00 |
| | Dog | 0 | 0 | 0 | 0 | 0 |
| Prodrug LXXII | Human | 0 | 0 | 0 | 0 | 0 |
| | Rat | 0 | 0 | 0 | 0.00595 | 0.0151 |
| | Dog | 0 | 0 | 0 | 0 | 0 |
| Prodrug LXXIII | Human | 0 | 0 | 0 | 0 | 0 |
| | Rat | 0 | 0 | 0 | 0 | 0 |
| | Dog | 0 | 0 | 0 | 0 | 0 |

6.2. Stability in Liver Microsomes

6.2.1. Experimental Procedure

Mixed-gender human liver microsomes, male Sprague-Dawley rat liver microsomes, and male Beagle dog liver microsomes were purchased from XenoTech. The reaction mixture, minus NADPH, was prepared as described below. In duplicate, the test article was added into the reaction mixture at a final concentration of 1 μM. The control compound, testosterone, was run simultaneously with the test article in a separate reaction. An aliquot of the reaction mixture (without cofactor) was equilibrated in a shaking water bath at 37° C. for 5 minutes. The reaction was initiated by the addition of cofactor, and the mixture was incubated in a shaking water bath at 37° C. Aliquots (200 μL) were withdrawn at 0, 10, 20, 30, and 60 minutes. Test article samples were immediately combined with 400 μL of ice-cold acetonitrile (ACN) to terminate the reaction. Testosterone samples were immediately combined with 400 μL of ice-cold 50/50 ACN/H2O containing 0.1% formic acid and internal standard to terminate the reaction. The samples were then mixed and centrifuged to precipitate proteins. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives and clearance were calculated using GraphPad software, fitting to a single-phase exponential decay equation.

6.2.2 Reaction Composition

Liver Microsomes 0.5 mg/mL
NADPH (cofactor) 1 mM
Potassium Phosphate, pH 7.4 100 mM
Magnesium Chloride 5 mM
Test Article 1 μM

6.2.3. Experimental Results

TABLE 5

Stability of Prodrugs in Liver Microsomes

| Test Article | Species | \multicolumn{5}{c}{Percent Remaining (AVG, n = 2)} | Half-life$^a$ (min) | $CL_{int}{}^b$ (mL/min/μg protein) |
|---|---|---|---|---|---|---|---|---|
| | | 0 min | 10 min | 20 min | 30 min | 60 min | | |
| Prodrug LXX | Human | 100* | <1.00 | <1.00 | <1.00 | <1.00 | <10 | >0.139 |
| | Rat | 100 | 31.7 | 3.50 | 1.24 | <1.00 | <10 (5.53) | >0.139 (0.250) |
| | Dog | —* | — | — | — | — | <10 | >0.139 |
| Prodrug LXXI | Human | 100 | 43.5 | 9.48 | 5.78 | 1.69 | <10 (7.32) | >0.139 (0.189) |
| | Rat | 100* | 5.68 | <1.00 | <1.00 | <1.00 | <10 (2.41) | >0.139 (0.575) |
| | Dog | 100* | 10.6 | <1.00 | <1.00 | <1.00 | <10 (3.05) | >0.139 (0.454) |
| Prodrug LXXII | Human | —* | — | — | — | — | <10 | >0.139 |
| | Rat | 100 | 55.6 | 18.5 | 10.4 | 3.66 | <10 (9.65) | >0.139 (0.144) |
| | Dog | —* | — | — | — | — | <10 | >0.139 |

$^a$When the calculated half-life is longer than the duration of the experiment, the half-life is expressed as > the longest incubation time. Then, if the calculated half-life is < 2x the duration of the experiment, the calculated half-life is listed in parentheses. Similarly, when the calculated half-life is < the first non-zero timepoint, the half-life is listed as <10, with the calculated half-life also listed in parentheses.
$^b$Intrinsic clearance ($CL_{int}$) was calculated based on $CL_{int}$ = k/P, where k is the elimination rate constant and P is the protein concentration in the incubation.
*Little to no prodrug was present in the time zero sample. It is likely this test article underwent non-CYP mediated degradation during the 5 minute pre-incubation period. Stability results should be interpreted with caution for these experiments.

TABLE 6

Formation of Treprostinil in Liver Microsomes

| Test Article Dosed | Species | \multicolumn{5}{c}{Concentration (μM) (AVG, n = 2)} |
|---|---|---|---|---|---|---|
| | | 0 min | 10 min | 20 min | 30 min | 60 min |
| Prodrug LXX | Human | 1.18 | 0.903 | 0.602 | 0.538 | 0.381 |
| | Rat | 0.336 | 0.595 | 0.764 | 0.653 | 0.699 |
| | Dog | 1.24 | 1.26 | 1.24 | 1.23 | 1.07 |
| Prodrug LXXI | Human | 0.0646 | 0.124 | 0.194 | 0.209 | 0.192 |
| | Rat | 0.301 | 0.490 | 0.638 | 0.590 | 0.595 |
| | Dog | 0.875 | 0.985 | 0.979 | 0.970 | 0.853 |
| Prodrug LXXII | Human | 0.989 | 0.829 | 0.543 | 0.485 | 0.349 |
| | Rat | 0.0413 | 0.0950 | 0.182 | 0.190 | 0.216 |
| | Dog | 1.07 | 1.07 | 1.04 | 1.05 | 0.897 |
| Prodrug LXXIII | Human | 0 | 0.00471 | 0.00629 | 0.00835 | 0.00762 |
| | Rat | 0.00 | 0.00495 | 0.00898 | 0.0117 | 0.0171 |
| | Dog | 0.00 | 0.00908 | 0.0186 | 0.0236 | 0.0294 |

TABLE 7

Half-life of Testosterone in Liver Microsomes

| Control Compound | Species | Half-life (min) | $CL_{int}$ (mL/min/mg protein) | Acceptable Range (t1/2, min) |
|---|---|---|---|---|
| Testosterone | Human | 29.2 | 0.0475 | ≤40 |
| | Rat | 1.71 | 0.809 | ≤15 |
| | Dog | 37.7 | 0.0368 | ≤41 |

6.3. Stability in Hepatocytes

6.3.1. Experimental Procedure

Mixed-gender human cryopreserved hepatocytes, male Sprague-Dawley rat cryopreserved hepatocytes, and male Beagle dog cryopreserved hepatocytes were purchased from XenoTech. The hepatocytes were thawed and prepared according to the vendor's instructions, pooled into Krebs Henseleit buffer (KHB, pH 7.4), and kept on ice prior to the experiments. The hepatocyte suspension was equilibrated in a shaking water bath at 37° C. for 3 minutes, and then the reaction was initiated by spiking the test article (in duplicate) into the hepatocyte suspension ($1.5 \times 10^6$ cells/mL) at a final test article concentration of 1 μM. The final DMSO content in the incubation mixture was ≤0.1%. The reaction mixture was incubated in a shaking water bath at 37° C. Positive controls, testosterone (1 μM) and 7-hydroxycoumarin (7-HC) (100 μM), were performed in parallel to confirm the activity of the hepatocytes. Aliquots of the test article were withdrawn (n=1) at 0, 15, 30, 60, and 120 minutes. Aliquots of testosterone were withdrawn (n=1) at 0, 5, 15, 30, 60, and 120 minutes. Aliquots of 7-HC were withdrawn (n=1) at 0 and 15 minutes. The reaction was immediately terminated by adding two volumes of ice-cold acetonitrile (ACN) to the test article samples and three volumes of ACN containing internal standard to the positive control samples. The samples were then mixed and centrifuged to precipitate proteins. An aliquot of the supernatant was then diluted with water and analyzed by LC-MS/MS against calibration standards prepared in a matched matrix. Testosterone samples were analyzed without calibration standards. All test article samples were analyzed for the dosed prodrugs as well as the drug, treprostinil. The test article concentration was compared to the concentration at time 0 to determine the percent of test article remaining at each time point. Half-lives and clearance values were calculated using GraphPad software, fitting to a single-phase exponential decay equation.

6.3.2. Experimental Results

TABLE 8

Stability of Prodrugs in Cryopreserved Hepatocytes

| Test Article | Species | \multicolumn{5}{c}{Percent Remaining (AVG, n = 2)} | Half-life$^a$ (min) | $CL_{int}^b$ (mL/min/mg protein) |
|---|---|---|---|---|---|---|---|---|
| | | 0 min | 15 min | 30 min | 60 min | 120 min | | |
| Prodrug LXX | Human | 100 | 1.57 | <1.00 | <1.00 | <1.00 | <15 (2.50) | >0.0308 (0.185) |
| | Rat | 100 | 7.28 | <1.00 | <1.00 | <1.00 | <15 (3.97) | >0.0308 (0.116) |
| | Dog | 100 | <1.00 | <1.00 | <1.00 | <1.00 | <15 | >0.0308 |
| Prodrug LXXI | Human | 100 | 32.5 | 8.06 | <1.00 | <1.00 | <15 (8.96) | >0.0308 (0.0516) |
| | Rat | 100 | <1.00 | <1.00 | <1.00 | <1.00 | <15 (1.56) | >0.0308 (0.295) |
| | Dog | 100 | 1.50 | <1.00 | <1.00 | <1.00 | <15 (2.47) | >0.0308 (0.187) |
| Prodrug LXXII | Human | 100 | <1.00 | <1.00 | <1.00 | <1.00 | <15 (1.67) | >0.0308 (0.276) |
| | Rat | 100 | 21.3 | 3.42 | <1.00 | <1.00 | <15 (6.63) | >0.0308 (0.0697) |
| | Dog | 100 | <1.00 | <1.00 | <1.00 | <1.00 | <15 | >0.0308 |

$^a$When the calculated half-life is longer than the duration of the experiment, the half-life is expressed as > the longest incubation time. Then, if the calculated half-life is < 2x the duration of the experiment, the calculated half-life is listed in parentheses. Similarly, when the calculated half-life is < the first non-zero timepoint, the half-life is listed as <15, with the calculated half-life also listed in parentheses if applicable.
$^b$Intrinsic clearance ($CL_{int}$) was calculated based on $CL_{int} = k/P$, where k is the elimination rate constant and P is the cell concentration in the incubation.

TABLE 9

Formation of Treprostinil in Cryopreserved Hepatocytes

| Test Article Dosed | Species | \multicolumn{5}{c}{Concentration (µM) (AVG, n = 2)} |
|---|---|---|---|---|---|---|
| | | 0 min | 15 min | 30 min | 60 min | 120 min |
| Prodrug LXX | Human | 0.00542 | 0.638 | 0.556 | 0.482 | 0.413 |
| | Rat | 0 | 0.606 | 0.579 | 0.484 | 0.405 |
| | Dog | 0.0959 | 0.736 | 0.597 | 0.511 | 0.445 |
| Prodrug LXXI | Human | 0 | 0.118 | 0.211 | 0.273 | 0.259 |
| | Rat | 0 | 0.422 | 0.403 | 0.347 | 0.292 |
| | Dog | 0.00293 | 0.501 | 0.408 | 0.348 | 0.303 |
| Prodrug LXXII | Human | 0.00458 | 0.562 | 0.491 | 0.433 | 0.364 |
| | Rat | 0 | 0.240 | 0.301 | 0.298 | 0.274 |
| | Dog | 0.0636 | 0.671 | 0.541 | 0.465 | 0.401 |
| Prodrug LXXIII | Human | 0 | 0.0163 | 0.0399 | 0.0848 | 0.158 |
| | Rat | 0 | 0.00970 | 0.0208 | 0.0431 | 0.0925 |
| | Dog | 0 | 0.0506 | 0.112 | 0.195 | 0.272 |

TABLE 10

Half-life of Testosterone in Cryopreserved Hepatocytes

| Species | Half-life (min) | Clint (mL/min/10$^6$ cells) | Half-life Acceptance Criteria |
|---|---|---|---|
| Human | 4.82 | 0.0959 | ≤5.0 |
| Rat | 1.03 | 0.448 | ≤5.0 |
| Dog | 6.50 | 0.0711 | ≤10.0 |

TABLE 11

Rates of Formation of Glucuronide and Sulfate of 7-Hydroxycoumarin in Cryopreserved Hepatocytes

| Species | Analyte | Formation Rate (pmol/min/10$^6$ cells) | Acceptable Range (pmol/min/10$^6$ cells) |
|---|---|---|---|
| Human | 7-HC-G | 97.7 | ≥50 |
| | 7-HC-S | 10.8 | ≥1.0 |
| Rat | 7-HC-G | 91.4 | ≥25 |
| | 7-HC-S | 24.7 | ≥5.0 |
| Dog | 7-HC-G | 114 | ≥50 |
| | 7-HC-S | 35.9 | ≥5.0 |

7-HC-G: 7-hydroxy coumarin glucuronide; 7-HC-S: 7 hydroxycoumarin sulfate 6.4. Stability in Simulated Intestinal Fluid 6.4.1. Experimental Procedure Studies were carried out in simulated intestinal fluid (SIF). SIF was prepared by dissolving 6.8 g of $KH_2PO_4$ in 250 mL of water, mixing, and then adding 77 mL of 0.2 N NaOH and 750 mL of water. Pancreatin (10 g) was added, mixed, and the pH was adjusted to pH 6.8 with 10 N NaOH. DMSO stocks were first prepared for the test articles. Aliquots of the DMSO solutions were dosed into 0.4 mL of matrix, which had been pre-warmed to 37° C., at a final test article concentration of 1 µM. The vials were kept in a benchtop Thermomixer® for the duration of the experiment. A separate tube was dosed for each time point in each matrix. At the appropriate times (0, 15, 30, 60, and 120 minutes), 0.8 mL of acetonitrile (ACN) containing 1% formic acid and internal standard was added directly to a single tube. Samples were mixed and then immediately stored at 4° C. until the end of the experiment. After the final time point was sampled, the plate was mixed and then centrifuged at 3000 rpm for 10 minutes. Aliquots of the supernatant were removed, diluted 1:1 into distilled water containing internal standard, and analyzed by LC-MS/MS against calibration standards prepared in a matched matrix. All samples were analyzed for the dosed prodrugs as well as the drug, treprostinil. The test article concentration was compared to the concentration at time 0 to determine the percent of test article remaining at each time point. Half-lives were calculated using GraphPad software, fitting to a single-phase exponential decay equation.

FLUOstar® plate reader, and the formation of calcein (Sigma) was monitored by fluorescence (490/515 nm). Calibration standards of calcein were prepared in distilled water by serial dilutions of a calcein DMSO stock at final concentrations ranging from 1 μM to 1 nM. All samples and standards were read concurrently (Table 15).

For each of the test articles, 495 μL of skin homogenate was added to triplicate centrifuge tubes. To each tube, 5 μL of a 100 μM solution of test article was added, for a final test

TABLE 12

Stability of Prodrugs in Simulated Intestinal Fluid

| Test Article | Matrix | Percent Remaining | | | | | Half-Life[a] |
| | | 0 min | 15 min | 30 min | 60 min | 120 min | (min) |
|---|---|---|---|---|---|---|---|
| Prodrug LXX | SIF | 100 | 97.2 | 104 | 93.6 | 86.2 | >120 |
| Prodrug LXXI | SIF | 100 | 96.2 | 100 | 91.9 | 83.5 | >120 |
| Prodrug LXXII | SIF | 100 | 111 | 107 | 108 | 109 | >120 |

[a]When the calculated half-life is longer than the duration of the experiment, the half-life is expressed as > the longest incubation time. Then, if the calculated half-life is < 2x the duration of the experiment, the calculated half-life is listed in parentheses.

TABLE 13

Formation of Treprostinil in Simulated Fluid

| Test Article Dosed | Matrix | Concentration (μM) | | | | |
| | | 0 min | 15 min | 30 min | 60 min | 120 min |
|---|---|---|---|---|---|---|
| Prodrug LXX | SIF | 0 | 0 | 0 | 0.00415 | 0.0720 |
| Prodrug LXXI | SIF | 0 | 0 | 0 | 0 | 0.0121 |
| Prodrug LXXII | SIF | 0 | 0 | 0 | 0 | 0.0126 |
| Prodrug LXXIII | SIF | 0 | 0 | 0 | 0 | 0 |

6.5. Stability in Human Subcutaneous Skin Homogenate

The objective of this study was to determine the stability of seven test articles in human subcutaneous skin homogenate.

6.5.1. Experimental Procedure

The stability of calcein-AM and test articles (Prodrugs IV, LXIV, LXVII, LXX, LXXI, LXXII and LXXIII) was assessed in subcutaneous skin homogenate (BioIVT, Lot information in Table 14). The pool of skin homogenate was prepared by combining equal volumes of three lots that were tested in the initial skin homogenate lot assessment experiments.

A stock solution of calcein-AM was first prepared at 5 mM in DMSO, followed by a serial dilution into methanol at a concentration of 100 μM. 495 μL of skin homogenate was thawed and warmed to 37° C. A 5 μL aliquot of the 100 μM calcein-AM solution was spiked into the skin homogenate, for a final calcein-AM dosing concentration of 1 μM. After briefly mixing, 150 μL aliquots were removed in triplicate and transferred to 96-well Falcon plates. The plates were placed onto a Thermomixer and maintained at 37° C., with gentle shaking for the duration of the experiment. At each time point (0, 15, 30, 60, and 120 minutes), the plate was removed from the Thermomixer and transferred to a article dosing concentration of 1 μM. The tubes were placed onto a Thermomixer and maintained at 37° C. with gentle shaking for the duration of the experiment. At each time point (0, 30, 60, and 120 minutes), a 100 μL aliquot was removed from each tube and combined with 200 μL of acetonitrile to stop the stability reaction. The tubes were mixed and centrifuged at 3000 rpm for 10 minutes. Aliquots of supernatant were removed and diluted 1:1 with distilled water containing internal standard (2 μM treprostinil-d4). Calibration standards for the treprostinil analysis were prepared for each test article in a surrogate matrix (supernatant from a mixture of 1:2 human plasma:acetonitrile), at concentrations ranging from 1 μM to 1 nM. Calibration standards were also diluted 1:1 with distilled water containing internal standard. Analytical conditions are outlined in Appendix 1. The disappearance of each individual test article was monitored, as well as the formation of treprostinil (Table 16 and Table 17).

TABLE 14

Skin Homogenate Lot Information

| Fraction | Gender | Age | Race |
|---|---|---|---|
| Subcutaneous | Female | 43 | Hispanic |
| Subcutaneous | Female | 31 | African American |
| Subcutaneous | Female | 37 | Caucasian |

6.5.2. Experimental Results

TABLE 15

Formation of Calcein in Pooled Human Skin Homogenate

| Test Article Dosed | Calcein Concentration (μM) (Avg, n = 3) | | | | |
| | 0 min | 15 min | 30 min | 60 min | 120 min |
|---|---|---|---|---|---|
| Calcein-AM | 0.00340 | 0.0243 | 0.0953 | 0.261 | 0.419 |

TABLE 16

Stability of Test Articles in Pooled Human Skin Homogenate

| Test Article | Percent Remaining (Avg, n = 3) | | | |
|---|---|---|---|---|
| | 0 min | 30 min | 60 min | 120 min |
| Prodrug IV | 100 | 90.4 | 86.3 | 78.1 |
| Prodrug LXIV | 100 | 93.6 | 88.3 | 72.6 |
| Prodrug LXVII | 100 | 79.2 | 61.6 | 35.0 |
| Prodrug LXX | 100 | 99.4 | 105 | 96.3 |
| Prodrug LXXI | 100 | 97.1 | 92.5 | 90.8 |
| Prodrug LXXIII | 100 | 86.2 | 71.2 | 64.0 |

TABLE 17

Measured Concentration of Treprostinil in Pooled Human Skin Homogenate

| Test Article Dosed | Measured Concentration (µM) (Avg, n = 3) | | | |
|---|---|---|---|---|
| | 0 min | 30 min | 60 min | 120 min |
| Prodrug IV | 0 | 0.0395 | 0.0771 | 0.153 |
| Prodrug LXIV | 0 | 0.0793 | 0.155 | 0.283 |
| Prodrug LXVII | 0 | 0.224 | 0.408 | 0.657 |
| Prodrug LXX | 0 | 0.0179 | 0.0411 | 0.0972 |
| Prodrug LXXI | 0 | 0 | 0.00262 | 0.00643 |
| Prodrug LXXII | 0 | 0.0200 | 0.0556 | 0.147 |
| Prodrug LXXIII | 0 | 0.00817 | 0.0216 | 0.0509 |

6.6. An In Vitro Assessment of the Pharmacology of Disubstituted Treprostinil Prodrugs LXX-LXXIII

6.6.1. Summary of Findings

Comparing the disubstituted prodrugs to treprostinil:

(A) Prodrugs LXX, LXXI and LXXII are inactive, and Prodrug LXXIII is approximately 200-fold less active at the prostaglandin I2 (PGI2) receptor (IP);

(B) Prodrugs LXX, LXXI and LXXIII are inactive, and Prodrug LXXII exhibits a non-traditional dose response curve at the prostaglandin E2 (PGE2) receptor 2 (EP2);

(C) Each of Prodrugs LXX-LXXIII exhibits a non-traditional dose-response curve, with Prodrugs LXX, LXXII and LXXIII being several hundred-fold less active and Prodrug LXXI approximately 2000-fold less active at the prostaglandin D2 (PGD2) receptor 1 (DP1);

(D) Each of Prodrugs LXX-LXXIII is inactive at the PGE2 receptor 1 (EP1).

6.6.2. Materials

Cells and control agonists: Cells and control agonists used in the study are summarized in the table below.

TABLE 18

Cell Lines and Control Agonists Used in the Study

| Species | Target | Parental | Assays | Control agonist |
|---|---|---|---|---|
| Human | DP1 | HEK293T | cAMP | PGD2 |
| Human | EP2 | HEK293T | cAMP | Iloprost |
| Human | IP1 | CHO-K1 | cAMP | Iloprost |
| Human | EP1 | HEK293T | Calcium | Iloprost |

TABLE 19

Compounds

| # | Compound ID | Mode |
|---|---|---|
| 1 | Treprostinil | Agonist |
| 2 | Prodrug LXX (Treprostinil diproprionic ester) | Agonist |
| 3 | Prodrug LXXI (Treprostinil dicarbonate ester) | Agonist |
| 4 | Prodrug LXXII (Treprostinil diacetate ester) | Agonist |
| 5 | Prodrug LXXIII (Treprostinil diphosphate ester) | Agonist |

Cyclic AMP assay kit: Multiscreen™ TR-FRET cAMP 1.0 No Wash Assay Kit (Multispan, Inc.)

Calcium assay kit: Multiscreen™ Calcium 1.0 No Wash Kit (Multispan, Inc., Cat #MSCA01-1)

Assay Buffer:
EP1 Calcium and DP1 cAMP Assays: HBSS plus 20 mM HEPES
EP2 and IP1 cAMP Assays: 1 mM IBMX in HBSS plus 20 mM HEPES Instruments: FlexStation III (Molecular Devices) and FLIPR 384 (Molecular Devices)

6.6.3 Methods

Cells were thawed from frozen cells and resuspended in assay buffer at desired concentrations. cAMP or Calcium assays were performed according to the manufacturer's protocol using Multiscreen™ TR-FRET cAMP 1.0 No Wash Assay Kit or Multiscreen™ Calcium 1.0 No Wash Kit.

Gas Cyclic AMP (cAMP) Assay: In agonist mode testing, cells were seeded in a 384-well plate at an appropriate density and then were treated with compounds and incubated at 37° C. for 20 minutes. The reaction was terminated by sequentially adding sequentially adding trFluor™ Eu-labeled cAMP and trFluor™ 650-labeled anti-cAMP antibody in lysis buffer. The plate was then incubated at room temperature for 30 minutes before reading fluorescent emissions at 620 nm and 665 with excitation at 314 nm on FlexStation III (Molecular Devices). All testing wells contained 0.1% DMSO in the final concentrations.

Calcium Assay: Cells were seeded in a 384-well plate at an appropriate density. The calcium assay was conducted according to the manufacturer's protocols (Multiscreen Calcium 1.0 No Wash Assay Kit). The calcium dye loading buffer was added to the cells and incubated for 1 hour at 37° C. For agonist mode, cells were injected with Iloprost control agonist or test compound by FLIPR and calcium mobilization was monitored for 180 seconds with compound injected into the wells at the 19th second. Fluorescent emissions were read at 525 nm with excitation at 490 nm in a FLIPR 384 instrument (Molecular Devices).

6.6.4. Data Analysis

Cyclic AMP (cAMP) assays: Cyclic AMP assay results are shown as "Ratio 665/620×10,000" (ratio of fluorescence at 665 nm and 620 nm×10,000). Data in graphs are represented in Mean±SD. Dose-dependent responses were fitted with sigmoidal dose-response curves allowing variable slopes using GraphPad Prism version 6 (Graphpad Prism).

Calcium Assay: Calcium assay results are expressed as "RFU" as defined in figure below. Data are represented in Mean±SEM. Dose-response curves were fitted using "Sigmoidal dose-response (variable slope)" function in GraphPad Prism 6. EC50 values were calculated based on the fitted curves.

6.6.5. Results

Prostaglandin receptor activity assessments with treprostinil and treprostinil analogues have been conducted, and a historical, positive control agonist for these receptors, iloprost (for IP, EP2 and EP1) or PGD2 (for DP1), was also included. These studies used cell lines overexpressing either human IP, EP2 or DP1, or EP1 receptors, and following incubation with varying concentrations of compounds, cAMP levels were measured using Fluorescence Resonance Energy Transfer (FRET). The 665/620 (acceptor/donor emission signals) ratio is inversely proportional to the concentration of cAMP.

Figure 11:
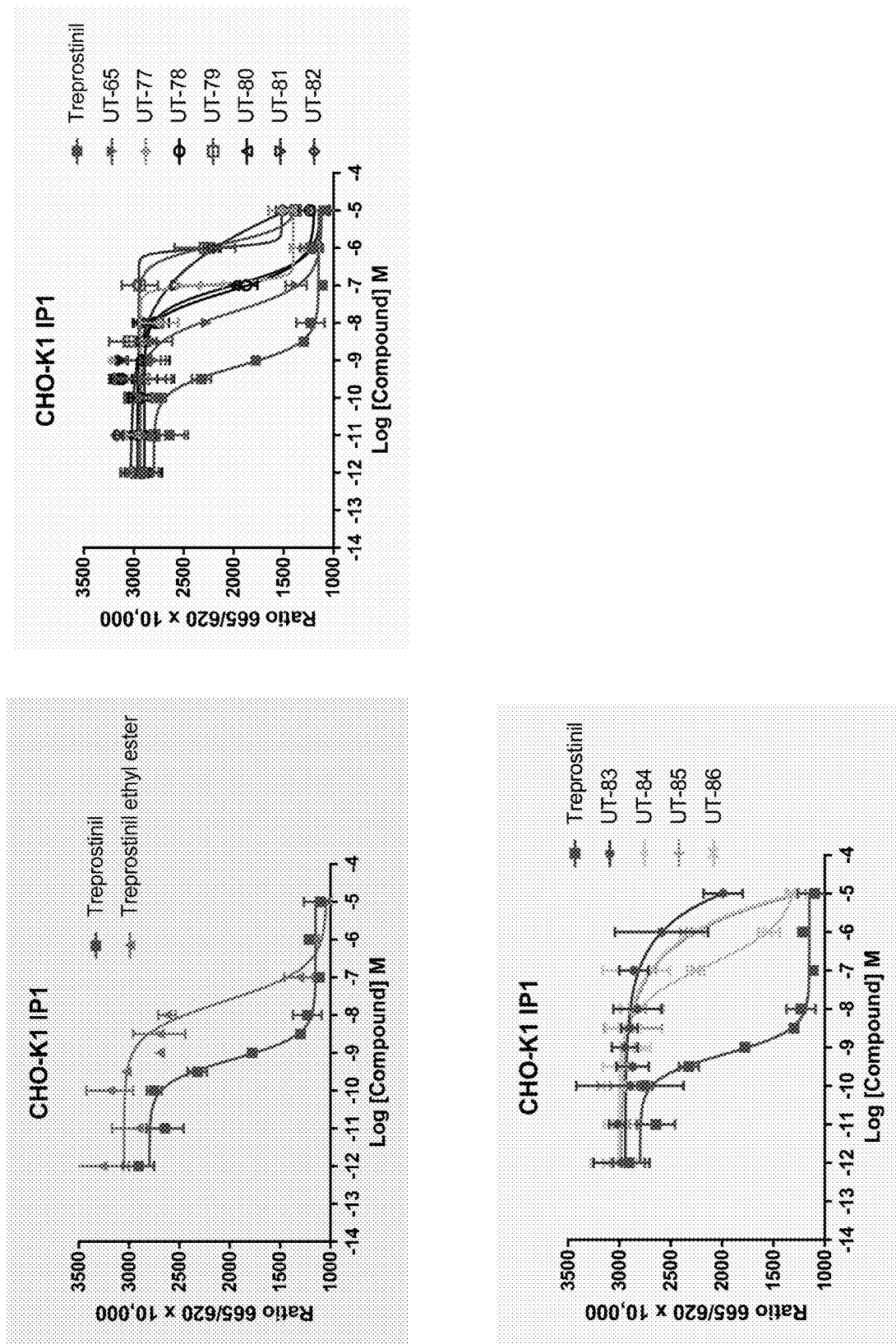
FIG. 11 presents plots comparing activities of selected treprostinil prodrugs against IP 1 receptor with that of treprostinil.
Figure 12:
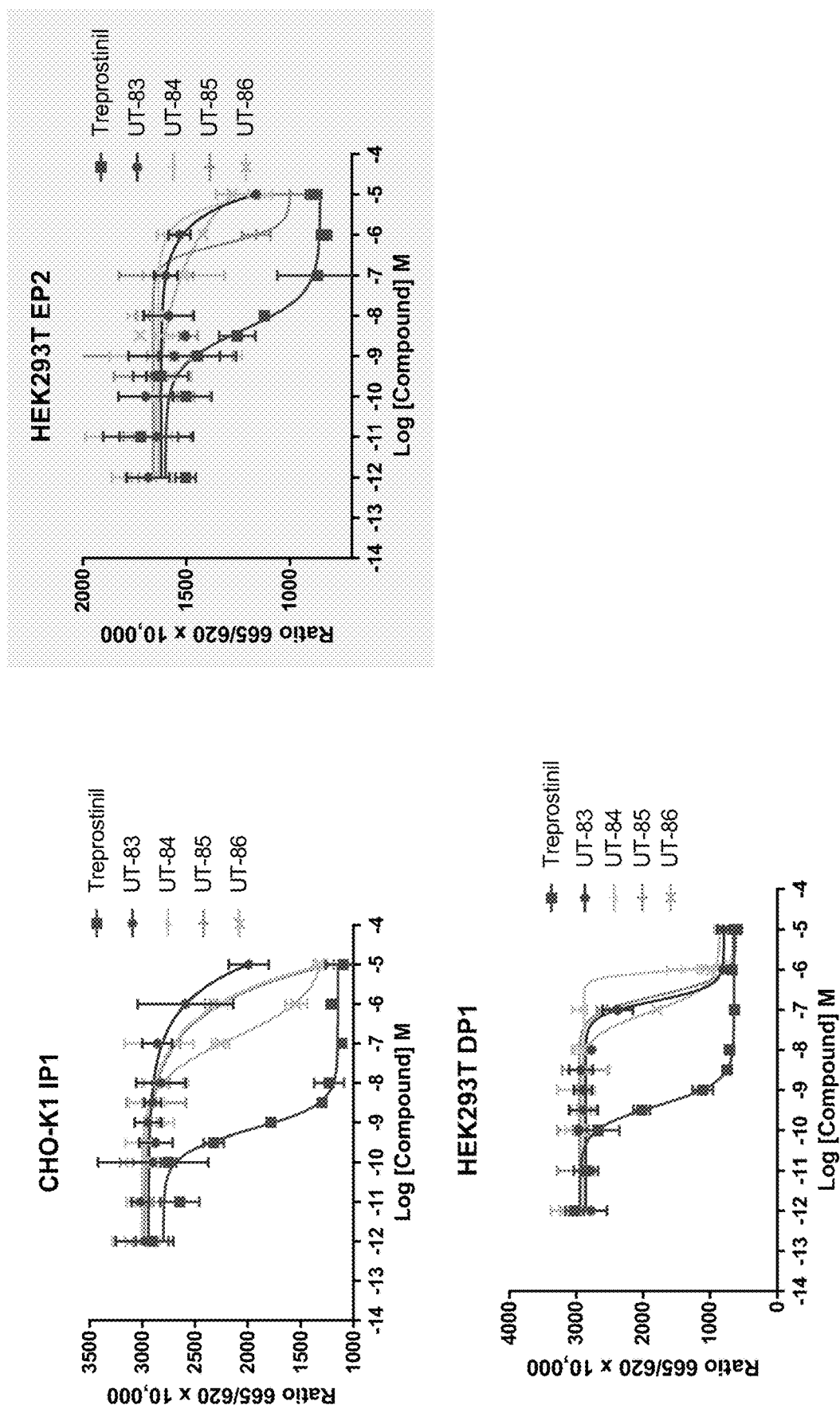
FIG. 12 presents plots comparing activities of selected treprostinil prodrugs against IP1, EP2 and DP1 receptors with those of treprostinil.

Results for treprostinil and its relative difference from the positive controls (iloprost and PGD2) were consistent with previous assessments. As shown below Tables 20 and 24-25 as well as in FIGS. 11 and 12 compared to treprostinil, the disubstituted analogs have lower activity and very different pharmacologic profiles as compared with treprostinil.

TABLE 20

EC50 Values in IP, EP2, DP1 and EP1 Receptor cAMP Assays

| Compound | $EC_{50}$ Fold Different from Treprostinil | | | |
|---|---|---|---|---|
| | IP Receptor | EP2 Receptor | DP1 Receptor | EP1 Receptor |
| Prodrug LXX | NC | NC | 410x* | NC |
| Prodrug LXXI | NC | NC | 2181x* | NC |
| Prodrug LXXII | NC | 133x* | 561x* | NC |
| Prodrug LXIII | 208x | NC | 217x* | NC |

DP1, PGD2 receptor 1; EC50, concentration that gives a half-maximal response; EP2, PGE2 receptor 2; EP1, PGE2 receptor 1; IP, PGI2 receptor
*Partial agonists or odd dose-response curves; NC = too inactive to realistically calculate.

Figure 9:
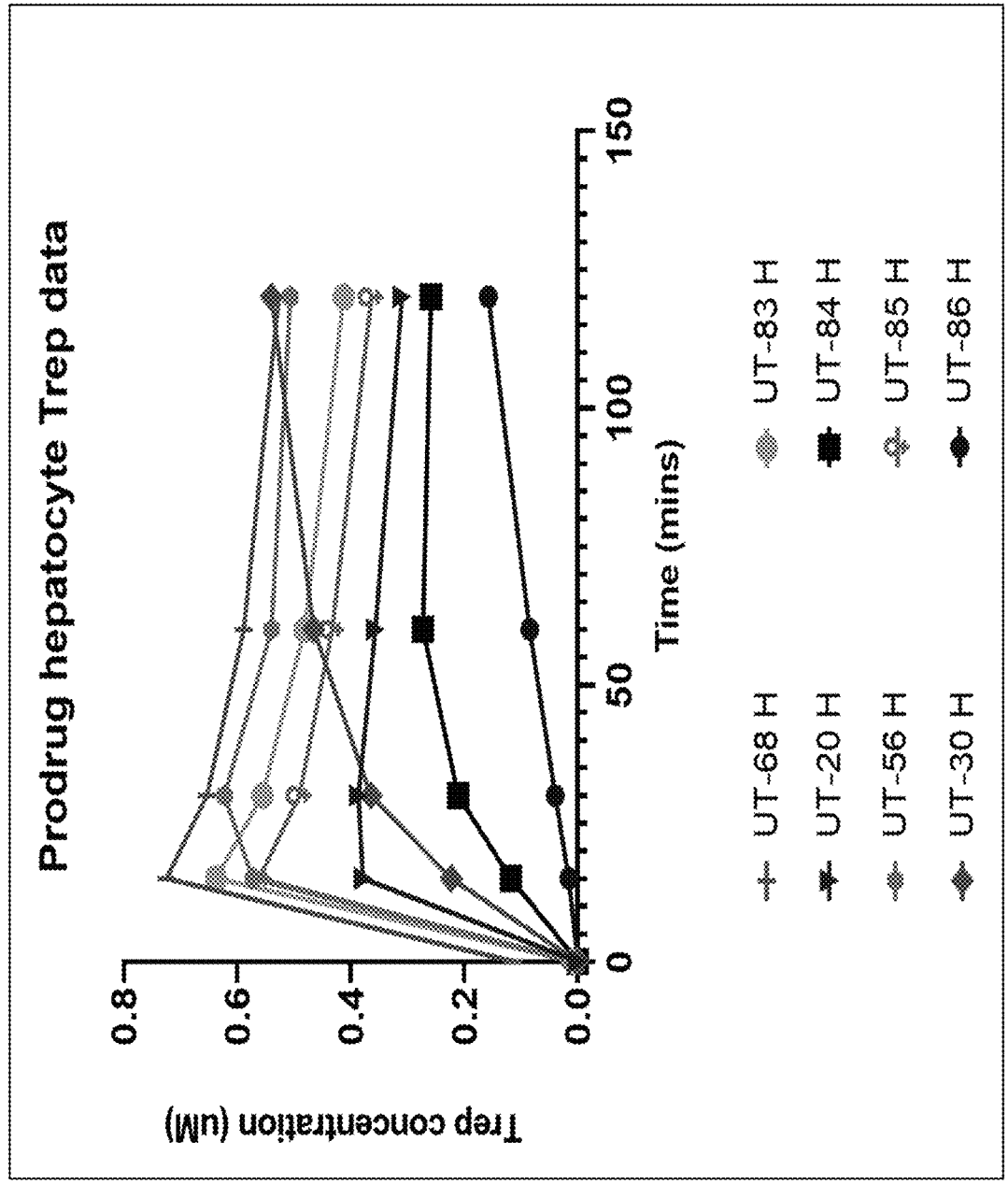
FIG. 9 is a plot presenting data for conversion to treprostinil in hepatocytes for selected treprostinil prodrugs.
Figure 10:
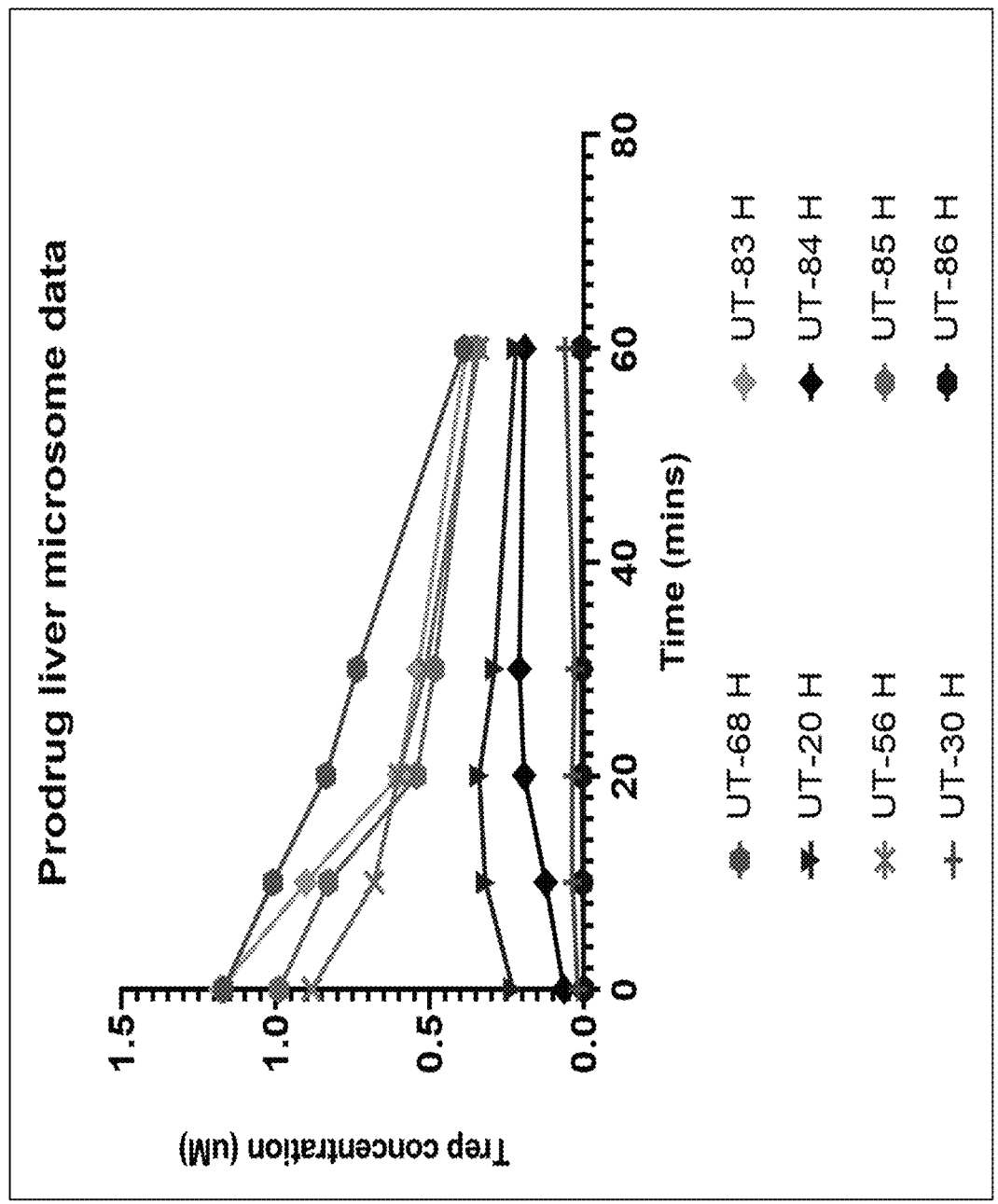

Data for prodrug conversion in hepatocytes is also presented in Table 21 and in FIG. 9.

TABLE 21

Prodrug conversion in hepatocytes

| Test Article Dosed | Species | Treprostinil Concentration (μM) | | | | | Mono AUC (umoles · min/L) | Dual AUC (umoles · min/L) |
|---|---|---|---|---|---|---|---|---|
| | | 0 min | 15 min | 30 min | 60 min | 120 min | | |
| Prodrug IV | Human | 0 | 0.379 | 0.387 | 0.357 | 0.310 | 39.8 | 26.6 |
| | Rat | 0.0652 | 0.714 | 0.652 | 0.598 | 0.575 | 70.0 | 39.8 |
| | Dog | 0 | 0.513 | 0.462 | 0.399 | 0.398 | 48.0 | 41.5 |
| Prodrug VI | Human | 0 | 0.223 | 0.365 | 0.466 | 0.540 | 48.7 | 9.7 |
| | Rat | 0.128 | 0.693 | 0.635 | 0.564 | 0.53 | 66.9 | 5.3 |
| | Dog | 0.0124 | 0.581 | 0.609 | 0.533 | 0.548 | 62.9 | 20.2 |
| Prodrug XLIII | Human | 0.00744 | 0.573 | 0.623 | 0.54 | 0.507 | 62.2 | 49.9 |
| | Rat | 0.00292 | 0.161 | 0.266 | 0.397 | 0.503 | 41.4 | 32.0 |
| | Dog | 0.0381 | 0.628 | 0.543 | 0.446 | 0.4 | 54.0 | 55.7 |
| Prodrug LV | Human | 0.113 | 0.725 | 0.654 | 0.589 | 0.527 | 68.8 | 56.2 |
| | Rat | 0.0159 | 0.506 | 0.48 | 0.424 | 0.391 | 49.3 | 56.1 |
| | Dog | 0.124 | 0.781 | 0.698 | 0.599 | 0.53 | 71.2 | 61.5 |
| Prodrug LXX | Human | 0.00542 | 0.638 | 0.556 | 0.482 | 0.413 | 56.2 | |
| | Rat | 0 | 0.606 | 0.579 | 0.484 | 0.405 | 56.1 | |
| | Dog | 0.0959 | 0.736 | 0.597 | 0.511 | 0.445 | 61.5 | |
| Prodrug LXXI | Human | 0 | 0.118 | 0.211 | 0.273 | 0.259 | 26.6 | |
| | Rat | 0 | 0.422 | 0.403 | 0.347 | 0.292 | 39.8 | |
| | Dog | 0.00293 | 0.501 | 0.408 | 0.348 | 0.303 | 41.5 | |
| Prodrug LXXII | Human | 0.00458 | 0.562 | 0.491 | 0.433 | 0.364 | 49.9 | |
| | Rat | 0 | 0.24 | 0.301 | 0.298 | 0.274 | 32.0 | |
| | Dog | 0.0636 | 0.671 | 0.541 | 0.465 | 0.401 | 55.7 | |
| Prodrug LXXIII | Human | 0 | 0.0163 | 0.0399 | 0.0848 | 0.158 | 9.7 | |
| | Rat | 0 | 0.0097 | 0.0208 | 0.0431 | 0.0925 | 5.3 | |
| | Dog | 0 | 0.0506 | 0.112 | 0.195 | 0.272 | 20.2 | |

Figure 10:
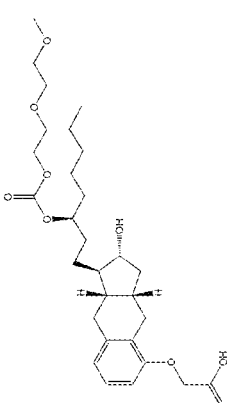
FIG. 10 is a plot presenting data for conversion to treprostinil in liver microsomes for selected treprostinil prodrugs.
Figure 10:
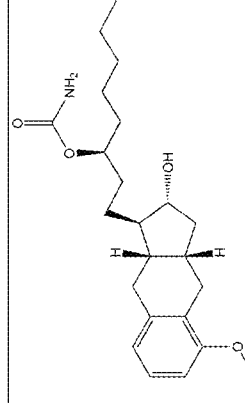
Figure 10:
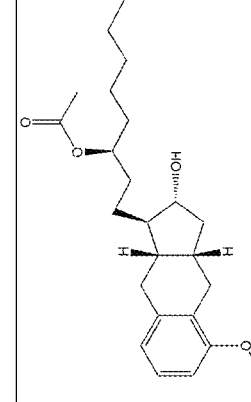
Figure 1V:
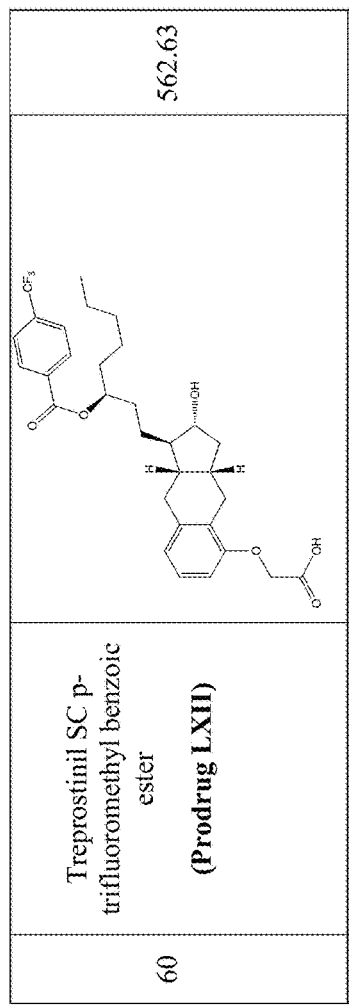
Figure 1V:
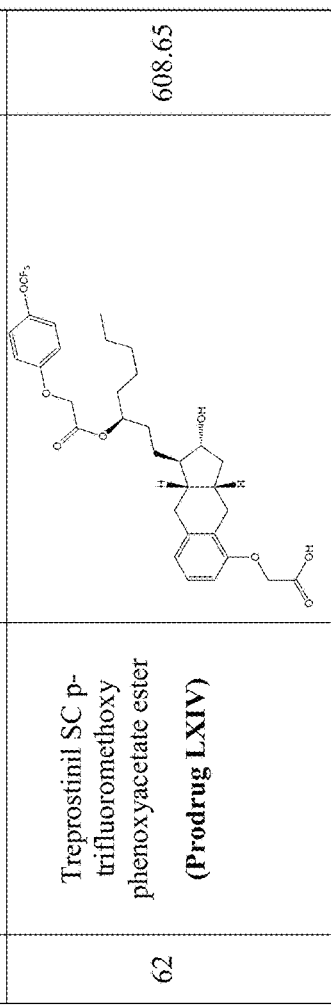
Figure 1V:
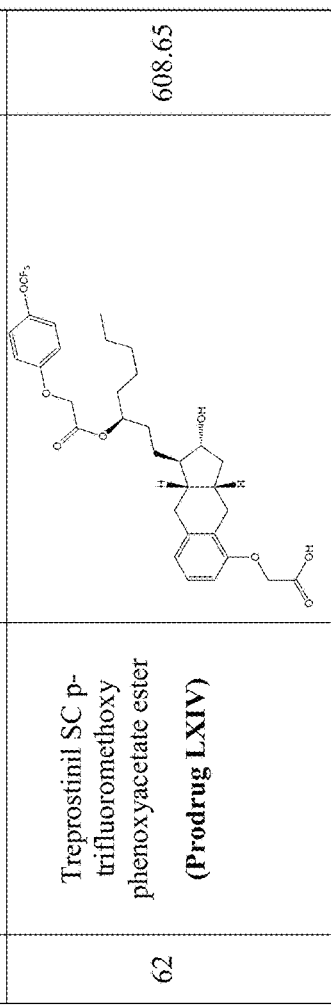
Figure 1X:
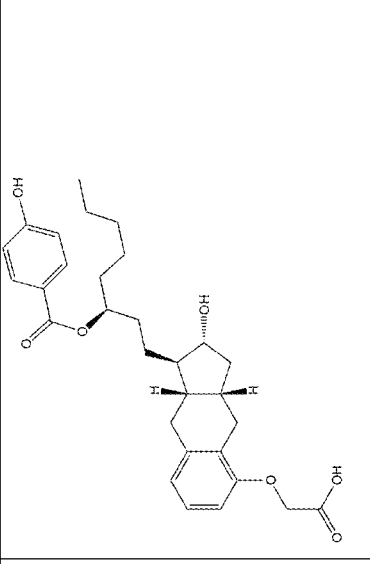
Figure 1X:
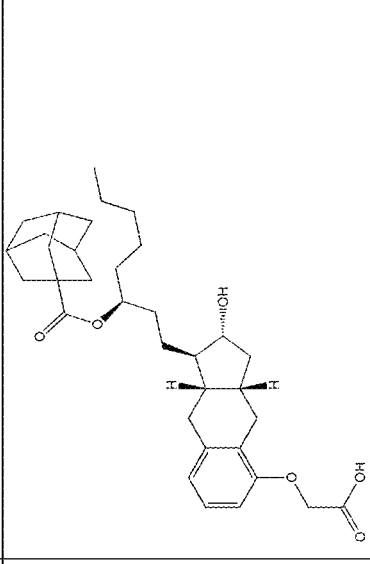
Figure 1X:
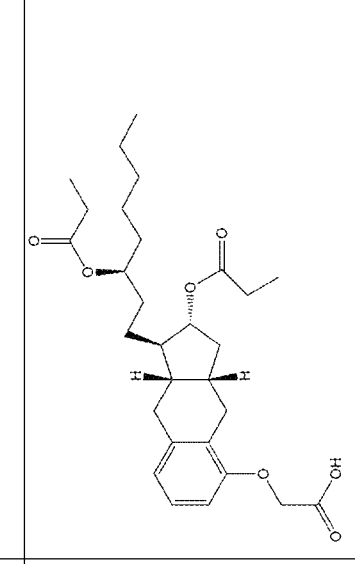
Figure 1Y:
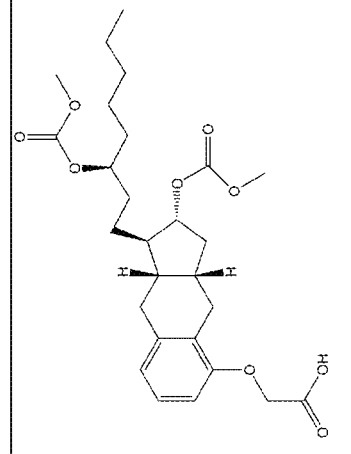
Figure 1Y:
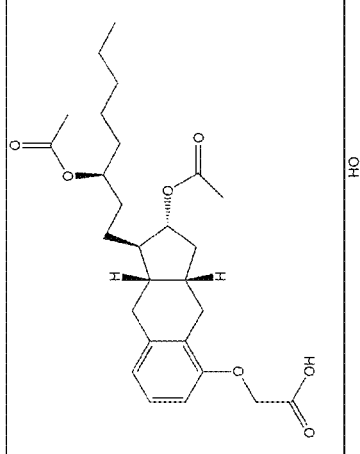
Figure 1Y:
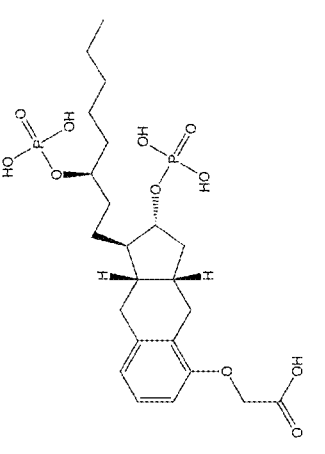

Data for prodrug conversion in liver microsomes is also presented in Table 22 and in FIG. 10.

TABLE 22

Prodrug conversion in liver microsomes.

| Test Article Dosed | Species | Treprostinil Concentration (μM) | | | | | Mono AUC (umoles · min/L) | Dual AUC (umoles · min/L) |
|---|---|---|---|---|---|---|---|---|
| | | 0 min | 15 min | 30 min | 60 min | 120 min | | |
| Prodrug IV | Human | 0.23 | 0.32 | 0.34 | 0.29 | 0.22 | 16.9 | 10.6 |
| | Rat | 0.89 | 0.88 | 0.85 | 0.82 | 0.77 | 49.7 | 33.5 |
| | Dog | 0.74 | 0.95 | 0.94 | 0.94 | 0.97 | 56.0 | 56.2 |

TABLE 22-continued

Prodrug conversion in liver microsomes.

| Test Article Dosed | Species | Treprostinil Concentration (μM) | | | | | Mono AUC (umoles · min/L) | Dual AUC (umoles · min/L) |
|---|---|---|---|---|---|---|---|---|
| | | 0 min | 15 min | 30 min | 60 min | 120 min | | |
| Prodrug VI | Human | 0.02 | 0.038 | 0.038 | 0.03 | 0.061 | 2.4 | 0.4 |
| | Rat | 0.27 | 0.39 | 0.46 | 0.53 | 0.73 | 31.4 | 0.6 |
| | Dog | 0.21 | 0.32 | 0.43 | 0.48 | 0.75 | 29.4 | 33.6 |
| Prodrug XLIII | Human | 0.883 | 0.681 | 0.602 | 0.513 | 0.341 | 32.6 | 10.0 |
| | Rat | 0.035 | 0.0741 | 0.111 | 0.145 | 0.206 | 8.0 | 60.9 |
| | Dog | 0.964 | 0.917 | 0.899 | 0.932 | 0.873 | 54.7 | 60.9 |
| Prodrug LV | Human | 1.17 | 1.01 | 0.837 | 0.736 | 0.389 | 44.9 | 37.4 |
| | Rat | 0.26 | 0.43 | 0.525 | 0.586 | 0.553 | 30.9 | 38.8 |
| | Dog | 0.971 | 0.961 | 0.934 | 0.915 | 0.743 | 53.3 | 71.9 |
| Prodrug LXX | Human | 1.18 | 0.903 | 0.602 | 0.538 | 0.381 | 37.4 | |
| | Rat | 0.336 | 0.595 | 0.764 | 0.653 | 0.699 | 38.8 | |
| | Dog | 1.24 | 1.26 | 1.24 | 1.23 | 1.07 | 71.9 | |
| Prodrug LXXI | Human | 0.0646 | 0.124 | 0.194 | 0.209 | 0.192 | 10.6 | |
| | Rat | 0.301 | 0.49 | 0.638 | 0.59 | 0.595 | 33.5 | |
| | Dog | 0.875 | 0.985 | 0.979 | 0.97 | 0.853 | 56.2 | |
| Prodrug LXXII | Human | 0.989 | 0.829 | 0.543 | 0.485 | 0.349 | 33.6 | |
| | Rat | 0.0413 | 0.095 | 0.182 | 0.19 | 0.216 | 10.0 | |
| | Dog | 1.07 | 1.07 | 1.04 | 1.05 | 0.897 | 60.9 | |
| Prodrug LXXIII | Human | 0 | 0.00471 | 0.00629 | 0.00835 | 0.00762 | 0.4 | |
| | Rat | 0 | 0.00495 | 0.00898 | 0.0117 | 0.0171 | 0.6 | |
| | Dog | 0 | 0.00908 | 0.0186 | 0.0236 | 0.0294 | 1.2 | |

Table 23. Prodrug conversion in skin homogenate for selected treprostinil prodrugs.

TABLE 23

Prodrug conversion in skin homogenate

| Test Article Dosed | Species | Treprostinil Concentration (μM) | | | | Mono AUC (umoles · min/L) | Dual AUC (umoles · min/L) |
|---|---|---|---|---|---|---|---|
| | | 0 min | 30 min | 60 min | 120 min | | |
| Prodrug IV | Human | 0 | 0.0443 | 0.0795 | 0.156 | 9.59 | 0.3108 |
| Prodrug VI | Human | 0 | 0.6 | 0.93 | 1.07 | 91.95 | 2.744 |
| Prodrug XLIII | Human | 0.0034 | 0.382 | 0.583 | 0.839 | 62.92 | 7.512 |
| Prodrug LV | Human | 0.0045 | 0.545 | 0.741 | 0.954 | 78.38 | 5.303 |
| Prodrug LXX | Human | 0 | 0.0179 | 0.0411 | 0.0972 | 5.303 | |
| Prodrug LXXI | Human | 0 | 0 | 0.00262 | 0.00643 | 0.3108 | |
| Prodrug LXXII | Human | 0 | 0.02 | 0.0556 | 0.147 | 7.512 | |
| Prodrug LXXIII | Human | 0 | 0.00817 | 0.0216 | 0.0509 | 2.744 | |

Tables 24-25 and FIGS. 11-12 present data for activity of selected treprostinil prodrugs against IP, EP1, EP2 and DP receptors in comparison to those of treprostinil.

TABLE 24

| | Activity | | | |
|---|---|---|---|---|
| | IP Relative to Tre | EP2 Relative to Tre | DP1 Relative to Tre | EP1 Relative to Tre |
| Prodrug VII | 875x | 110,000x | 600x | Not tested |
| Prodrug IV | 175x | 674x | 204x | Not tested |
| Prodrug VI | 5x | 4x | 2x | 5x |
| Prodrug VI repeat | 1.5x | 9x | 2x | 42x |
| Prodrug XLIII | 632x | 461x | 272x | 20x* |
| Prodrug LV | 54x | 50x | 94x | 122x* |

TABLE 24-continued

| | Activity | | | |
|---|---|---|---|---|
| | IP Relative to Tre | EP2 Relative to Tre | DP1 Relative to Tre | EP1 Relative to Tre |
| Treprostinil ethyl ester | 35x | 11x | 18x | 30x |
| Prodrug LII | 27x | 26x | 73x | 133x* |
| Prodrug LXIV | 162x* | 24x* | 38x | 0.03x* |
| Prodrug LXV | 99x | 187x* | 89x | 64x* |
| Prodrug LXVI | 1803x* | ⊗ | 1527x | 0.01x* |
| Prodrug LXVII | 148x | 34x* | 184x | ⊗ |
| Prodrug LXVIII | ⊗ | 2619x | 1048x | ⊗ |
| Prodrug LXIX | 1470x* | 236x* | 1897x | ⊗ |

TABLE 24-continued

| | Activity | | | |
|---|---|---|---|---|
| | IP Relative to Tre | EP2 Relative to Tre | DP1 Relative to Tre | EP1 Relative to Tre |
| | Di-Substituted | | | |
| Prodrug LXX | ⊗ | ⊗ | 410x | ⊗ |
| Prodrug LXXI | ⊗ | ⊗ | 2181x* | ⊗ |
| Prodrug LXXII | ⊗ | 133x* | 561x | ⊗ |
| Prodrug LXXIII | 208x | ⊗ | 217x | ⊗ |

Relative to treprostinil $EC_{50}$ values
*Partial agonists or ambiguous dose-response curves
⊗ = too high to realistically calculate

TABLE 25

| | Activity | | | |
|---|---|---|---|---|
| | IP Relative to Tre | EP2 Relative to Tre | DP1 Relative to Tre | EP1 Relative to Tre |
| Prodrug VII | 875x | 110,000x | 600x | Not tested |
| Prodrug IV | 175x | 674x | 204x | Not tested |
| Prodrug LXX | ⊗ | ⊗ | 410x | ⊗ |
| Prodrug LXXI | ⊗ | ⊗ | 2181x* | ⊗ |
| Prodrug LXXII | ⊗ | 133x* | 561x | ⊗ |
| Prodrug LXXIII | 208x | ⊗ | 217x | ⊗ |

Relative to treprostinil $EC_{50}$ values
*Partial agonists or ambiguous dose-response curves
⊗ = too high to realistically calculate Tables 26, 27 and 28 present data for hydrolysis of selected treprostinil prodrugs at pH 6, 7 and 8, respectively, and 40 C.

TABLE 26

Hydrolysis of selected treprostinil prodrugs to treprostinil at pH 6 and 40 C.

| Prodrug | % Area, t = 1 week | % Area, t = 2 weeks | % Area, t = 3 weeks |
|---|---|---|---|
| Prodrug LXIV | 0.72 | 1.2 | 1.5 |
| Prodrug LXV | 0.13 | 0.29 | 0.39 |
| Prodrug LXVI | 0.47 | 1.2 | 1.9 |
| Prodrug LXVII | 0.00 | 0.00 | 0.00 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.00 |
| Prodrug LXXII | 0.00 | 0.00 | 0.00 |
| Prodrug LXXIII | 0.00 | 0.00 | 0.00 |

TABLE 27

Hydrolysis of selected treprostinil prodrugs to treprostinil at pH 7 and 40 C.

| Prodrug | % Area t = 1 week | % Area t = 2 weeks | % Area t = 3 weeks |
|---|---|---|---|
| Prodrug LXIV | 0.46 | 0.93 | 1.2 |
| Prodrug LXV | 0.96 | 1.9 | 2.7 |
| Prodrug LXVI | 0.05 | 1.0 | 1.5 |
| Prodrug LXVII | 0.00 | 0.00 | 0.00 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.00 |
| Prodrug LXXII | 0.00 | 0.00 | 0.00 |
| Prodrug LXXIII | 0.00 | 0.00 | 0.00 |

TABLE 28

Hydrolysis of selected treprostinil prodrugs to treprostinil at pH 8 and 40 C.

| Prodrug | % Area (t = 1 week) | % Area (t = 2 weeks) | % Area (t = 3 weeks) |
|---|---|---|---|
| Prodrug LXIV | 1.8 | 3.9 | 5.8 |
| Prodrug LXV | 6.0 | 11.4 | 16.9 |
| Prodrug LXVI | 0.73 | 1.6 | 2.6 |
| Prodrug LXVII | 0.00 | 0.23 | 0.27 |
| Prodrug LXVIII | 0.00 | 0.00 | 0.00 |
| Prodrug LXIX | 0.00 | 0.00 | 0.00 |
| Prodrug LXX | 0.00 | 0.00 | 0.00 |
| Prodrug LXXI | 0.00 | 0.00 | 0.38 |
| Prodrug LXXII | 0.00 | 0.00 | 0.00 |
| Prodrug LXXIII | 0.00 | 0.00 | 0.00 |

Example 7

7.1. Synthesis of Treprostinil Mono Substituted Prodrugs

Scheme 16: Synthesis of Prodrugs XXXII-XXXVII, XLIII-XLIV, XLVIII, XLIX, XLVIII, XLIX, LIV, and LV

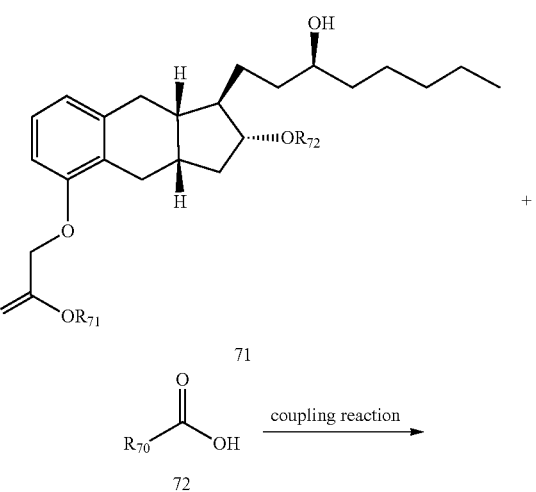

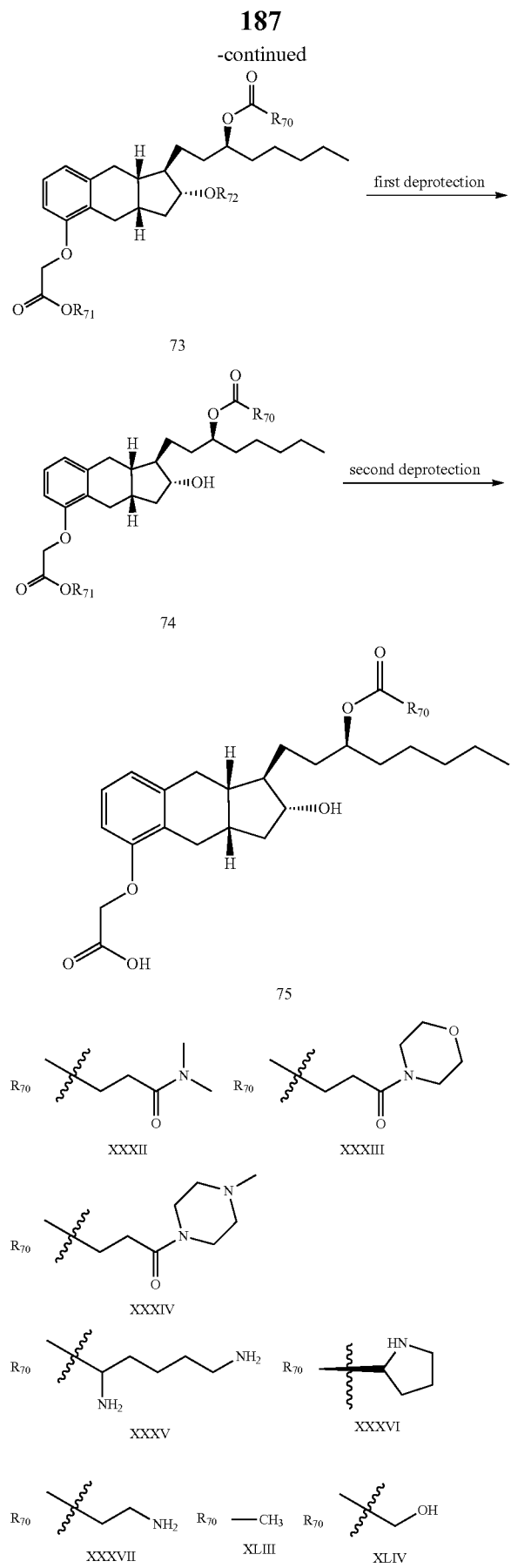

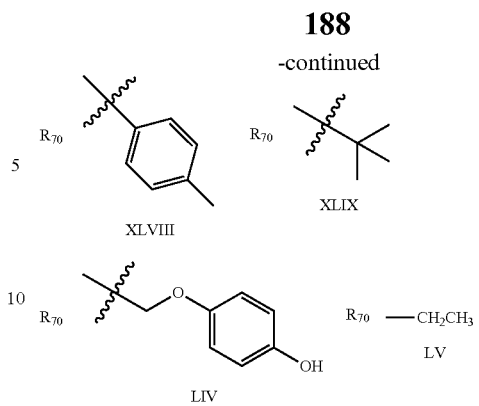

In Scheme 16, $R_{72}$ may be triethylsilyl (TES) or another silyl ester, such as trimethylsilyl, t-butyldimethylsilyl, t-butyldiphenylsilyl, phenyldimethylsilyl, while $R_{71}$ may be benzyl or a substituted benzyl, i.e. a benzyl group substituted at one or more meta, ortho or para positions with one or more substituents, which may be independently selected from the group consisting of —NO2, —CN, halogen (e.g., —F, —Cl, —Br or —I), (C1-C3)alkyl, halo(C1-C3)alkyl, (C1-C3)alkoxy and halo(C1-C3)alkoxy.

7.1.1. Experimental

General Procedure for Syntheses of Treprostinil Side Chain Substituted Mono-TES Benzyl Ester (73) (Coupling Reaction):

To a stirring solution of treprostinil mono-TES benzyl ester (71) (1.0 eq) in dichloromethane (DCM) (10 v/wt)) were added acid (72) (1.2 eq), diisopropylethylamine (DIPEA) (2.5 eq) or triethylamine (2.5 eq) and 4-N,N-dimethylaminopyridine (DMAP) (0.2 eq). After stirring for 10 min, EDCI.HCl (2.5 eq) was added and the mixture stirred at room temperature under argon for 3 h. Water was added and the aqueous layer was extracted with DCM. The combined organic extracts were washed with brine, dried over sodium sulfate, filtered, and concentrated the filtrate in vacuo to give crude product. It was purified by silica gel column chromatography to give treprostinil side chain substituted mono-TES benzyl ester (73). The compound 73 were characterized by $^1$H NMR and LCMS. Purities were determined by HPLC.

General Procedure for the Syntheses of Treprostinil Side Chain Substituted Benzyl Ester (74) (First Deprotection or Desilylation)

To a stirring solution of treprostinil side chain substituted mono-TES benzyl ester (74) (1.0 eq) in THF (15 v/wt) and water (3 v/wt) was added HCl solution (2N) (1.0 eq) and the mixture was stirred at room temperature for 1 h. Water and EtOAc were added. The aqueous layer was extracted with ethyl acetate. The combined organic layers were washed with water, brine, dried over sodium sulfate, filtered, and concentrated the filtrate in vacuo to give crude product. It was purified on silica gel column chromatography to obtain treprostinil side chain substituted benzyl ester (74). The compound 74 were characterized by $^1$H NMR and LCMS. Purities were determined by HPLC.

General Procedure for the Syntheses of Treprostinil Side Chain Esters (75) (Second Deprotection or Debenzylation)

To a stirring solution of treprostinil side chain substituted benzyl ester (74). (1.0 eq) in ethyl acetate (20 v/wt) was added 5% palladium on carbon (25 wt %). The system was evacuated under house vacuum and replaced with hydrogen (repeated this process for two more times). The system was connected to hydrogen balloon and stirred at room temperature for 1 h. It was filtered through a Celite pad and washed with ethyl acetate. The filtrate was concentrated in vacuo to give treprostinil side chain esters (75). The compound 75 were characterized by IR, $^1$H NMR, $^{13}$C NMR and LCMS. Purities were determined by HPLC.

Similarly following the general procedures described above, prodrugs XXXII, XXXIII, XXXIV, XXXV, XXXVI, XXXVII, XLIII, XLIV, XLVIII, XLIX, LIV and LV were synthesized.

XXXII, treprostinil side chain succinic ester dimethylamide.
XXXIII, treprostinil side chain succinic ester morpholinamide.
XXXIV, treprostinil side chain succinic ester N-methylpiperazine.
XXXV, treprostinil side chain lysine ester.
XXXVI, treprostinil side chain proline ester.
XXXVII, treprostinil side chain β-alanine ester.
XLIII, treprostinil side chain acetate.
XLIV, treprostinil side chain hydroxy acetic ester.
XLVIII, treprostinil side chain p-toluic ester.
XLIX, treprostinil side chain trimethylacetic ester.
LIV, treprostinil side chain (4-hydroxyphenoxy)acetic ester.
LV, treprostinil side chain propionic ester.

Scheme 17: Syntheses of Treprostinil Side Chain Monosubstituted Carbamates (Prodrugs XXXXIII and XLII)

In

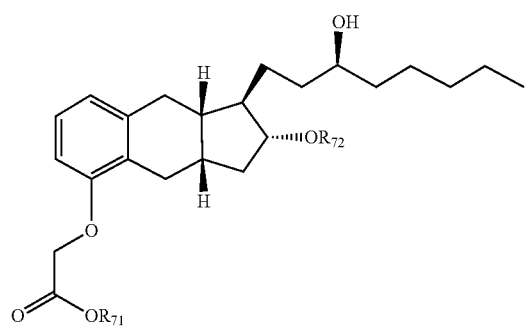

71

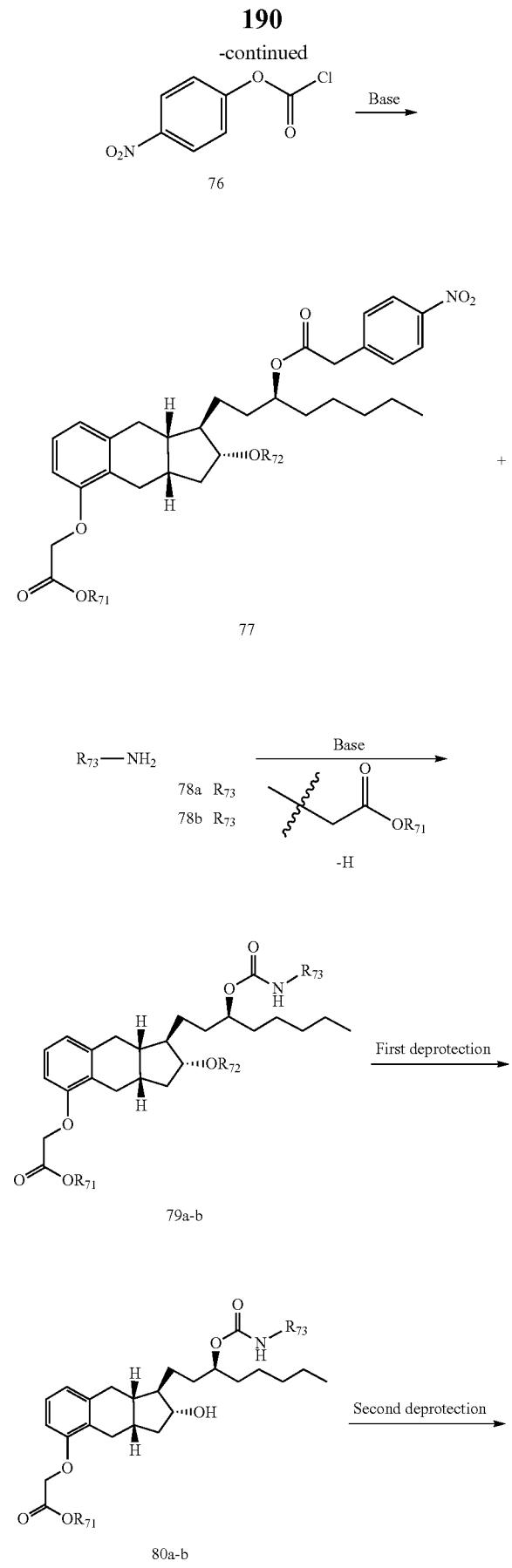

-continued

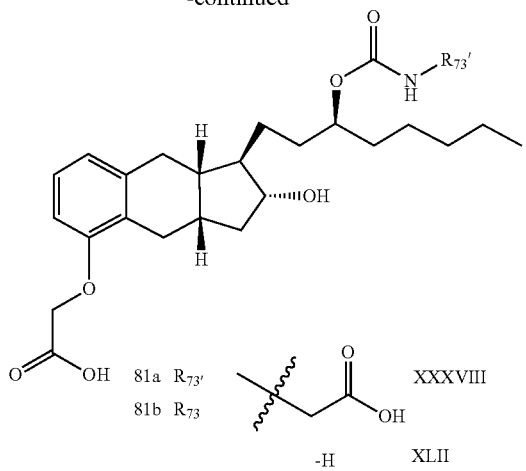

In Scheme 17, $R_{71}$ and $R_{72}$ are the same as in Scheme 16.

Procedure for the Synthesis of Treprostinil Mono-TES Benzyl Ester Side Chain (4-Nitrophenol) Carbonate (77)

To a stirring solution of treprostinil mono-TES benzyl ester (71) (1.0 eq) in THF (15 v/wt) at room temperature under argon was added pyridine (5.0 eq). The solution was cooled to 0° C. Then, a solution of 4-nitrophenol chloroformate (76) (1.5 eq) in THF (7 v/wt) was added drop wise and stirred at room temperature for 2 h. Water was added and the aqueous layer was extracted with EtOAc. The combined organic layers washed with brine, dried over sodium sulfate, filtered, concentrated the filtrate in vacuo to give crude product. It was purified on silica gel column chromatography to afford treprostinil mono-TES benzyl ester side chain (4-nitrophenol) carbonate (77). The compound 77 was characterized by $^1$H NMR and LCMS.

General Procedure for the Syntheses of Treprostinil Mono-TES Benzyl Ester Side Chain Carbamate (79a-b)

79a: To a stirring solution of treprostinil mono-TES benzyl ester side chain (4-nitrophenol) carbonate (7) (1.0 eq) in THE (20 v/wt) and water (1 v/wt) was added benzyl glycine hydrochloride (78a) (1.1 eq) and potassium carbonate (1.2 eq). The mixture was stirred at room temperature overnight.

79b: To a stirring solution of treprostinil mono-TES benzyl ester side chain (4-nitrophenol) carbonate (7) (1.0 eq) in THE (20 v/wt) was added ammonia solution (7 N in methanol) (78b) (10 eq). The mixture was stirred at room temperature for 4 h.

Water and ethyl acetate were added and layers separated. The aqueous layer was extracted with ethyl acetate. The combined organic extracts were washed with brine, dried over sodium sulfate, filtered, and concentrated the filtrate in vacuo to give crude product. It was purified on silica gel column chromatography to give the treprostinil mono-TES benzyl ester side chain carbamate (79a-b). The compound 79a-b were characterized by $^1$H NMR and LCMS.

General Procedure for the Synthesis of Treprostinil Benzyl Ester Side Chain Carbamates (80a-b)

First Deprotection or Desilylation

Using the general procedure described for compound 74 treprostinil benzyl ester side chain carbamates (80a-b) were prepared and characterized.

General Procedure for the Synthesis of Treprostinil Side Chain Carbamates (81a-b) (Second Deprotection or Debenzylation)

Similarly following the general procedures described for compound 75, treprostinil benzyl ester side chain carbamates (81a-b) were prepared and characterized. Thus were prepared prodrugs XXXVIII and XLII.

XXXVIII, treprostinil side chain glycine carbamate (81a).

XLII, treprostinil side chain carbamate (81b).

Scheme 18: Synthesis of Treprostinil Side Chain Monosubstituted Carbonate (Prodrugs XXXXIX)

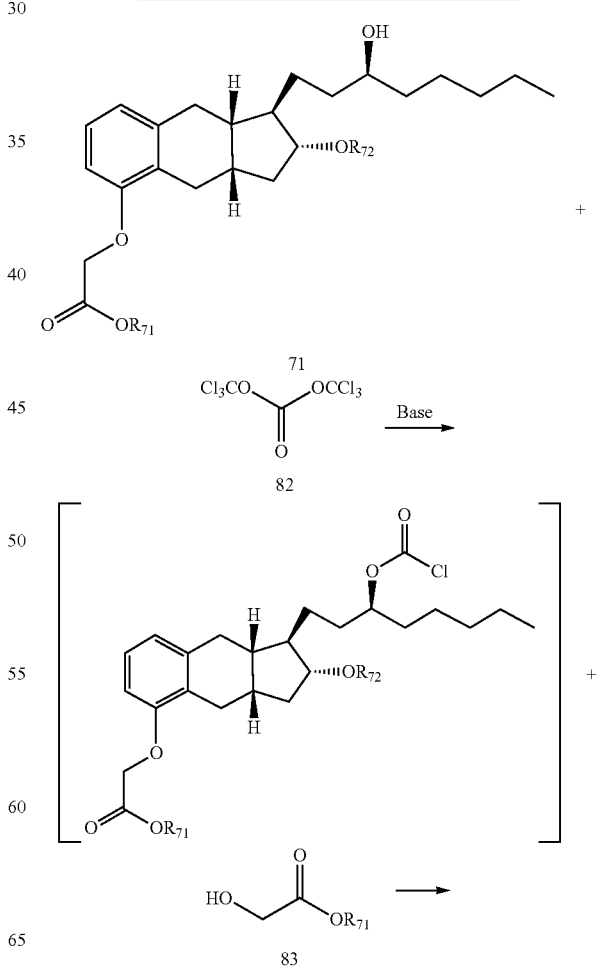

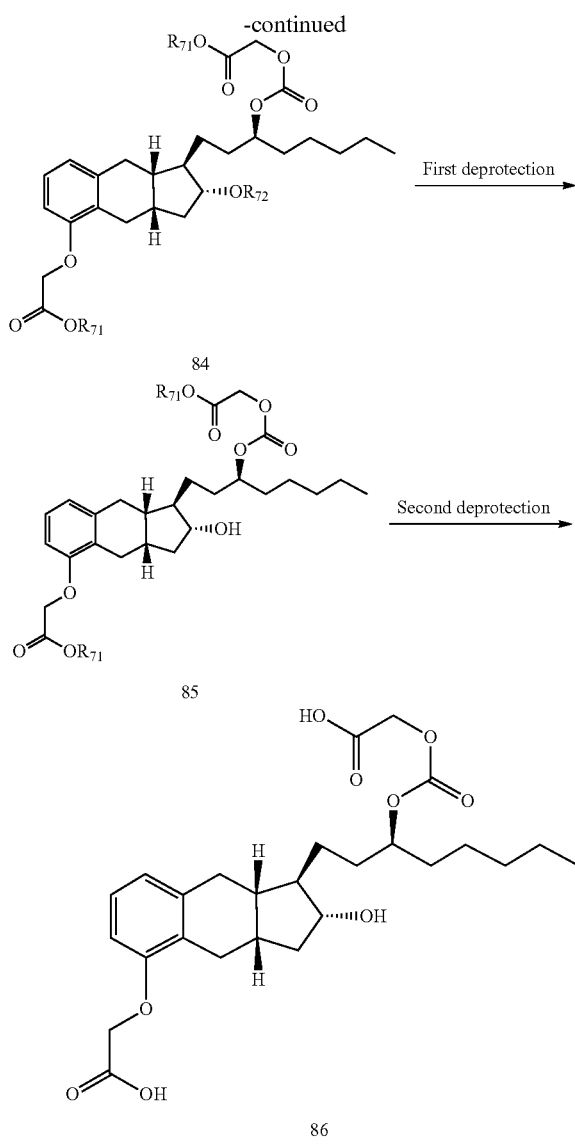

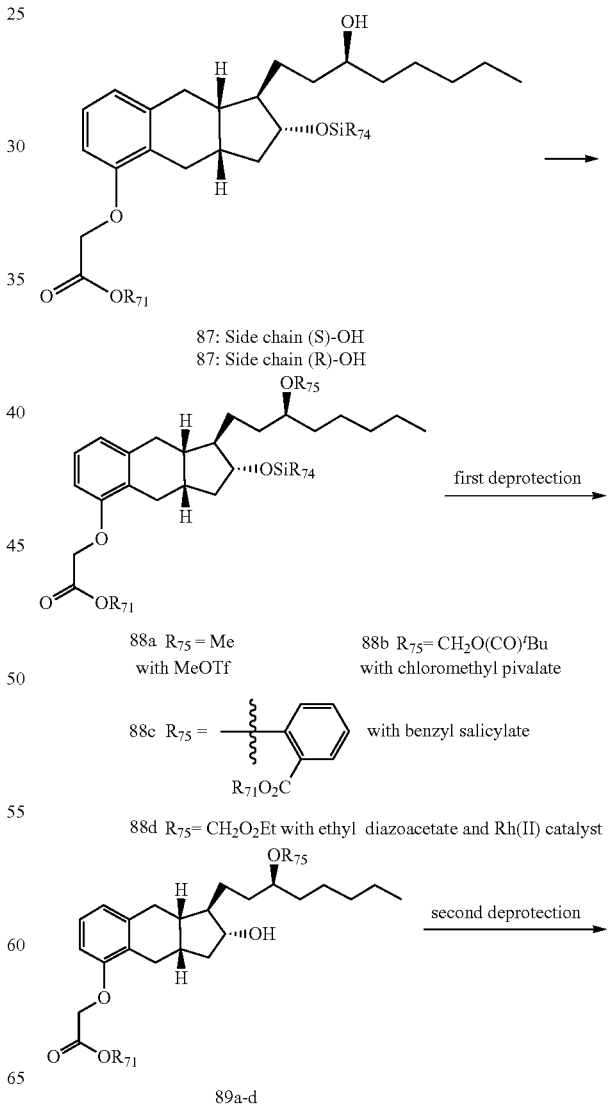

In Scheme 18, $R_{71}$ and $R_{72}$ are the same as in Schemes 16-17.

Procedure for the Syntheses of Treprostinil Mono-TES Benzyl Ester Side Chain Benzyl Glycolate Carbonate (84)

To a stirring solution of triphosgen (82) (1.0 eq) in toluene (10 v/wt) at 0° C. under argon was added a solution of treprostinil mono-TES benzyl ester (71) (1.0 eq) and pyridine (1.1 eq) in toluene (10 v/wt) through addition funnel. The mixture was stirred for 3 h. To this, was added a solution of benzyl glycolate (83) (10 eq) and pyridine (10 eq) in toluene (5 v/wt). The mixture was stirred overnight. Saturated sodium bicarbonate solution and ethyl acetate were added and stirred for 10 min. The layers were separated. The aqueous layer was extracted with ethyl acetate. The combined organic extracts were washed with brine, dried over sodium sulfate, filtered, and concentrated the filtrate in vacuo to give the crude product. It was purified on silica gel column chromatography to give triprostinil mono-TES benzyl ester side chain benzyl glycolate carbonate (84). The compound 84 was characterized by $^1$H NMR and LCMS. The purity was determined by HPLC.

Procedure for the Synthesis of Treprostinil Benzyl Ester Side Chain Benzyl Glycolate Carbonate (85)

First Deperotection or Desilylation

Using the general procedure described for compound 74, treprostinil benzyl ester side chain benzyl glycolate carbonate (85) was prepared and characterized.

Procedure for the Synthesis of Treprostinil Side Chain Glycolate Carbonate (16) (Prodrug XXXIX)

Second Deprotection or Debenzylation

Using the general procedure described for compound 75, treprostinil side chain glycolate carbonate (86) (Prodrug XXXIX) was prepared and characterized accordingly.

-continued

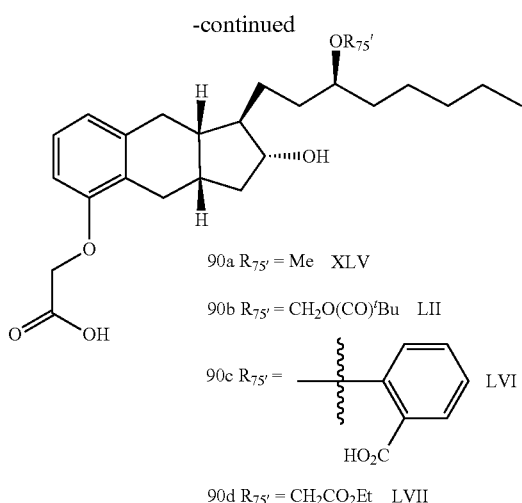

90a R$_{75'}$ = Me    XLV

90b R$_{75'}$ = CH$_2$O(CO)$^t$Bu    LII

90c R$_{75'}$ = 
[2-carboxyphenyl group]    LVI

90d R$_{75'}$ = CH$_2$CO$_2$Et    LVII

The first reaction in Scheme 19 may be alkylation or Mitsunobu or diazoacetate coupling performed in the presence of a base. In Scheme 19, R$_{71}$ may be the same as in Schemes 16-18. SiR$_{74}$ may be a silyl ester, such as triethylsilyl, trimethylsilyl, t-butyldimethylsilyl, t-butyldiphenylsilyl, phenyldimethylsilyl. In some embodiments, R$_{74}$ may be Et$_3$ or t-BuMe$_2$. Procedure for the synthesis of treprostinil mono-TBDMS benzyl ester side chain methyl ether (88a, R$_{74}$=t-BuMe$_2$):

To a stirring solution of treprostinil mono-TBDMS benzyl ester (87, R$_{74}$=t-BuMe$_2$) (1.0 eq) and 4-methyl-bis(2,6-tert-butyl)pyri dine (15 eq) in DCM (30 v/wt) was added methyl triflate (10 eq). The mixture was stirred at 35° C. in oil bath for 6 h. Water was added and layers were separated. The aqueous layer was extracted with DCM. The combined organic layers were washed with brine, dried over sodium sulfate, filtered, and concentrated the filtrate in vacuo to give the crude product. It was purified on by column chromatography to give treprostinil mono-TBDMS benzyl ester side chain methyl ether (88a, R$_{74}$=t-BuMe$_2$). The compound (88a, R$_{74}$=t-BuMe$_2$) was characterized by $^1$H NMR and LCMS. The purity was determined by HPLC.

Procedure for the Synthesis of Treprostinil Mono-TES Benzyl Ester Side Chain Methyl Pivalate Ether (88b, R$_{74}$=Et$_3$)

To a stirring solution of treprostinil mono-TES benzyl ester (71) (=87, R$_{74}$=Eh) (1.0 eq) in anhydrous DMF (6.5 v/wt) at room temperature were added cesium carbonate (6.0 eq), sodium iodide (5.0 eq) and chloromethyl pivalate (5.0 eq). The resulting mixture was stirred at room temperature for three days. It was filtered and the filtrate was concentrated in vacuo to give crude product. It was purified on silica gel column chromatography to give the treprostinil mono-TES benzyl ester side chain methyl pivalate ether (88b, R$_{74}$=Et$_3$). The compound (88b, R$_{74}$=Et$_3$) was characterized by $^1$H NMR and LCMS. The purity was determined by HPLC.

Procedure for the Synthesis of Treprostinil Mono-TBDMS Benzyl Ester Side Chain Benzoate Ether (88c, R$_{74}$=t-BuMe$_2$)

To a stirring solution of 3'AU90 mono-TBDMS (87', R$_{74}$=t-BuMe$_2$)(1.0 eq.) and benzyl bromide (2.0 eq) in DMF (15 v/wt) was added potassium carbonate (3.0 eq) and sodium iodide (3 mol %). The solution was stirred at room temperature overnight. The mixture was filtered and the filtrate was concentrated in vacuo to give crude product which was purified on silica gel column chromatography to afford pure product 3'AU90 mono-TBDMS benzyl ester which was characterized by $^1$H NMR and LCMS. The purity was checked by HPLC.

To a stirring solution of 3'AU90 mono-TBDMS benzyl ester (1.0 eq), 2-benzyl salicylate (5.0 eq) and triphenyl phosphine (2.0 eq) in THF (25 v/wt) at 0° C. under argon was added dropwise DIAD (2.0 eq) in THF (8 v/wt) solution via addition funnel. The reaction mixture stirred at that temperature under argon overnight (slowly warm-up to room temperature). Water and EtOAc were added and layers were separated. The aqueous layer was extracted with EtOAc. Combined EtOAc layers were washed with brine, dried over sodium sulfate, filtered, and concentrated the filtrate in vacuo to give crude product. It was purified on silica gel column chromatography to give treprostinil mono-TBDMS benzyl ester side chain benzoate ether (88c, R$_{74}$=t-BuMe$_2$) which was characterized by $^1$H NMR and LCMS. The purity was determined by HPLC.

Procedure for the Synthesis of Treprostinil Mono-TBDMS Benzyl Ester Side Chain Ethyl Acetate Ether (88d, R$_{74}$=t-BuMe$_2$)

To a suspension of treprostinil mono-TBDMS benzyl ester (87, R$_{74}$=t-BuMe$_2$) (1.0 eq) and rhodium (II) acetate dimer (10 mol %) in anhydrous toluene (10 v/wt) at 80° C. under argon was added a solution of 15 wt. % toluene solution of ethyl diazoacetate (4.0 eq) in toluene (1 v/v) dr op wise over a period of 75 min. After 6 h, the reaction was complete. The reaction mixture was concentrated in vacuo. This was purified by column chromatography on silica gel to afford treprostinil mono-TBDMS benzyl ester side chain ethyl acetate ether (88d, R$_{74}$=t-BuMe$_2$). This compound (88d, R$_{74}$=t-BuMe$_2$) was characterized by $^1$H NMR.

General Procedure for the Syntheses of Treprostinil Benzyl Ester Side Chain Ethers (89a, 89c, 89d)

To a stirring solution of treprostinil mono-TMDMS benzyl ester side chain ether (88a or 88c or 88d, R$_{74}$=t-BuMe$_2$) (1.0 eq) in THF (20 v/wt) in a plastic tube was added HF.Py (10 eq). The solution was stirred at room temperature for 4 h. Saturated aq. sodium bicarbonate solution was added slowly to pH~7 followed by ethyl acetate, stirred for 10 min, separated layers. The aqueous layer was extracted with ethyl acetate. The combined organic extracts were washed with brine, dried over sodium sulfate, filtered and concentrated the filtrate in vacuo to give the crude product. It was purified by silica gel column chromatography to give treprostinil benzyl ester side chain ethers (89a, 89c, 89d). These compounds 89a, 89c, 89d were characterized by $^1$H NMR and LCMS. The purities were determined by HPLC.

Procedure for the Synthesis of Treprostinil Benzyl Ester Side Chain Methyl Pivalate Ether (89b)

First Deprotection or Desilylation

Using the general procedure described for compound 74, treprostinil benzyl ester side chain methyl pivalate ether (89b) was prepared and characterized.

Procedure for the Synthesis of Treprostinil Side Chain Ethers (90a-d) (Second Deprotection or Debenzylation)
Similarly using the general procedure described for compound 75, treprostinil side chain ethers (90a-d) were prepared and characterized accordingly.
Scheme 20: Syntheses of Treprostinil Side Chain Ethers (Prodrugs XLVI and L)
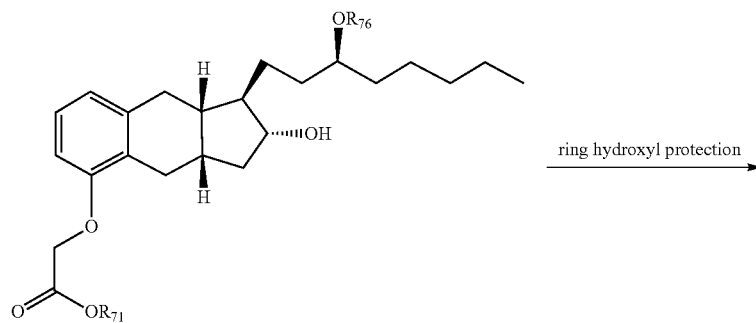
91
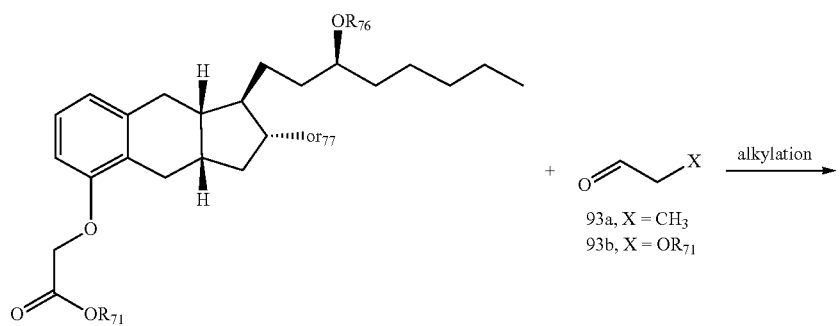
92
93a, X = CH₃
93b, X = OR₇₁
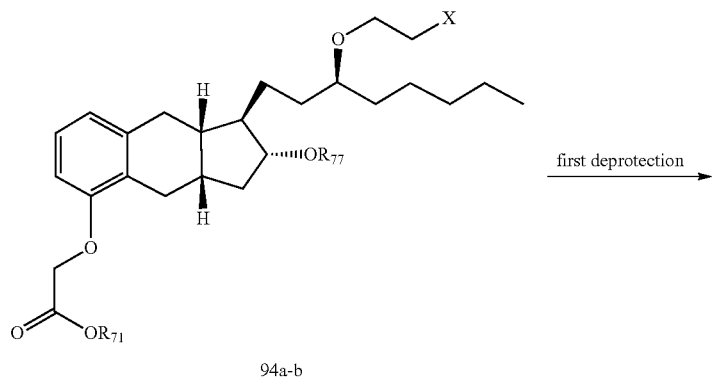
94a-b

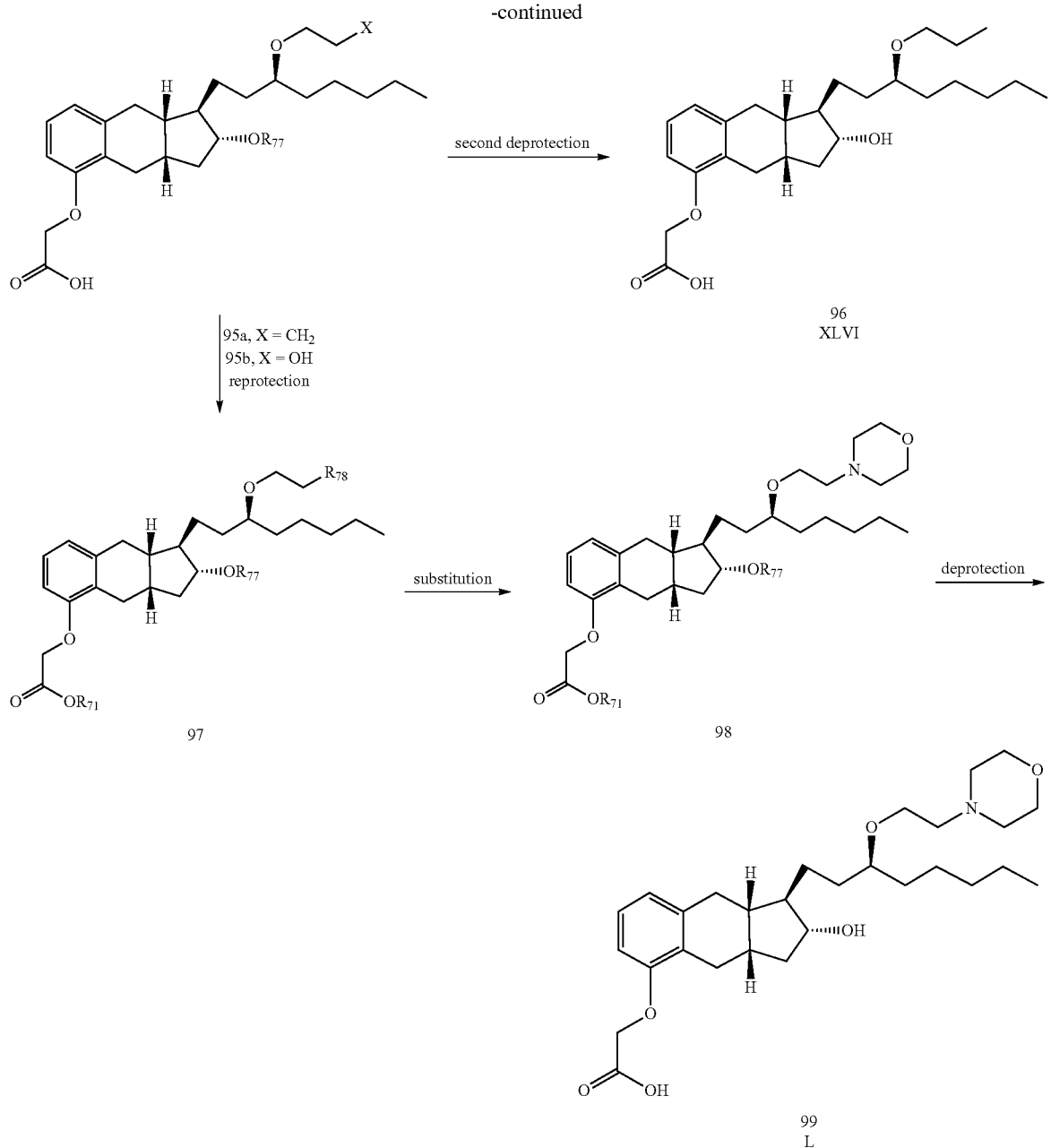

In Scheme 20, $R_{71}$ may be the same as in Schemes 16-19. $R_{76}$ may be a silyl ester, such as triethylsilyl, trimethylsilyl, t-butyldimethylsilyl, t-butyldiphenylsilyl, phenyl dimethyl silyl. In some embodiments, $R_{76}$ may be t-butyldimethylsilyl. $R_{77}$ may be a hydroxyl protective group, such as acetyl or benzoyl. $R_{78}$ may be a sulfonate group such as methyl sulphonate (mesylate) or p-toluenesulphonate (tosylate).

Synthesis of Treprostinil Benzyl Ester Acetate Side Chain TBDMS Ether (92)

To a solution of treprostinil benzyl ester side chain TBDMS ether (91) (1.0 eq) and dimethylaminopyridine (DMAP) (2.6 eq) in anhydrous dichloromethane (10 v/wt) was added acetic anhydride (2.0 eq) under argon at ambient temperature. After 1 h, the reaction was complete. The reaction mixture was evaporated in vacuo to obtain crude product. The crude compound was purified by column chromatography using silica gel to afford treprostinil benzyl ester acetate side chain TBDMS ether (92). The compound 92 was characterized by $^1$H NMR.

General Procedure for the Syntheses of Treprostinil Benzyl Ester Acetate Side Chain Ethers (94a-b)

To a solution of treprostinil benzyl ester side chain TBDMS acetate (92) (1.0 eq) in acetonitrile (20 v/wt) was added triethylsilane (1.5 eq). To this mixture a solution of bismuth bromide (7 mol %) in acetonitrile (2 v/wt) was added under argon. Then propionaldehyde (1.5 eq) was added slowly over a period of 5 min. The reaction mixture was stirred at room temperature under argon for 20 min. The reaction mixture was quenched with sat. aq. sodium bicarbonate solution and was extracted with ethyl acetate. The precipitate was filtered. The filtrate was dried over anhydrous Na$_2$SO$_4$, filtered and concentrate in vacuo to obtain crude product. The crude product was purified by silica gel column chromatography to obtain pure treprostinil benzyl ester acetate side chain ethers (94a-b). These compounds 94a-b were characterized by $^1$H NMR and LCMS.

General Procedure for the Syntheses of Treprostinil Acetate Side Chain Ethers (95a-b) (First Deprotection or Debenzylation)

Similarly using the general procedure described for compound 75, treprostinil acetate side chain ether acetates (95a-b) were prepared and characterized accordingly.

Procedure for the Synthesis of Treprostinil Side Chain Propyl Ether (96) (Prodrug XLVI)

To a solution of treprostinil acetate side chain propyl ether (95a) (1.0 eq) in methanol (25 v/wt) was added a solution of potassium hydroxide (4.0 eq) in water (6 v/wt). This was stirred at room temperature overnight. The reaction mixture was evaporated in vacuo and the residue was dissolved in water. The pH of this solution was adjusted to pH 2-3 with 1N HCl and then extracted with ethyl acetate. The organic layer was separated washed with brine, dried over sodium sulfate and evaporated in vacuo to obtain crude product. The crude product was purified by silica gel column chromatography to obtain treprostinil side chain propyl ether (96) (Prodrug XLVI). The compound 96 was characterized by IR, $^1$H NMR, $^{13}$C NMR and LCMS. The purity was determined by HPLC.

Procedure for the Synthesis of Treprostinil Benzyl Ester Side Chain Mesyloxy Ethyl Ether (97)

To a stirring solution of treprostinil hydroxy ethyl ether (95b) (1.0 eq) and benzyl bromide (1.1 eq) in acetone (40 v/wt) was added K$_2$CO$_3$ (2.0 eq). The mixture was stirred under argon overnight and the reaction was found not complete. NaI (25 mol %) and additional benzyl bromide (1.1 eq) were added and stirring was continued for another 5 h. The mixture was passed through a Celite pad and washed with acetone. The filtrate was concentrated in vacuo to provide crude product. This crude product was purified on silica gel column chromatography to obtain treprostinil benzyl ester side chain hydroxy ethyl ether which was characterized by $^3$H NMR, $^{13}$C NMR and LCMS. The purity was determined by HPLC.

To a stirring solution of treprostinil benzyl ester side chain hydroxy ethyl ether (1.0 eq) and triethylamine (6.0 eq) in DCM (40 v/wt) at 0-5° C. under argon was added methyl sulfonyl chloride (6.0 eq) in DCM (2 v/wt) dropwise. The mixture was stirred under argon for 1 h and the reaction was found to be complete. The mixture was concentrated in vacuo and the crude product was purified by silica gel column chromatography to give treprostinil benzyl ester side chain mesyloxy ethyl ether (97). The compound 97 was characterized by $^3$H NMR, $^{13}$C NMR and LCMS. The purity was determined by HPLC.

Procedure for the Synthesis of Treprostinil Benzyl Ester Side Chain Morpholine Ethyl Ether (28)

To a stirring solution of treprostinil benzyl ester side chain mesyloxy ethyl ether (97) (1.0 eq) and DIPEA (10 eq) in anhydrous CH$_3$CN (20 v/wt) was added morpholine (10 eq). The mixture was heated to 60-70° C. under argon for 11 h, then it was cooled to RT and concentrated in vacuo and the crude product was purified on silica gel column chromatography to obtain desired treprostinil benzyl ester side chain morpholine ethyl ether (98). The compound 98 was characterized by IR, $^1$H NMR, $^{13}$C NMR and LCMS. The purity was determined by HPLC.

Procedure for the Synthesis of Treprostinil Side Chain Morphine Ethyl Ether (99) (Prodrug L)

To a stirring solution of treprostinil benzyl ester side chain morpholine ethyl ether (98) (1.0 eq) in methanol (25 v/wt) was added 5% palladium on carbon (50% water) (25 wt %). The mixture was evacuated and replaced with hydrogen (from hydrogen balloon) for three times and stirred under H$_2$ atmosphere for 3 h. The mixture was passed through a Celite pad and washed with methanol. The solvent was removed in vacuo to give white solid. This was dissolved in methanol (25 v/wt). then NaOH (5.0 eq) in H$_2$O (5 v/wt) was added. The mixture was stirred under argon at RT for 4 h until the reaction was complete. To the mixture was added water, the mixture was extracted with MTBE. Then the aqueous was adjusted to pH 1-2 with 2N HCl and extracted with EtOAc. The extracts were washed with brine and dried over Na$_2$SO$_4$. The solvent was removed in vacuo to give pure treprostinil side chain morpholine ethyl ether (99) (Prodrug L). The compound 99 was characterized by $^3$H NMR, $^{13}$C NMR and LCMS. The purity was determined by HPLC.

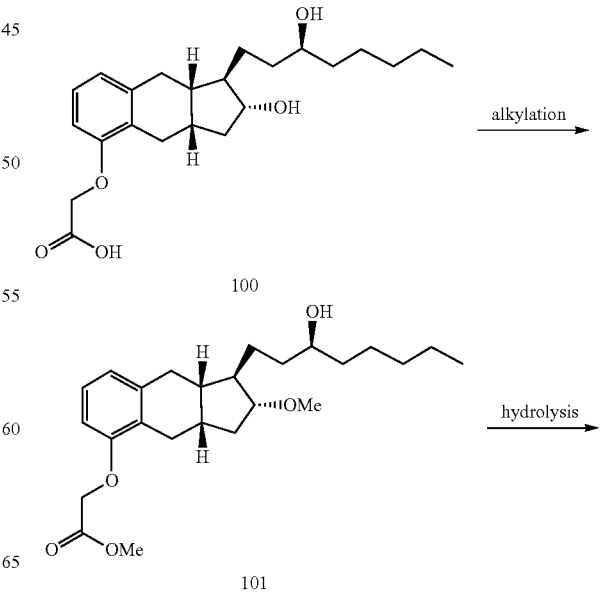

Scheme 21: Synthesis of Treprostinil Cyclopentyl Methyl Ether (Prodrug LIII)

-continued

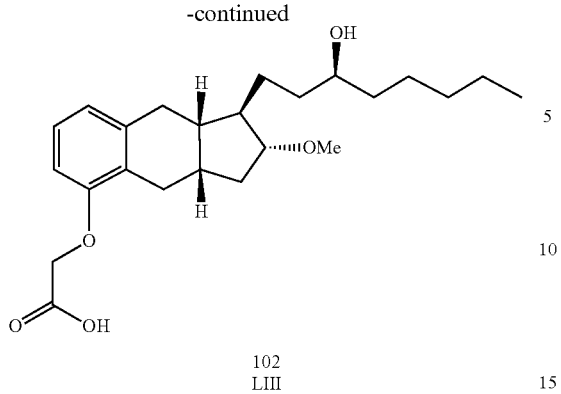

102
LIII

Procedure for the Synthesis of Treprostinil Methyl Ester Cyclopentyl Methyl Ether (101)

To a stirring solution of treprostinil (100) (1.0 eq) in anhydrous DMSO (20 v/wt) at room temperature were added potassium hydroxide (9.0 eq), and methyl iodide (20 eq). The resulting mixture was stirred at room temperature overnight. It was filtered and the filtrate was concentrated in vacuo to give crude product. Water and DCM were added, the layers separated. Aqueous layer was extracted with DCM. Combined organic layers washed with water, brine, dried over sodium sulfate, filtered, and concentrated in vacuo to give crude product. It was purified on silica gel column chromatography to give the treprostinil methyl ester cyclopentyl methyl ether (101). The compound 101 was characterized by $^1$H NMR and LCMS. The purity was determined by HPLC.

Synthesis of Treprostinil Cyclopentyl Methyl Ether (102) (Prodrug LXIII)

To a stirring solution of treprostinil methyl ester cyclopentyl methyl ether (101) (1.0 eq) in methanol (20 v/wt) was added sodium hydroxide (10 eq) in water (2 v/wt). The resulting mixture was stirred at room temperature for 6 h. The solvent was evaporated in vacuo. Water was added to the residue and extracted the basic solution by MTBE. The aqueous layer was cooled to 0° C. and adjusted pH~2 using 2N HCl. EtOAc was used to extract the acidic solution. The combined organic layers washed by brine, dried over sodium sulfate, filtered and concentrated the filtrate in vacuo to give crude product. It was dissolved in EtOAc and added to hexanes slowly to form solid, which was filtered and then dried overnight in the air to obtain treprostinil cyclopentyl methyl ether (102) (Prodrug LIII). The compound 102 was characterized by IR, $^1$H NMR, $^{13}$C NMR and LCMS. The purity was determined by HPLC.

Example 8

Syntheses of Treprostinil Disubstituted Prodrugs LXX-LXXIII

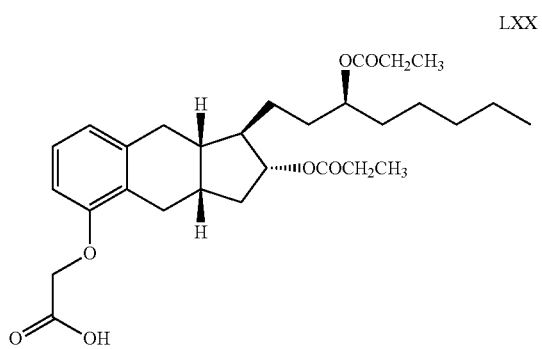

LXX

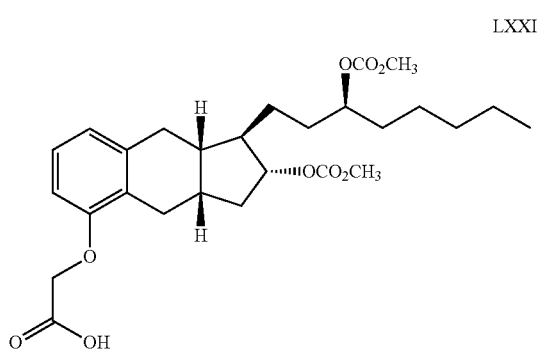

LXXI

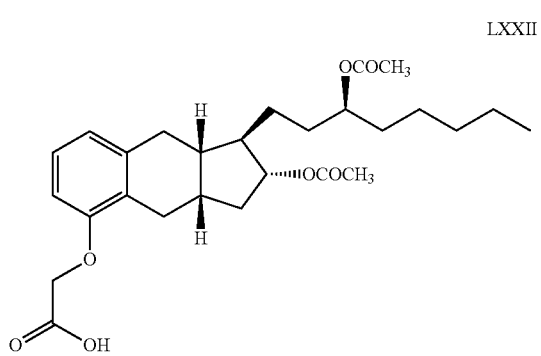

LXXII

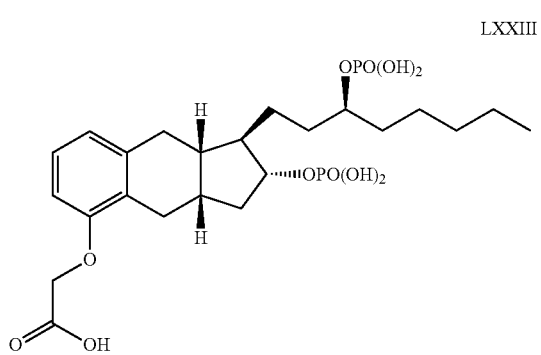

LXXIII

Scheme 22: Synthesis of Treprostinil Disubstituted Prodrug LXX-LXXIII

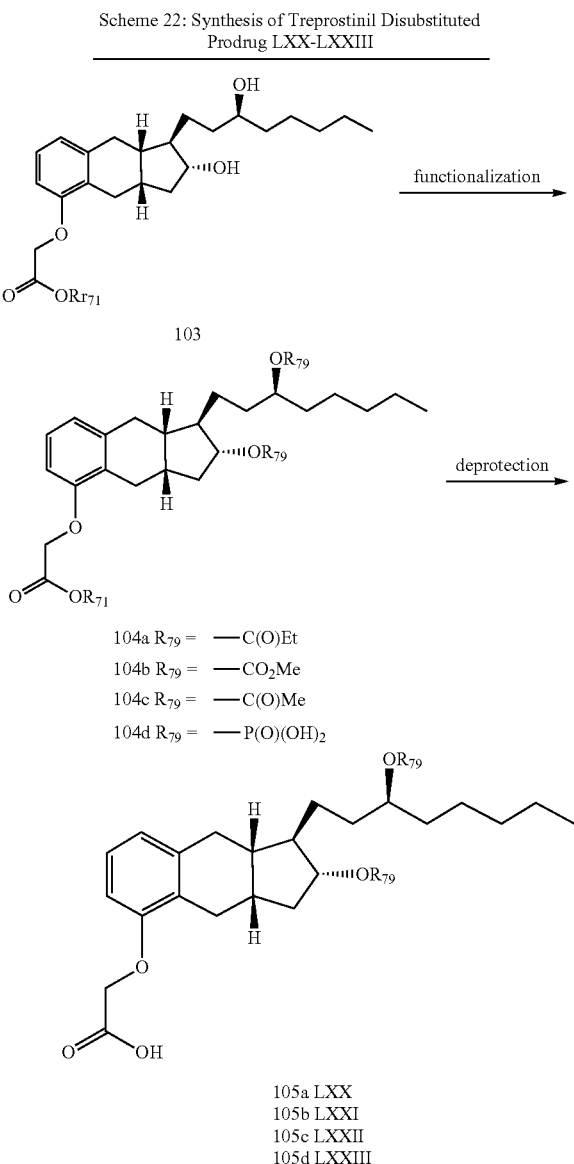

104a $R_{79}$ = —C(O)Et
104b $R_{79}$ = —CO$_2$Me
104c $R_{79}$ = —C(O)Me
104d $R_{79}$ = —P(O)(OH)$_2$

105a LXX
105b LXXI
105c LXXII
105d LXXIII

In Scheme 22, $R_{71}$ may be the same as in Schemes 16-20. The functionalization reaction may be, for example, acylation, carbonylation or phosphorylation.

EXPERIMENTAL

General Procedure for the Synthesis of Treprostinil Benzyl Ester Diacylate (104a and 104c) (Acylation)

To a stirring solution of treprostinil benzyl ester (103) (1.0 eq.) and DMAP (4.0 eq) in dichloromethane (DCM) (20 v/wt) was added propionic anhydride (2.5 eq) (for 104a) or acetic anhydride (2.5 eq) (for 104c). The resulting mixture was stirred at room temperature for 1 h. The solvent was removed in vacuo to give crude product. It was purified on silica gel column chromatography to give treptostinil benzyl ester diacylate (104a or 104c). These compounds (104a, 104c) were characterized by $^1$H NMR and LCMS. The purities were determined by HPLC.

Procedure for the Synthesis of Treprostinil Benzyl Ester Di Carbonate (104b)

To a solution of treprostinil benzyl ester (103) (1.0 eq) in anhydrous pyridine (5 v/wt) at 0 to 5° C. under argon was added dropwise a solution of methyl chloroformate (6.0 eq) in anhydrous dichloromethane (5 v/wt) over a period of 5 min. After complete addition, the reaction mixture was stirred at 0° C. to room temperature for 2 h. The mixture was treated with water and then extracted with dichloromethane. The dichloromethane extracts were washed with water, brine, dried over Na$_2$SO$_4$, filtered, and concentrated in vacuo to give crude oil. The crude product was purified by silica gel column chromatography to give the pure treprostinil benzyl ester di carbonate (104b) as white solid. The pure product was characterized by IR, $^1$H NMR, $^{13}$C NMR, DEPT-135 and LC-MS. The purity was determined by HPLC.

Procedure for the Synthesis of Treprostinil Benzyl Ester Di(Dibenzyl)Phosphate) (104d)

To a stirring solution of treprostinil benzyl ester (103) (1.0 eq) was added 1H-tetrazole (4.0 eq) (0.45 M in acetonitrile) through addition funnel under argon. The resulting mixture was stirred at room temperature for 10 min and dibenzyl-N,N-diisopropylphosphoramidite (3.0 eq) in DCM (7 v/wt) was added dropwise. The mixture was stirred at room temperature for 2 h. The reaction at this stage was complete and the system was cooled to −78° C. (dry ice-acetone). 3-Chloroperoxybenzoic acid (mCPBA) (70-75%) (4.2 eq) was added in one portion and stirred at that temperature for 2 h. The reaction was complete and sodium sulfite solution (10%) was added and stirred overnight (slowly warm up to room temperature). The DCM layer was checked by peroxide 100 test tip to make sure that there is no peroxide in solution (wash more time with sodium sulfite solution (10%) if peroxide exists). The DCM layer was washed with brine, dried over sodium sulfate, filtered, and concentrated in vacuo to give crude product. It was purified by silica gel column chromatography to give treprostinil benzyl ester di(dibenzyl)phosphate (104d). The compound 104d was characterized by $^3$H NMR and LCMS. The purity was determined by HPLC.

General Procedure for the Synthesis of Treprostinil Disubstituted Prodrugs (105a-d) (Deprotection or Debenzylation)

To a solution of treprostinil benzyl ester disubstituted prodrugs (104a-d) (1.0 eq) in ethyl acetate (20 v/wt) (and 1 v/wt water in case of 104d) was added 5% palladium on carbon (~50% water) (25 wt %) under argon. The mixture was evacuated under house vacuum and replaced by hydrogen (filled in a balloon) at room temperature and this process was repeated three times. The reaction mixture was stirred under the atmosphere of hydrogen at room temperature for 2.5 h. The mixture was filtered through Celite pad and washed with EtOAc. The filtrate was evaporated in vacuo to give pure treprostinil disubstituted prodrugs (105a-d) The pure products were characterized by IR, $^1$H NMR, $^{13}$C NMR, DEPT-135 ($^{31}$P NMR for 105d) and LC-MS. The purities were determined by HPLC.

Similarly following the general procedure described above, treprostinil disubstituted prodrugs LXX-LXXIII were synthesized. LXX, treprostinil dipropionate (105a);

LXXI, treprostinil dicarbonate (105b), LXXII, treprostinil diacetate (105c), LXXIII, treprostinil diphosphate (105d).

Additional Embodiments

1. A compound having the following formula:

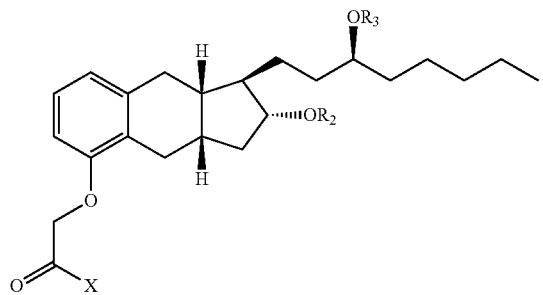

or a pharmaceutically acceptable salt of the compound, wherein X is $OR_9$, each of $R_9$, $R_2$ and $R_3$ is selected from H and a second drug moiety with a proviso that each of $R_9$, $R_2$ and $R_3$ is not H.

2. The compound of embodiment 1, wherein $R_9$ is H, one of $R_2$ and $R_3$ is H and the other of $R_2$ and $R_3$ is a second drug moiety.

3. The compound of embodiment 2, wherein $R_2$ is H and $R_3$ is a second drug moiety.

4. The compound of embodiment 2, wherein $R_2$ is a second drug moiety and $R_3$ is H 5. The compound of any one of embodiments 1-4, wherein the second drug moiety is a pain relief drug moiety.

6. The compound of embodiment 5, wherein the second drug moiety is a nonsteroidal anti-inflammatory drug moiety.

7. The compound of embodiment 6, wherein the nonsteroidal anti-inflammatory drug moiety is selected from the group consisting of aspirin, naproxene and ibuprofen.

8. A compound having the following formula:

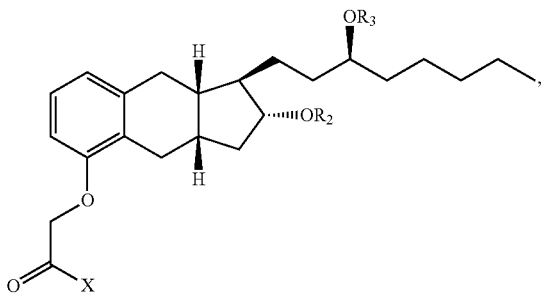

wherein X is OH, and $R_2$ and $R_3$ form together a carbonyl containing group or a phosphorous containing group.

9. The compound of embodiment 8, wherein $R_2$ and $R_3$ form together

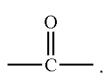

10. The compound of embodiment 8, wherein $R_2$ and $R_3$ form together

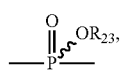

wherein $R_{23}$ is H, substituted or un substituted alkyl, substituted or unsubstituted alkenyl, substituted or unsubstituted cycloalkyl, and substituted or unsubstituted aryl.

11. A compound having the following formula

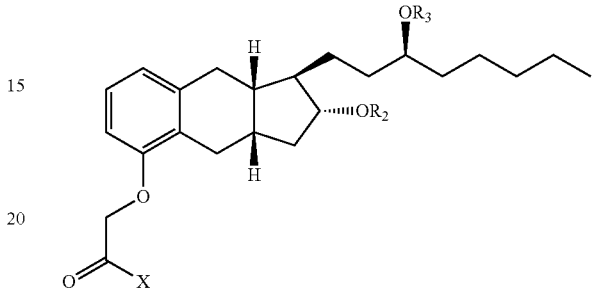

or a pharmaceutically salt of the compound, wherein X is $OR_9$, wherein $R_9$ is a phosphorous containing group having the following formula

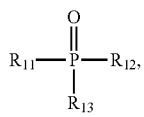

wherein $R_{11}$ is absent, or $R_{11}$ is a substituted or unsubstituted alkyl, and each of $R_{12}$ and $R_{13}$ are independently selected from H, substituted or un substituted alkyl, substituted or unsubstituted alkenyl, substituted or unsubstituted cycloalkyl, and substituted or unsubstituted aryl, $R_2$ and $R_3$ are each independently selected from H, phosporous containing groups, alkyls, or groups such that $OR_2$ or $OR_3$ form an ester containing group.

12. The compound of embodiment 11, wherein $R_{12}$, Rn, $R_2$ and $R_3$ are each H, and $R_{11}$ is $C_{1-4}$ alkyl.

13. A compound having the following formula

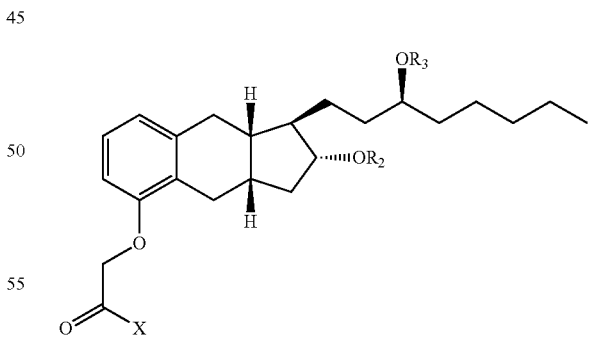

wherein X is OH, $R_2$ and $R_3$ are each individually selected from H or

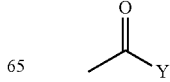

wherein Y is a) NR$_4$R$_5$, wherein R$_4$ and R$_5$ form a substituted or unsubstituted C$_3$-C$_8$ cycloalkyl group and b) OR$_4$, wherein R$_4$ is a C$_{1-6}$ alkyl group optionally substituted with a carboxy or hydroxy group, with a proviso that both R$_2$ and R$_3$ are not H.

14. The compound of embodiment 13, wherein R$_3$ is H.
15. The compound of embodiment 13, wherein R$_2$ is H.
16. The compound of embodiment 15, wherein R$_3$ is

wherein Y is NR$_4$R$_5$, wherein R$_4$ and R$_5$ form a substituted or unsubstituted C$_3$-C$_8$ cycloalkyl group.

17. The compound of embodiment 16, wherein R$_4$ and R$_5$ form a C$_3$-C$_8$ cycloalkyl group substituted with one or more substituent selected from substituted or unsubstituted alkyl groups and substituted or unsubstituted cycloalkyl groups.

18. The compound of embodiment 15, wherein R$_3$ is

wherein Y is OR$_4$, R$_4$ is a C$_{1-6}$ alkyl group optionally substituted with a carboxy or hydroxy group.

19. A compound having a formula selected from the group consisting of:

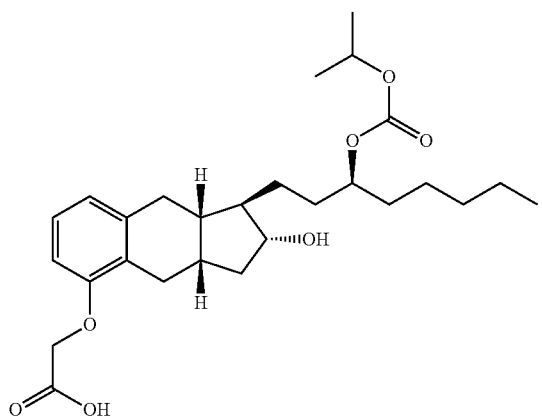

;

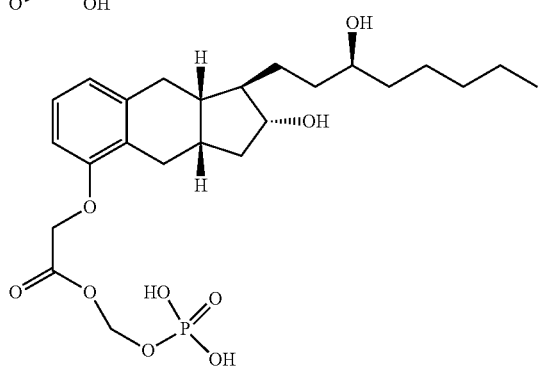

;

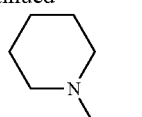

-continued

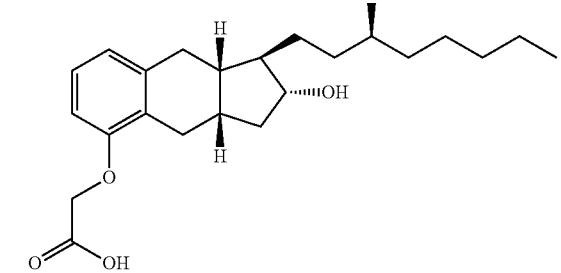

;

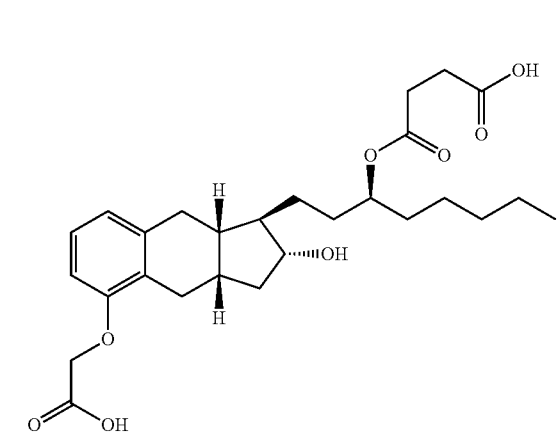

;

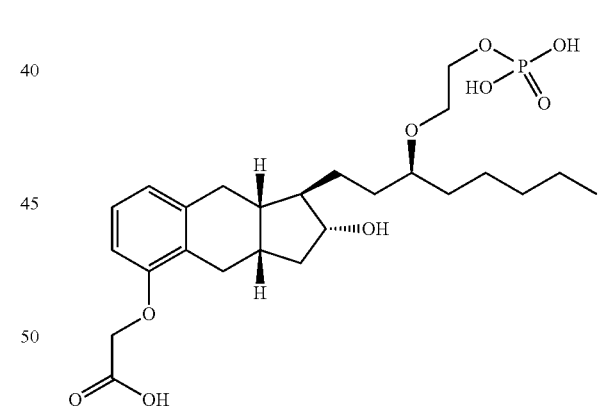

;

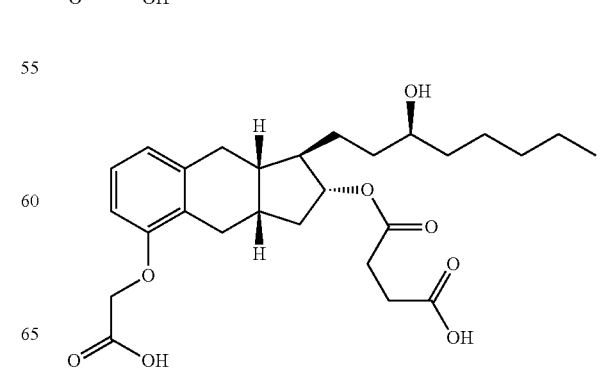

;

211
-continued

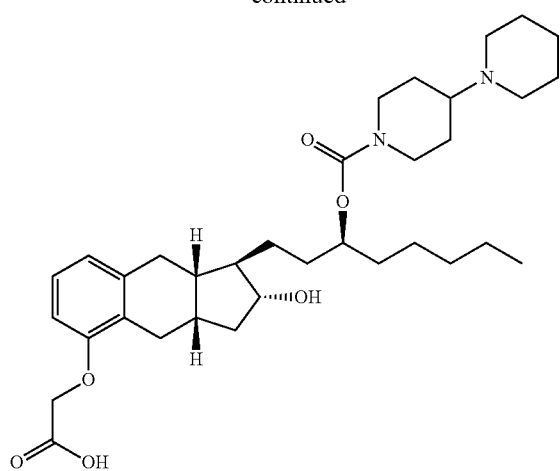

212
-continued

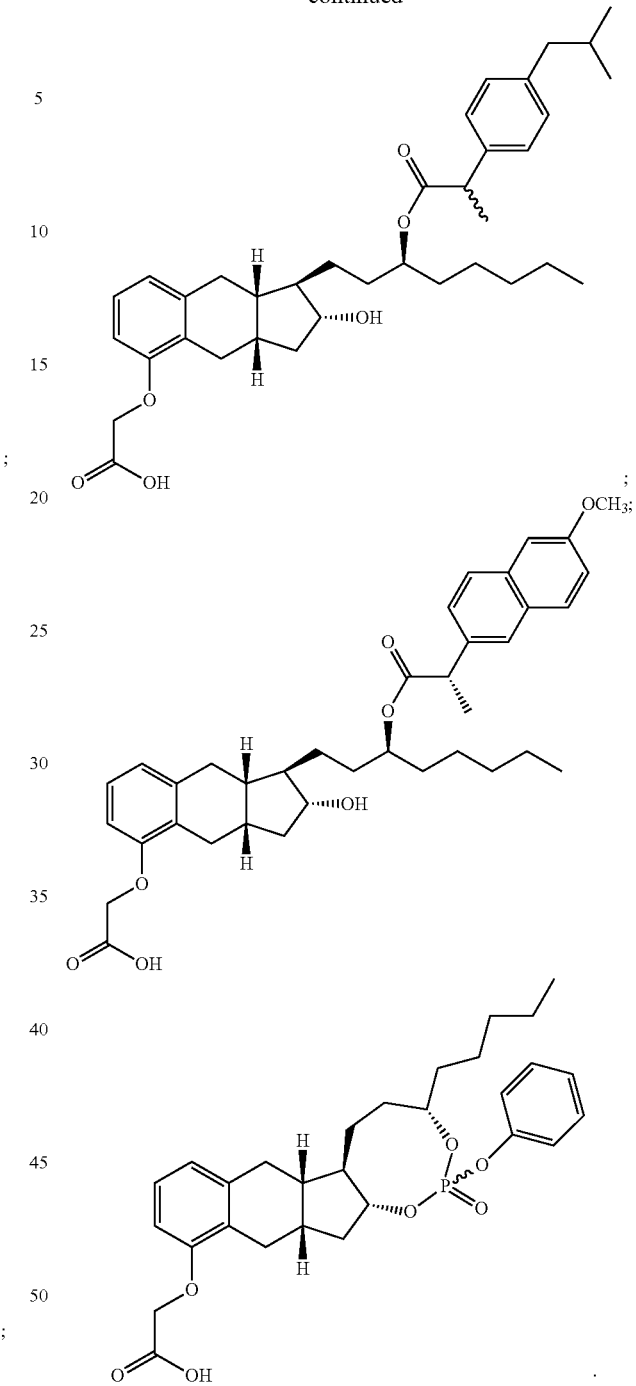

20. A pharmaceutical composition, comprising (A) an effective amount of the compound of any one of embodiments 1-19 and (B) a pharmaceutically acceptable carrier.
21. The pharmaceutical composition of embodiment 20, which is an oral pharmaceutical composition.
22. The pharmaceutical composition of embodiment 20, which is a subcutaneous pharmaceutical composition.
23. A method of treating a disease or condition comprising administering to a subject the composition of embodiment 20.
24. The method of embodiment 23, wherein the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma.

25. The method of embodiment 23, wherein the disease is pulmonary hypertension.
26. The method of any one of embodiments 23-25, wherein the composition is administered orally.
27. The method of embodiment 26, wherein the subject has detectable treprostinil plasma levels for at least 24 hours upon said administering.
28. The method of any one of embodiments 23-25, wherein the composition is administered by an injection.
29. The method of embodiment 28, wherein the administering is performed subcutaneously.
30. The method of embodiment 29, wherein said administering is continuous subcutaneous administering.
31. The method of any one of embodiments 28-30, wherein said administering results in no or less pain at a site of the injection compared to administering treprostinil.
32. The method of any one of embodiments 23-31, wherein the subject is a human being.
33. A method of treating a disease or condition comprising administering to a subject a prodrug of treprostinil, wherein upon said administering said prodrug converts to a metabolic product, which consists essentially of treprostinil.
34. The method of embodiment 33, wherein said metabolic product consists of treprostinil.
35. The method of embodiment 33 or 34, wherein said administering is performed orally.
36. The method of embodiment 35, wherein the subject has detectable treprostinil plasma levels for at least 24 hours after said administering.
37. The method of any one of embodiments 32-36, wherein the prodrug is a compound having the following formula:

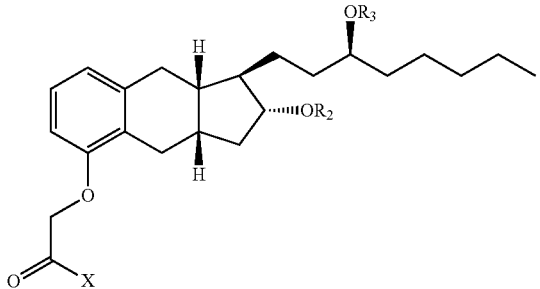

or a pharmaceutically acceptable salt of the compound, wherein X is $OR_9$, $R_9$ and $R_2$ is H, $R_3$ is a non-hydrogen group.

38. The method of embodiment 37, wherein $R_3$ is a phosphorous containing group or wherein $OR_3$ is an ester group.
39. The method of embodiment 38, wherein $R_3$ is phosphorous containing group having the following formula

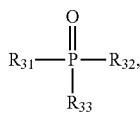

wherein $R_{31}$ is absent, or $R_{31}$ is a substituted or unsubstituted alkyloxy, and each of $R_{32}$ and $R_{33}$ are independently selected from H, substituted or unsubstituted alkyloxy, substituted or unsubstituted alkenyloxy, substituted or unsubstituted cycloalkyloxy, and substituted or unsubstituted aryloxy.

40. The method of embodiment 39, wherein $R_{31}$ is $C_{1-5}$ alkyl and each of $R_{32}$ and $R_{33}$ are H.
41. The method of embodiment 38, wherein $OR_3$ is an ester of an amino acid.
42. The method of embodiment 41, wherein the amino acid is alanine, valine or glycine.
43. The method of embodiment 38, wherein $OR_3$ is an ester of a second drug moiety.
44. The method of embodiment 43, wherein the second drug moiety is a pain relief drug moiety.
45. The method of embodiment 44, wherein the second drug moiety is a nonsteroidal anti-inflammatory drug moiety.
46. The method of embodiment 45, wherein the second drug moiety is selected from the group consisting aspirin, naproxene and ibuprofen.
47. The method of embodiment 37, wherein $R_3$ is

wherein Y is $OR_4$ or $NR_4R_5$, wherein each of $R_4$ and $R_5$ is independently selected from H and $C_{1-4}$ alkyl.

48. The method of embodiment 37, wherein $R_3$ is

wherein Y is $NR_4R_5$, wherein $R_4$ and $R_5$ form a substituted or unsubstituted $C_3$-$C_8$ cycloalkyl group.

49. The method of embodiment 48, wherein $R_4$ and $R_5$ form a $C_3$-$C_8$ cycloalkyl group substituted with one or more substituent selected from substituted or unsubstituted alkyl groups and substituted or unsubstituted cycloalkyl groups.

50. The method of embodiment 37, wherein $R_3$ is

wherein Y is $OR_4$, $R_4$ is a $C_{1-6}$ alkyl group optionally substituted with a carboxy or alkoxy group.

51. The method of one of embodiments 33-37, wherein the prodrug is selected from the group consisting of:
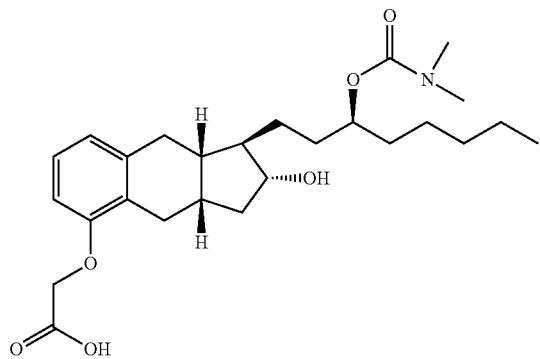
;
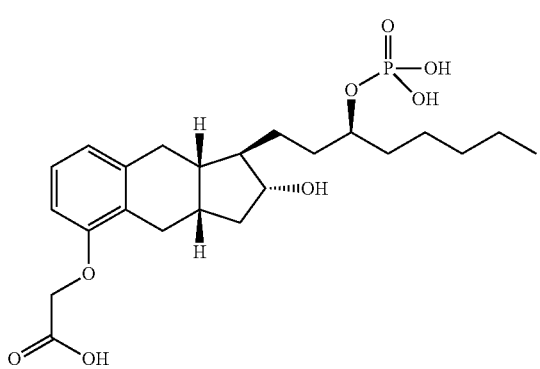
;
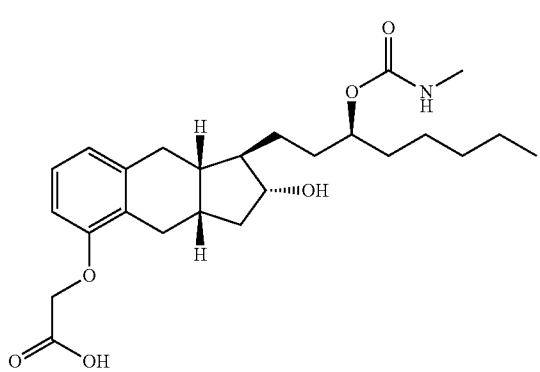
;
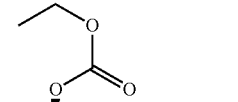
;
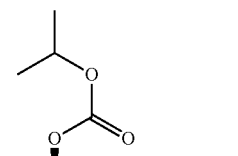
;
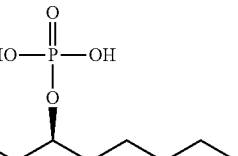
;
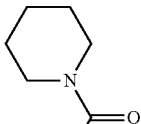
;

217
-continued
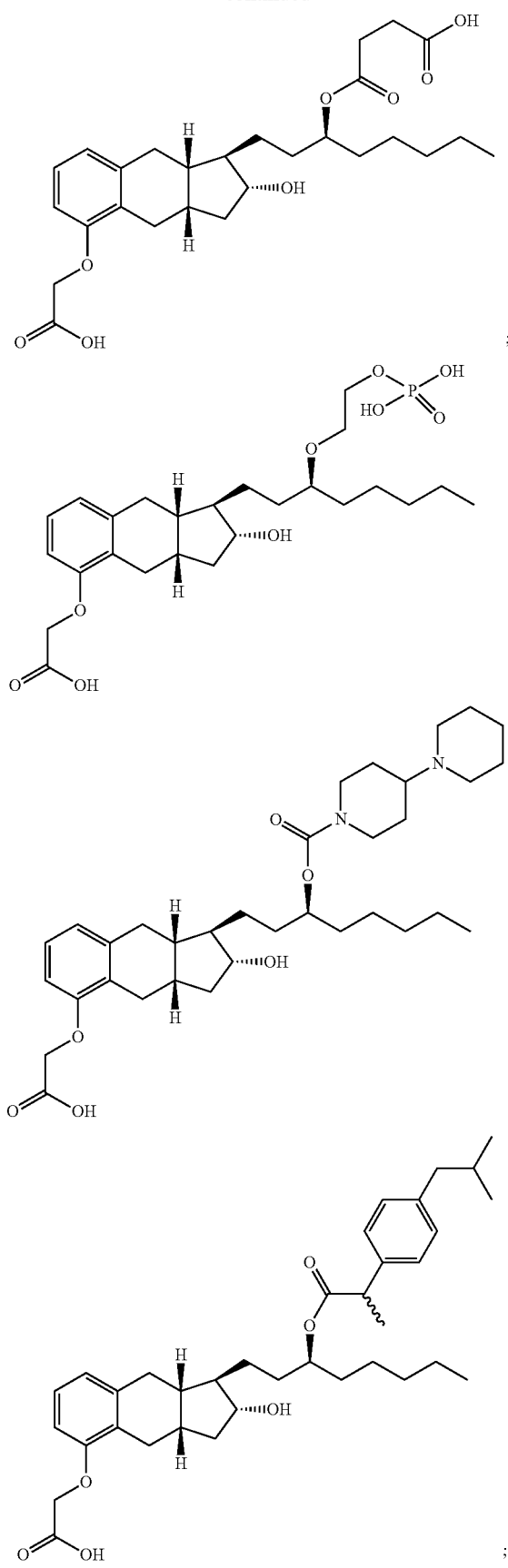
218
-continued
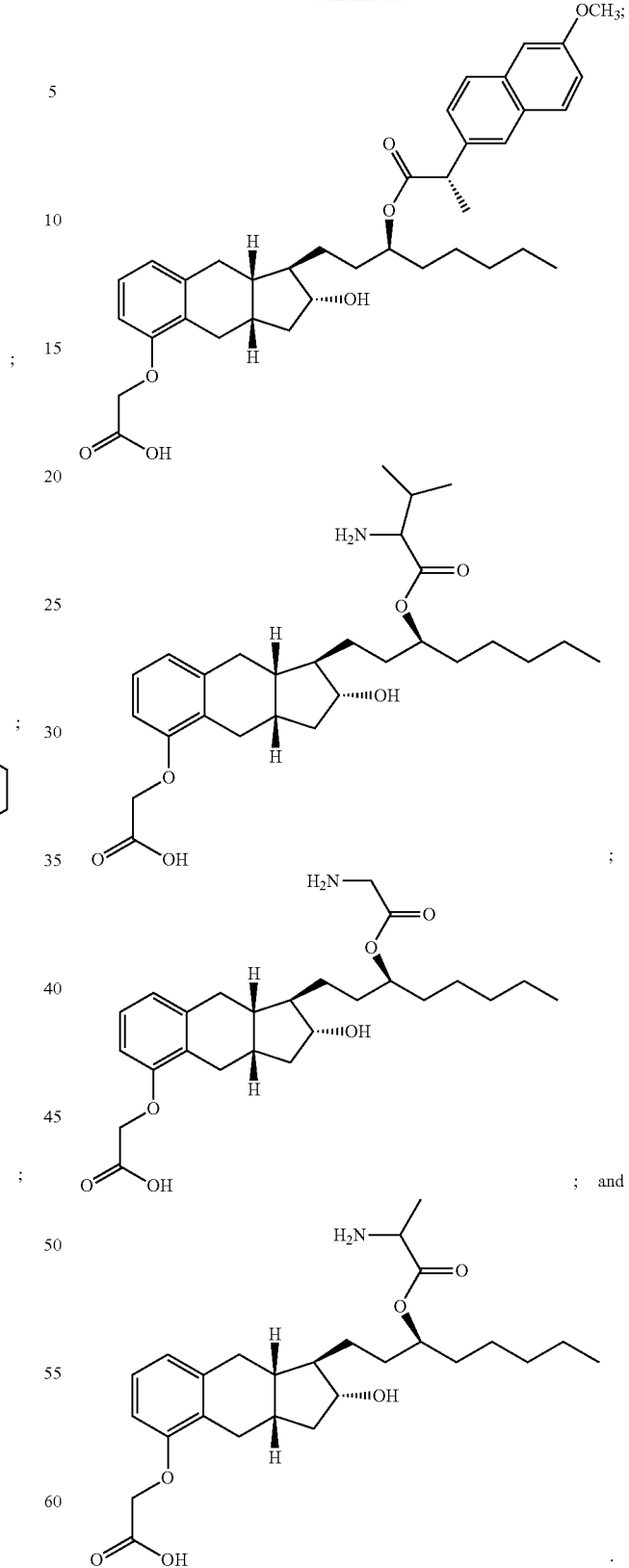
52. The method of any one of embodiments 33-51, wherein the disease or condition is one or more selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma.
53. The method of embodiment 53, wherein the disease is pulmonary hypertension.
54. The method of any one of embodiments 33-53, wherein the subject is a human being.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:

1. A compound having the following formula:

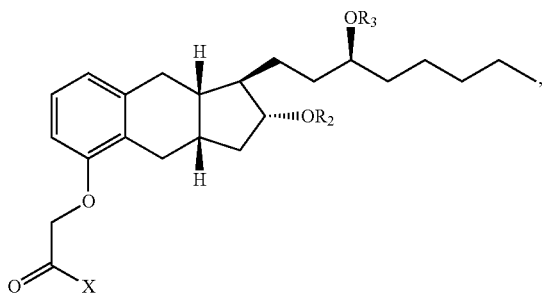

or a pharmaceutically acceptable salt thereof, wherein:
X is OR$^{14}$;
R$^{14}$ is a H;
one of R$^2$ and R$^3$ is a second drug moiety and the other one of R$^2$ and R$^3$ is H, wherein the second drug moiety is a pain relief drug moiety or a nonsteroidal anti-inflammatory drug moiety.

2. A pharmaceutical composition, comprising (A) an effective amount of the compound of claim 1 and (B) a pharmaceutically acceptable carrier.

3. A method of treating pulmonary hypertension comprising administering to a subject in need thereof the composition of claim 2.

4. The method of claim 3, wherein the composition is administered orally.

5. The method of claim 3, wherein the subject has detectable treprostinil plasma levels for at least 24 hours following said administration.

6. The method of claim 3, wherein the composition is administered by an injection.

7. The method of claim 6, wherein the administration is performed subcutaneously.

8. The method of claim 7, wherein said administration is continuous subcutaneous administration.

9. The method of claim 6, wherein said administration results in no or less pain at a site of the injection compared to administering treprostinil.

10. The method of claim 3, wherein the subject is a human being.

11. The method of claim 3, wherein upon said administration said compound converts to a metabolic product, which consists essentially of treprostinil.

12. The method of claim 11, wherein said metabolic product consists of treprostinil.

13. The method of claim 3, wherein the second drug moiety is a pain relief drug moiety.

14. The method of claim 3, wherein the second drug moiety is a nonsteroidal anti-inflammatory drug moiety.

15. The method of claim 14, wherein the second drug moiety is selected from the group consisting aspirin, naproxene and ibuprofen.

16. The method of claim 3, wherein the compound is

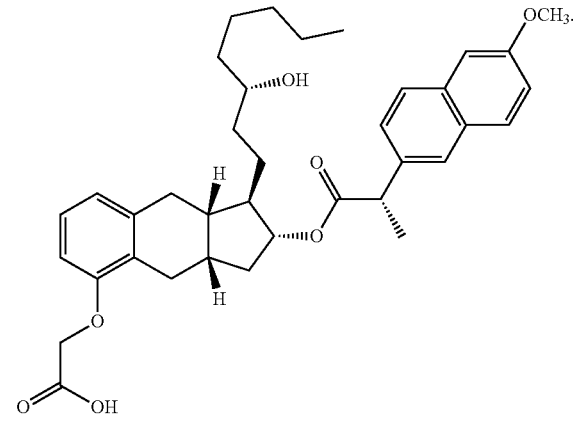 [SMILES: CCCCC[C@H](O)CC[C@@H]1[C@H]2Cc3cccc(OCC(=O)O)c3C[C@H]2C[C@H]1OC(=O)[C@@H](C)c1ccc2cc(OC)ccc2c1]

* * * * *